US012441799B2

(12) United States Patent
Tipton et al.

(10) Patent No.: US 12,441,799 B2
(45) Date of Patent: *Oct. 14, 2025

(54) ACTIVATABLE ANTI-CTLA-4 ANTIBODIES AND USES THEREOF

(71) Applicants: Bristol-Myers Squibb Company, Princeton, NJ (US); CytomX Therapeutics, Inc., South San Francisco, CA (US)

(72) Inventors: Kimberly Ann Tipton, South San Francisco, CA (US); James William West, South San Francisco, CA (US); Shrikant Deshpande, Fremont, CA (US); John J. Englehardt, El Cerrito, CA (US)

(73) Assignees: Bristol-Myers Squibb Company, Princeton, NJ (US); CytomX Therapeutics, Inc., South San Francisco, CA (US)

( * ) Notice: Subject to any disclaimer, the term of this patent is extended or adjusted under 35 U.S.C. 154(b) by 1097 days.

This patent is subject to a terminal disclaimer.

(21) Appl. No.: 17/399,729

(22) Filed: Aug. 11, 2021

(65) Prior Publication Data

US 2022/0089734 A1 Mar. 24, 2022

Related U.S. Application Data

(63) Continuation of application No. 16/347,522, filed as application No. PCT/US2017/059740 on Nov. 2, 2017, now Pat. No. 11,117,968.

(60) Provisional application No. 62/417,212, filed on Nov. 3, 2016.

(51) Int. Cl.
*C07K 16/28* (2006.01)
*A61K 39/395* (2006.01)

(52) U.S. Cl.
CPC ........ *C07K 16/2818* (2013.01); *A61K 39/395* (2013.01); *C07K 2317/24* (2013.01); *C07K 2317/41* (2013.01); *C07K 2317/50* (2013.01); *C07K 2317/76* (2013.01); *C07K 2317/92* (2013.01); *C07K 2317/94* (2013.01)

(58) Field of Classification Search
CPC . C07K 2317/41; C07K 2319/50; A61P 35/00; A61K 2039/505
See application file for complete search history.

(56) References Cited

U.S. PATENT DOCUMENTS

| | | | |
|---|---|---|---|
| 3,773,919 | A | 11/1973 | Boswell et al. |
| 4,522,811 | A | 6/1985 | Eppstein et al. |
| 5,151,510 | A | 9/1992 | Stec et al. |
| 6,808,710 | B1 | 10/2004 | Wood et al. |
| 6,984,720 | B1 | 1/2006 | Korman et al. |
| 7,465,790 | B2 | 12/2008 | Waldmann et al. |
| 7,488,802 | B2 | 2/2009 | Collins et al. |
| 7,605,238 | B2 | 10/2009 | Korman et al. |
| 7,666,817 | B2 | 2/2010 | Daugherty et al. |
| 7,943,743 | B2 | 5/2011 | Korman et al. |
| 8,008,449 | B2 | 8/2011 | Korman et al. |
| 8,168,757 | B2 | 5/2012 | Finnefrock et al. |
| 8,217,149 | B2 | 7/2012 | Irving et al. |
| 8,354,509 | B2 | 1/2013 | Carven et al. |
| 8,513,390 | B2 | 8/2013 | Stagliano et al. |
| 8,518,404 | B2 | 8/2013 | Daugherty et al. |
| 8,529,898 | B2 | 9/2013 | Daugherty et al. |
| 8,541,203 | B2 | 9/2013 | Daugherty et al. |
| 8,563,269 | B2 | 10/2013 | Stagliano et al. |
| 8,779,105 | B2 | 7/2014 | Korman et al. |
| 8,809,504 | B2 | 8/2014 | Lauermann |
| 8,846,042 | B2 | 9/2014 | Zhou |
| 8,900,587 | B2 | 12/2014 | Carven et al. |
| 9,120,853 | B2 | 9/2015 | Lowman et al. |
| 9,127,053 | B2 | 9/2015 | West et al. |
| 9,169,321 | B2 | 10/2015 | Daugherty et al. |
| 9,453,078 | B2 | 9/2016 | Stagliano et al. |

(Continued)

FOREIGN PATENT DOCUMENTS

| | | | |
|---|---|---|---|
| EP | 1324771 | B1 | 7/2003 |
| EP | 2282773 | B1 | 1/2014 |

(Continued)

OTHER PUBLICATIONS

Jenkins, K. (2015). Rational Design of a Tumor-Activated CTLA4 Antagonist Prodrug (Doctoral dissertation, City of Hope's Irell & Manella Graduate School of Biomedical Sciences). (Year: 2015).*

(Continued)

*Primary Examiner* — Julie Wu
*Assistant Examiner* — Bryan William Heck
(74) *Attorney, Agent, or Firm* — Sterne, Kessler, Goldstein &Fox P.L.L.C.

(57) ABSTRACT

Provided herein are activatable anti-human CTLA-4 antibodies comprising a heavy chain comprising a VH domain and a light chain comprising a masking moiety (MM), a cleavable moiety (CM), and a VL domain. Such activatable anti-human CTLA-4 antibodies have CTLA-4 binding activity in the tumor microenvironment, where the masking moiety is removed by proteolytic cleavage of the cleavable moiety by tumor-specific proteases, but exhibit greatly reduced binding to CTLA-4 outside the tumor. In this way, the activatable anti-human CTLA-4 antibodies of the present invention retain anti-tumor activity while reducing the side effects associated with anti-CTLA-4 activity outside the tumor.

14 Claims, 26 Drawing Sheets

Figure 1A:
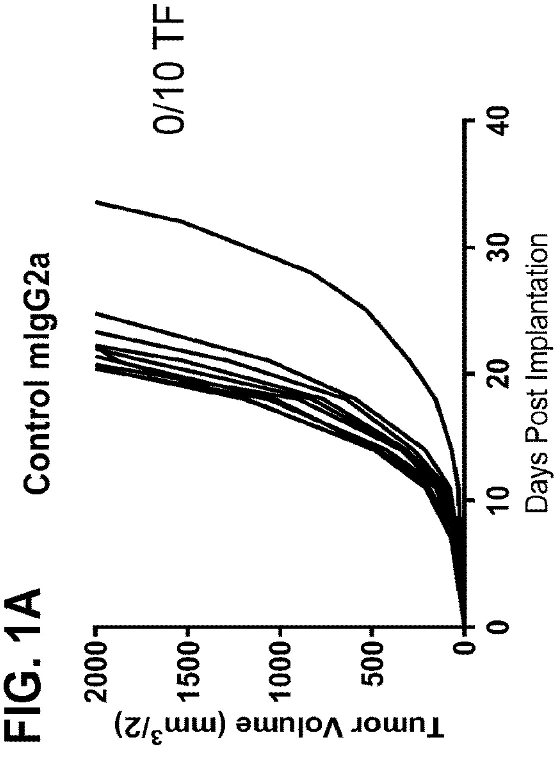

Specification includes a Sequence Listing.

(56) References Cited

U.S. PATENT DOCUMENTS

| | | | |
|---|---|---|---|
| 9,580,507 | B2 | 2/2017 | Korman et al. |
| 10,059,762 | B2 | 8/2018 | Stagliano et al. |
| 10,077,300 | B2 | 9/2018 | Daugherty et al. |
| 10,118,961 | B2 | 11/2018 | Stagliano et al. |
| 11,117,968 | B2 | 9/2021 | Tipton et al. |
| 2004/0109855 | A1 | 6/2004 | Waldmann et al. |
| 2004/0110704 | A1 | 6/2004 | Yamane et al. |
| 2005/0260186 | A1 | 11/2005 | Bookbinder et al. |
| 2006/0104968 | A1 | 5/2006 | Bookbinder et al. |
| 2009/0062142 | A1 | 3/2009 | Daugherty et al. |
| 2009/0304719 | A1 | 12/2009 | Daugherty et al. |
| 2010/0189651 | A1 | 7/2010 | Stagliano et al. |
| 2011/0081354 | A1 | 4/2011 | Korman et al. |
| 2012/0149061 | A1 | 6/2012 | Stagliano et al. |
| 2012/0207756 | A1 | 8/2012 | Stagliano et al. |
| 2012/0237512 | A1 | 9/2012 | Daugherty et al. |
| 2012/0237977 | A1 | 9/2012 | Daugherty et al. |
| 2012/0244154 | A1 | 9/2012 | Daugherty et al. |
| 2012/0276086 | A1 | 11/2012 | Black et al. |
| 2013/0309230 | A1 | 11/2013 | Stagliano et al. |
| 2014/0024810 | A1 | 1/2014 | Stagliano et al. |
| 2014/0045195 | A1 | 2/2014 | Daugherty et al. |
| 2015/0056206 | A1 | 2/2015 | Zhou |
| 2015/0079109 | A1 | 3/2015 | Li et al. |
| 2015/0322119 | A1 | 11/2015 | Englehardt et al. |
| 2016/0122425 | A1 | 5/2016 | Daugherty et al. |
| 2016/0185875 | A1 | 6/2016 | Cheng et al. |
| 2016/0193332 | A1 | 7/2016 | Lowman et al. |
| 2016/0228546 | A1 | 8/2016 | Stagliano et al. |
| 2016/0272708 | A1 | 9/2016 | Chen |
| 2016/0289324 | A1 | 10/2016 | Moore et al. |
| 2016/0311903 | A1 | 10/2016 | West et al. |
| 2017/0081397 | A1 | 3/2017 | Stagliano et al. |
| 2018/0215806 | A1 | 8/2018 | Williams et al. |
| 2019/0055321 | A1 | 2/2019 | Krystek, Jr. et al. |
| 2019/0119370 | A1 | 4/2019 | Stagliano et al. |
| 2019/0169245 | A1 | 6/2019 | Williams et al. |
| 2019/0211089 | A1 | 7/2019 | Daugherty et al. |

FOREIGN PATENT DOCUMENTS

| | | | | |
|---|---|---|---|---|
| EP | 3059319 | A1 | 8/2016 | |
| JP | 2006340714 | A | 12/2006 | |
| WO | WO-9411026 | A2 | 5/1994 | |
| WO | WO-9954342 | A1 | 10/1999 | |
| WO | WO-2001091798 | A2 | 12/2001 | |
| WO | WO-2002030460 | A2 | 4/2002 | |
| WO | WO-03035835 | A2 | 5/2003 | |
| WO | WO-2004009638 | A1 | 1/2004 | |
| WO | WO-2006089231 | A2 | 8/2006 | |
| WO | WO-2007105027 | A1 | 9/2007 | |
| WO | WO-2008052030 | A2 | 5/2008 | |
| WO | WO-2008156712 | A1 | 12/2008 | |
| WO | WO-2009025846 | A2 | 2/2009 | |
| WO | WO-2010081173 | A2 | 7/2010 | |
| WO | WO-2011066389 | A1 | 6/2011 | |
| WO | WO-2012145493 | A1 | 10/2012 | |
| WO | WO-2013079174 | A1 | 6/2013 | |
| WO | WO-2013173223 | A1 | 11/2013 | |
| WO | WO-2013181634 | A2 | 12/2013 | |
| WO | WO-2014089113 | A1 * | 6/2014 | ............. A61P 35/00 |
| WO | WO-2014179664 | A2 | 11/2014 | |
| WO | WO-2014193973 | A2 | 12/2014 | |
| WO | WO-2014194302 | A2 | 12/2014 | |
| WO | WO-2014206107 | A1 | 12/2014 | |
| WO | WO-2015035606 | A1 | 3/2015 | |
| WO | WO-2015085847 | A1 | 6/2015 | |
| WO | WO-2015112800 | A1 | 7/2015 | |
| WO | WO-2015112900 | A1 | 7/2015 | |
| WO | WO-2016004383 | A1 | 1/2016 | |
| WO | WO-2016014974 | A2 | 1/2016 | |
| WO | WO-2016106159 | A1 | 6/2016 | |
| WO | WO-2016115275 | A1 | 7/2016 | |
| WO | WO-2016118629 | A1 | 7/2016 | |
| WO | WO-2016149201 | A2 | 9/2016 | |
| WO | WO-2016197367 | A1 | 12/2016 | |
| WO | WO-2017020291 | A1 | 2/2017 | |
| WO | WO-2017020858 | A1 | 2/2017 | |
| WO | WO-2017024465 | A1 | 2/2017 | |
| WO | WO-2017024515 | A1 | 2/2017 | |
| WO | WO-2017025016 | A1 | 2/2017 | |
| WO | WO-2017025051 | A1 | 2/2017 | |
| WO | WO-2017034916 | A1 | 3/2017 | |
| WO | WO-2017040790 | A1 | 3/2017 | |
| WO | WO-2017106061 | A1 | 6/2017 | |
| WO | WO-2017123557 | A1 | 7/2017 | |
| WO | WO-2017132827 | A1 | 8/2017 | |
| WO | WO-2017133540 | A1 | 8/2017 | |
| WO | WO-2018085555 | A1 | 5/2018 | |
| WO | WO-2018213335 | A1 | 11/2018 | |
| WO | WO-2019036433 | A2 | 2/2019 | |

OTHER PUBLICATIONS

DrugBank ID: DB06186; "ipilimumab" (https://go.drugbank.com/drugs/DB06186) Retrieved Feb. 6, 2025. First deposited Mar. 19, 2008. (Year: 2008).*

Affara, N.I., et al., "Delineating Protease Functions During Cancer Development," Methods in Molecular Biology, 539:1-32, Humana Press, United States (2009).

Ascierto, P.A., et al., "Anti-ctla4 Monoclonal Antibodies: the Past and the Future in Clinical Application," Journal of translational medicine, 9:196, BioMed Central, England (2011).

Attia, P., et al., "Autoimmunity Correlates With Tumor Regression in Patients with Metastatic Melanoma Treated with Anti-Cytotoxic T-Lymphocyte Antigen-4," Journal of Clinical Oncology, 23(25):6043-6053, American Society of Clinical Oncology, United States (2005).

Baitsch, L., et al., "Extended Co-expression of Inhibitory Receptors by Human Cd8 T-cells Depending on Differentiation, Antigen-specificity and Anatomical Localization," PLoS One, 7(2):e30852, Public Library of Science, United States (2012).

Baldrick, P, "Pharmaceutical Excipient Development: the Need for Preclinical Guidance," Regulatory Toxicology and Pharmacology 32(2):210-218, Elsevier, Netherlands (2000).

Bowie, J.U., et al., "A Method to Identify Protein Sequences That Fold Into a Known Three-dimensional Structure," Science 253(5016):164-170, American Association for the Advancement of Science, United States (1991).

Bruhns, P., et al., "Specificity and Affinity of Human Fcgamma Receptors and Their Polymorphic Variants for Human IgG Subclasses," Blood 113(16):3716-3725, American Society of Hematology, United States (2009).

Charman, W.N., et al., "Lipids, Lipophilic Drugs, and Oral Drug Delivery—some Emerging Concepts," Journal of Pharmaceutical Sciences 89(8):967-978, Elsevier, United States (2000).

Chothia, C. and Lesk, A.M., "Canonical Structures for the Hypervariable Regions of Immunoglobulins," Journal of Molecular Biology 196(4):901-917, Elsevier Science, United States (1987).

Chothia, C., et al., "Conformations of Immunoglobulin Hypervariable Regions," Nature 342(6252):877-883, Nature Publishing Group, England (1989).

Corse, E and Allison, J.P., "Cutting Edge: CTLA-4 on Effector T Cells Inhibits In Trans," Journal of Immunology, 189(3):1123-1127, American Association of Immunologists, United States (2012).

Database Embase [Online] Elsevier Science Publishers. Amsterdam, NL; Jul. 1, 2017 (Jul. 1, 2017). Korman, A.J et al: "Next-generation anti-CTLA-4 antibodies", XP002779025, Database accession No. EMB-619155523.

Database Embase [Online] Elsevier Science Publishers. Amsterdam. NL; Jan. 1, 2018 (Jan. 1, 2018). Price K D et al: "Nonclinical safety evaluation of two distinct second-generation variants of anti-CTLA4 monoclonal antibody, ipilimumab. In monkeys", XP002779024, Database accession No. EMB-620384233.

Davies, D.R., et al., "Antibody-Antigen Complexes," Annual Review of Biochemistry 59:439-473, Annual Reviews, United States (1990).

Di Giacomo, A.M., et al., "The Emerging Toxicity Profiles of Anti-CTLA-4 Antibodies across Clinical Indications," Seminars in Oncology, 37(5):499-507, W.B. Saunders, United States (2010).

(56) References Cited

OTHER PUBLICATIONS

Flies, D.B., et al., "Blockade of the B7-H1/PD-1 Pathway for Cancer Immunotherapy," The Yale Journal of Biology and Medicine 84(4):409-421, Yale Journal of Biology and Medicine, United States (2011).

Gorelik, L., et al., Preclinical Characterization of a Novel Fully Human IgG1 anti-PD-L1 mAb CK-301, American Association for Cancer Research Annual Meeting (AACR), Abstract 4606 (2016).

Herbst, R.S., et al., "A Study of MPDL3280A, an Engineered PD-L1 Antibody in Patients with Locally Advanced or Metastatic Tumors," Journal of Clinical Oncology 31(Suppl):Abstract 3000, American Society of Clinical Oncology, United States (2013).

Hodi, F.S., et al., "Immunologic and Clinical Effects of Antibody Blockade of Cytotoxic T Lymphocyte-Associated Antigen 4 In Previously Vaccinated Cancer Patients," Proceedings of the National Academy of Sciences of the United States of America, 105(8):3005-3010, National Academy of Sciences, United States (2008).

Hodi, F.S., et al., "Improved Survival with Ipilimumab in Patients with Metastatic Melanoma," The New England Journal of Medicine 363(8):711-723, Massachusetts Medical Society, United States (2010).

Hoos, A., et al., "Development of Ipilimumab: Contribution to a New Paradigm for Cancer Immunotherapy," Seminars in oncology, 37(5):533-546, W.B. Saunders, United States (2010).

Hurwitz, A.A., et al., "Specific Blockade of Ctla-4/b7 Interactions Results in Exacerbated Clinical and Histologic Disease in an Actively-induced Model of Experimental Allergic Encephalomyelitis,"73(1-2):57-62, Elsevier/North-Holland, Netherlands (1997).

International Preliminary Report on Patentability for Application No. PCT/US2017/059740, mailed on May 7, 2019, 7 pages.

International Search Report and Written Opinion for Application No. PCT/US2017/059740, mailed on Mar. 23, 2018, 11 pages.

Keler, T. et al., "Activity and Safety of CTLA-4 Blockade combined with Vaccines in Cynomolgus Macaques", The J. of Immunology, vol. 171, pp. 6251-6259 (2003).

Krummel, M.F and Allison, J.P., "CD28 and CTLA-4 have Opposing Effects on the Response of T Cells to Stimulation," Journal of Experimental Medicine, 182(2):459-465, Rockefeller University Press, United States (1995).

Ku, G.Y., et al., "Single-Institution Experience with Ipilimumab In Advanced Melanoma Patients In The Compassionate Use Setting: Lymphocyte Count After 2 Doses Correlates With Survival," Cancer, 116(7):1767-1775, Wiley, United States (2010).

Laplanche, L.A., et al., "Phosphorothioate-modified Oligodeoxyribonucleotides. lii. Nmr and Uv Spectroscopic Studies of the Rp-rp, Sp-sp, and Rp-sp Duplexes, [d(Ggsaattcc)]2, Derived From Diastereomeric O-ethyl Phosphorothioates," Nucleic Acids Research 14(22):9081-9093, Oxford University Press, England (1986).

Leach, D.R., et al., "Enhancement of Antitumor Immunity by CTLA-4 blockade," Science 271(5256):1734-1736, American Association for the Advancement of Science, United States (1996).

Liakou, C.I., et al., "CTLA-4 Blockade Increases Ifngamma-Producing Cd4+Icoshi Cells to Shift the Ratio of Effector to Regulatory T Cells in Cancer Patients," Proceedings of the National Academy of Sciences of the United States of America, 105(39):14987-14992, National Academy of Sciences, United States (2008).

Liu, S.Y., et al., "Ongoing Clinical Trials of PD-1 and PD-L1 Inhibitors for Lung Cancer in China,"Journal of Hematology & Oncology, 10(1):136, Biomed Central, England (2017).

Maker, A.V., et al., "Analysis of the Cellular Mechanism of Antitumor Responses and Autoimmunity in Patients Treated With Ctla-4 Blockade," Journal of Immunology, 175(11):7746- 7754, American Association of Immunologists, United States (2005).

Malmqvist, M. "Biospecific interaction analysis using biosensor technology", Nature, 1993, vol. 361, p. 186-187.

Mellman, I., et al., "Cancer Immunotherapy Comes of Age," Nature 480(7378):480-489, Nature Publishing Group, England (2011).

Mook, O.R., et al., "In Situ Localization of Gelatinolytic Activity in the Extracellular Matrix of Metastases of Colon Cancer in Rat Liver Using Quenched Fluorogenic Dq-Gelatin," Journal of Histochemistry and Cytochemistry, 51(6):821-829, SAGE Publications, United States (2003).

Mossner, E., et al., "Increasing the Efficacy of CD20 Antibody Therapy Through the Engineering of A New Type II Anti-CD20 Antibody with Enhanced Direct and Immune Effector Cell-Mediated B-Cell Cytotoxicity," Blood 115(22):4393-4402, American Society of Hematology, United States (2010).

Murthy, R.V., et al., "Legumain Expression In Relation to Clinicopathologic and Biological Variables in Colorectal Cancer," Clinical Cancer Research, 11(6):2293-2299, The Association, United States (2005).

Natsume, A., et al., "Improving Effector Functions of Antibodies for Cancer Treatment: Enhancing ADCC and CDC," Drug Design, Development and Therapy 3:7-16, Dove Press Limited, New Zealand (2009).

NCI Drug Dictionary, pembrolizumab, accessed on Dec. 1, 2016, retrieved from the Internet URL: https://www.cancer.gov/drugdictionary?cancer-drug?cdrid=695789, 3 pages.

Nielsen, B.S., et al., "Urokinase Plasminogen Activator Is Localized In Stromal Cells in Ductal Breast Cancer," Laboratory Investigation, 81(11):1485-1501, Nature Publishing Group, United States (2001).

Nimmerjahn, F. and Ravetch, J.V., "Divergent Immunoglobulin G Subclass Activity Through Selective Fc Receptor Binding," Science 310(5753):1510-1512, American Association for the Advancement of Science, United States (2005).

Onishi, Y., et al., "Foxp3+ Natural Regulatory T Cells Preferentially Form Aggregates On Dendritic Cells in Vitro and Actively Inhibit Their Maturation," Proceedings of the National Academy of Sciences of the United States of America, 105(29):10113-10118, National Academy of Sciences, United States (2008).

Pardoll, D.M., "Immunology Beats Cancer: A Blueprint for Successful Translation," Nature Immunology, 13(12):1129-1132, Nature America, Inc, United States (2012).

Pardoll, D.M., "The Blockade of Immune Checkpoints in Cancer Immunotherapy," Nature Reviews Cancer 12(4):252-264, Nature Publishing Group, England (2012).

Pearlman and Nguyen, "Analysis of protein drugs," Chapter 6, In Peptide and Protein Drug Delivery, 1st ed., [In Advances in Parenteral Sciences, vol. 4] (Lee, ed.) (Marcel Dekker, Inc., New York, 1991) pp. 247-301.

Peggs, K.S., et al., "Cell Intrinsic Mechanisms of T-cell Inhibition and Application to Cancer Therapy," Immunological Reviews, 224:141-65, Blackwell, England (2008).

Pei-Show Juo., The Concise Dictionary of Biomedicine and Molecular Biology, 2nd Edition, CRC Press, United States (2002).

Perrin, P.J., et al., "CTLA-4 Blockade Enhances Clinical Disease and Cytokine Production during Experimental Allergic Encephalomyelitis," Journal of Immunology, 157(4):1333-1336, American Association of Immunologists, United States (1996).

Powell, M.F., et al., "Compendium of Excipients for Parenteral Formulations," PDA Journal of Pharmaceutical Science and Technology / PDA 52(5):238-311, PDA (Parenteral Drug Association), United States (1998).

Quezada, S.A., et al., "CTLA4 Blockade and GM-CSF Combination Immunotherapy Alters the Intratumor Balance of Effector and Regulatory T Cells," Journal of Clinical Investigation, 116(7):1935-1945, American Society for Clinical Investigation, United States (2006).

Qureshi, O.S., et al., "Trans-Endocytosis of CD80 and CD86: a Molecular Basis for the Cell-Extrinsic Function of CTLA-4," Science, 332(6029):600-603, American Association for the Advancement of Science, United States (2011).

Read, S., et al., "Cytotoxic T Lymphocyte-Associated Antigen 4 Plays An Essential Role In The Function of CD25(+)CD4(+) Regulatory Cells That Control Intestinal Inflammation," Journal of Experimental Medicine, 192(2):295-302, Rockefeller University Press, United States (2000).

Ribas, A., et al., "Tremelimumab (Cp-675,206), a Cytotoxic T Lymphocyte Associated Antigen 4 Blocking Monoclonal Antibody in Clinical Development for Patients With Cancer," The oncologist, 12(7):873-883, AlphaMed Press, United States (2007).

(56) References Cited

OTHER PUBLICATIONS

Rudd, C.E., et al., "Cd28 and Ctla-4 Coreceptor Expression and Signal Transduction," Immunological Reviews, 229(1):12-26, Blackwell, England (2009).
Ryan, J.M., et al., "Enhancing the Safety of Antibody-Based Immunomodulatory Cancer Therapy Without Compromising Therapeutic Benefit: Can We Have Our Cake And Eat It Too?," Expert Opinion on Biological Therapy, 16(5):655-674, Taylor & Francis, England (2016).
Shields, R.L., et al., "Lack of Fucose on Human IgG1 N-linked Oligosaccharide Improves Binding to Human Fcgamma RIII and Antibody-Dependent Cellular Toxicity," The Journal of Biological Chemistry 277(30):26733-26740, American Society for Biochemistry and Molecular Biology, United States (2002).
Stec et al. "Automated Solid-Phase Synthesis, Separation, and Stereochemistry of Phosphorothioate Analogues ofOligodeoxyribonucleotides", J. Am. Chern. Soc., 1984, vol. 106, No. 20, p. 6077-6079.
Stein, C.A., et al., "Physicochemical Properties of Phosphorothioate Oligodeoxynucleotides," Nucleic Acids Research 16(8):3209-3221, Oxford University Press, England (1988).
Tarentino, A.L., et al., "The Isolation and Structure of the Core Oligosaccharide Sequences of IgM," Biochemistry 14(25):5516-5523, American Chemical Society, United States (1975).
Thornton, J.M., et al. "Protein Structure. Prediction of Progress at Last," Nature, 354(6349):105-106, Nature Publishing Group, England (1991).
Uhlmann and Peyman "Antisense Oligonucleotides: A New Therapeutic Principle", Chemical Reviews, 1990, vol. 90, No. 4, p. 543-584.
Umana, P., et al., "Engineered Glycoforms of an Antineuroblastoma IgG1 with Optimized Antibody-Dependent Cellular Cytotoxic Activity," Nature Biotechnology 17(2):176-180, Nature America Publishing, United States (1999).
Vitetta et al., "Redesigning Nature's Poisons to Create Anti-Tumor Reagents", Science, 1987, vol. 238, p. 1098-1104.
Walunas, T. et al., "CTLA-4 can function as a Negative Regulator bf T Cell Activation", Immunity, vol. 1, pp. 405-413 (1994).
Wang W. "Lyophilization and development of solid protein pharmaceuticals." International Journal of Pharmaceutics, 2000, vol. 203, p. 1-60.
Wang, C., et al., "In Vitro Characterization of the Anti-PD-1 Antibody Nivolumab, BMS-936558, and in Vivo Toxicology in Non-human Primates," Cancer Immunology Research 2(9):846-856, American Association for Cancer Research, United States (2014).
Wang, C.J., et al., "Cutting Edge: Cell-Extrinsic Immune Regulation by CTLA-4 Expressed on Conventional T Cells," Journal of Immunology, 189(3):1118-1122, American Association of Immunologists, United States (2012).
Weber, J., "Immune Checkpoint Proteins: a New Therapeutic Paradigm for Cancer—preclinical Background: Ctla-4 and Pd-1 Blockade," Seminars in oncology, 37(5):430-439, W.B. Saunders, United States (2010).
Wing, K., et al., "CTLA-4 Control Over Foxp3+ Regulatory T Cell Function," Science 322(5899):271-275, American Association for the Advancement of Science, United States (2008).
Yamane, O., et al., "Establishment of FUT8 Knockout Chinese Hamster Ovary Cells: an Ideal Host Cell Line for Producing Completely Defucosylated Antibodies With Enhanced Antibody-dependent Cellular Cytotoxicity," Biotechnology and Bioengineering , 87(5):614-622, Wiley, United States, (2004).
Zhang, F., et al., "Structural Basis of a Novel PD-L1 Nanobody for Immune Checkpoint Blockade,"Cell Discovery, 3:17004, Nature Publishing Group, England (2017).
Zon et al. "Phosphorothioate oligonucleotides: chemistry, purification, analysis, scale-up and future directions", Anti Cancer Drug Design, 1991, vol. 6, p. 539-568.
Zon., et al., Oligonucleotides and Analogues: A Practical Approach, pp. 87-108 (F. Eckstein, Ed., Oxford University Press, Oxford England (1991).
Blank, C.U., et al., "Therapeutic use of anti-CTLA-4 antibodies," International Immunology 27(1): 3-10, Japanese Society for Immunology, Japan (2014).
Contardi, E., et al., " CTLA-4 is constitutively expressed on tumor cells and can trigger apoptosis upon ligand interaction," Int J. Cancer 117: 538-550, Wiley-Liss, United States (2005).
Lute, K.D., et al., "Human CTLA4 knock-in mice unravel the quantitative link between tumor immunity and autoimmunity induced by anti-CTLA-4 antibodies," Blood 106(9): 3127-3133, American Society of Hematology, United States (2005).

* cited by examiner

YV04-2001-YV1
YV06-2001-YV1
YV09-2001-YV1
YV23-2001-YV1
YV1
A450
nM

YV27-2001-YV1
YV29-2001-YV1
YV32-2001-YV1
YV33-2001-YV1
YV1
A450
nM

YV35-2001-YV1
YV41-2001-YV1
YV1
A450
nM

YV24-2001-YV1
YV39-2001-YV1
YV51-2001-YV1
YV52-2001-YV1
YV53-2001-YV1
YV1
A450
nM

YV54-2001-YV1
YV55-2001-YV1
YV56-2001-YV1
YV57-2001-YV1
YV58-2001-YV1
YV1
A450
nM

| Sample | EC50 (nM) |
|---|---|
| Ipi YV39 2011 | 22 |
| Ipilimumab | 0.54 |
| Ipi YV39 2011 MMP monoclipped | 2.8 |
| Ipi YV39 2011 MMP clipped | 0.65 |
| Ipi YV39 2011 µPA clipped | 0.76 |

Spleen Ki-67 on Tregs

Spleen-ICOS on Tregs

FIG. 19

| | | IgG1 | NF |
|---|---|---|---|
| | FcR | Ipi (nM) | Ipi NF (nM) |
| Human FcR | hCD64 | 0.2 | 0.18 |
| | hCD32a-H131 | 920 | 900 |
| | hCD32a-R131 | 1100 | 730 |
| | hCD32b | >5000 | 4200 |
| | hCD16a-V158 | 310 | 9.5 |
| | hCD16a-F158 | 4600 | 190 |
| | hCD16B-NA1 | >5000 | 1800 |
| | hCD16B-NA2 | 4200 | 110 |
| Cyno FcR | cyCD64 | 11 | 5.6 |
| | cyCD32a | 2700 | 2300 |
| | cyCD32b | 1900 | 2000 |
| | cyCD16 | **370** | **7.5** |
| Mouse FcR | mCD64 | 62 | 69 |
| | mCD32 | 1300 | 1100 |
| | mCD16 | 3100 | 2700 |
| | mFcγRIV | 29 | 6.3 |

ACTIVATABLE ANTI-CTLA-4 ANTIBODIES AND USES THEREOF

CROSS REFERENCE TO RELATED APPLICATIONS

This application is a continuation of U.S. application Ser. No. 16/347,522 (issued as U.S. Pat. No. 11,117,968), which is a U.S. National Stage Application of International Application No. PCT/US2017/059740, filed Nov. 2, 2017, which claims the priority benefit of U.S. Provisional Application No. 62/417,212, filed Nov. 3, 2016, each of which is hereby incorporated by reference in its entirety.

REFERENCE TO SEQUENCE LISTING SUBMITTED ELECTRONICALLY VIA EFS-WEB

The content of the electronically submitted sequence listing (Name: 3338_0590002_Seglisting_ST25.txt; Size: 528,133 bytes; and Date of Creation: Aug. 10, 2021) is herein incorporated by reference in its entirety.

BACKGROUND OF THE INVENTION

The immune system is capable of controlling tumor development and mediating tumor regression. This requires the generation and activation of tumor antigen-specific T cells. Multiple T-cell co-stimulatory receptors and T-cell negative regulators, or co-inhibitory receptors, act in concert to control T-cell activation, proliferation, and gain or loss of effector function. Among the earliest and best-characterized T-cell co-stimulatory and co-inhibitory molecules are CD28 and CTLA-4. Rudd et al. (2009) *Immunol. Rev.* 229: 12. CD28 provides co-stimulatory signals to T-cell receptor engagement by binding to B7-1 and B7-2 ligands on antigen-presenting cells, while CTLA-4 provides a negative signal down-regulating T-cell proliferation and function. CTLA-4, which also binds the B7-1 (CD80) and B7-2 (CD86) ligands but with higher affinity than CD28, acts as a negative regulator of T-cell function through both cell autonomous (or intrinsic) and cell non-autonomous (or extrinsic) pathways. Intrinsic control of CD8 and CD4 T effector (Teff) function is mediated by the inducible surface expression of CTLA-4 as a result of T-cell activation, and inhibition of T-cell proliferation and cytokine proliferation by multivalent engagement of B7 ligands on opposing cells. Peggs et al. (2008) *Immunol. Rev.* 224:141.

Anti-CTLA-4 antibodies, when cross-linked, suppress T cell function in vitro. Krummel & Allison (1995) *J. Exp. Med* 182:459; Walunas et al. (1994) *Immunity* 1:405. Regulatory T cells ($T_{regs}$), which express CTLA-4 constitutively, control effector T cell (Teff) function in a non-cell autonomous fashion. $T_{regs}$ that are deficient for CTLA-4 have impaired suppressive ability (Wing et al. (2008) *Science* 322:271) and antibodies that block CTLA-4 interaction with B7 can inhibit $T_{reg}$ function (Read et al. (2000) *J. Exp. Med* 192:295; Quezada et al. (2006) *J. Clin. Invest.* 116:1935). More recently, Teffs have also been shown to control T cell function through extrinsic pathways (Corse & Allison (2012) *J. Immunol.* 189:1123; Wang et al. (2012) *J. Immunol.* 189:1118). Extrinsic control of T cell function by $T_{regs}$ and Teffs occurs through the ability of CTLA-4-positive cells to remove B7 ligands on antigen-presenting cells, thereby limiting their co-stimulatory potential. Qureshi et al. (2011) *Science* 332: 600; Onishi et al. (2008) *Proc. Nat'l Acad Sci.* (USA) 105:10113. Antibody blockade of CTLA-4/B7 interactions is thought to promote Teff activation by interfering with negative signals transmitted by CTLA-4 engagement; this intrinsic control of T-cell activation and proliferation can promote both Teff and $T_{reg}$ proliferation (Krummel & Allison (1995) *J. Exp. Med* 182:459; Quezada et al. (2006) *J. Clin. Invest.* 116:1935). In early studies with animal models, antibody blockade of CTLA-4 was shown to exacerbate autoimmunity. Perrin et al. (1996) *J. Immunol.* 157:1333; Hurwitz et al. (1997) *J. Neuroimmunol.* 73:57. By extension to tumor immunity, the ability of anti-CTLA-4 to cause regression of established tumors provided a dramatic example of the therapeutic potential of CTLA-4 blockade. Leach et al. (1996) *Science* 271:1734.

Human antibodies to human CTLA-4, ipilimumab and tremelimumab, were selected to inhibit CTLA-4-B7 interactions (Keler et al. (2003) *J. Immunol.* 171:6251; Ribas et al. (2007) *Oncologist* 12:873) and have been tested in a variety of clinical trials for multiple malignancies. Hoos et al. (2010) *Semin. Oncol.* 37:533; Ascierto et al. (2011) *J. Transl. Med* 9:196. Tumor regressions and disease stabilization were frequently observed, and treatment with these antibodies has been accompanied by adverse events with inflammatory infiltrates capable of affecting a variety of organ systems. In 2011, ipilimumab, which has an IgG1 constant region, was approved in the US and EU for the treatment of unresectable or metastatic melanoma based on an improvement in overall survival in a phase III trial of previously treated patients with advanced melanoma. Hodi et al. (2010) *N. Engl. J. Med.* 363:711.

Treatment with ipilimumab has, however, been hampered by dose limiting toxicities, such as colitis. Di Giacomo et al. (2010) *Seminars in Oncology* 37:499. Accordingly, the need exists for improved anti-CTLA-4 antibodies, such as modified forms of ipilimumab, with reduced toxicity but with comparable anti-tumor efficacy. Such improved anti-CTLA-4 antibodies may be more effective anti-tumor agents than current antibodies.

SUMMARY OF THE INVENTION

Provided herein are activatable anti-human CTLA-4 antibodies comprising a heavy chain comprising a VH domain and a light chain comprising a masking moiety (MM), a cleavable moiety (CM), and a VL domain. Such activatable anti-human CTLA-4 antibodies have CTLA-4 binding activity in the tumor microenvironment, where the masking moiety is removed by proteolytic cleavage of the cleavable moiety by tumor-specific proteases, but exhibit greatly reduced binding to CTLA-4 outside the tumor. In this way, the activatable anti-human CTLA-4 antibodies of the present invention retain anti-tumor activity while reducing the side effects associated with anti-CTLA-4 activity outside the tumor.

Provided herein are improved anti-CTLA-4 antibodies, such as an improved ipilimumab, in particular an activatable antibody that when activated binds Cytotoxic T-Lymphocyte Antigen 4 (CTLA-4). In some embodiments, the activatable anti-human CTLA-4 antibody comprises:

(i) a heavy chain comprising a heavy chain variable domain (VH) comprising complementarity determining regions (CDRs) CDRH1: SYTMH (SEQ ID NO: 557); CDRH2: FISYDGNNKYYADSVKG (SEQ ID NO: 558); and CDRH3: TGWLGPFDY (SEQ ID NO: 559); and (ii) a light chain comprising:

(a) a light chain variable domain (VL) comprising CDRL1: RASQSVGSSYLA (SEQ ID NO: 560);

CDRL2: GAFSRAT (SEQ ID NO: 561); and CDRL3: QQYGSSPWT (SEQ ID NO: 562);

(b) a cleavable moiety (CM); and (c) a masking moiety (MM), wherein the light chain has the structural arrangement from N-terminus to C-terminus as follows: MM-CM-VL.

In some embodiments, an activatable anti-human CTLA-4 antibody comprises:

(i) a heavy chain comprising a heavy chain variable domain (VH) comprising CDRH1: SYTMH (SEQ ID NO: 557); CDRH2: FISYDGNNKYYADSVKG (SEQ ID NO: 558); and CDRH3: TGWLGPFDY (SEQ ID NO: 559); and (ii) a light chain comprising, from N-terminus to C-Terminus:

(a) a masking moiety (MM);

(b) a cleavable moiety (CM); and (c) a light chain variable domain (VL) comprising CDRL1: RASQSVGSSYLA (SEQ ID NO: 560); CDRL2: GAFSRAT (SEQ ID NO: 561); and CDRL3: QQYGSSPWT (SEQ ID NO: 562).

In some embodiments, the activatable antibody comprises a heavy chain and a light chain such that the light chain has the structural arrangement, from N-terminus to C-terminus of the light chain, MM-CM-VL. As used herein, the N-terminal fragment that is joined to the VL domain is referred to as the prodomain and comprises MM and CM.

In some embodiments, the activatable antibody comprises a complete antibody, i.e., an antibody comprising two mature full-length heavy chains and two mature full-length light chains. In some embodiments, the activatable antibody comprises a Fab fragment, a $F(ab')_2$ fragment, an scFv, or a scAb. In some embodiments, the activatable antibody comprises a monoclonal antibody.

In some embodiments, the CM functions as a substrate for a protease. In some embodiments, the CM is selected from the group of CMs provided in Table 3. In some embodiments, the CM is selected from the group consisting of 2001 (SEQ ID NO: 297), 2003 (SEQ ID NO: 298), 2005 (SEQ ID NO: 299), 2006 (SEQ ID NO: 300), 2007 (SEQ ID NO: 301), 2008 (SEQ ID NO: 302), 2009 (SEQ ID NO: 303), 2011 (SEQ ID NO: 304), 2012 (SEQ ID NO: 305), 3001 (SEQ ID NO: 306), 3006 (SEQ ID NO: 307), 3007 (SEQ ID NO: 308), 3008 (SEQ ID NO: 309), 3009 (SEQ ID NO: 310), 3011 (SEQ ID NO: 311), and 3012 (SEQ ID NO: 312). In some embodiments, the CM is 2001 (SEQ ID NO: 297). In some embodiments, the CM is 2011 (SEQ ID NO: 304). In some embodiments, the CM is 2012 (SEQ ID NO: 305).

In some embodiments, the MM is selected from the group consisting of the MMs provided in Tables 4-6. In some embodiments, the MM is selected from the group consisting of YV01 (SEQ ID NO: 1), YV02 (SEQ ID NO: 2), YV03, (SEQ ID NO: 3), YV04 (SEQ ID NO: 4), YV09, (SEQ ID NO: 9), YV23 (SEQ ID NO: 23), YV24 (SEQ ID NO: 24), YV35 (SEQ ID NO: 35), YV39 (SEQ ID NO: 39), YV51 (SEQ ID NO: 51), YV61 (SEQ ID NO: 60), YV62 (SEQ IDNO: 61), YV63 (SEQ ID NO: 62), YV64 (SEQ ID NO: 63), YV65 (SEQ ID NO: 64), and YV66 (SEQ ID NO: 65); and the CM is selected from the group consisting of 2001, 2006, 2007, 2008, 2009, 2011, and 2012. In some embodiments, the MM is YV39 and the CM is 2011. In some embodiments, the MM is YV39 and the CM is 2012. In some embodiments, the MM is YV39 and the CM is 2001.

In some embodiments, the activatable antibody comprises a heavy chain comprising the amino acid sequence of SEQ ID NO: 353 and a light chain comprising an amino acid sequence selected from the group consisting of SEQ ID NOs: 356 to 529. In some embodiments, the activatable anti-CTLA-4 antibodies comprise a light chain having a prodomain and VL corresponding to the prodomain and VL of SEQ ID NOs: 356 to 529. In some embodiments, the activatable anti-CTLA-4 antibodies comprise a light chain having a prodomain and VL of SEQ ID NOs: 564, 565, or 563. In one embodiment, the activatable anti-CTLA-4 antibody comprises a light chain having a prodomain and VL of SEQ ID NO: 564.

In some embodiments, the activatable anti-CTLA-4 antibodies comprise a heavy chain variable domain amino acid sequence that is at least 90%, 91%, 92%, 93%, 94%, 95%, 96%, 97%, 98% or 99% identical to SEQ ID NO: 345. In some embodiments, the activatable anti-CTLA-4 antibodies comprise a light chain variable domain amino acid that is at least 90%, 91%, 92%, 93%, 94%, 95%, 96%, 97%, 98% or 99% identical to an amino acid sequence selected from the group consisting of SEQ ID NOs: 564, 565, and 563.

In some embodiments, the activatable antibody comprises a combination of heavy chain sequence SEQ ID NO: 353 and light chain sequence SEQ ID NO: 449, 473, or 383. In some embodiments, the activatable antibody comprises a combination of heavy chain sequence SEQ ID NO: 349 and light chain sequence SEQ ID NO: 448, 472, or 382.

Provided herein is an activatable anti-CTLA-4 antibody that, when activated, specifically binds to human CTLA-4 and is referred to as an activated activatable anti-CTLA-4 antibody. In some embodiments, the activated activatable anti-CTLA-4 antibody binds to CTLA-4 with the same binding affinity as ipilimumab. Also provided herein is an activatable anti-CTLA-4 antibody that does not bind to CTLA-4 as effectively as ipilimumab since the activatable anti-CTLA-4 antibody comprises a heavy chain and a light chain comprising a prodomain comprising a MM and CM linked to the ipilimumab light chain such that the prodomain reduces the ability of the ipilimumab to bind to CTLA-4

In some embodiments, the activatable antibody binds to human CTLA-4 with an $EC_{50}$ of 1 μg/mL or higher as measured by flow cytometry. In some embodiments, the activatable anti-CTLA-4 antibodies bind to CTLA-4 with an $EC_{50}$ of 5 μg/mL or higher, 10 μg/mL or higher, 20 μg/mL or higher, or 40 μg/mL or higher.

In some embodiments, the MM is a polypeptide of no more than 40 amino acids in length. In some embodiments, the MM is a polypeptide that is no more than 50% identical to any natural binding partner of the antibody. In some embodiments, the MM does not comprise more than 25% amino acid sequence identity to CTLA-4. In some embodiments, the MM does not comprise more than 10% amino acid sequence identity to CTLA-4.

Activatable anti-CTLA-4 antibodies of the disclosure are activated when the cleavable moiety is cleaved by a protease. In some embodiments, the protease is produced by a tumor that is in proximity to T cells that express CTLA-4. In some embodiments, the protease is produced by a tumor that is co-localized with T cells that express CTLA-4. In some embodiments, the protease is selected from the group of proteases provided in Table 1 provided below. In some embodiments, the protease is selected from the group consisting of a matrix metalloprotease (MMP), a thrombin, a neutrophil elastase, a cysteine protease, a legumain, and a serine protease, such as a matriptase or a urokinase (uPA). In some embodiments, the protease is selected from the group consisting of MMP1, MMP2, MMP3, MMP8, MMP9, MMP11, MMP13, MMP14, MMP17, legumain, matriptase, and uPA, or a combination of one or more of such proteases. In some embodiments, the CM is cleaved by a matrix metalloprotease (MMNP) and a serine protease. In some embodiments, the CM is cleaved by a matrix metalloprotease (MMIP), a serine protease and a legumain.

TABLE 1

| Exemplary Proteases and/or Enzymes |
|---|
| ADAMS, ADAMTS, e.g. |
| ADAM8 |
| ADAM9 |
| ADAM10 |
| ADAM12 |
| ADAM15 |
| ADAM17/TACE |
| ADAMDEC1 |
| ADAMTS1 |
| ADAMTS4 |
| ADAMTS5 |
| Aspartate proteases, e.g., |
| BACE |
| Renin |
| Aspartic cathepsins, e.g., |
| Cathepsin D |
| Cathepsin E |
| Caspases, e.g., |
| Caspase 1 |
| Caspase 2 |
| Caspase 3 |
| Caspase 4 |
| Caspase 5 |
| Caspase 6 |
| Caspase 7 |
| Caspase 8 |
| Caspase 9 |
| Caspase 10 |
| Caspase 14 |
| Cysteine cathepsins, e.g., |
| Cathepsin B |
| Cathepsin C |
| Cathepsin K |
| Cathepsin L |
| Cathepsin S |
| Cathepsin V/L2 |
| Cathepsin X/Z/P |
| Cysteine proteinases, e.g., |
| Cruzipain |
| Legumain |
| Otubain-2 |
| KLKs, e.g., |
| KLK4 |
| KLK5 |
| KLK6 |
| KLK7 |
| KLK8 |
| KLK10 |
| KLK11 |
| KLK13 |
| KLK14 |
| Metallo proteinases, e.g., |
| Meprin |
| Neprilysin |
| PSMA |
| BMP-1 |
| MMPs, e.g., |
| MMP1 |
| MMP2 |
| MMP3 |
| MMP7 |
| MMP8 |
| MMP9 |
| MMP10 |
| MMP11 |
| MMP12 |
| MMP13 |
| MMP14 |
| MMP15 |
| MMP16 |
| MMP17 |
| MMP19 |
| MMP20 |
| MMP23 |
| MMP24 |
| MMP26 |
| MMP27 |
| Serine proteases, e.g., |
| activated protein C |
| Cathepsin A |
| Cathepsin G |
| Chymase |
| coagulation factor proteases |
| (e.g., FVIIa, FIXa, FXa, FXIa, FXIIa) |
| Elastase |
| Granzyme B |
| Guanidinobenzoatase |
| HtrA1 |
| Human Neutrophil Elastase |
| Lactoferrin |
| Marapsin |
| NS3/4A |
| PACE4 |
| Plasmin |
| PSA |
| tPA |
| Thrombin |
| Tryptase |
| uPA |
| Type II Transmembrane |
| Serine Proteases (TTSPs), e.g., |
| DESC1 |
| DPP-4 |
| FAP |
| Hepsin |
| Matriptase-2 |
| MT-SP1/Matriptase |
| TMPRSS2 |
| TMPRSS3 |
| TMPRSS4 |

Provided herein are activatable anti-CTLA-4 antibodies that further comprise one or more linker peptides. In some embodiments, the linker peptide is between the MM and the CM. In some embodiments, the linker peptide is between the CM and the VL. In some embodiments, the activatable antibody comprises a first linker peptide (LP1) and a second linker peptide (LP2). In some embodiments, the activatable antibody comprises a heavy chain and a light chain such that the light chain has the structural arrangement, from N-terminus to C-terminus of the light chain, MM-LP1-CM-LP2-VL. In some embodiments, the LP1 and the LP2 are not identical to each other. In some embodiments, the LP1 and the LP2 are identical to each other. In some embodiments, the prodomain comprises MM-LP1-CM-LP2.

In some embodiments, the LP1 and/or the LP2 comprise a glycine-serine polymer. In some embodiments, the LP1 and/or the LP2 comprise an amino acid sequence selected from the group consisting of $(GS)_n$(SEQ ID NO: 532), $(GGS)_n$(SEQ ID NO: 533), $(GSGGS)_n$(SEQ ID NO: 534), and $(GGGS)_n$(SEQ ID NO: 535), where n is an integer of at least one. In some embodiments, the LP1 comprises the amino acid sequence GGGSSGGS (SEQ ID NO: 542). In some embodiments, the LP2 comprises the amino acid sequence GGGS (SEQ ID NO: 543).

Provided herein are activatable anti-CTLA-4 antibodies that also comprise a spacer. In some embodiments, the spacer is joined directly to the MM and has the structural arrangement from N-terminus to C-terminus as follows: spacer-MM-CM-VL. In some embodiments, the spacer comprises an amino acid sequence selected from the group consisting of QGQSGQG (SEQ ID NO: 544), GQSGQG (SEQ ID NO: 545), QGQSGS (SEQ ID NO: 546), QGQSGQ (SEQ ID NO: 547), QSGQG (SEQ ID NO: 548), GQSGS (SEQ ID NO: SEQ ID NO: 549), QGQSG (SEQ ID NO: 550), SGQG (SEQ ID NO: 551), QSGS (SEQ ID NO: 552), QGQS (SEQ ID NO: 553), GQG, SGS, QGQ, QG, GS, G, S, and Q. In some embodiments, the spacer and the MM comprise the amino acid sequence QGQSGSCRTQ-LYGYNLCPY (SEQ ID NO: 556).

Also provided herein are activatable antibodies that comprise a toxic agent, such as a dolastatin, an auristatin, an auristatin E, a monomethyl auristatin E (MMAE), a maytansinoid, a duocarmycin, a calicheamicin, a pyrrolobenzodiazepine, or a derivative thereof. In some embodiments, the toxic agent is conjugated to the activatable antibody via a linker. In some embodiments, the linker is a cleavable linker. In some embodiments, the linker is a non-cleavable linker.

Provided herein are activatable anti-CTLA-4 antibodies that comprises a detectable moiety. In some embodiments, the detectable moiety is a diagnostic agent.

Provided herein are pharmaceutical compositions comprising an activatable anti-CTLA-4 antibody described herein. In some embodiments, the pharmaceutical composition comprises an additional therapeutic agent.

Also provided herein are isolated nucleic acid molecules encoding the heavy and/or light chains of the activatable anti-CTLA-4 antibodies described herein, vectors that comprise one or more of the isolated nucleic acid molecules, and methods of producing an activatable antibody by culturing a cell comprising the vector or vectors under conditions that lead to expression of the activatable antibody.

Provided herein are methods of manufacturing an activatable antibody, the methods comprising: (a) culturing a cell comprising a nucleic acid construct that encodes the activatable antibody described herein under conditions that lead to expression of the activatable antibody, and (b) recovering the activatable antibody.

Provided herein are methods of reducing CTLA-4 activity comprising administering an effective amount of the activatable antibody described herein or pharmaceutical compositions comprising an activatable anti-CTLA-4 antibody described herein to a subject in need thereof.

Provided herein are methods of blocking binding of a natural ligand to CTLA-4 comprising administering an effective amount of the activatable antibodies described herein or pharmaceutical compositions comprising an activatable anti-CTLA-4 antibody described herein to a subject in need thereof.

Provided herein are methods of treating, alleviating a symptom of, or delaying the progression of a CTLA-4-related disorder comprising administering a therapeutically effective amount of the activatable antibodies described herein or the pharmaceutical compositions comprising an activatable anti-CTLA-4 antibody described herein to a subject in need thereof. In some embodiments, the CTLA-4 related disorder is a cancer. In some embodiments, the cancer is a melanoma, such as unresectable or metastatic melanoma, breast cancer, colorectal cancer, gastric cancer, glioblastoma, head and neck cancer, lung cancer, ovarian cancer, endometrial cancer, pancreatic cancer, prostate cancer, renal cancer, sarcoma, or skin cancer. In some embodiments, the CTLA-4 related disorder is a disorder known to be treatable with ipilimumab.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

BRIEF DESCRIPTION OF THE DRAWINGS/FIGURES

Figure 1B:
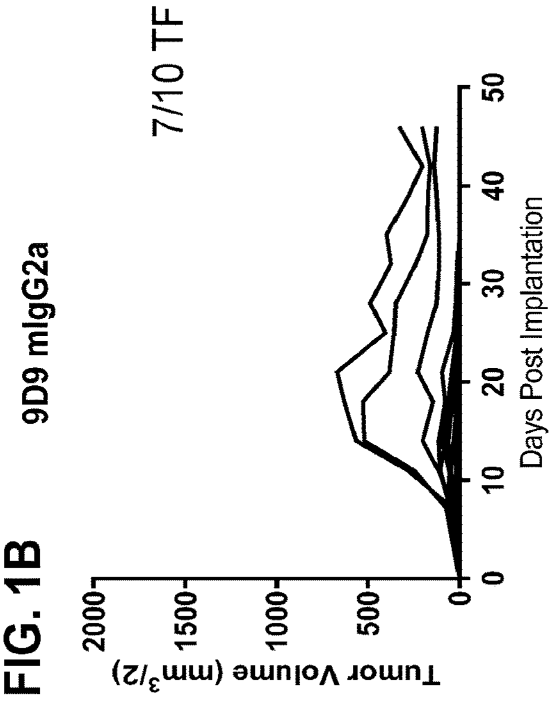
Figure 1C:
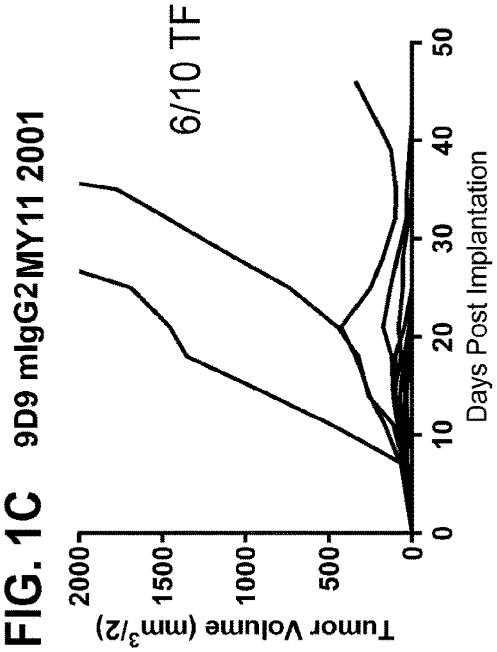

FIGS. 1A to 1C show tumor volumes as a function of days post tumor implantation in mice (n=10) treated with (i) an unrelated mouse IgG2a antibody (FIG. 1A), (ii) a mouse anti-CTLA-4 (9D9) IgG2a antibody (FIG. 2B), or (iii) an activatable 9D9 antibody (FIG. 1C). All antibodies and activatable antibodies were dosed at 25 μg/mouse. The activatable 9D9 antibody comprises MY11 (SEQ ID NO: 294) as the masking moiety and 2001 (SEQ ID NO: 297) as the cleavable moiety. "TF" indicates the number of tumor free mice at the end of each experiment. The unrelated mouse IgG2a antibody and the mouse anti-CTLA-4 (9D9) IgG2a antibody were used as controls.

Figure 2A:
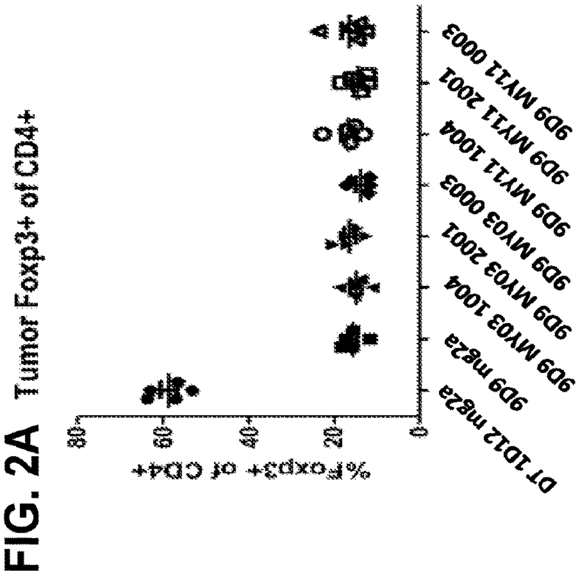
Figure 2B:
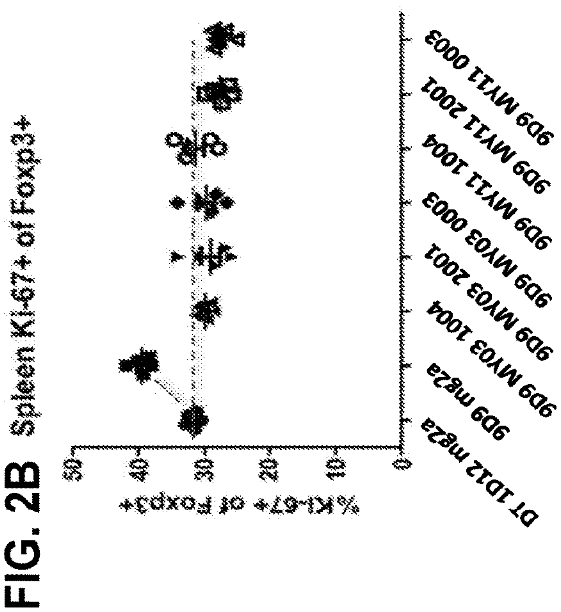
Figure 2C:
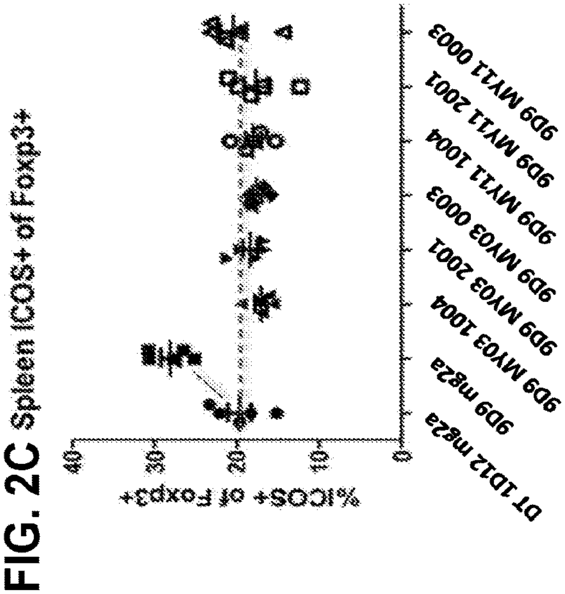

FIGS. 2A to 2C show the frequency of regulatory T cells in the tumor (FIG. 2A) and proliferation and activation of regulatory T cells in the spleen (FIGS. 2B and 2C) of mice treated with different activatable mouse anti-CTLA-4 (9D9) IgG2a antibodies. The different activatable 9D9 antibodies comprise (i) either MY03 (SEQ ID NO: 293) or MY11 (SEQ ID NO: 294) as the masking moiety and (2) 0003 (SEQ ID NO: 320), 1004 (SEQ ID NO: 323), or 2001 (SEQ ID NO: 297) as the cleavable moiety. The unrelated mouse IgG2a antibody ("DT 1D12 mg2a") and the mouse anti-CTLA-4 (9D9) IgG2a antibody ("9D9 mg2a") were used as controls. In FIG. 2A, the frequency of regulatory T cells is shown as a percentage of total CD4+ T cells that are Foxp3+ in the tumor. FIGS. 2B and 2C show the frequency of proliferating (Ki-67+) and activated (ICOS+) regulatory T cells, as a percentage of Foxp3+ T cells, in the spleen, respectively.

Figures 3A, 3B, 3C, 3D, 3E:
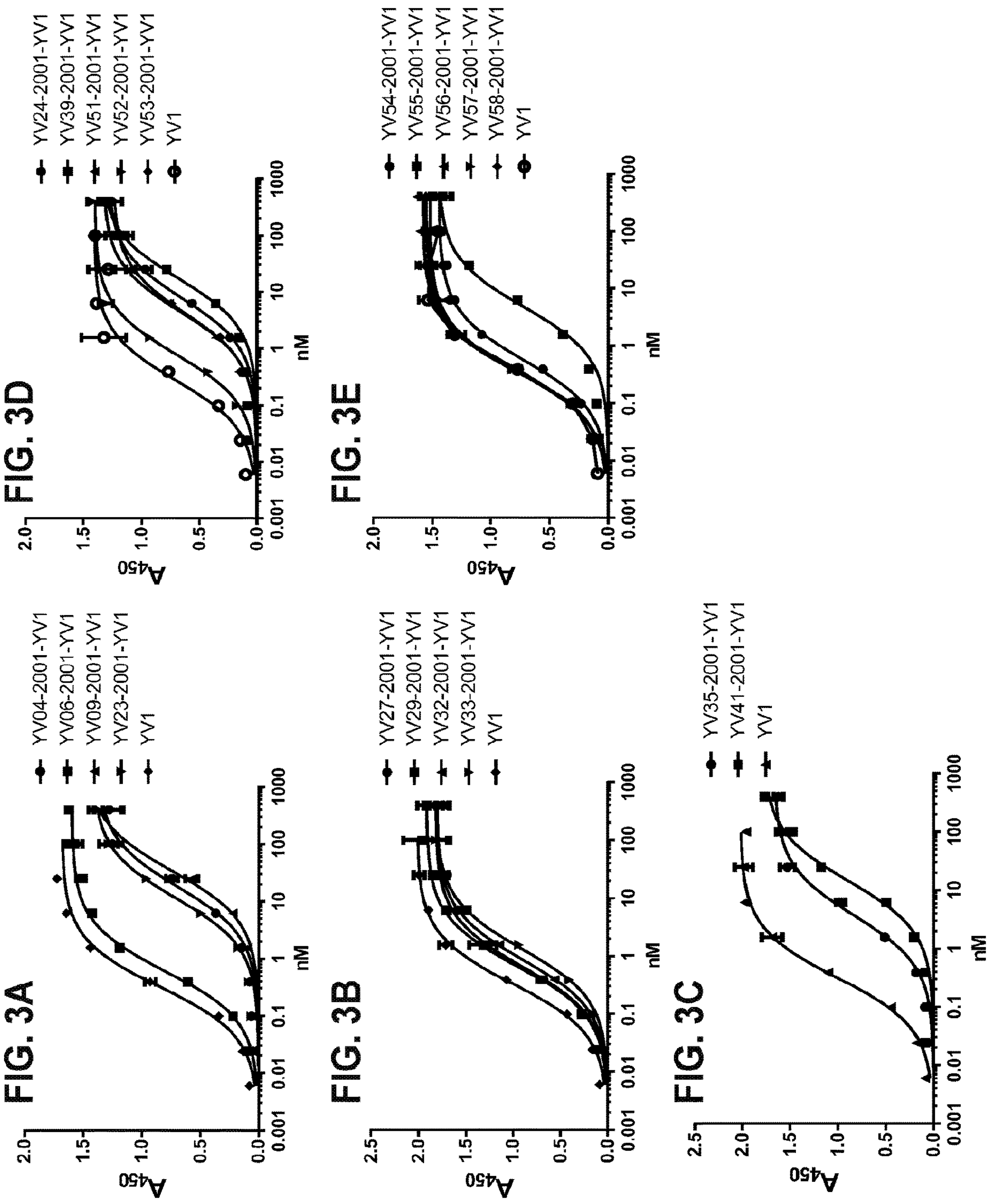

FIGS. 3A to 3E show the ability of different anti-CTLA-4 activatable antibodies (human IgG1 isotype) to bind to human CTLA-4, as measured in vitro with an ELISA binding assay. Ipilimumab ("YV1") was used as a control in all experiments. In FIG. 3A, the anti-CTLA-4 activatable antibodies comprise YV04 (SEQ ID NO: 4), YV06 (SEQ ID NO: 6), YV09 (SEQ ID NO: 9), or YV23 (SEQ ID NO: 23) as the masking moiety. In FIG. 3B, the anti-CTLA-4 activatable antibodies comprise YV27 (SEQ ID NO: 27), YV29 (SEQ ID NO: 29), YV32 (SEQ ID NO: 32), or YV33 (SEQ ID NO: 33) as the masking moiety. In FIG. 3C, the anti-CTLA-4 activatable antibodies comprise YV35 (SEQ ID NO: 35) or YV41 (SEQ ID NO: 41) as the masking moiety. In FIG. 3D, the anti-CTLA-4 activatable antibodies comprise YV24 (SEQ ID NO: 24), YV39 (SEQ ID NO: 39), YV51 (SEQ ID NO: 51), YV52 (SEQ ID NO: 52), or YV53 (SEQ ID NO: 53) as the masking moiety. In FIG. 3E, the anti-CTLA-4 activatable antibodies comprise YV54 (SEQ ID NO: 54), YV55 (SEQ ID NO: 55), YV56 (SEQ ID NO: 56), YV57 (SEQ ID NO: 57), or YV58 (SEQ ID NO: 58) as the masking moiety. In FIGS. 3A to 3E, all the anti-CTLA-4 activatable antibodies comprise 2001 (SEQ ID NO: 297) as the cleavable moiety.

Figure 4A:
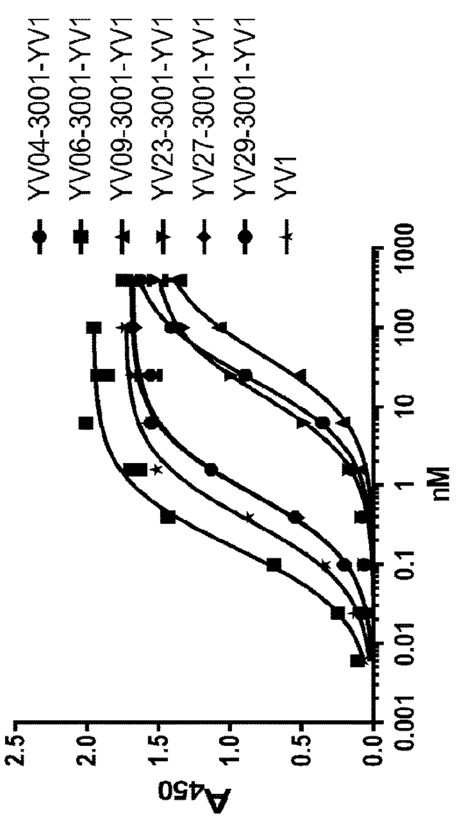
Figure 4B:
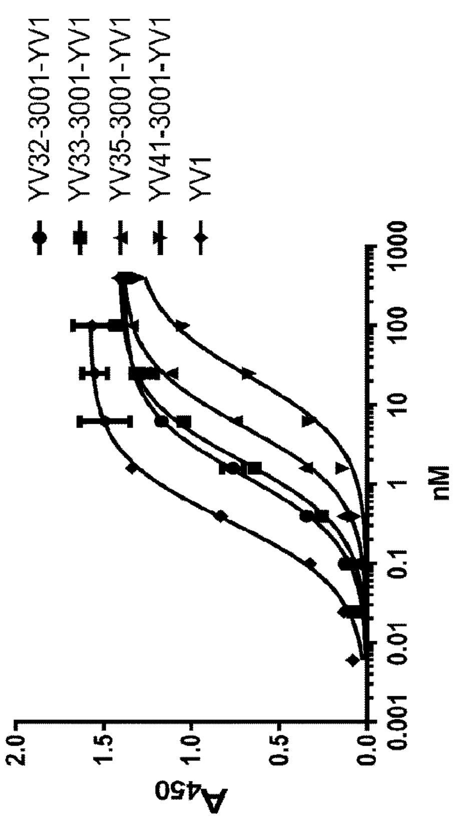
Figure 4C:
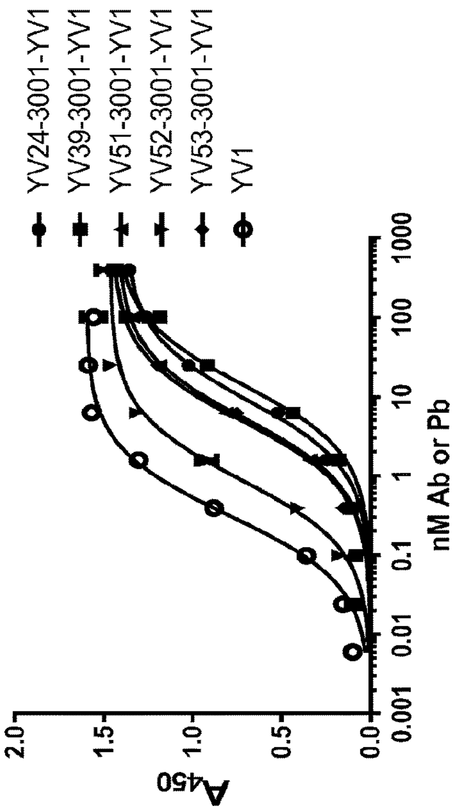
Figure 4D:
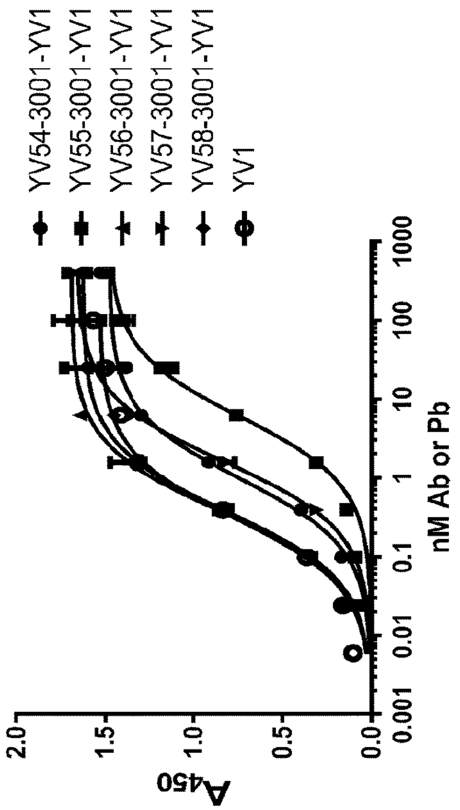

FIGS. 4A to 4D show the ability of additional anti-CTLA-4 activatable antibodies (human IgG1 isotype) to bind to human CTLA-4, as measured in vitro with an ELISA binding assay. Ipilimumab ("YV1") was used as a control in all experiments. In FIG. 4A, the anti-CTLA-4 activatable antibodies comprise YV04, YV06, YV09, YV23, YV27, or YV29 as the masking moiety. In FIG. 4B, the anti-CTLA-4 activatable antibodies comprise YV32, YV33, YV35, or YV41 as the masking moiety. In FIG. 4C, the anti-CTLA-4 activatable antibodies comprise YV24, YV39, YV51, YV52, or YV53 as the masking moiety. In FIG. 4D, the anti-CTLA-4 activatable antibodies comprise YV54, YV55, YV56, YV57, or YV58 as the masking moiety. In FIGS. 4A to 4D, all the anti-CTLA-4 activatable antibodies comprise 3001 as the cleavable moiety.

Figure 5A:
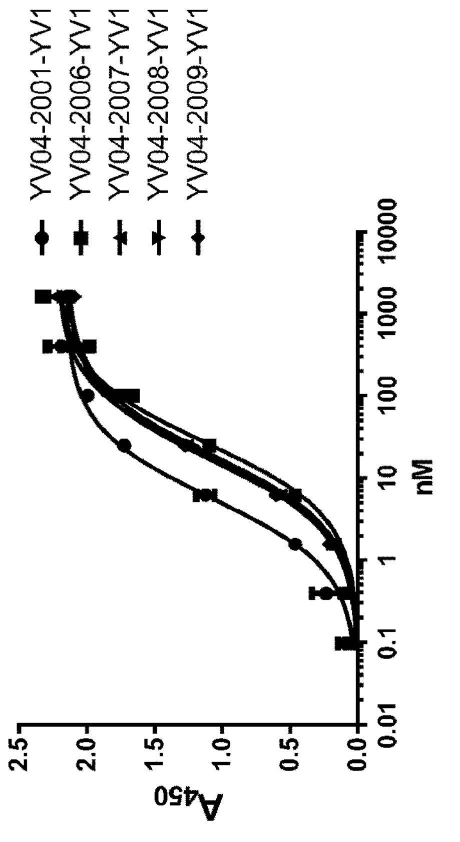
Figure 5B:
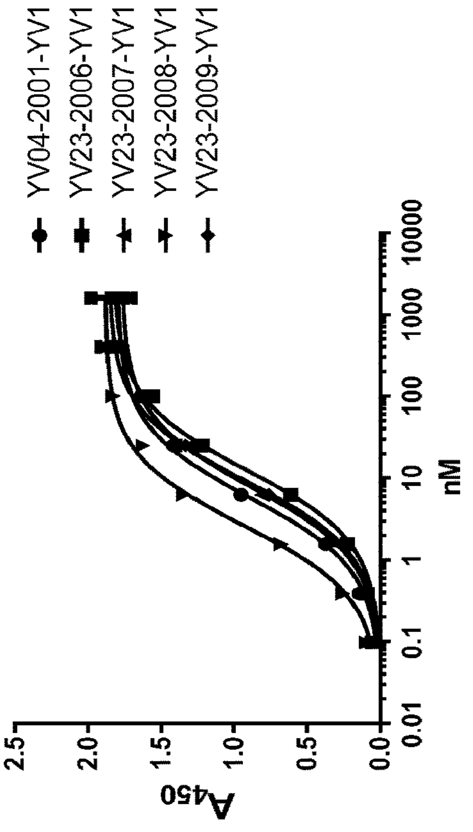
Figure 5C:
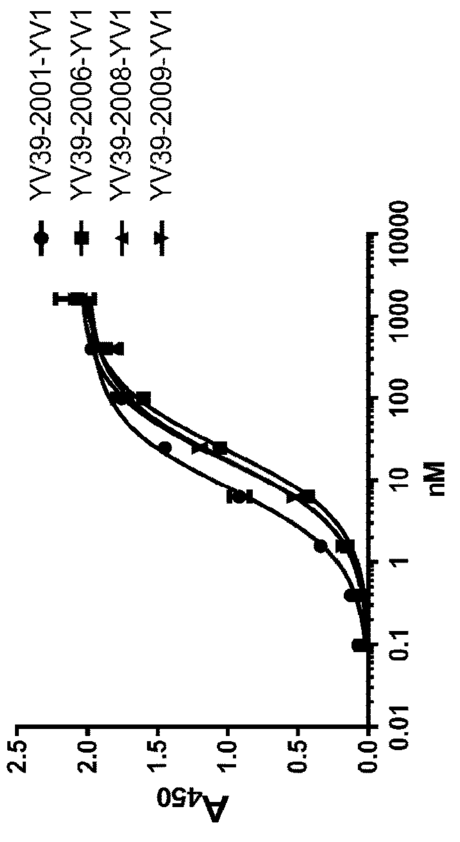
Figure 5E:
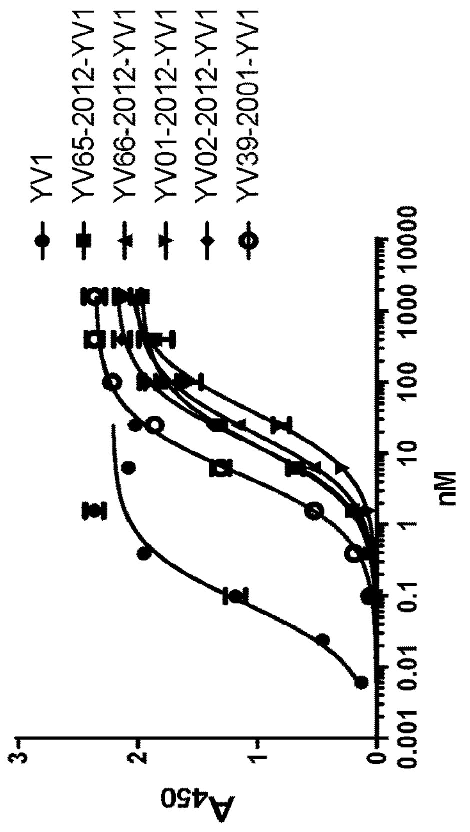
Figure 5D:
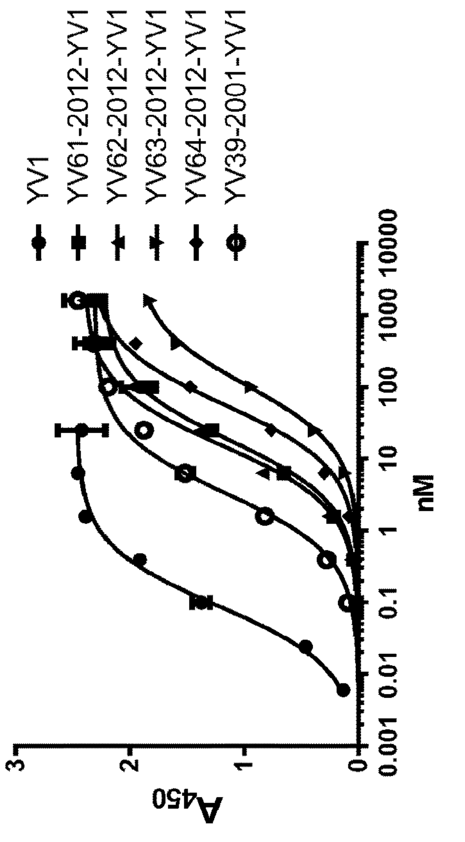
Figure 5F:
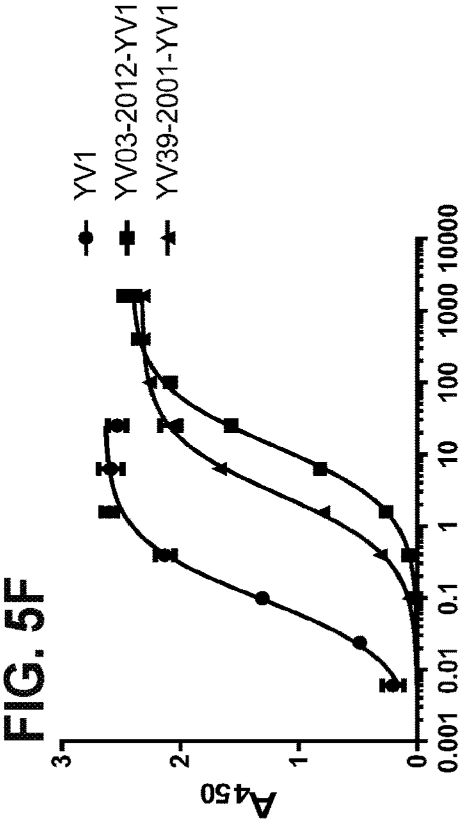

FIGS. 5A to 5F show the ability of several anti-CTLA-4 activatable antibodies (mouse IgG2a isotype) to bind to human CTLA-4, as measured in vitro with an ELISA binding assay. Ipilimumab ("YV1") was used as a control. In FIG. 5A, the anti-CTLA-4 activatable antibodies comprise YV04 as the masking moiety and 2001 (SEQ ID NO: 297), 2006 (SEQ ID NO: 300), 2007 (SEQ ID NO: 301), 2008 (SEQ ID NO: 302), or 2009 (SEQ ID NO: 303) as the cleavable moiety. In FIG. 5B, the anti-CTLA-4 activatable antibodies comprise YV04 or YV23 as the masking moiety, and 2001, 2006, 2007, 2008, or 2009 as the cleavable moiety. In FIG. 5C, the anti-CTLA-4 activatable antibodies comprise YV39 as the masking moiety and 2001, 2006, 2008, or 2009 as the cleavable moiety. In FIG. 5D, the anti-CTLA-4 activatable antibodies comprise YV61 (SEQ ID NO: 60), YV62 (SEQ ID NO: 61), YV63 (SEQ ID NO: 62), YV64 (SEQ ID NO: 63), or YV39 (SEQ ID NO: 39) as the masking moiety and 2001 or 2012 as the cleavable moiety. In FIG. 5E, the anti-CTLA-4 activatable antibodies comprise YV65 (SEQ ID NO: 64), YV66 (SEQ ID NO: 65), YV01 (SEQ ID NO: 1), YV02 (SEQ ID NO: 2), or YV39 (SEQ ID NO: 39) as the masking moiety and 2001 or 2012 as the cleavable moiety. In FIG. 5F, the anti-CTLA-4 activatable antibodies comprise YV39 or YV03 (SEQ ID NO: 3) as the masking moiety and 2001 or 2012 as the cleavable moiety.

Figure 6A:
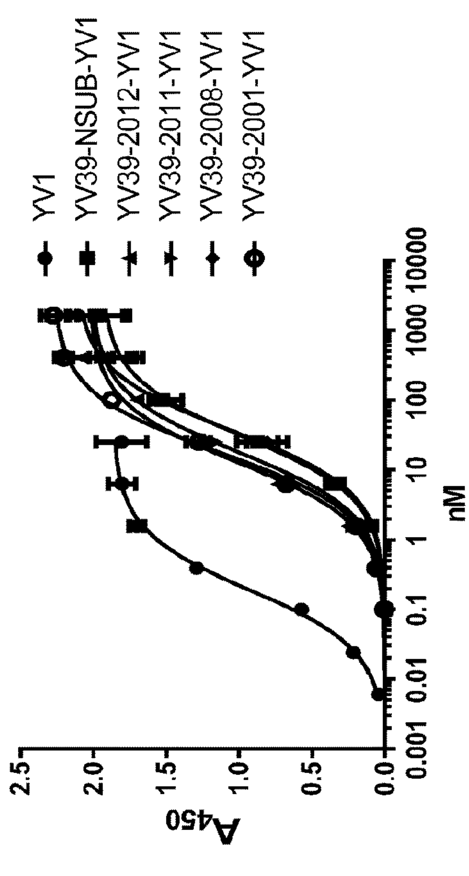
Figure 6B:
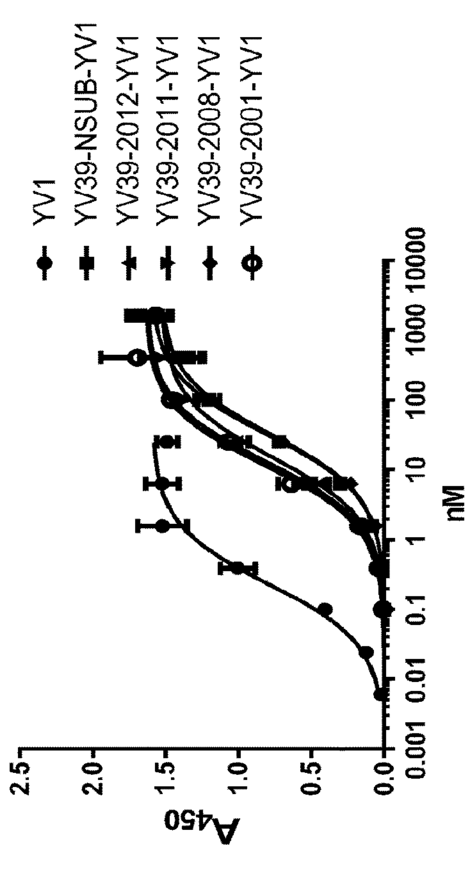

FIGS. 6A and 6B compares the ability of anti-CTLA-4 activatable antibodies having either a mouse IgG2a isotype (FIG. 6A) or human IgG1 isotype (FIG. 6B) to bind to human CTLA-4, as measured in vitro with an ELISA binding assay. Ipilimumab ("YV1") was used as a control. In both FIGS. 6A and 6B, the anti-CTLA-4 activatable antibodies comprise YV39 as the masking moiety and 2001, 2008, 2011, or 2012 as the cleavable moiety. In a modified antibody of the disclosure (YV39-NSUB), the cleavable moiety was replaced with a protease resistant linker ("NSUB") comprising the amino acid sequence GGSGGSGGGSGGGS (SEQ ID NO: 570).

Figure 7B:
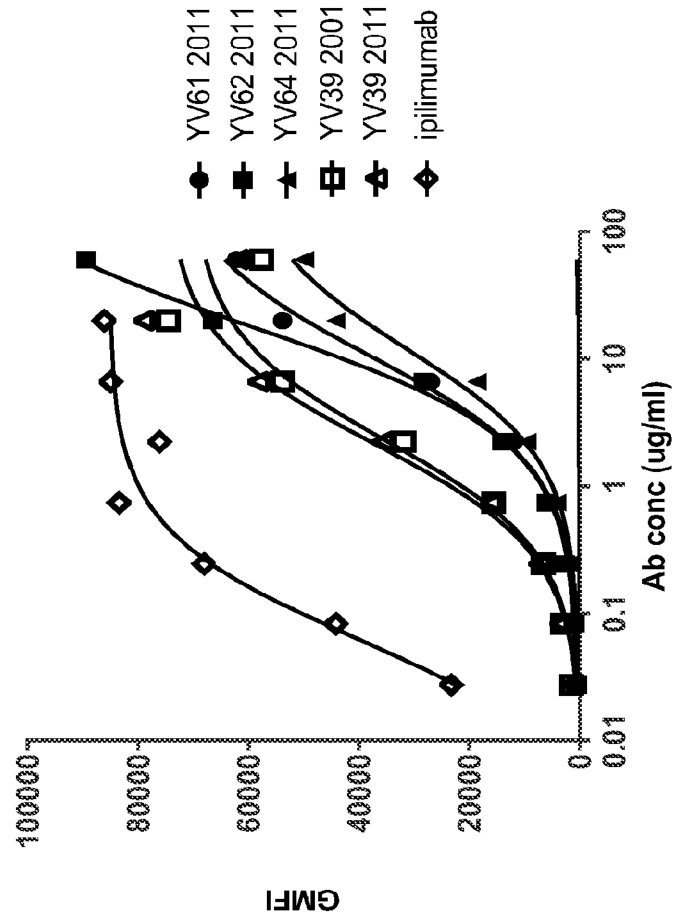
Figure 7A:
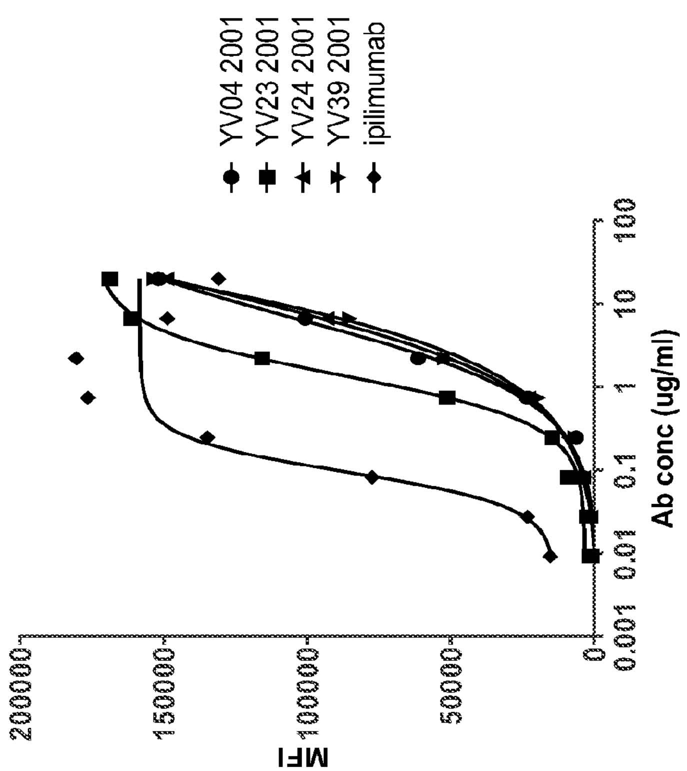
Figures 7C, 7D:
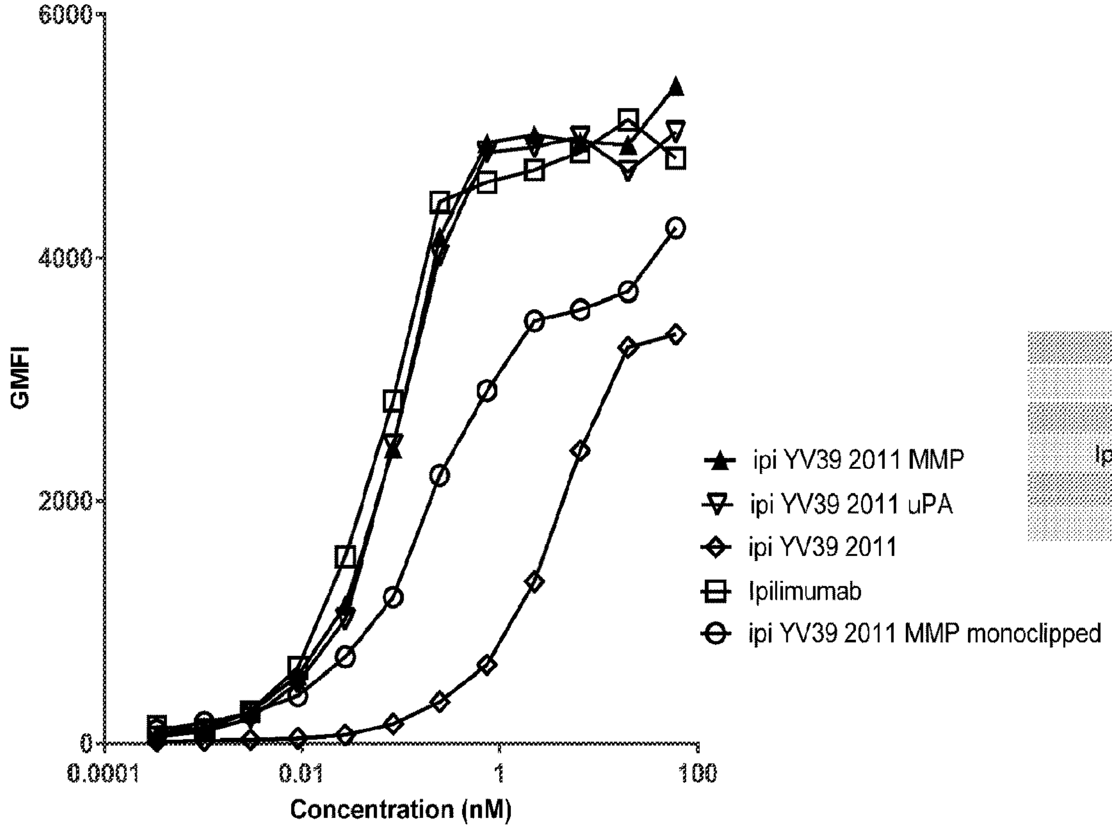

FIGS. 7A to 7D show the ability of different anti-CTLA-4 activatable antibodies to bind 58 $\alpha^-\beta^-$ cells overexpressing human CTLA-4, as measured via flow cytometry. Binding is presented as arbitrary fluorescence units (mean fluorescence intensity, MFI, or geometric mean fluorescence intensity, gMFI) as a function of the concentration of anti-CTLA-4 antibody added. In FIG. 7A, the anti-CTLA-4 activatable antibodies comprise YV04, YV23, YV24, or YV39 as the masking moiety and 2001 as the cleavable moiety. In FIG. 7B, the anti-CTLA-4 activatable antibodies comprise YV61, YV62, YV64, or YV39 as the masking moiety and 2001 or 2011 as the cleavable moiety. In FIG. 7C, the anti-CTLA-4 activatable antibodies comprise YV39 as the masking moiety and for the cleavable moiety, 2011 ("Ipi YV39 2011") or three variants of Ipi YV39 2011: (i) mono-clipped ("Ipi YV39 MMP monoclipped"), (ii) fully clipped by MMP ("Ipi YV39 MMP"), or (iii) fully clipped by uPA ("Ipi YV39 2011 uPA"). FIG. 7D provides the EC50 values for the different activatable antibodies shown in FIG. 7C. Ipilimumab was used as a control for FIGS. 7A to 7D.

Figure 8:
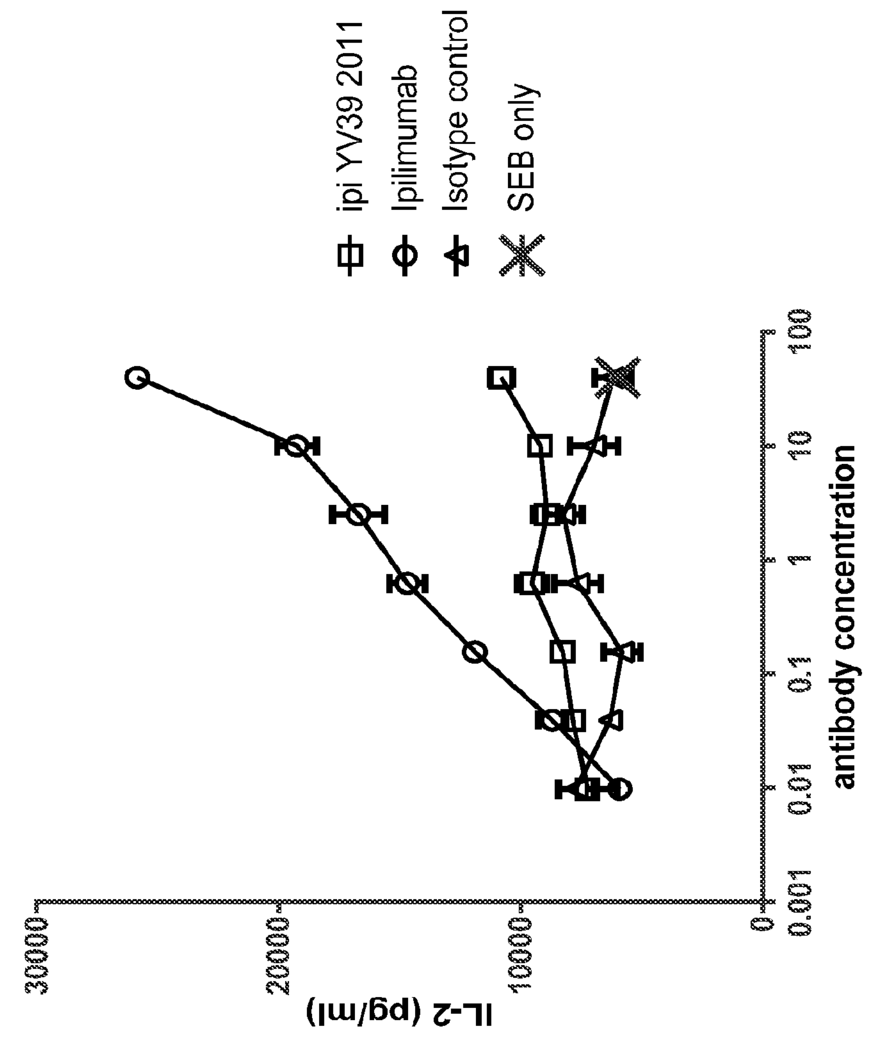

FIG. 8 shows the activity of the anti-CTLA-4 activatable antibody comprising YV39 as the masking moiety and 2011 as the cleavable moiety ("Ipi YV39 2011") (square) at different concentrations, as measured in vitro with an SEB (Staphylococcal enterotoxin B) assay. Antibody activity is shown via IL-2 production by the human PBMCs after SEB stimulation. An unrelated human IgG1 isotype (triangle), ipilimumab (circle), and SEB only stimulation (x-mark) were used as controls.

FIGS. 9A to 9F show tumor volume as a function of days post tumor implantation in human CTLA-4 knock-in mice (n=10) treated with different anti-human CTLA-4 activatable antibodies (mouse IgG2a isotype) dosed once at 10 mg/kg. An unrelated mouse IgG2a antibody (FIG. 9A) and ipilimumab with a mouse IgG2a isotype (FIG. 9B) were used as controls. In FIGS. 9C to 9F, the activatable antibodies comprise YV04, YV23, YV24, and YV39, respectively, as the masking moiety and 2001 as the cleavable moiety.

FIGS. 10A to 10F show tumor volume as a function of days post tumor implantation in human CTLA-4 knock-in mice (n=10) treated with different anti-human CTLA-4 activatable antibodies (human IgG1 isotype). The antibodies were dosed once at 200 g/mouse on day 7 post-implantation. An unrelated human IgG1 antibody (FIG. 10A) and ipilimumab with a human IgG1 isotype (FIG. 10B) were used as controls. In FIGS. 10C to 10F, the activatable antibodies comprise YV39 as the masking moiety and 2001, 2012, 2011, or 2008 as the cleavable moiety. Cleavable moieties 2012, 2011, and 2008 have been modified to overcome a deamidation site in 2001.

Figure 11A:
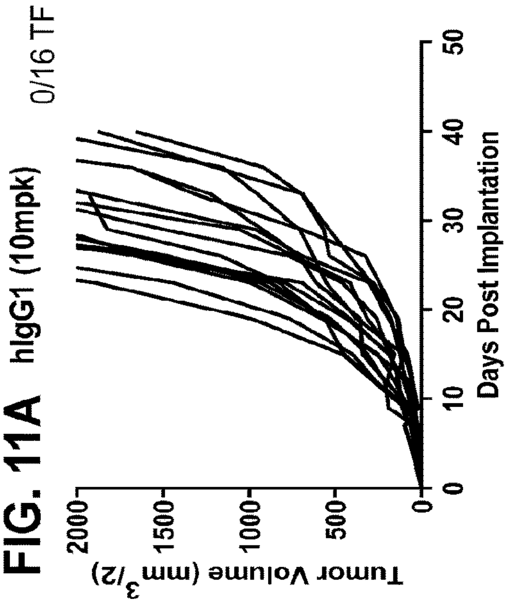
Figure 11B:
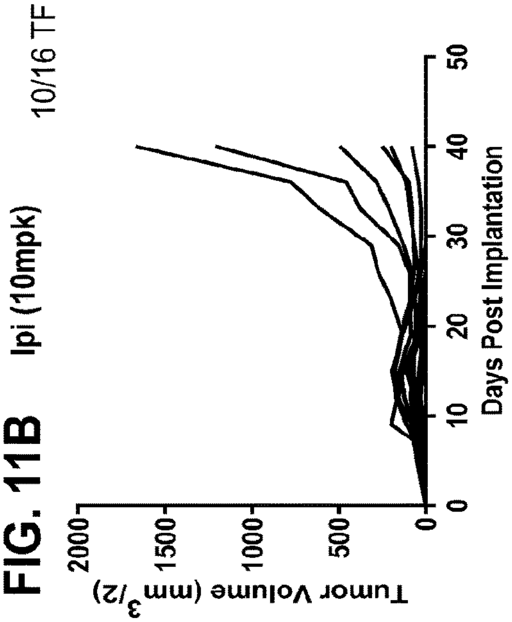
Figure 11C:
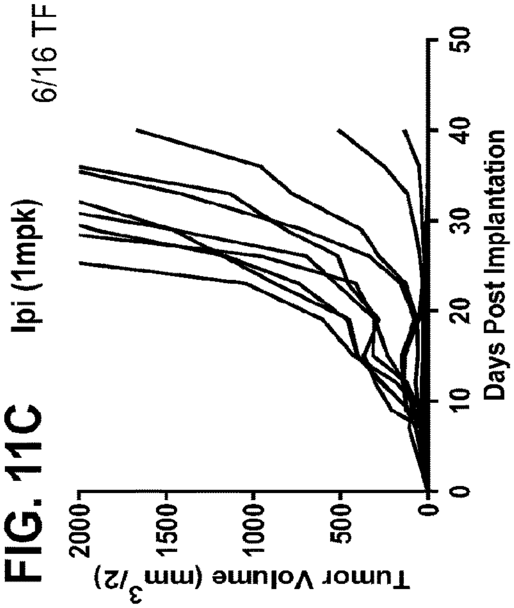
Figure 11D:
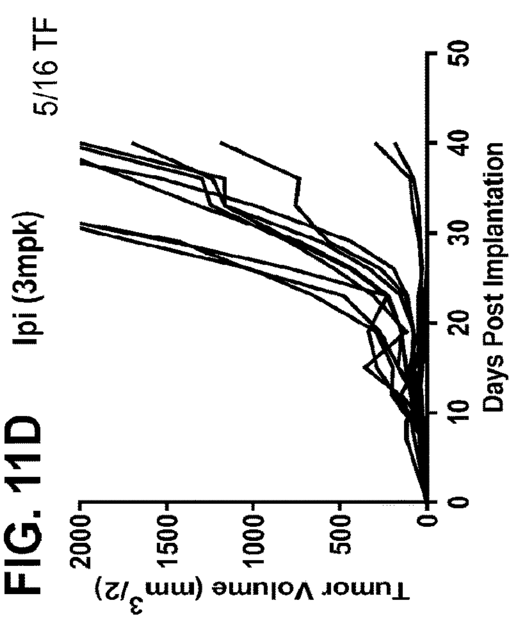
Figure 11E:
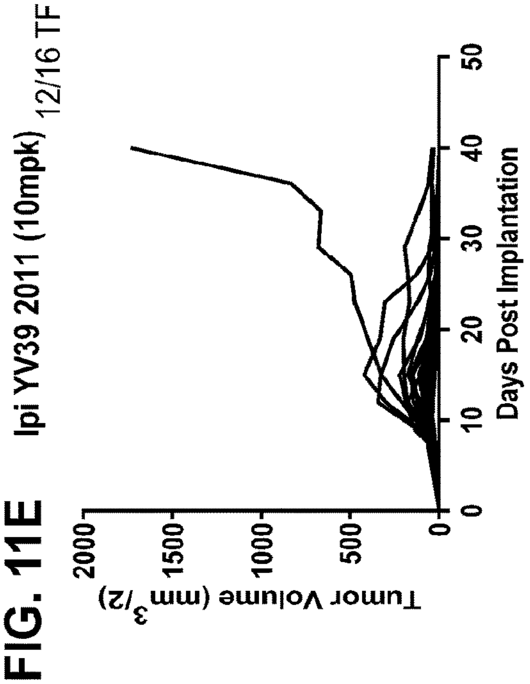
Figure 11F:
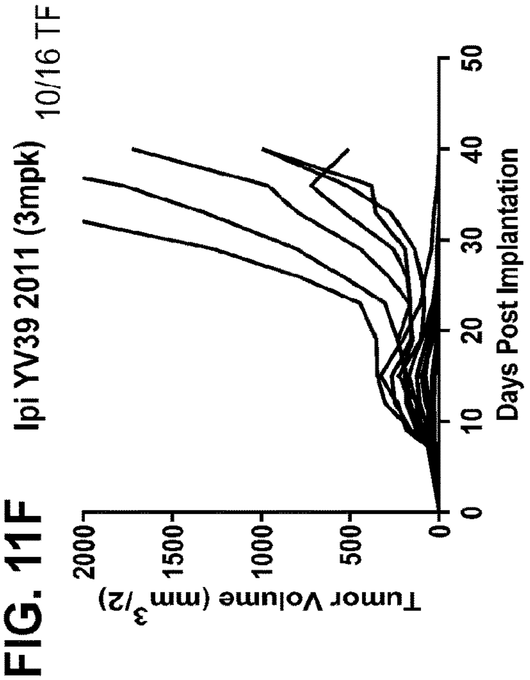
Figure 11G:
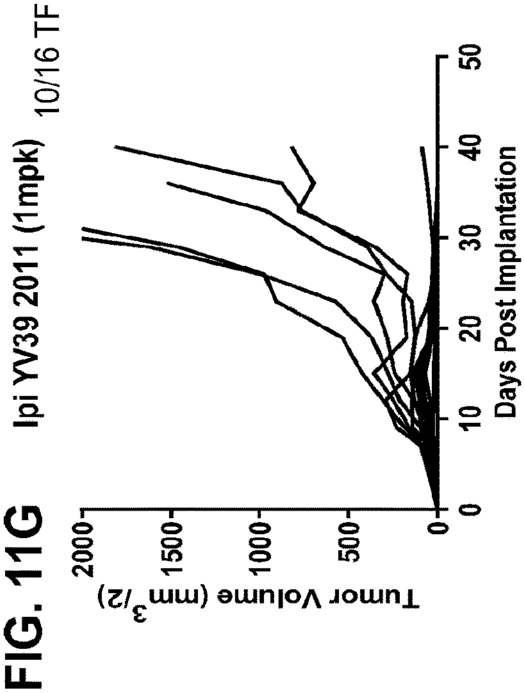

FIGS. 11A to 11G show tumor volume as a function of days post tumor implantation in human CTLA-4 knock-in mice (n=16) treated with different doses of an anti-CTLA activatable antibody comprising YV39 as the masking moiety and 2011 as the cleavable moiety ("Ipi YV39 2011") (FIGS. 11E to 11G). The antibody was dosed once at 10 mg/kg (FIG. 11E), 3 mg/kg (FIG. 11F), or 1 mg/kg (FIG. 11G) on day 7 post tumor implantation. Control animals were treated with ipilimumab (10 mg/kg, 3 mg/kg, or 1 mg/kg; FIGS. 11B to 11D, respectively) or an unrelated human IgG1 antibody (FIG. 11A).

Figure 12B:
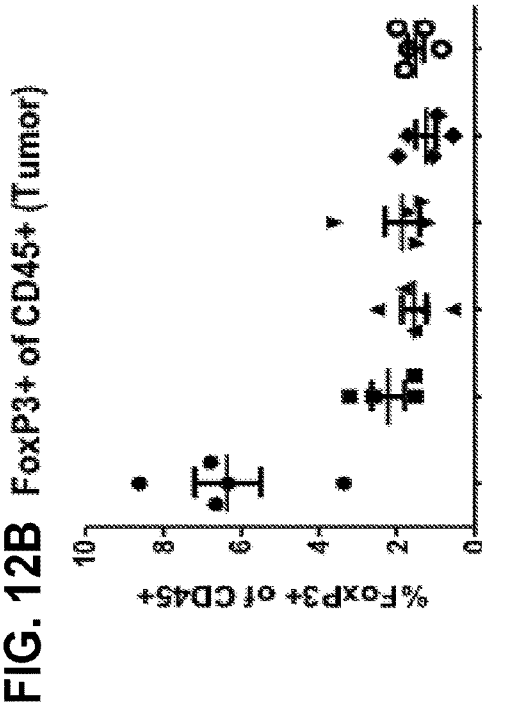
Figure 12A:
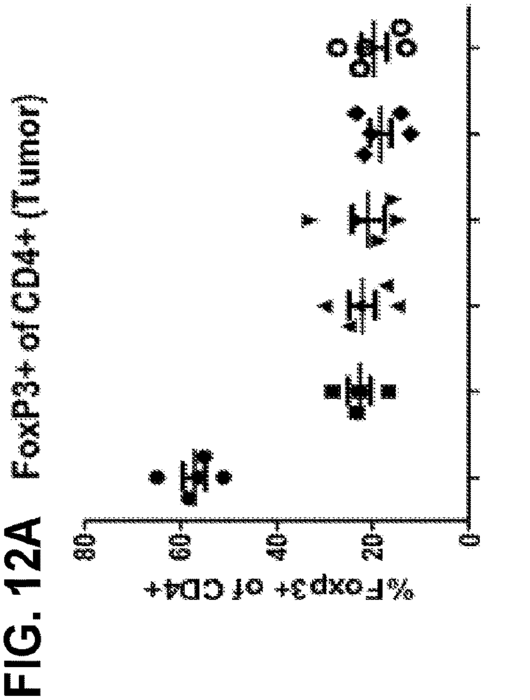
Figure 12C:
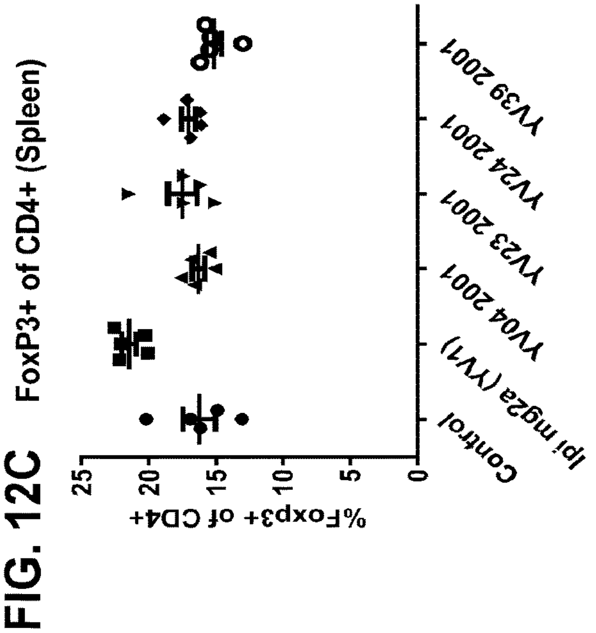
Figure 12D:
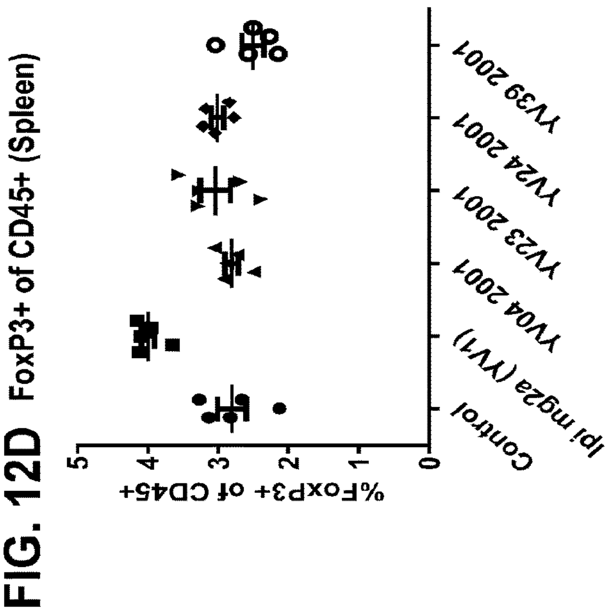
Figure 12E:
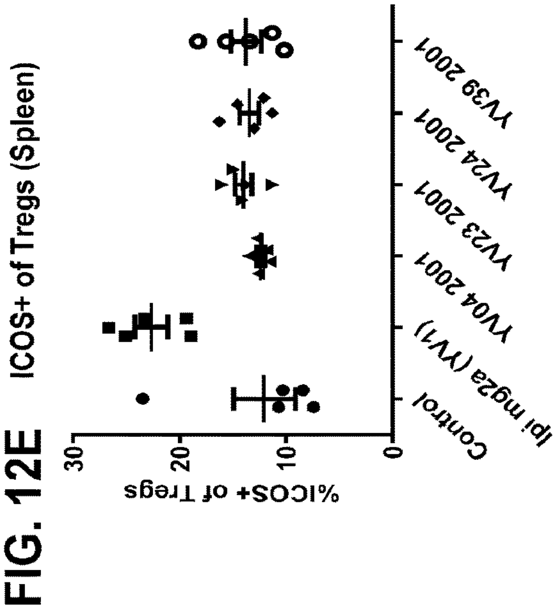
Figure 12F:
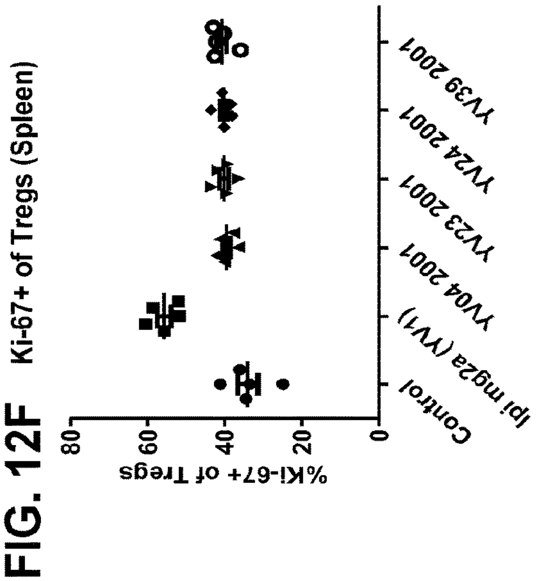

FIGS. 12A to 12D show the frequency of regulatory T cells in the tumor (FIGS. 12A and 12B) or the spleen (FIGS. 12C and 12D) in human CTLA-4 knock-in mice (n=10) treated with different anti-human CTLA-4 activatable antibodies with a mouse IgG2a isotype. All antibodies were dosed once at 10 mg/kg. The activatable antibodies comprise YV04, YV23, YV24, or YV39 as the masking moiety and 2001 as the cleavable moiety. The labels on the abscissas of FIGS. 12C and 12D also apply to FIGS. 12A and 12B, respectively. An unrelated human IgG1 antibody and ipilimumab with a mouse IgG2a isotype were used as controls. In FIGS. 12A and 12C, the frequency of regulatory T cells is shown as a percentage of total CD4+ T cells that are Foxp3+. In FIGS. 12B and 12D, the frequency of regulatory T cells is shown as a percentage of total CD45+ T cells that are Foxp3+. FIGS. 12E and 12F show the frequency of activated (ICOS+) cells and proliferating (Ki-67+) cells is shown as a percentage of regulatory T cells in the spleen.

Figure 13A:
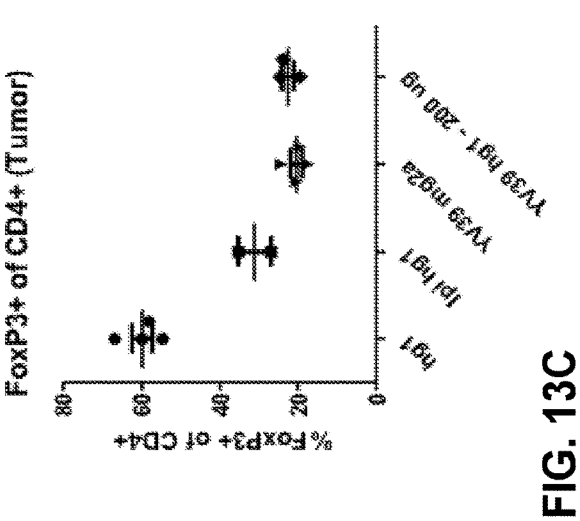
Figure 13B:
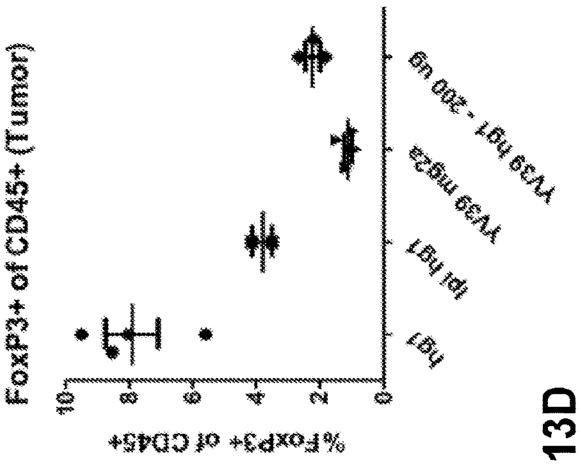
Figure 13C:
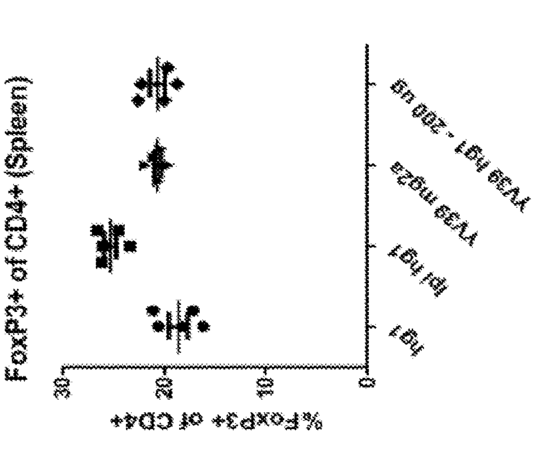
Figure 13D:
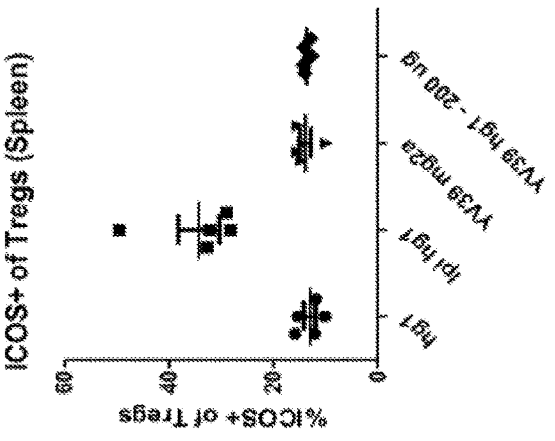
Figure 13E:
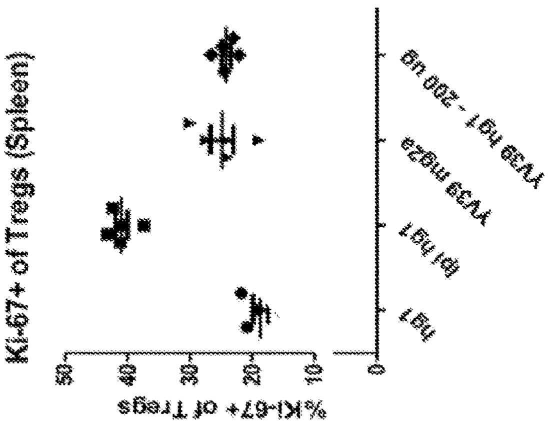

FIGS. 13A to 13C show the frequency of regulatory T cells in the tumor (FIGS. 13A and 13B) or the spleen (FIG. 13C) in human CTLA-4 knock-in mice treated with anti-CTLA-4 activatable antibody. The activatable antibody used comprises YV39 as the masking moiety and were either a mouse IgG2a isotype or human IgG1 isotype. An unrelated human IgG1 antibody and ipilimumab with a human IgG1 isotype were used as controls. In FIGS. 13A and 13C, the frequency of regulatory T cells is shown as a percentage of total CD4+ T cells that are Foxp3+. In FIG. 13B, the frequency of regulatory T cells is shown as a percentage of total CD45+ T cells that are Foxp3+. FIGS. 13D and 13E show the frequency of proliferating (Ki-67+) and activated (ICOS+) cells as a percentage of regulatory T cells in the spleen.

Figure 14B:
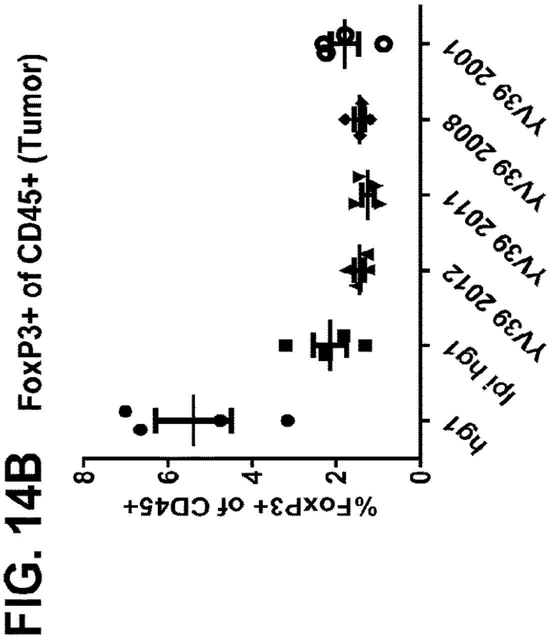
Figure 14A:
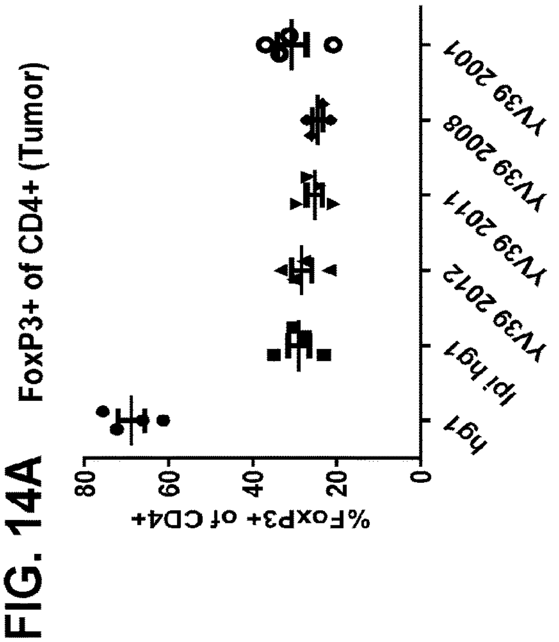
Figure 14C:
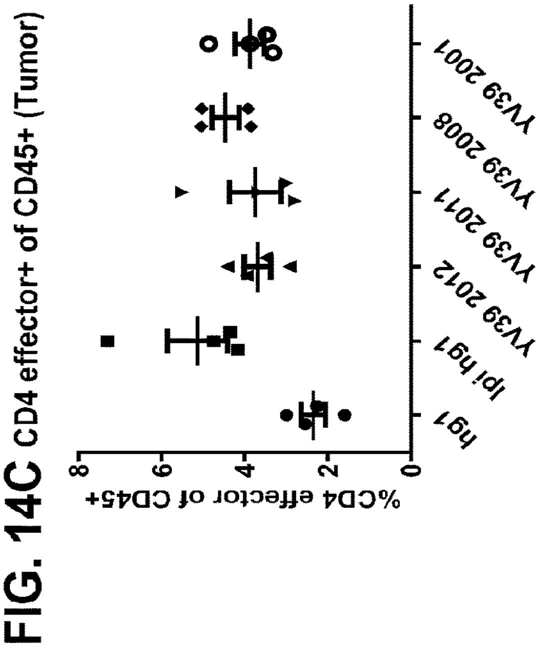
Figure 14E:
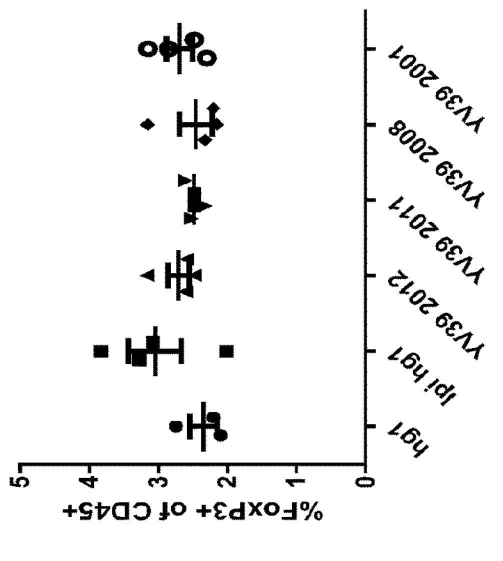
Figure 14D:
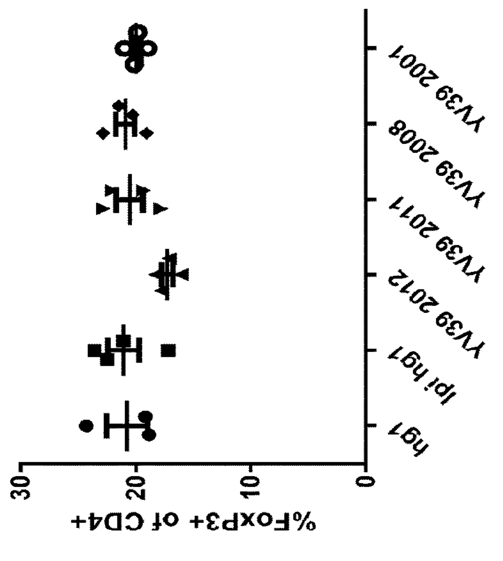
Figure 14G:
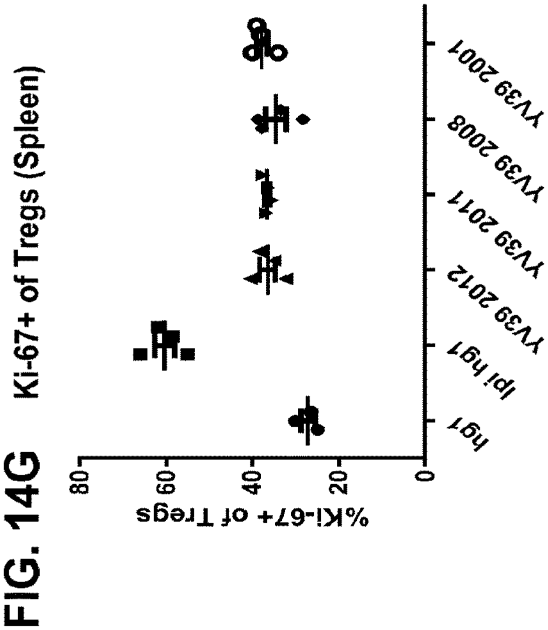
Figure 14F:
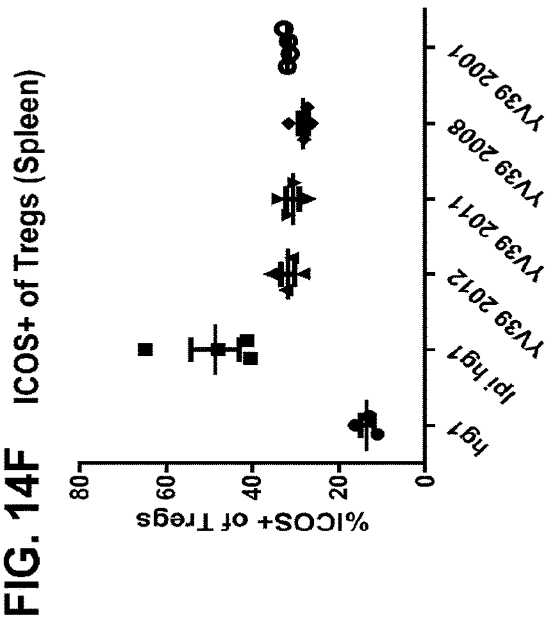
Figure 15:
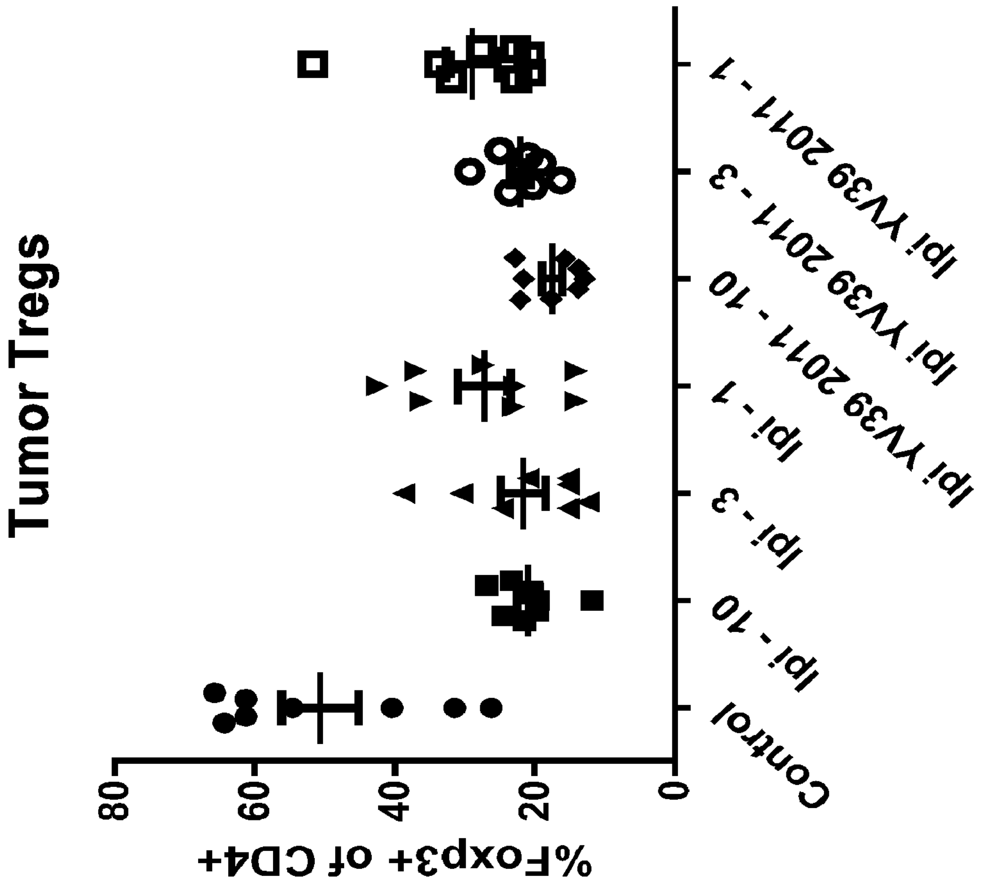

FIGS. 14A to 14C show the frequency of regulatory T cells (FIGS. 14A and 14B) or CD4+ effector T cells (FIG. 14C) in the tumors of mice treated with different anti-CTLA-4 activatable antibodies. FIGS. 14D and 14E show the regulatory T cells in the spleen. The anti-CTLA-4 activatable antibodies comprise YV39 as the masking moiety and 2012, 2011, 2008, or 2001 as the cleavable moiety. An unrelated human IgG1 antibody and ipilimumab with a human IgG1 isotype were used as controls. In FIGS. 14A and 14D, the frequency of regulatory T cells is shown as a percentage of total CD4+ T cells that are Foxp3+. In FIGS. 14B and 14E, the frequency of regulatory T cells is shown as a percentage of total CD45+ T cells that are Foxp3+. FIG. 14C shows the frequency of CD4+ effector T cells as a percentage of the total CD45+ T cells in the tumor. FIGS. 14F and 14G show the percentages of proliferating (Ki-67+) and activated (ICOS+) regulatory T cells in the spleen FIG. 15 shows the frequency of regulatory T cells in the tumors of human CTLA-4 knock-in mice (n=8) treated with different doses of either ipilimumab or an anti-CTLA-4 activatable antibody comprising YV39 as the masking moiety and 2011 as the cleavable moiety ("Ipi YV39 2011"). The antibodies were dosed once at 10 mg/kg, 3 mg/kg, or 1 mg/kg on day 7 post tumor implantation. An unrelated human IgG1 antibody was used as a control.

Figure 16B:
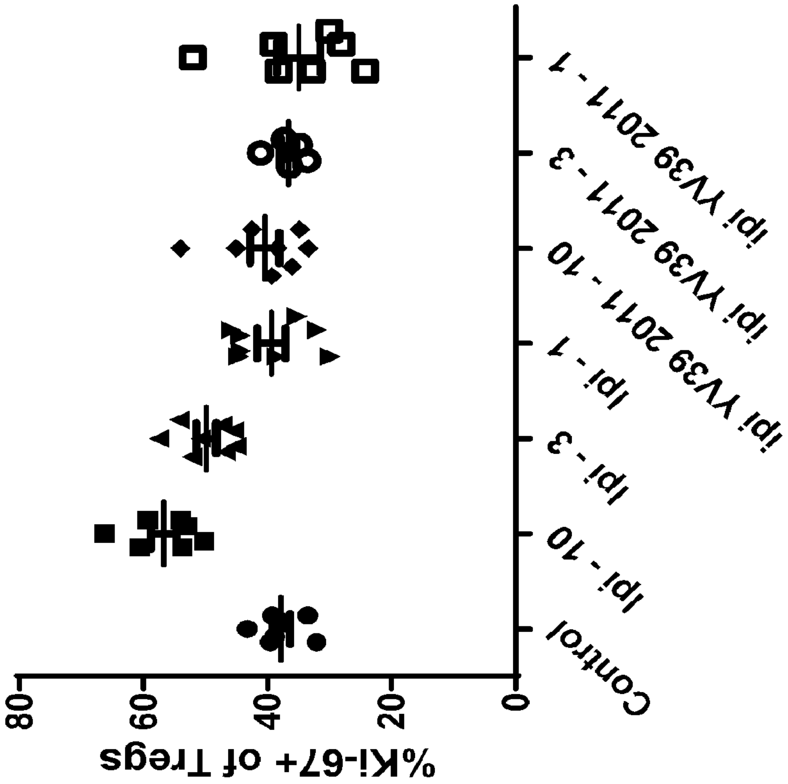
Figure 16A:
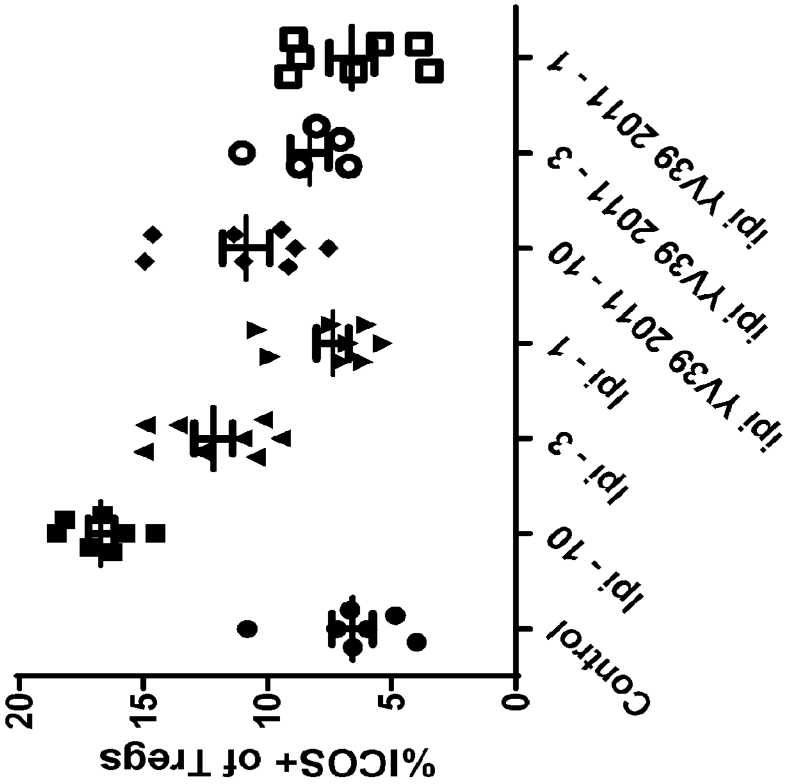

FIGS. 16A and 16B show the percentages of activated (ICOS+) and proliferating (Ki-67+) regulatory T cells in the spleen of human CTLA-4 knock-in mice (n=8) treated with different doses of either ipilimumab or an anti-CTLA-4 activatable antibody comprising YV39 as the masking moiety and 2011 as the cleavable moiety ("Ipi YV39 2011"). The antibodies were dosed once at 10 mg/kg, 3 mg/kg, or 1 mg/kg on day 7 post tumor implantation. An unrelated human IgG1 antibody was used as a control.

Figure 17A:
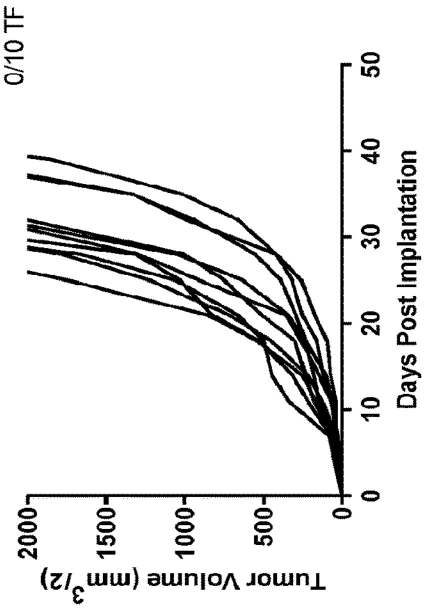
Figure 17B:
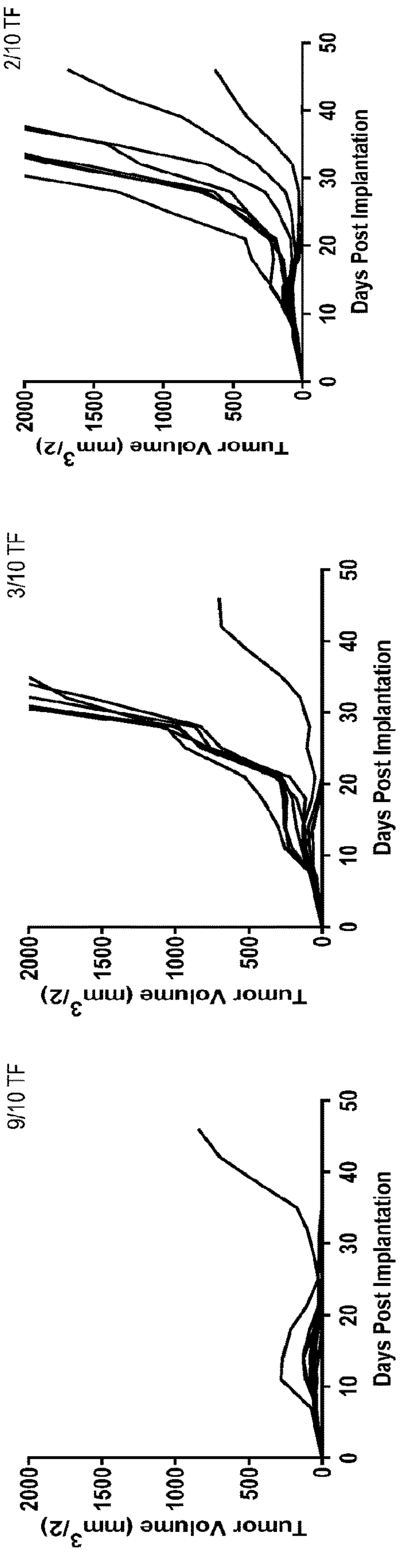
Figure 17C:
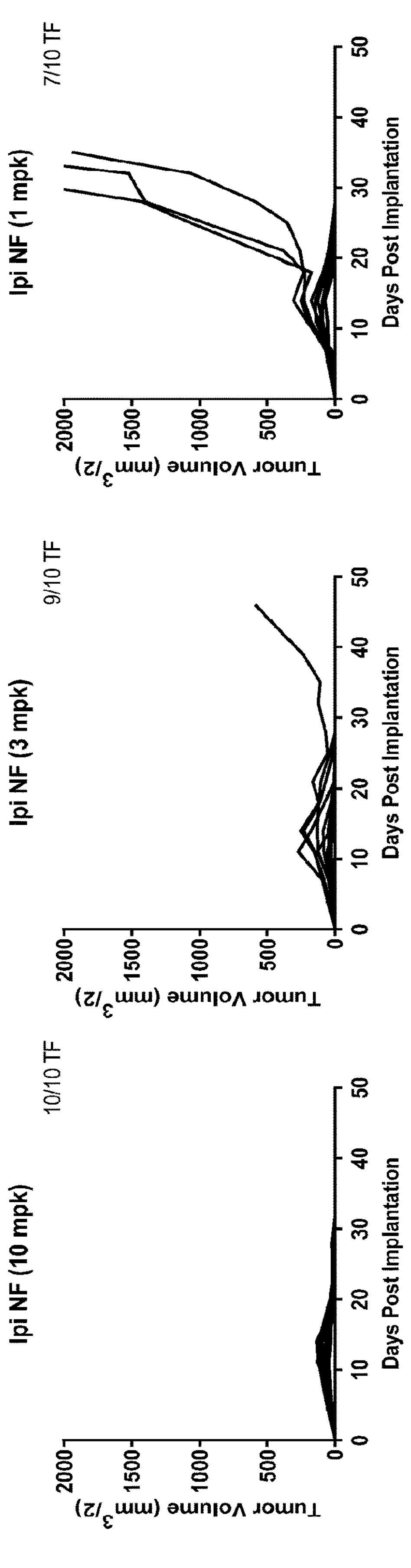
Figure 17D:
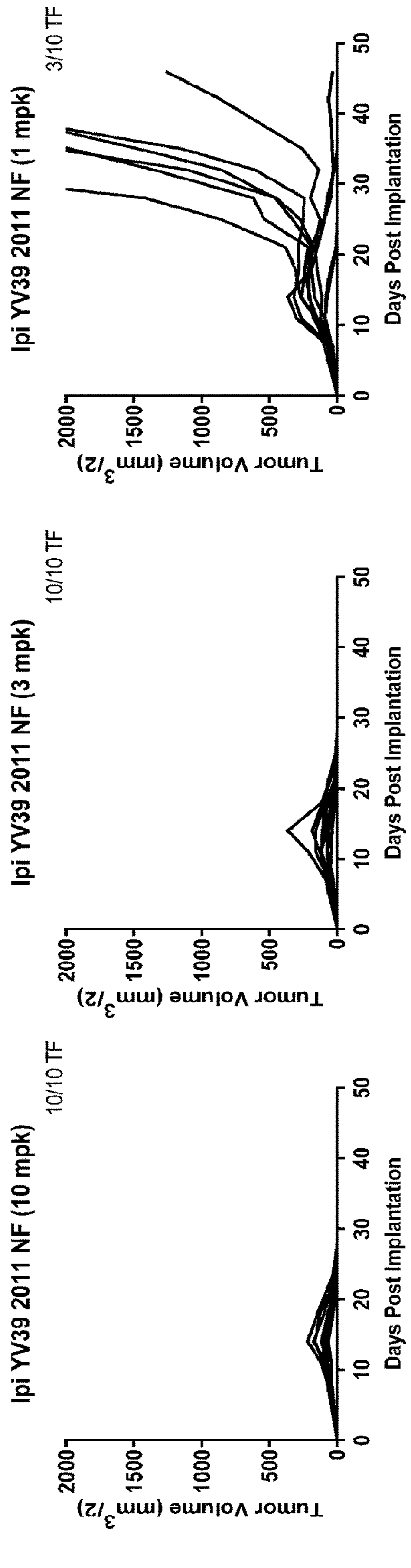

FIGS. 17A to 17D show tumor volume as a function of days post tumor implantation in human CTLA-4 knock-in mice (n=10) treated with different doses of ipilimumab ("Ipi") (FIG. 17B), a nonfucosylated version of ipilimumab ("Ipi NF") (FIG. 17C), or a nonfucosylated version of an anti-CTLA-4 activatable antibody comprising YV39 as the masking moiety and 2011 as the cleavable moiety ("Ipi YV39 2011 NF") (FIG. 17D). The antibodies were dosed once at 10 mg/kg, 3 mg/kg, or 1 mg/kg (left panel, middle panel, and right panel, respectively, in FIGS. 17B to 17D). Control animals received an unrelated human IgG1 antibody (FIG. 17A).

Figure 18:
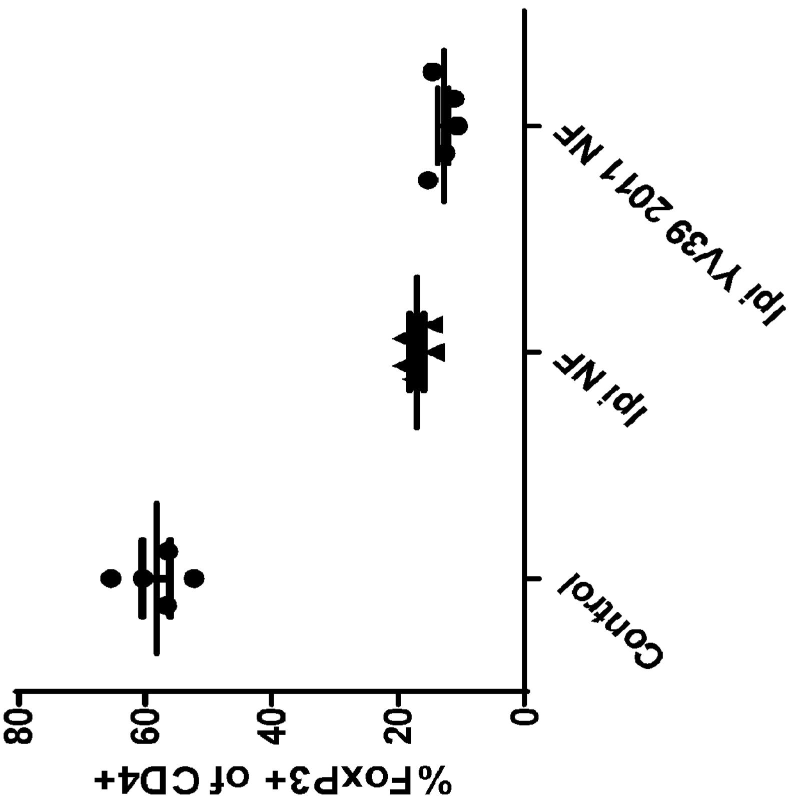

FIG. 18 shows the frequency of regulatory T cells in the tumors of human CTLA-4 knock-in mice (n=5) treated with either the nonfucosylated version of ipilimumab ("Ipi NF") or a nonfucosylated version of the anti-CTLA-4 activatable antibody comprising YV39 as the masking moiety and 2011 as the cleavable moiety ("NF Ipi YV39 2011"). The antibodies were dosed once at 200 μg/mouse on day 7 post tumor implantation. An unrelated human IgG1 antibody was used as a control.

FIG. 19 shows the binding affinities (Kd) for both ipilimumab ("Ipi") and a nonfucosylated version of ipilimumab ("Ipi NF") to various human, cyno, and mouse Fc receptors.

Figure 20:
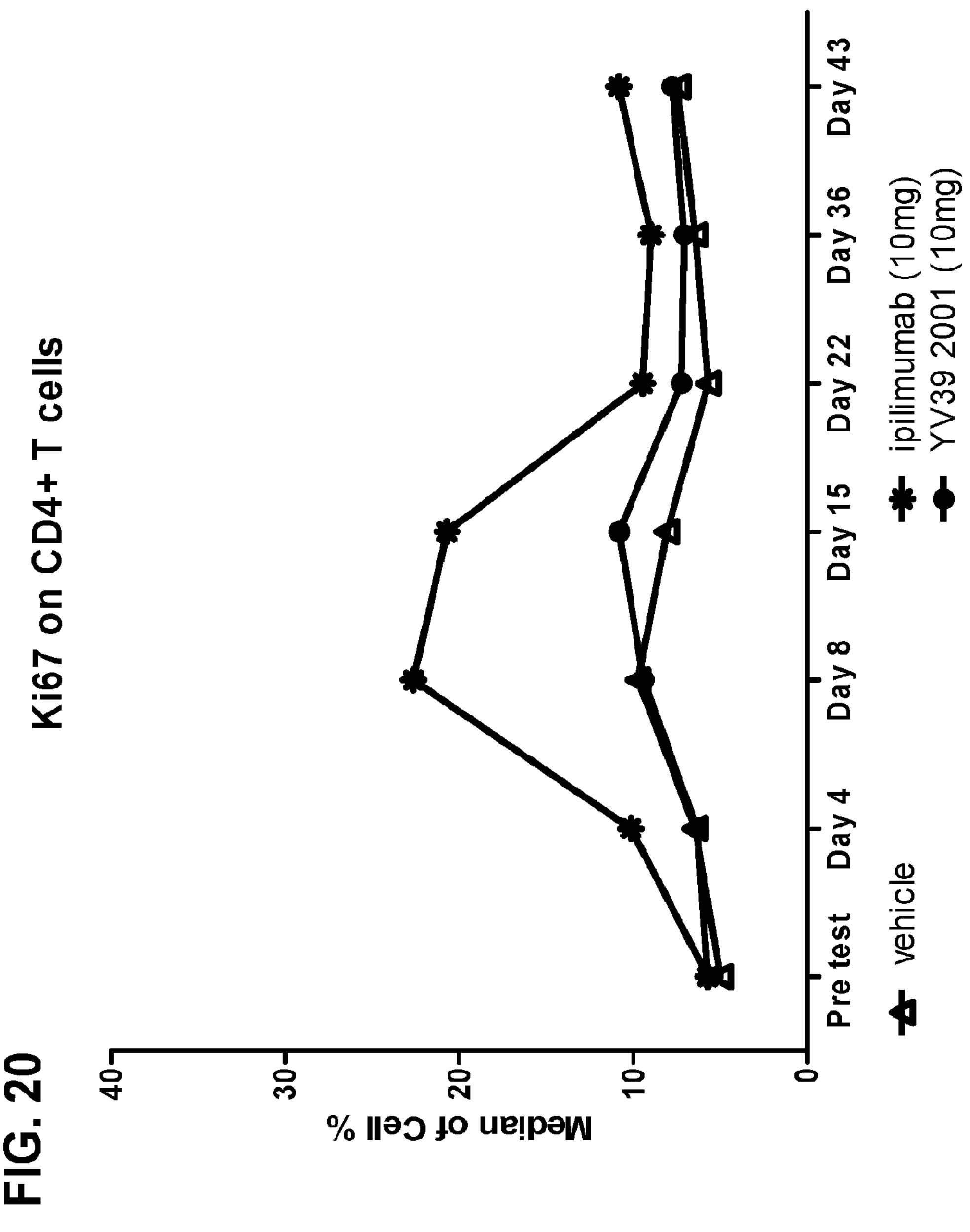

FIG. 20 shows the median percentage of Ki67+CD4+ T cells in the blood of cynomolgus monkeys after treatment with an anti-CTLA-4 activatable antibody. The anti-CTLA-4 activatable antibody comprises YV39 as the masking moiety and 2001 as the cleavable moiety. Vehicle and ipilimumab were used as controls.

DETAILED DESCRIPTION OF INVENTION

In order that the present description can be more readily understood, certain terms are first defined. Additional definitions are set forth throughout the detailed description.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systéme International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "cytotoxic T-lymphocyte antigen 4" or "CTLA-4" as used herein refers to a receptor that is a member of the immunoglobulin superfamily that is expressed by activated T cells and transmits an inhibitory signal to T cells. CTLA-4 is homologous to the T-cell co-stimulatory protein, CD28, and both molecules bind to CD80 and CD86, also called B7-1 and B7-2 respectively, on antigen-presenting cells. CTLA4 is also found in regulatory T cells and contributes to its inhibitory function. CTLA-4 is also referred to as cytotoxic T-lymphocyte-associated protein 4, CD152, Insulin-dependent Diabetes Mellitus 12 (IDDM12), Celiac Disease 3 (CELIAC3), GRD4, and GSE. The term "CTLA-4" includes any variants or isoforms of CTLA-4 which are naturally expressed by cells.

The term "T cell" as used herein is defined as a thymus-derived lymphocyte that participates in a variety of cell-mediated immune reactions. The term "regulatory T cell" as used herein refers to a $CD4^+CD25^+FoxP3^+$ T cell with suppressive properties. "Treg" is the abbreviation used herein for a regulatory T cell.

The term "helper T cell" as used herein refers to a $CD4^+$ T cell; helper T cells recognize antigen bound to MHC Class II molecules. There are at least two types of helper T cells, Th1 and Th2, which produce different cytokines. Helper T cells become $CD25^+$ when activated, but only transiently become FoxP3+.

The term "cytotoxic T cell" as used herein refers to a $CD8^+$ T cell; cytotoxic T cells recognize antigen bound to MHC Class I molecules.

The term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($Kd>10^{-6}$). Antibodies include, but are not limited to, polyclonal, monoclonal, chimeric, domain antibody, single chain, Fab, and F(ab')2 fragments, scFvs, and a Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as IgG1, IgG2, and others. Furthermore, in humans, the light chain may be a kappa chain or a lambda chain.

As used herein, the term "activatable antibody" refers to an antibody that also comprises a masking moiety (MM) and a cleavable moiety (CM), wherein the MM is joined to the VL of the antibody via the CM, which is cleavable by a protease. As used herein, a "prodomain" comprises the N-terminal fragment that is joined to the VL domain of the anti-human CTLA-4 activatable antibodies and, as such, comprises the MM and CM. In some embodiments, the light chain of the activatable antibody has the structural arrangement from N-terminus to C-terminus as follows: MM-CM-VL. In some embodiments, the prodomain is joined to the VH domain of the anti-human CTLA-4 antibody. An activatable antibody is designed to be cleaved by upregulated proteolytic activity present in most if not all cancers. Such proteolytic cleavage, or activation, removes the prodomain and releases an active antibody, i.e., an activated activatable antibody. Protease activation of activatable antibodies in normal tissue is significantly reduced due to the tight control of proteolytic activity in normal tissues. As such, activatable antibodies remain largely inert in circulation and in normal tissues.

An activatable antibody, in view of its prodomain masking the antigen binding domain thereby inhibiting the ability of the antigen binding domain to bind to its target, has a lower affinity for binding to the target than does an activated activatable antibody, in which the MM has been removed by proteolytic cleavage of the CM thereby releasing an active antibody. Such released antibody exhibits higher affinity for binding to its target. In some embodiments, the MM interacts specifically with the antigen binding domain of ipilimumab to reduce the antibody's ability to bind to its target. When the MM is removed by proteolytic cleavage of the activatable antibody, the released antibody binds to its target with an affinity similar to the parental ipilimumab.

Schematic representations of activatable antibodies of the present invention, e.g. MM-CM-VL, are not intended to be exclusive. Other sequence elements, such as linkers, spacers and signal sequences, may be present before, after, or between the listed sequence elements in such schematic representations. It is also to be appreciated that a prodomain comprising a MM and a CM can be joined to a VH of an antibody instead of to a VL of an antibody such that the heavy chain has the structural arrangement from N-terminus to C-terminus as follows: MM-CM-VH.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site, or domain, capable of immunoreacting with a particular epitope of the antigen characterized by a unique binding affinity for it. Monoclonal antibody molecules will typically comprise two heavy chains and two light chains.

The term "antigen binding domain" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk *J. Mol. Biol.* 196:901-917 (1987), Chothia et al. *Nature* 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is 1 M; preferably 100 nM and most preferably 10 nM.

As used herein, the terms "specific binding," "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($k_{on}$) and the "off rate constant" ($k_{off}$) can be determined by calculation of the concentrations and the actual rates of association and dissociation. (See *Nature* 361:186-87 (1993)). The ratio of $k_{off}/k_{on}$ enables the cancellation of all parameters not related to affinity, and is equal to the dissociation constant $K_d$. (See, generally, Davies et al. (1990) *Annual Rev Biochem* 59:439-473). An antibody of the present invention is said to specifically bind to CTLA-4, when the equilibrium binding constant ($K_d$) is ≤1 μM, preferably ≤100 nM, more preferably ≤10 nM, and most preferably ≤100 pM to about 1 pM, as measured by assays such as radioligand binding assays or similar assays known to those skilled in the art.

The term "isolated polynucleotide" as used herein refers to a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. *Nucl. Acids Res.* 14:9081 (1986); Stec et al. *J. Am. Chem. Soc.* 106:6077 (1984), Stein et al. *Nucl. Acids Res.* 16:3209 (1988), Zon et al. *Anti Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Gren, Eds., Sinauer Associates, Sunderland Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% sequence identity. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. In the case of an antibody, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a CDR or framework region. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis in regions of the activatable antibody other than in the cleavable linker comprising the CM, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts). A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. *Nature* 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long' more preferably at least 20 amino acids long, usually at least 50 amino acids long, and even more preferably at least 70 amino acids long. The term "analog" as used herein refers to polypeptides which comprise a segment of at least 25 amino acids that has substantial identity to a portion of a deduced amino acid sequence and which has specific binding to CTLA-4, under suitable binding conditions. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$ $^{99}Tc$, $^{111}In$, $^{125}I$, $^{131}I$) fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

As used herein, "treatment" is an approach for obtaining beneficial or desired clinical results. Beneficial or desired clinical results may include, but are not limited to, any one or more of: alleviation of one or more symptoms, diminishment of extent of disease, stabilized (i.e., not worsening) state of disease, preventing or delaying spread (e.g., metastasis) of disease, preventing or delaying occurrence or recurrence of disease, delay or slowing of disease progression, amelioration of the disease state, and remission (whether partial or total). Also encompassed by "treatment" is a reduction of pathological consequence of a proliferative disease such as cancer. The methods provided herein contemplate any one or more of these aspects of treatment.

The term "effective amount" used herein refers to an amount of a compound or composition, when used alone or in combination with a second therapy, is sufficient to treat a specified disorder, condition or disease such as ameliorate, palliate, lessen, and/or delay one or more of its symptoms. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. An effective amount can be administered in one or more administrations.

As used herein, by "combination therapy" is meant that a first agent be administered in conjunction with another agent. "In conjunction with" refers to administration of one treatment modality in addition to another treatment modality. As such, "in conjunction with" refers to administration of one treatment modality before, during, or after delivery of the other treatment modality to the individual.

The term "pharmaceutical agent or drug" as used herein refers to a chemical compound or composition capable of inducing a desired therapeutic effect when properly administered to a subject.

As used herein, by "pharmaceutically acceptable" or "pharmacologically compatible" is meant a material that is not biologically or otherwise undesirable, e.g., the material may be incorporated into a pharmaceutical composition administered to an individual or subject without causing any significant undesirable biological effects or interacting in a deleterious manner with any of the other components of the composition in which it is contained. Pharmaceutically acceptable carriers or excipients have for example met the required standards of toxicological and manufacturing testing and/or are included on the Inactive Ingredient Guide prepared by the U.S. Food and Drug administration.

The terms "cancer", "cancerous", or "malignant" refer to or describe the physiological condition in mammals that is typically characterized by unregulated cell growth. Examples of cancer include, for example, melanoma, such as unresectable or metastatic melanoma, leukemia, lymphoma, blastoma, carcinoma and sarcoma. More particular examples of such cancers include chronic myeloid leukemia, acute lymphoblastic leukemia, Philadelphia chromosome positive acute lymphoblastic leukemia (Ph+ ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia (AML), and chronic lymphocytic leukemia (CMIL).

"Leukemia" refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease—acute or chronic; (2) the type of cell involved; myeloid (myelogenous), lymphoid (lymphogenous), or monocytic; and (3) the increase or non-increase in the number of abnormal cells in the blood—leukemic or aleukemic (subleukemic). Leukemia includes, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia. In certain aspects, the present invention provides treatment for chronic myeloid leukemia, acute lymphoblastic leukemia, and/or Philadelphia chromosome positive acute lymphoblastic leukemia (Ph+ ALL).

I. Anti-CTLA-4 Activatable Antibodies

The present invention provides improved anti-CTLA-4 antibodies that are as efficacious as the traditional anti-CTLA-4 antibodies (e.g., ipilimumab) but with a greater, i.e., improved, safety profile. Specifically, the improved anti-CTLA-4 antibodies are activatable monoclonal antibodies (mAbs) that specifically bind human CTLA-4 when activated. These improved anti-CTLA-4 antibodies, also referred to herein as activatable anti-CTLA-4 antibodies or CTLA-4 activatable antibodies, are used in methods of treating, preventing, delaying the progression of, ameliorating and/or alleviating a symptom of a disease or disorder, including but not limited to, a disease or disorder associated with aberrant CTLA-4 expression and/or activity. For example, the activatable anti-CTLA-4 antibodies are used in methods of treating, preventing, delaying the progression of, ameliorating and/or alleviating a symptom of a cancer or other neoplastic condition. Activatable antibodies are described in, for example, U.S. Pat. Nos. 8,513,390, 8,518,404; 9,120,853; 9,127,053 and International Publ. No. WO 2016/149201.

In some embodiments, the activatable anti-CTLA-4 antibodies provided herein comprise (i) ipilimumab or antigen binding domain thereof (AB), such as an ipilimumab variable light chain (VL), (ii) a cleavable moiety (CM), and (iii) a masking moiety (MM). In some embodiments, the VL is coupled to the MM, such that coupling of the MM reduces the ability of the ipilimumab to bind to CTLA-4. In some embodiments, the MM is coupled to the VL via a cleavable moiety (CM) (also known as a substrate linker) that includes a substrate for a protease, for example, a protease that is over-expressed in the tumor microenvironment.

Antibody or Antigen Binding Fragment Thereof

In some embodiments, the antibody or antigen binding domain thereof (AB) comprises the complementarity determining regions (CDRs) of the anti-CTLA-4 antibody ipilimumab, identified as 10D1 in U.S. Pat. Nos. 6,984,720 and 7,605,238, which are hereby incorporated by reference in their entireties. Ipilimumab (also formerly known as MDX-010 and BMS-734016) is marketed as YERVOY® and has been approved for the treatment of metastatic melanoma and is in clinical testing in other cancers. See Hoos et al. (2010) *Semin. Oncol.* 37:533; Hodi et al. (2010) *N. Engl. J. Med.* 363:711; Pardoll (2012) *Nat. Immunol.* 13(12): 1129.

Ipilimumab has a human IgG1 isotype, which binds best to most human Fc receptors (Bruhns et al. (2009) *Blood* 113: 3716) and is considered equivalent to murine IgG2a with respect to the types of activating Fc receptors that it binds. Since IgG1 binds to the activating receptor CD16 (FcγRIIIa) expressed by human NK cells and monocytes, ipilimumab can mediate ADCC. The IgG1-isotype ipilimumab was originally isolated directly from a hybridoma but was subsequently cloned and expressed in Chinese hamster ovary (CHO) cells. Notwithstanding the consideration that an isotype that mediates ADCC and/or CDC might be undesirable in an antibody targeting a receptor on T cells that seeks to upregulate an immune response, the IgG1 isotype of the antibody was retained, in part, because it enhanced vaccine response in cynomolgus monkey and was considered functional. Ipilimumab has been shown to increase the numbers of activated T cells in the blood, as evidenced, for example, by a significant increase in the expression of HLA-DR on the surface of post-treatment $CD4^+$ and $CD8^+$ cells as well as increases in absolute lymphocyte count (Ku et al. (2010) *Cancer* 116:1767; Attia et al. (2005) *J. Clin. Oncol.* 23:6043; Maker et al. (2005) *J. Immunol.* 175:7746; Berman et al. (2009) *J. Clin. Oncol.* 27(suppl):15s.3020; Hamid et al. (2009) *J. Clin. Oncol.* 27(suppl): 15s.9008), indicating that depletion of T cells does not occur in the periphery in man. Ipilimumab demonstrated only modest levels of ADCC of activated T cells using IL-2-activated PBMCs as effector cells; however, use of $T_{regs}$ as targets was not tested. Minor changes in peripheral $T_{reg}$ frequency in the blood of patients treated with ipilimumab have been observed (Maker et al. (2005) *J. Immunol.* 175:7746), but little information of the effect of ipilimumab on intratumoral $T_{regs}$ is available. However, a positive correlation between a high $CD8^+$ to $T_{reg}$ ratio and tumor necrosis in biopsies from metastatic melanoma lesions from patients treated with ipilimumab have been described. Hodi et al. (2008) *Proc. Nat'l Acad. Sci.* (USA) 105:3005. In addition, tumor tissue from ipilimumab-treated bladder cancer patients had lower percentages of $CD4^+$ $Foxp3^+$ T cells than tumors from untreated bladder cancer patients. Liakou et al. (2008) *Proc. Nat'l Acad. Sci.* (USA) 105:14987.

In some embodiments, the activatable anti-CTLA-4 antibody comprises a combination of a variable heavy chain CDR1 (VH CDR1, also referred to herein as CDRH1), CDR2 (VH CDR2, also referred to herein as CDRH2), and CDR3 (VH CDR3, also referred to herein as CDRH3), and a variable light chain CDR1 (VL CDR1, also referred to herein as CDRL1), CDR2 (VL CDR2, also referred to herein as CDRL2), and CDR3 (VL CDR3, also referred to herein as CDRL3). These CDR sequences are provided at Table 2.

TABLE 2

CDR Sequences of heavy and light chains for Ipilimumab

| CHAIN | CDR1 | CDR2 | CDR3 |
|---|---|---|---|
| LIGHT | RASQSVGSSYLA (SEQ ID NO: 560) | GAFSRAT (SEQ ID NO: 561) | QQYGSSPWT (SEQ ID NO: 562) |
| HEAVY | SYTMH (SEQ ID NO: 557) | FISYDGNNKYYADSVKG (SEQ ID NO: 558) | TGWLGPFDY (SEQ ID NO: 559) |

Ipilimumab-VL chain (SEQ ID NO: 344)

EIVLTQSPGTLSLSPGERATLSCRASQSVGSSYLAWYQQKPGQAPRLLI

YGAFSRATGIPDRFSGSGSGTDFTLTISRLEPEDFAVYYCQQYGSSPWT

FGQGTKVEIK

Ipilimumab-VH chain (SEQ ID NO: 345)

QVQLVESGGGVVQPGRSLRLSCAASGFTFSSYTMHWVRQAPGKGLEWVT

FISYDGNNKYYADSVKGRFTISRDNSKNTLYLQMNSLRAEDTAIYYCAR

TGWLGPFDYWGQGTLVTVSS

Various other sequences, as indicated, are provided below.

Human Kappa constant LC (SEQ ID NO: 346)

RTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGEC

-continued

Mouse Kappa constant light chain (SEQ ID NO: 347)

RADAAPTVSIFPPSSEQLTSGGASVVCFLNNFYPKDINVKWKIDGSERQNGVLNS

WTDQDSKDSTYSMSSTLTLTKDEYERHNSYTCEATHKTSTSPIVKSFNRNEC

Ipilimumab - Human Kappa LC (SEQ ID NO: 348)

EIVLTQSPGTLSLSPGERATLSCRASQSVGSSYLAWYQQKPGQAPRLLIYGAFSRA

TGIPDRFSGSGSGTDFTLTISRLEPEDFAVYYCQQYGSSPWTFGQGTKVEIKRTVA

APSVFIFPPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC

Ipilimumab - Mouse Kappa LC (SEQ ID NO: 349)

EIVLTQSPGTLSLSPGERATLSCRASQSVGSSYLAWYQQKPGQAPRLLIYGAFSRA

TGIPDRFSGSGSGTDFTLTISRLEPEDFAVYYCQQYGSSPWTFGQGTKVEIKRADA

APTVSIFPPSSEQLTSGGASVVCFLNNFYPKDINVKWKIDGSERQNGVLNSWTDQ

DSKDSTYSMSSTLTLTKDEYERHNSYTCEATHKTSTSPIVKSFNRNEC

Human IgG1 constant HC (SEQ ID NO: 350)

ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKRVEPKSCDKTHTCPP

CPAPELLGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKSLSLSP

G

Mouse IgG1 constant HC (SEQ ID NO: 351)

ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDKTHTCP

PCPAPELLGGPSVFLFPPKPKDTLMISRTPEVTCVVVDVSHEDPEVKFNWYVDGV

EVHNAKTKPREEQYASTYRVVSVLTVLHQDWLNGKEYKCKVSNKALPAPIEKTI

SKAKGQPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQKSLSLS

PG

Mouse IgG2a constant HC (SEQ ID NO: 352)

AKTTAPSVYPLAPVCGDTTGSSVTLGCLVKGYFPEPVTLTWNSGSLSSGVHTFPA

VLQSDLYTLSSSVTVTSSTWPSQSITCNVAHPASSTKVDKKIEPRGPTIKPCPPCKC

PAPNLLGGPSVFIFPPKIKDVLMISLSPIVTCVVVDVSEDDPDVQISWFVNNVEVH

TAQTQTHREDYNSTLRVVSALPIQHQDWMSGKEFKCKVNNKDLPAPIERTISKPK

GSVRAPQVYVLPPPEEEMTKKQVTLTCMVTDFMPEDIYVEWTNNGKTELNYKN

TEPVLDSDGSYFMYSKLRVEKKNWVERNSYSCSVVHEGLHNHHTTKSFSRTPGK

Ipilimumab-VH-Human IgG1 constant HC (SEQ ID NO: 353)

QVQLVESGGGVVQPGRSLRLSCAASGFTFSSYTIVIHWVRQAPGKGLEWVTFISYD

GNNKYYADSVKGRFTISRDNSKNTLYLQMNSLRAEDTAIYYCARTGWLGPFDY

WGQGTLVTVSSASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKVDKRVEP

-continued

KSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNH

YTQKSLSLSPG

Ipilimumab-VH-Mouse IgG1 constant HC
(SEQ ID NO: 354)

QVQLVESGGGVVQPGRSLRLSCAASGFTFSSYTIVIHWVRQAPGKGLEWVTFISYD

GNNKYYADSVKGRFTISRDNSKNTLYLQMNSLRAEDTAIYYCARTGWLGPFDY

WGQGTLVTVSSASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKVDKKVE

PKSCDKTHTCPPCPAPELLGGPSVFLFPPKPKDTLMISRTPEVTCVVVDVSHEDPE

VKFNWYVDGVEVHNAKTKPREEQYASTYRVVSVLTVLHQDWLNGKEYKCKVS

NKALPAPIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHEALH

NHYTQKSLSLSPG

Ipilimumab-VH-Mouse IgG2a constant HC
(SEQ ID NO: 355)

QVQLVESGGGVVQPGRSLRLSCAASGFTFSSYTIVIHWVRQAPGKGLEWVTFISYD

GNNKYYADSVKGRFTISRDNSKNTLYLQMNSLRAEDTAIYYCARTGWLGPFDY

WGQGTLVTVSSAKTTAPSVYPLAPVCGDTTGSSVTLGCLVKGYFPEPVTLTWNS

GSLSSGVHTFPAVLQSDLYTLSSSVTVTSSTWPSQSITCNVAHPASSTKVDKKIEP

RGPTIKPCPPCKCPAPNLLGGPSVFIFPPKIKDVLMISLSPIVTCVVVDVSEDDPDV

QISWFVNNVEVHTAQTQTHREDYNSTLRVVSALPIQHQDWMSGKEFKCKVNNK

DLPAPIERTISKPKGSVRAPQVYVLPPPEEEMTKKQVTLTCMVTDFMPEDIYVEW

TNNGKTELNYKNTEPVLDSDGSYFMYSKLRVEKKNWVERNSYSCSVVHEGLHN

HEITTKSFSRTPGK

In some embodiments, the antibody comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence comprises 1, 2, 3, 4 or more amino acid sequence differences compared with the CDR sequences shown in Table 2, including conservative amino acid differences.

In some embodiments, the activatable anti-CTLA-4 antibody comprises a heavy chain variable domain that is at least 90%, 91%, 92%, 93%, 94%, 95%, 96%, 97%, 98%, 99% or more identical to the group consisting of SEQ ID NO: 345. In some embodiments, the activatable anti-CTLA-4 antibody comprises a light chain variable domain, not including any MM, CM, linker, spacer or other sequence added in creation of the activatable form of the antibody, that is at least 90%, 91%, 92%, 93%, 94%, 95%, 96%, 97%, 98%, 99% or more identical to the group consisting of SEQ ID NOs: 563 to 565.

In some embodiments, the antibody or antigen-binding fragment thereof that binds CTLA-4 in the activatable antibodies can include modifications, particularly in the Fc region of the antibody or antigen-binding fragment thereof. For example, the interaction of antibodies with FcγRs can be enhanced by modifying the glycan moiety attached to each Fc fragment at the N297 residue. In particular, the absence of core fucose residues strongly enhances ADCC via improved binding of IgG to activating FcγRIIIA without altering antigen binding or CDC. Natsume et al. (2009) *Drug Des. Devel. Ther.* 3:7. There is convincing evidence that afucosylated tumor-specific antibodies translate into enhanced therapeutic activity in mouse models in vivo. Nimmerjahn & Ravetch (2005) *Science* 310:1510; Mossner et al. (2010) *Blood* 115:4393.

Modification of antibody glycosylation can be accomplished by, for example, expressing the antibody in a host cell with altered glycosylation machinery. Cells with altered glycosylation machinery have been described in the art and can be used as host cells in which to express recombinant antibodies of this disclosure to thereby produce an antibody with altered glycosylation. For example, the cell lines Ms704, Ms705, and Ms709 lack the fucosyltransferase gene, FUT8 (α-(1,6) fucosyltransferase) (see U.S. Pat. App. Publication No. 20040110704; Yamane-Ohnuki et al. (2004) *Biotechnol. Bioeng.* 87: 614), such that antibodies expressed in these cell lines lack fucose on their carbohydrates. As another example, EP 1176195 also describes a cell line with a functionally disrupted FUT8 gene as well as cell lines that have little or no activity for adding fucose to the N-acetylglucosamine that binds to the Fc region of the antibody, for example, the rat myeloma cell line YB2/0 (ATCC CRL 1662). PCT Publication WO 03/035835 describes a variant CHO cell line, Lec13, with reduced ability to attach fucose to Asn (297)-linked carbohydrates, also resulting in hypofucosylation of antibodies expressed in that host cell. See also Shields et al. (2002) *J. Biol. Chem.* 277:26733. Antibodies with a modified glycosylation profile can also be produced in chicken eggs, as described in PCT Publication No. WO 2006/089231. Alternatively, antibodies with a modified glycosylation profile can be produced in plant cells, such as Lemna. See e.g. U.S. Publication No. 2012/0276086. PCT Publication No. WO 99/54342 describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies. See also Umaña et al. (1999) *Nat. Biotech.* 17:176. Alternatively, the fucose residues of the antibody may be cleaved off using a fucosidase enzyme. For example, the enzyme alpha-L-fucosidase removes fucosyl residues from antibodies. Tarentino et al. (1975) *Biochem.* 14:5516. Core fucosylation may also be reduced by culturing antibody-producing cells in the presence of small molecule fucose analogs, such as those described at EP2282773B1, or in the presence of castanospermine, as described at WO 08/052030.

Cleavable Moiety

In some embodiments, the CM is specific for a protease, which is useful in leveraging the dysregulated protease activity in tumor cells for targeted activatable antibody activation at the site of treatment and/or diagnosis. Numerous studies have demonstrated the correlation of aberrant protease levels, e.g., uPA, legumain, MT-SP1, matrix metalloproteases (MMPs), in solid tumors. (See e.g., Murthy R V, et al. "Legumain expression in relation to clinicopathologic and biological variables in colorectal cancer." *Clin Cancer Res.* 11 (2005): 2293-2299; Nielsen B S, et al. "Urokinase plasminogen activator is localized in stromal cells in ductal breast cancer." *Lab Invest* 81 (2001): 1485-1501; Look O R, et al. "In situ localization of gelatinolytic activity in the extracellular matrix of metastases of colon cancer in rat liver using quenched fluorogenic DQ-gelatin." *J Histochem Cytochem.* 51 (2003): 821-829).

A general overview of this process is discussed in U.S. Pat. Nos. 7,666,817, 8,513,390, and 9,120,853 and International Publication Nos. WO 2016/118629 and WO 2016/149201, which are hereby incorporated by reference in their entireties. The cleavable moiety selection process is used to identify cleavable moieties that have a number of desirable characteristics. For example, the selected cleavable moieties are systemically stable (i.e., stable in the systemic circulation of a subject), are generally not susceptible to cleavage by circulating proteases such as plasmin, thrombin, tissue plasminogen activator (tPA) or a kallikrein (KLK) such as KLK-5 and/or KLK-7, are non-toxic, are generally not susceptible to cleavage at potential sites of toxicity such as the skin by proteases such as ADAM 9, ADAM 10, ADAM 17 and/or kallikreins, such as KLK-5 and KLK-7, and are active at an intended site of treatment and/or diagnosis. In some embodiments, the identified cleavable moieties are selected for proteases that are overexpressed at an intended site of therapy and/or diagnosis but are not typically expressed at or in normal, healthy or otherwise non-diseased or non-damaged tissue, and then the selected substrates are subsequently counter-screened against proteases expressed in normal, e.g., non-diseased, tissue. Exemplary proteases and/or enzymes are provided in Table 1 as indicated earlier.

In some embodiments, the cleavable moiety is selected from the group consisting of 2001 and 3001, and derivatives thereof. In some embodiments, the cleavable moiety is selected from the group consisting of 2001 (SEQ ID NO: 297), 2006 (SEQ ID NO: 300), 2007 (SEQ ID NO: 301), 2008 (SEQ ID NO: 302), 2009 (SEQ ID NO: 303), 2012 (SEQ ID NO: 305), 2011 (SEQ ID NO: 304), 2003 (SEQ ID NO: 298), 3001 (SEQ ID NO: 306), 3006 (SEQ ID NO: 307), 3007 (SEQ ID NO: 308), 3008 (SEQ ID NO: 309), 3009 (SEQ ID NO: 310), 3012 (SEQ ID NO: 312), 3011 (SEQ ID NO: 311), and 2005 (SEQ ID NO: 299). Table 3 provides additional cleavable moieties that may be used with the activatable anti-CTLA-4 antibodies disclosed herein.

TABLE 3

Anti-CTLA-4 Activatable Cleavable Moieties

| SEQUENCE IDENTIFIER | CM Sequence |
|---|---|
| 313 | LSGRSDNH |
| 314 | LSGRSANPRG |
| 315 | TGRGPSWV |
| 316 | PLTGRSGG |
| 317 | TARGPSFK |
| 318 | NTLSGRSENHSG |
| 319 | NTLSGRSGNHGS |
| 320 | TSTSGRSANPRG |
| 321 | TSGRSANP |
| 322 | VHMPLGFLGP |
| 306 | AVGLLAPPGGLSGRSDNH |
| 307 | AVGLLAPPGGLSGRSDDH |
| 308 | AVGLLAPPGGLSGRSDIH |
| 309 | AVGLLAPPGGLSGRSDQH |
| 310 | AVGLLAPPGGLSGRSDTH |
| 338 | AVGLLAPPGGLSGRSDYH |
| 339 | AVGLLAPPGGLSGRSANI |
| 340 | AVGLLAPPGGLSGRSDNI |
| 312 | AVGLLAPPGGLSGRSANP |
| 311 | AVGLLAPPGGLSGRSDNP |
| 299 | AVGLLAPPSGRSANPRG |
| 323 | AVGLLAPP |
| 324 | AQNLLGMV |
| 325 | QNQALRMA |
| 326 | LAAPLGLL |
| 327 | STFPFGMF |
| 328 | ISSGLLSS |

TABLE 3-continued

Anti-CTLA-4 Activatable Cleavable Moieties

| SEQUENCE IDENTIFIER | CM Sequence |
|---|---|
| 329 | PAGLWLDP |
| 330 | VAGRSMRP |
| 331 | VVPEGRRS |
| 332 | ILPRSPAF |
| 333 | MVLGRSLL |
| 334 | VAGRSMRP |
| 335 | QGRAITFI |
| 336 | SPRSIMLA |
| 337 | SMLRSMPL |
| 297 | ISSGLLSGRSDNH |
| 300 | ISSGLLSGRSDDH |
| 301 | ISSGLLSGRSDIH |
| 302 | ISSGLLSGRSDQH |
| 303 | ISSGLLSGRSDTH |
| 341 | ISSGLLSGRSDYH |
| 342 | ISSGLLSGRSANI |
| 343 | ISSGLLSGRSDNI |
| 305 | ISSGLLSGRSANP |
| 304 | ISSGLLSGRSDNP |
| 298 | ISSGLLSGRSANPRG |

Masking Moiety

The activatable anti-CTLA-4 antibodies provided herein comprise a masking moiety (MM). In some embodiments, the MM is an amino acid sequence that is coupled, or otherwise attached, to the anti-CTLA-4 antibody and is positioned within the activatable anti-CTLA-4 antibody construct such that the MM reduces the ability of the anti-CTLA-4 antibody to specifically bind CTLA-4. In some embodiments, the MM binds specifically to the antigen binding domain. Suitable MMs are identified using any of a variety of known techniques. For example, peptide MMs are identified using the methods described in U.S. Patent Application Publication Nos. 2009/0062142 by Daugherty et al. and 2012/0244154 by Daugherty et al., the contents of which are hereby incorporated by reference in their entirety.

In some embodiments, the MM is selected from the group consisting of YV01 to YV58 and YV60 to YV66 and comprises an amino acid sequence selected from Table 4 below.

TABLE 4

Anti-CTLA4 Masking Moieties (MM)

| SEQUENCE IDENTIFIER | MM SEQUENCE |
|---|---|
| 1 | DFSCLHSMYNVCLDP |
| 2 | QPCAQMYGYSMCPHT |

TABLE 4-continued

Anti-CTLA4 Masking Moieties (MM)

| SEQUENCE IDENTIFIER | MM SEQUENCE |
|---|---|
| 3 | LHCRTQMYGYNLCPY |
| 4 | LHCRTQLYGYNLCPY |
| 5 | CTYSFFNVC |
| 6 | CAQMYGYSMC |
| 7 | CPNHPMC |
| 8 | GTACTYSFFNVCLDP |
| 9 | FGTACPNHPMCHDWQ |
| 10 | SACAYWMFGVNLCPY |
| 11 | CRTQLYGYNLC |
| 12 | CRTQIYGYNLC |
| 13 | LHCRTQIYGYNLCPY |
| 14 | CPNHPMCHDWQ |
| 15 | GTACPNHPMCHDWQ |
| 16 | CAYWMFGVNLCPY |
| 17 | QECHLYMYGVNLCPY |
| 18 | CHLYMYGVNLCPY |
| 19 | GQCQFYMFGYNLCPY |
| 20 | LSTCMYSFFNVCLDP |
| 21 | CLHSMYNVCLDP |
| 22 | CLHSMYNVC |
| 23 | CLHSLYNVCLDP |
| 24 | CLHSAYNVCLDP |
| 25 | CMYSFFNVCLDP |
| 26 | CMYSFFNVC |
| 27 | QPCAQMYGYSMC |
| 28 | CAQLYGYSMCPHT |
| 29 | CAQMYGYSMCAHT |
| 30 | CAQMYGYSMCPAT |
| 31 | CAQMYGYSMCPHT |
| 32 | CPNHPLCHDWQ |
| 33 | CPNHPMCADWQ |
| 34 | CPNHPMCHAWQ |
| 35 | CPNHPMCHDAQ |
| 36 | CPNHPMCHDWA |
| 37 | GTACPNHPMC |
| 38 | LHCRTQLYGYNLC |
| 39 | CRTQLYGYNLCPY |

TABLE 4-continued

| Anti-CTLA4 Masking Moieties (MM) | |
|---|---|
| SEQUENCE IDENTIFIER | MM SEQUENCE |
| 40 | CRTQLYGYNLCAY |
| 41 | CRTQLYGYNLCPA |
| 42 | FGTACPNHPLCHDWQ |
| 43 | CPNHPLCHDFQ |
| 44 | CPNHPLCHDYQ |
| 45 | CPNHPLCPY |
| 46 | CPNHPLCPA |
| 47 | CMYSFFNVCYP |
| 48 | CMYSFFNVCYA |
| 49 | CLYSFFNVCYP |
| 50 | CLYSFFNVCYA |
| 51 | FGAACPNHPICHDWQ |
| 52 | FGAACPNHPLCHDWQ |
| 53 | FGAACPNHPMCHDAQ |
| 54 | CLHSAYNACLDP |
| 55 | CAHSAYNVCLDP |
| 56 | CLHSAYNVCADP |
| 57 | CLHSAYNVCLAP |
| 58 | CLHSAYNVCLDA |
| 59 | KNTCTYVMYNVCLDP |
| 60 | YISDCPYHPMCHDYQ |
| 61 | FRNTCPYHPMCHDYR |
| 62 | RECHMWMFGVNLCPY |
| 63 | AVCHMYMYGYNLCPF |
| 64 | RSCPQMYGYSMCPHT |
| 65 | QPCAQMFGYSMCPHT |
| 66 | TAKCTYSFFNVCLDP |
| 67 | DFSCLYSMYNVCLDP |
| 68 | DVSCMYMMYNFCLDP |
| 69 | CPNHPMC |
| 70 | CMYSFFNVCPY |
| 71 | CMYSFFNVCPA |
| 72 | CTYSFFNVCPY |
| 73 | CTYSFFNVCPA |
| 74 | GFPCMYSMFNVCLDP |
| 75 | GLSCMYSMYGYCLDP |
| 76 | IPCDYWMFGVNLCPY |

TABLE 4-continued

| Anti-CTLA4 Masking Moieties (MM) | |
|---|---|
| SEQUENCE IDENTIFIER | MM SEQUENCE |
| 77 | QVCHAYMYGYNLCPY |
| 78 | RMYCTYSFYNVCLDP |
| 79 | ALSCMYIMYNVCLDP |
| 80 | DFSCMYVMFNVCLDP |
| 81 | DFSCVYSMFNVCLDP |
| 82 | DMNTCPNHPMCYDYR |
| 83 | DMNTCPRHPMCHDYH |
| 84 | DSRCMYVMYNVCLDP |
| 85 | EHLCTYSFYNVCLDP |
| 86 | ELSCVYSMFGFCLDP |
| 87 | FTNNCPYHPMCHDYL |
| 88 | GFSCTYIMYDVCLDP |
| 89 | GSSCMYSMYNVCLDP |
| 90 | HFSCMYIMYNVCLDP |
| 91 | LHCGMWMFGVNLCPK |
| 92 | LPCQMWMFGHNLCPH |
| 93 | LPCTMYMYGYNLCPY |
| 94 | LTCHHWMFGVNLCPY |
| 95 | NFSCMYSMFNVCLDP |
| 96 | NNHCMYSFFNICLDP |
| 97 | NRSCMYIMYNVCLDP |
| 98 | NSCTMFMFGVNLCPY |
| 99 | NTCELYMFGVNLCPY |
| 100 | QHCDMWMFGYNLCPY |
| 101 | QHCPMYMFGYNLCPF |
| 102 | QVCHIQMYGFDLCPH |
| 103 | RACDYWMYGVNLCPY |
| 104 | RQCHMQMFGYDLCPF |
| 105 | SGSCLYSFYNVCLDP |
| 106 | SNGCTYSFFNVCLDP |
| 107 | STCAQMYGYSMCPH |
| 108 | SYKCLYSFYNVCLDP |
| 109 | VLYCTYVMYNVCLDP |
| 110 | VNCGMWMFGYNLCPK |
| 111 | YGSCLYSFYNICLDP |
| 112 | YPCAQMYGYSMCPHT |
| 113 | AACDLWMFGVNLCPY |
| 114 | AFCTLAPYNQACIAN |

TABLE 4-continued

| Anti-CTLA4 Masking Moieties (MM) | |
|---|---|
| SEQUENCE IDENTIFIER | MM SEQUENCE |
| 115 | AGSCLYSMYNVCLDP |
| 116 | ALCENTMYGYHLCPW |
| 117 | ALSCMYIMYGVCLDP |
| 118 | APVCDVLMFGFCMQP |
| 119 | AQVCSIMMYGTCLMP |
| 120 | ASTCMYSFYNVCLDP |
| 121 | AVCEFWMFGFNLCPY |
| 122 | DANTCPNHPMCYDYH |
| 123 | DFSCIYIMFDVCLDP |
| 124 | DFSCMYVMYGFCLDP |
| 125 | DFTCMYSMYNVCLDP |
| 126 | DFTCTYSMYNVCLDP |
| 127 | DHYCTYIMYSICLDP |
| 128 | DICTNFMFGVNLCPY |
| 129 | DINTCPYHPMCHDYH |
| 130 | DKNTCPLHPMCHDYR |
| 131 | DMNMCPNHPMCHDWH |
| 132 | DMNSCPNHPMCHDYH |
| 133 | DMNSCPNHPMCYDYR |
| 134 | DMNTCPNHPMCFDYR |
| 135 | DMNTCPNHPMCHDFQ |
| 136 | DMNTCPNHPMCHDYR |
| 137 | DMNTCPNHPMCYDYH |
| 138 | DMNTCPNHPMCYDYK |
| 139 | DMSTCPNHPMCHDYM |
| 140 | DRNMCPYHPMCYDYR |
| 141 | DSCAFMMFGVNLCPY |
| 142 | DSCRSVFDMVWNCWN |
| 143 | DTPNCPHHPMCHNHM |
| 144 | DVSCLYVMYSVCLDP |
| 145 | DWCASMMFGYNLCPY |
| 146 | EFSCMYSMFNVCLDP |
| 147 | EHCDVWMFGFNLCPY |
| 148 | EPCDYWMFGVNLCPY |
| 149 | EQCTMWMYGFNLCPY |
| 150 | ESACSLRMYEVCLQP |
| 151 | ESCASMYGYSMCPRT |

TABLE 4-continued

| Anti-CTLA4 Masking Moieties (MM) | |
|---|---|
| SEQUENCE IDENTIFIER | MM SEQUENCE |
| 152 | ESCSYWMFGYNLCPY |
| 153 | FSNTCPHHPMCYDYR |
| 154 | FWNTCPHHPMCHDYK |
| 155 | FYQNCYPPTWCSMFS |
| 156 | GECSYWMFGYNLCPY |
| 157 | GGSCMYSFFNICLDP |
| 158 | GGSCVYVMYNVCLDP |
| 159 | GHCLMHMYGYNLCPK |
| 160 | GHCRMSMYEMTLCPR |
| 161 | GISCVHIMFNFCLDP |
| 162 | GLCVMYMFGVNLCPY |
| 163 | GSCDYWMFGYNLCPY |
| 164 | GSYCMYVMYNVCLDP |
| 165 | GTKCIYSFYNVCLDP |
| 166 | GTSTCPYHPMCHDYR |
| 167 | GTTCTYSFFNVCLDP |
| 168 | GVCHFFMYGVSMCPA |
| 169 | GVPCWYSMYNVCLDP |
| 170 | GVSCMYSMFNICLDP |
| 171 | HAKCVYSFFNVCLDP |
| 172 | HDSCMYSMYNFCLDP |
| 173 | HGNTCPNHPMCHDYQ |
| 174 | HKGCLYSFYNICLDP |
| 175 | HKGCLYSFYNVCLDP |
| 176 | HLSCMYIMYNVCLDP |
| 177 | HSSCIYSMFNVCLDP |
| 178 | HTNMCPYHPMCYDYK |
| 179 | HTPCTYSFFNVCLDP |
| 180 | IMNTCPYHPMCHDYQ |
| 181 | IVPCTYMMFGVCLQP |
| 182 | KKCDYWFYGVNLCPY |
| 183 | KNTCVYSFFNVCLDP |
| 184 | KPCAQMYGYSMCPHP |
| 185 | KPSCMYSFFNVCLDP |
| 186 | KRPCMYSFYNVCLDP |
| 187 | KTSCMYSFYNICLDP |
| 188 | KTTCTYSFFNVCLDP |
| 189 | LDCQMYWWFGACGDM |

TABLE 4-continued

Anti-CTLA4 Masking Moieties (MM)

| SEQUENCE IDENTIFIER | MM SEQUENCE |
|---|---|
| 190 | LHCAIYMYGYNLCPF |
| 191 | LHCPFQMYGYNLCPH |
| 192 | LHCSMYMYGFNLCPN |
| 193 | RECMAYMYGYNLCPY |
| 194 | RHCQMHMFGYDLCPY |
| 195 | LIHCRYVMYGMCLEP |
| 196 | LLPCEVMGPSRCKHD |
| 197 | LPCHAYMYGYSLCPY |
| 198 | LPCLAYMYGVNLCPN |
| 199 | LPCMAYMFGFNLCPH |
| 200 | LPCNFHMFGFNLCPY |
| 201 | LQCAMYMYGYNLCPY |
| 202 | LSSCTYSFFNVCLDP |
| 203 | LTCPFQMYGYNLCPY |
| 204 | LTSQCSPWYWCQIYD |
| 205 | LYCPYMMYGYNLCPY |
| 206 | LYHCTYSFYNVCLDP |
| 207 | LYRCIYSFYNVCLDP |
| 208 | MGCSMRMWGMELCPE |
| 209 | MKCDYWLYGYNLCPY |
| 210 | MNHCTLHMYNICMDP |
| 211 | MNPECPHHPMCHNSN |
| 212 | MPACTYSFFNICLDP |
| 213 | MPQCHVIMYNLCLDP |
| 214 | MSTCTYSFFNVCLDP |
| 215 | MTCNYWFYGVNLCPY |
| 216 | MYCHQSMFGFRMCPD |
| 217 | NACAQMYGYSMCPHT |
| 218 | NDCDISMFDQSLCPY |
| 219 | NFSCVYVMFNVCLDP |
| 220 | NFTCALTMYEVCLDP |
| 221 | NLCHAFMFGFNLCPY |
| 222 | NLNNCPHHPMCHDYQ |
| 223 | NPPCMYSFFNICLDP |
| 224 | NSACTYSFFNVCLDP |
| 225 | NVCTVSMFGVMLCPS |
| 226 | PACATLMYSVPLCPA |

TABLE 4-continued

Anti-CTLA4 Masking Moieties (MM)

| SEQUENCE IDENTIFIER | MM SEQUENCE |
|---|---|
| 227 | PAPCMYSFYNVCLDP |
| 228 | PLCAEMYGYSMCPHN |
| 229 | PQCHLYMYGYNLCPY |
| 230 | PRPCMYSFYNVCLDP |
| 231 | QHCPFQMYGYNLCPY |
| 232 | QHCQMHMFGYNLCPY |
| 233 | QHSCMYSFFNVCLDP |
| 234 | QKCHSYLYGVNLCPY |
| 235 | QKCNMFMFGYNLCPY |
| 236 | QMNDCPNHPMCHDYH |
| 237 | QPCAQMYGYSMCPAT |
| 238 | QPCAQMYGYSMCPRT |
| 239 | RECHFFFYGVNLCPY |
| 240 | LNCGMFMYGYNLCPY |
| 241 | RLCTSYMFGYNLCPQ |
| 242 | RLSCMYSMFNVCLDP |
| 243 | RNCPFVMFGVNLCPY |
| 244 | RNGCMYSFFNVCLDP |
| 245 | RNGCVYSFFNVCLDP |
| 246 | RPCHLYMFGYNLCPD |
| 247 | RPCHSYMYGINLCPY |
| 248 | RSCDMIMFGFNLCPY |
| 249 | RSCPMWFYGVNLCPY |
| 250 | RSTVCFYDFCGPWER |
| 251 | RTCHFYMYGVNLCPY |
| 252 | RTCSMVMFGVNLCPY |
| 253 | SGKCTYSFFNVCLDP |
| 254 | SIVCDLYWEATCLRP |
| 255 | SLSCTYSFFNICLDP |
| 256 | SMNTCPYHPMCFDYK |
| 257 | SQCWMWMYGYNLCPK |
| 258 | SSSCMYSFFNVCLDP |
| 259 | STACTYSFYNVCLDP |
| 260 | STCAQMYGYSMCPHT |
| 261 | STRCVYSFYNVCLDP |
| 262 | TACGAWMFGVNLCPY |
| 263 | TGACMYSFYNVCLDP |
| 264 | TLSCMYSMYNVCLDP |

TABLE 4-continued

| Anti-CTLA4 Masking Moieties (MM) | |
|---|---|
| SEQUENCE IDENTIFIER | MM SEQUENCE |
| 265 | TSCTVTMYQISMCPY |
| 266 | VGGCRHSFYNVCLDP |
| 267 | VHCQMYMYGYNLCPY |
| 268 | VHNCMYSFFNVCLDP |
| 269 | VMCKLHMYGIPVCPK |
| 270 | VNFCNYSMYGICLLP |
| 271 | VNFCYACYCMSCVFS |
| 272 | VNQCTYSFFNVCLDP |
| 273 | VPCPFHMFGYNLCPY |
| 274 | VRCQMWMYGFNLCPH |
| 275 | VRPCTYSFFNVCLDP |
| 276 | VSGCTYSFFNICLDP |
| 277 | YCSSWDTMTIPACNN |
| 278 | YDCDLSMFGIEMCPQ |
| 279 | YGNTCPFHPMCHDYK |
| 280 | YGYCMYSFFNVCLDP |
| 281 | YHCTMHMFGYNLCPF |
| 282 | YMNTCPNHPMCFDYQ |
| 283 | YMNTCPYHPMCHDYL |
| 284 | YMNTCPYHPMCHDYR |
| 285 | YNNCTYSFFNVCLDP |
| 286 | YPGCQYSFFNVCLDP |
| 287 | YRSCTHIMYNVCLDP |
| 288 | YSFCDMLMYDVCLVP |
| 289 | YSIDCGLSWWCGGMT |
| 290 | YSTTCPYHPMCHDYH |
| 291 | YVNTCPHHPMCHDYH |
| 292 | YVNTCPYHPMCHDYN |

In some embodiments, the $K_d$ of the activatable anti-CTLA-4 antibody, comprising a MM disclosed herein, towards the target is at least 2, 3, 4, 5, 10, 25, 50, 100, 250, 500, 1,000 times greater than, or between 5-10, 10-100, 10-200, 10-500, 10-1,000 times greater than the $K_d$ of the AB not modified with a MM or of the parental AB towards the target.

In some embodiments, the MM is not a natural binding partner of the activatable antibody. In some embodiments, the MM contains no or substantially no homology to any natural binding partner of the activatable antibody. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the activatable antibody. In some embodiments, the MM is no more than 50%, 25%, 20%, or 10% identical to any natural binding partner of the activatable antibody. In some embodiments, the MM is no more than 5%, 10%, 15%, 20%, 25%, 30%, 35%, 40%, 45%, 50%, 55%, 60%, 65%, 70%, 75%, or 80% identical to human CTLA-4. In some embodiments, the MM is no more than 50%, 25%, 20%, or 10% identical to human CTLA-4.

Exemplary Activatable Anti-CTLA-4 Antibodies

Particular antibodies described herein are activatable anti-CTLA-4 antibodies comprising any combination of the masking moieties, cleavable moieties, light chain variable domains (VL) (or the corresponding CDRs), and heavy chain variable domains (VH) (or the corresponding CDRs) provided in Tables 2-6. In some embodiments, the activatable anti-CTLA-4 antibody comprises a light chain comprising YV01 (SEQ ID NO: 1) as the masking moiety, LSGRSDNH (SEQ ID NO: 313) as the cleavable moiety, and the light chain variable domain (VL) of ipilimumab (SEQ ID NO: 344). In some embodiments, the activatable anti-CTLA-4 antibody comprises a light chain comprising YV01 (SEQ ID NO: 1) as the masking moiety, ISSGLLSGRSDNH (2001) (SEQ ID NO: 297) as the cleavable moiety, and the CDRs of the light chain variable domain (VL) of ipilimumab (SEQ ID NOs: 560, 561, and 562, respectively). In some embodiments, the activatable anti-CTLA-4 antibody comprises the heavy chain variable domain (VH) of ipilimumab (SEQ ID NO: 345) or just the corresponding CDRs (SEQ ID NOs: 557, 558, and 559).

In some embodiments, the activatable anti-CTLA-4 comprises YV39 (SEQ ID NO: 39) as the masking moiety, and ISSGLLSGRSDNP ("2011") (SEQ ID NO: 304) as the cleavable moiety, and the heavy and light chain variable domains of ipilimumab ((SEQ ID NOs: 345 and 344, respectively), wherein the MM and CM are linked to the VL in the arrangement MM-CM-VL.

In some embodiments, the activatable anti-CTLA-4 antibody includes a signal peptide. The signal peptide can be linked to the activatable anti-CTLA-4 antibody by a spacer. In some embodiments, the spacer is conjugated to the activatable antibody in the absence of a signal peptide. In some embodiments, the spacer is joined directly to the MM of the activatable antibody. In some embodiments, the spacer has amino acid sequence QGQSGS (SEQ ID NO: 546). In some embodiments, an activatable antibody comprises a spacer of sequence QGQSGS (SEQ ID NO: 546) joined directly to a MM sequence CRTQLYGYNLCPY (YV39) (SEQ ID NO: 39) in the structural arrangement from N-terminus to C-terminus of "spacer-MM-CM-VL" or "spacer-MM-CM-AB."

In some embodiments, the activatable anti-CTLA-4 antibody comprises a linker peptide (LP) between the MM and the CM. In some embodiments, the activatable anti-CTLA-4 antibody comprises a linker peptide between the CM and the antibody or antigen binding domain thereof (AB). In some embodiments, the activatable anti-CTLA-4 antibody comprises a first linker peptide (LP1) and a second linker peptide (LP2), and wherein the activatable anti-CTLA-4 antibody has the structural arrangement from N-terminus to C-terminus as follows: MM-LP1-CM-LP2-AB. In some embodiments, the light chain of the activatable anti-CTLA-4 antibody has the structural arrangement from N-terminus to C-terminus as follows: MM-LP1-CM-LP2-VL. In some embodiments, the two linker peptides need not be identical to each other. Examples of linker peptides that may be used with the activatable anti-CTLA-4 antibodies as disclosed herein are provided in U.S. Patent Publication No. 2016/0193332 and International Publication No. WO 2016/149201, ibid.

The disclosure also comprises a modified anti-CTLA-4 antibody that comprises a MM that is joined to the light chain of the antibody via a non-protease cleavable linker. In some embodiments, the non-protease cleavable linker comprises the amino acid sequence set forth in SEQ ID NO: 570. In some embodiments, such a modified anti-CTLA-4 antibody has a light chain comprising YV39 and a non-protease cleavable linker. In some embodiments, the light chain of the modified anti-CTLA-4 antibody comprises the amino acid sequence:

(SEQ ID NO: 530)
QGQSGSCRTQLYGYNLCPYGGGSSGGSGGSGGSGGGSGGGSGGSEIVLT
QSPGTLSLSPGERATLSCRASQSVGSSYLAWYQQKPGQAPRLLIYGAFSR
ATGIPDRFSGSGSGTDFTLTISRLEPEDFAVYYCQQYGSSPWTFGQGTKV
EIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLS
SPVTKSFNRGEC
or (SEQ ID NO: 531)
CRTQLYGYNLCPYGGGSSGGSGGSGGSGGGSGGGSGGSEIVLTQSPGTL
SLSPGERATLSCRASQSVGSSYLAWYQQKPGQAPRLLIYGAFSRATGIPD
RFSGSGSGTDFTLTISRLEPEDFAVYYCQQYGSSPWTFGQGTKVEIKRTV
AAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSF
NRGEC.

Linkers suitable for use in compositions described herein are generally ones that provide flexibility of the activatable anti-CTLA-4 antibody to facilitate the inhibition of the binding of the activatable antibody to the target. Such linkers are generally referred to as flexible linkers (also referred to as linker peptides herein). Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, or 20 amino acids in length.

Exemplary flexible linkers include glycine polymers (G)n, glycine-serine polymers (including, for example, (GS)n, (GSGGS)n (GSGGS is SEQ ID NO: 534) and (GGGS)n (GGGS is SEQ ID NO: 535), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible linkers include, but are not limited to Gly-Gly-Ser-Gly (SEQ ID NO: 536), Gly-Gly-Ser-Gly-Gly (SEQ ID NO: 537), Gly-Ser-Gly-Ser-Gly (SEQ ID NO: 538), Gly-Ser-Gly-Gly-Gly (SEQ ID NO: 539), Gly-Gly-Gly-Ser-Gly (SEQ ID NO: 540), Gly-Ser-Ser-Ser-Gly (SEQ ID NO: 541), and the like. The ordinarily skilled artisan will recognize that design of an activatable antibodies can include linkers that are all or partially flexible, such that the linker can include a flexible linker as well as one or more portions that confer less flexible structure to provide for a desired activatable antibodies structure.

In some embodiments, the activatable anti-CTLA-4 antibodies comprise the VL and VH (or the corresponding CDRs) of ipilimumab and a combination of MMs and CMs provided in Table 5 below, such that any MM in column 2 can be combined with any CM in column 4.

TABLE 5

Activatable anti-CTLA-4 Antibody Combinations

| SEQ ID NO. | Masking Moiety (MM) | SEQ ID NO. | Cleavable Moiety (CM) |
|---|---|---|---|
| 1 | (YV01) DFSCLHSMYNVCLDP | 313 | LSGRSDNH |
| 2 | (YV02) QPCAQMYGYSMCPHT | 314 | LSGRSANPRG |
| 3 | (YV03) LHCRTQMYGYNLCPY | 315 | TGRGPSWV |
| 4 | (YV04) LHCRTQLYGYNLCPY | 316 | PLTGRSGG |
| 5 | (YV05) CTYSFFNVC | 317 | TARGPSFK |
| 6 | (YV06) CAQMYGYSMC | 318 | NTLSGRSENHSG |
| 7 | (YV07) CPNHPMC | 319 | NTLSGRSGNHGS |
| 8 | (YV8) GTACTYSFFNVCLDP | 320 | TSTSGRSANPRG |
| 9 | (YV09) FGTACPNHPMCHDWQ | 321 | TSGRSANP |
| 10 | (YV10) SACAYWMFGVNLCPY | 322 | VHMPLGFLGP |
| 11 | (YV11) CRTQLYGYNLC | 323 | AVGLLAPP |
| 12 | (YV12) CRTQIYGYNLC | 324 | AQNLLGMV |
| 13 | (YV13) LHCRTQIYGYNLCPY | 325 | QNQALRMA |
| 14 | (YV14) CPNHPMCHDWQ | 326 | LAAPLGLL |
| 15 | (YV15) GTACPNHPMCHDWQ | 327 | STFPFGMF |
| 16 | (YV16) CAYWMFGVNLCPY | 328 | ISSGLLSS |
| 17 | (YV17) QECHLYMYGVNLCPY | 329 | PAGLWLDP |
| 18 | (YV18) CHLYMYGVNLCPY | 330 | VAGRSMRP |
| 19 | (YV19) GQCQFYMFGYNLCPY | 331 | VVPEGRRS |
| 20 | (YV20) LSTCMYSFFNVCLDP | 332 | ILPRSPAF |
| 21 | (YV21) CLHSMYNVCLDP | 333 | MVLGRSLL |
| 22 | (YV22) CLHSMYNVC | 334 | VAGRSMRP |
| 23 | (YV23) CLHSLYNVCLDP | 335 | QGRAITFI |
| 24 | (YV24) CLHSAYNVCLDP | 336 | SPRSIMLA |
| 25 | (YV25) CMYSFFNVCLDP | 337 | SMLRSMPL |
| 26 | (YV26) CMYSFFNVC | 297 | ISSGLLSGRSDNH |
| 27 | (YV27) QPCAQMYGYSMC | 300 | ISSGLLSGRSDDH |
| 28 | (YV28) CAQLYGYSMCPHT | 301 | ISSGLLSGRSDIH |
| 29 | (YV29) CAQMYGYSMCAHT | 302 | ISSGLLSGRSDQH |

TABLE 5-continued

Activatable anti-CTLA-4 Antibody Combinations

| SEQ ID NO. | Masking Moiety (MM) | SEQ ID NO. | Cleavable Moiety (CM) |
|---|---|---|---|
| 30 | (YV30) CAQMYGYSMCPAT | 303 | ISSGLLSGRSDTH |
| 31 | (YV31) CAQMYGYSMCPHT | 341 | ISSGLLSGRSDYH |
| 32 | (YV32) CPNHPLCHDWQ | 342 | ISSGLLSGRSANI |
| 33 | (YV33) CPNHPMCADWQ | 343 | ISSGLLSGRSDNI |
| 34 | (YV34) CPNHPMCHAWQ | 305 | ISSGLLSGRSANP |
| 35 | (YV35) CPNHPMCHDAQ | 304 | ISSGLLSGRSDNP |
| 36 | (YV36) CPNHPMCHDWA | 298 | ISSGLLSGRSANPRG |
| 37 | (YV37) GTACPNHPMC | 306 | AVGLLAPPGGLSGRSDNH |
| 38 | (YV38) LHCRTQLYGYNLC | 307 | AVGLLAPPGGLSGRSDDH |
| 39 | (YV39) CRTQLYGYNLCPY | 308 | AVGLLAPPGGLSGRSDIH |
| 40 | (YV40) CRTQLYGYNLCAY | 309 | AVGLLAPPGGLSGRSDQH |
| 41 | (YV41) CRTQLYGYNLCPA | 310 | AVGLLAPPGGLSGRSDTH |
| 42 | (YV42) FGTACPNHPLCHDWQ | 338 | AVGLLAPPGGLSGRSDYH |
| 43 | (YV43) CPNHPLCHDFQ | 339 | AVGLLAPPGGLSGRSANI |
| 44 | (YV44) CPNHPLCHDYQ | 340 | AVGLLAPPGGLSGRSDNI |
| 45 | (YV45) CPNHPLCPY | 312 | AVGLLAPPGGLSGRSANP |
| 46 | (YV46) CPNHPLCPA | 311 | AVGLLAPPGGLSGRSDNP |
| 47 | (YV47) CMYSFFNVCYP | 299 | AVGLLAPSGRSANPRG |
| 48 | (YV48) CMYSFFNVCYA | | |
| 49 | (YV49) CLYSFFNVCYP | | |
| 50 | (YV50) CLYSFFNVCYA | | |
| 51 | (YV51) FGAACPNHPICHDWQ | | |
| 52 | (YV52) FGAACPNHPLCHDWQ | | |
| 53 | (YV53) FGAACPNHPMCHDAQ | | |
| 54 | (YV54) CLHSAYNACLDP | | |
| 55 | (YV55) CAHSAYNVCLDP | | |
| 56 | (YV56) CLHSAYNVCADP | | |
| 57 | (YV57) CLHSAYNVCLAP | | |
| 58 | (YV58) CLHSAYNVCLDA | | |
| 59 | (YV60) KNTCTYVMYNVCLDP | | |
| 60 | (YV61) YISDCPYHPMCHDYQ | | |
| 61 | (YV62) FRNTCPYHPMCHDYR | | |
| 62 | (YV63) RECHMWMFGVNLCPY | | |
| 63 | (YV64) AVCHMYMYGYNLCPF | | |
| 64 | (YV65) RSCPQMYGYSMCPHT | | |
| 65 | (YV66) QPCAQMFGYSMCPHT | | |

In some embodiments, the activatable anti-CTLA-4 antibodies comprise the specific combination of MMs and CMs provided in Table 6 below.

TABLE 6

Exemplary Activatable Anti-CTLA-4 Antibody Combination

| Comb. No. | Masking Moiety (MM) | Cleavable Moiety (CM) |
|---|---|---|
| 1 | CRTQLYGYNLCPY (SEQ ID NO: 39) | ISSGLLSGRSDNH (SEQ ID NO: 297) |
| 2 | CRTQLYGYNLCPY (SEQ ID NO: 39) | ISSGLLSGRSDNP (SEQ ID NO: 304) |
| 3 | CRTQLYGYNLCPY (SEQ ID NO: 39) | ISSGLLSGRSANP (SEQ ID NO: 305) |
| 4 | CRTQLYGYNLCPY (SEQ ID NO: 39) | ISSGLLSGRSDQH (SEQ ID NO: 302) |
| 5 | CRTQLYGYNLCPY (SEQ ID NO: 39) | ISSGLL SGRSDDH (SEQ ID NO: 300) |
| 6 | CRTQLYGYNLCPY (SEQ ID NO: 39) | ISSGLLSGRSDTH (SEQ ID NO: 303) |
| 7 | LHCRTQMYGYNLCPY (SEQ ID NO: 3) | ISSGLLSGRSDNH (SEQ ID NO: 297) |
| 8 | LHCRTQMYGYNLCPY (SEQ ID NO: 3) | AVGLLAPPGGLSGRSDNH (SEQ ID NO: 306) |
| 9 | LHCRTQMYGYNLCPY (SEQ ID NO: 3) | ISSGLLSGRSDDH (SEQ ID NO: 300) |
| 10 | LHCRTQMYGYNLCPY (SEQ ID NO: 3) | ISSGLLSGRSDIH (SEQ ID NO: 301) |
| 11 | LHCRTQMYGYNLCPY (SEQ ID NO: 3) | ISSGLLSGRSDQH (SEQ ID NO: 302) |
| 12 | LHCRTQMYGYNLCPY (SEQ ID NO: 3) | ISSGLLSGRSDTH (SEQ ID NO: 303) |
| 13 | CAQMYGYSMC (SEQ ID NO: 06) | ISSGLLSGRSDNH (SEQ ID NO: 297) |
| 14 | CAQMYGYSMC (SEQ ID NO: 06) | AVGLLAPPGGLSGRSDNH (SEQ ID NO: 306) |
| 15 | FGTACPNHPMCHDWQ (SEQ ID NO: 09) | ISSGLLSGRSDNH (SEQ ID NO: 297) |
| 16 | FGTACPNHPMCHDWQ (SEQ ID NO: 09) | AVGLLAPPGGLSGRSDNH (SEQ ID NO: 306) |
| 17 | CLHSLYNVCLDP (SEQ ID NO: 23) | ISSGLLSGRSDNH (SEQ ID NO: 297) |
| 18 | CLHSLYNVCLDP (SEQ ID NO: 23) | ISSGLLSGRSDDH (SEQ ID NO: 300) |
| 19 | CLHSLYNVCLDP (SEQ ID NO: 23) | ISSGLLSGRSDIH (SEQ ID NO: 301) |
| 20 | CLHSLYNVCLDP (SEQ ID NO: 23) | ISSGLLSGRSDQH (SEQ ID NO: 302) |
| 21 | CLHSLYNVCLDP (SEQ ID NO: 23) | ISSGLLSGRSDTH (SEQ ID NO: 303) |
| 22 | CLHSLYNVCLDP (SEQ ID NO: 23) | AVGLLAPPGGLSGRSDNH (SEQ ID NO: 306) |
| 23 | CLHSAYNVCLDP (SEQ ID NO: 24) | ISSGLLSGRSDNH (SEQ ID NO: 297) |

TABLE 6-continued

| Exemplary Activatable Anti-CTLA-4 Antibody Combination | | |
|---|---|---|
| Comb. No. | Masking Moiety (MM) | Cleavable Moiety (CM) |
| 24 | CLHSAYNVCLDP (SEQ ID NO: 24) | AVGLLAPPGGLSGRSDNH (SEQ ID NO: 306) |
| 25 | QPCAQMYGYSMC (SEQ ID NO: 27) | ISSGLLSGRSDNH (SEQ ID NO: 297) |
| 26 | QPCAQMYGYSMC (SEQ ID NO: 27) | AVGLLAPPGGLSGRSDNH (SEQ ID NO: 306) |
| 27 | CAQMYGYSMCAHT (SEQ ID NO: 29) | ISSGLLSGRSDNH (SEQ ID NO: 297) |
| 28 | CAQMYGYSMCAHT (SEQ ID NO: 29) | AVGLLAPPGGLSGRSDNH (SEQ ID NO: 306) |
| 29 | CPNHPLCHDWQ (SEQ ID NO: 32) | ISSGLLSGRSDNH (SEQ ID NO: 297) |
| 30 | CPNHPLCHDWQ (SEQ ID NO: 32) | AVGLLAPPGGLSGRSDNH (SEQ ID NO: 306) |
| 31 | CPNHPMCADWQ (SEQ ID NO: 33) | ISSGLLSGRSDNH (SEQ ID NO: 297) |
| 32 | CPNHPMCADWQ (SEQ ID NO: 33) | AVGLLAPPGGLSGRSDNH (SEQ ID NO: 306) |
| 33 | CPNHPMCHDAQ (SEQ ID NO: 35) | ISSGLLSGRSDNH (SEQ ID NO: 297) |
| 34 | CPNHPMCHDAQ (SEQ ID NO: 35) | AVGLLAPPGGLSGRSDNH (SEQ ID NO: 306) |
| 35 | CRT QLYGYNLCPY (SEQ ID NO: 39) | AVGLLAPPGGLSGRSDNH (SEQ ID NO: 306) |
| 36 | CRTQLYGYNLCPA (SEQ ID NO: 41) | ISSGLLSGRSDNH (SEQ ID NO: 297) |
| 37 | CRTQLYGYNLCPA (SEQ ID NO: 41) | AVGLLAPPGGLSGRSDNH (SEQ ID NO: 306) |
| 38 | FGAACPNHPICHDWQ (SEQ ID NO: 51) | ISSGLLSGRSDNH (SEQ ID NO: 297) |
| 39 | FGAACPNHPICHDWQ (SEQ ID NO: 51) | AVGLLAPPGGLSGRSDNH (SEQ ID NO: 306) |
| 40 | FGAACPNHPLCHDWQ (SEQ ID NO: 52) | ISSGLLSGRSDNH (SEQ ID NO: 297) |
| 41 | FGAACPNHPLCHDWQ (SEQ ID NO: 52) | AVGLLAPPGGLSGRSDNH (SEQ ID NO: 306) |
| 42 | FGAACPNHPMCHDAQ (SEQ ID NO: 53) | ISSGLLSGRSDNH (SEQ ID NO: 297) |
| 43 | FGAACPNHPMCHDAQ (SEQ ID NO: 53) | AVGLLAPPGGLSGRSDNH (SEQ ID NO: 306) |
| 44 | CLHSAYNACLDP (SEQ ID NO: 54) | ISSGLLSGRSDNH (SEQ ID NO: 297) |
| 45 | CLHSAYNACLDP (SEQ ID NO: 54) | AVGLLAPPGGLSGRSDNH (SEQ ID NO: 306) |
| 46 | CAHSAYNVCLDP (SEQ ID NO: 55) | ISSGLLSGRSDNH (SEQ ID NO: 297) |
| 47 | CAHSAYNVCLDP (SEQ ID NO: 55) | AVGLLAPPGGLSGRSDNH (SEQ ID NO: 306) |
| 48 | CLHSAYNVCADP (SEQ ID NO: 56) | ISSGLLSGRSDNH (SEQ ID NO: 297) |

TABLE 6-continued

| Exemplary Activatable Anti-CTLA-4 Antibody Combination | | |
|---|---|---|
| Comb. No. | Masking Moiety (MM) | Cleavable Moiety (CM) |
| 49 | CLHSAYNVCADP (SEQ ID NO: 56) | AVGLLAPPGGLSGRSDNH (SEQ ID NO: 306) |
| 50 | CLHSAYNVCLAP (SEQ ID NO: 57) | ISSGLLSGRSDNH (SEQ ID NO: 297) |
| 51 | CLHSAYNVCLAP (SEQ ID NO: 57) | AVGLLAPPGGLSGRSDNH (SEQ ID NO: 306) |
| 52 | CLHSAYNVCLDA (SEQ ID NO: 58) | ISSGLLSGRSDNH (SEQ ID NO: 297) |
| 53 | CLHSAYNVCLDA (SEQ ID NO: 58) | AVGLLAPPGGLSGRSDNH (SEQ ID NO: 306) |
| 54 | YISDCPYHPMCHDYQ (SEQ ID NO: 60) | ISSGLLSGRSDNH (SEQ ID NO: 297) |
| 55 | FRNTCPYHPMCHDYR (SEQ ID NO: 61) | ISSGLLSGRSDNH (SEQ ID NO: 297) |
| 56 | AVCHMYMYGYNLCPF (SEQ ID NO: 63) | ISSGLLSGRSDNH (SEQ ID NO: 297) |
| 57 | RSCPQMYGYSMCPHT (SEQ ID NO: 64) | ISSGLLSGRSANP (SEQ ID NO: 305) |
| 58 | QPCAQMFGYSMCPHT (SEQ ID NO: 65) | ISSGLLSGRSANP (SEQ ID NO: 305) |

In some embodiments, the activatable anti-CTLA-4 antibodies described herein also include an agent conjugated to the activatable antibody. In some embodiments, the conjugated agent is a therapeutic agent, such as an anti-neoplastic agent. In some embodiments, the agent is conjugated to a carbohydrate moiety of the activatable antibody, preferably where the carbohydrate moiety is located outside the antigen-binding region of the antibody or antigen-binding fragment in the activatable antibody. In some embodiments, the agent is conjugated to a sulfhydryl group of the antibody or antigen-binding fragment in the activatable antibody. In some embodiments, the agent is conjugated to an amino group of the antibody or antigen-binding fragment of the activatable antibody. In some embodiments, the agent is conjugated to a carboxylic acid group of the antibody or antigen-binding fragment of the activatable antibody.

In some embodiments, the agent is a cytotoxic agent such as a toxin (e.g., an enzymatically active toxin of bacterial, fungal, plant, or animal origin, or fragments thereof), or a radioactive isotope (i.e., a radioconjugate).

In some embodiments, the conjugated activatable antibody can be modified for site-specific conjugation through modified amino acid sequences inserted or otherwise included in the activatable antibody sequence. These modified amino acid sequences are designed to allow for controlled placement and/or dosage of the conjugated agent within a conjugated activatable anti-CTLA-4 antibody. For example, the activatable antibody can be engineered to include cysteine substitutions at positions on light and heavy chains that provide reactive thiol groups and do not negatively impact protein folding and assembly, nor alter antigen binding. In some embodiments, the activatable antibody can be engineered to include or otherwise introduce one or more non-natural amino acid residues within the activatable antibody to provide suitable sites for conjugation. In some embodiments, the activatable antibody can be engineered to include or otherwise introduce enzymatically activatable peptide sequences within the activatable antibody sequence.

In some embodiments, the agent is a detectable moiety such as, for example, a label or other marker. For example, the agent is or includes a radiolabeled amino acid, one or more biotinyl moieties that can be detected by marked avidin (e.g., streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties are attached by linker molecules.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutarelde-hyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies of the invention. (See, e.g., "Conjugate Vaccines", Contributions to Microbiology and Immunology, J. M. Cruse and R. E. Lewis, Jr (eds), Carger Press, New York, (1989), the entire contents of which are incorporated herein by reference).

II. Uses of Anti-CTLA-4 Activatable Antibodies

Therapeutic formulations of the invention, which include an activatable anti-CTLA-4 antibody, are used to prevent, treat or otherwise ameliorate a disease or disorder, including but not limited to, a disease or disorder associated with aberrant CTLA-4 expression and/or activity. For example, therapeutic formulations of the invention, which include an activatable anti-CTLA-4 antibody, are used as cancer immunotherapy, e.g., potentiating an endogenous immune response in a subject afflicted with a cancer so as to thereby treat the subject, which method comprises administering to the subject therapeutically effective amount of any of the activatable anti-CTLA-4 antibodies described herein.

Examples of cancers that may be treated using the immunotherapeutic methods of the disclosure include bone cancer, pancreatic cancer, skin cancer, cancer of the head or neck, breast cancer, lung cancer, cutaneous or intraocular malignant melanoma, unresectable or metastatic melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, a hematological malignancy, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, metastatic cancers, and any combinations of said cancers. In some embodiments, the cancer is selected from MEL, RCC, squamous NSCLC, non-squamous NSCLC, CRC, CRPC, squamous cell carcinoma of the head and neck, and carcinomas of the esophagus, ovary, gastrointestinal tract and breast. The present methods are also applicable to treatment of metastatic cancers.

Other cancers include hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers.

Increased proteolysis is known to be a hallmark of cancer. (See e.g., Affara N I, et al. "Delineating protease functions during cancer development." *Methods Mol Biol.* 539 (2009): 1-32). Progression, invasion and metastasis of tumors result from several interdependent processes in which proteases are implicated. This process is described generally in U.S. Publication No. 2016/0193332 A1, which is incorporated in its entirety.

In some embodiments of these methods for treating a cancer subject, the activatable antibodies of the present invention, e.g. activatable ipilimumab, is administered to the subject as monotherapy. In some embodiments, stimulation or blockade of immunomodulatory targets may be effectively combined with standard cancer treatments, including chemotherapeutic regimes, radiation, surgery, hormone deprivation and angiogenesis inhibitors. The activatable anti-CTLA-4 antibody can be linked to an anti-neoplastic agent (as an immunoconjugate) or can be administered separately from the agent. In the latter case (separate administration), the antibody can be administered before, after or concurrently with the agent or can be co-administered with other known therapeutic agents. Chemotherapeutic drugs include, among others, doxorubicin (ADRIAMYCIN®), cisplatin, carboplatin, bleomycin sulfate, carmustine, chlorambucil (LEUKERAN®), cyclophosphamide (CYTOXAN®; NEOSAR®), lenalidomide (REVLIMID®), bortezomib (VELCADE®), dexamethasone, mitoxantrone, etoposide, cytarabine, bendamustine (TREANDA®), rituximab (RITUXAN®), ifosfamide, vincristine (ONCOVIN®), fludarabine (FLUDARA®), thalidomide (THALOMID®), alemtuzumab (CAMPATH®, ofatumumab (ARZERRA®), everolimus (AFINITOR®, ZORTRESS®), and carfilzomib (KYPROLIS™). Co-administration of anti-cancer agents that operate via different mechanisms can help overcome the development of resistance to drugs or changes in the antigenicity of tumor cells.

Activatable anti-CTLA-4 antibodies of the present invention, such as the activatable ipilimumab, may also be used in combination with other immunomodulatory agents, such as antibodies against other immunomodulatory receptors or their ligands. Several other co-stimulatory and inhibitory receptors and ligands that regulate T cell responses have been identified. Examples of stimulatory receptors include Inducible T cell Co-Stimulator (ICOS), CD137 (4-1BB), CD134 (OX40), CD27, Glucocorticoid-Induced TNFR-Related protein (GITR), and Herpes Virus Entry Mediator (HVEM), whereas examples of inhibitory receptors include Programmed Death-1 (PD-1), Programmed Death Ligand-1 (PD-L1), B and T Lymphocyte Attenuator (BTLA), T cell Immunoglobulin and Mucin domain-3 (TIM-3), Lymphocyte Activation Gene-3 (LAG-3), adenosine A2a receptor (A2aR), Killer cell Lectin-like Receptor G1 (KLRG-1), Natural Killer Cell Receptor 2B4 (CD244), CD160, T cell Immunoreceptor with Ig and ITIM domains (TIGIT), and the receptor for V-domain Ig Suppressor of T cell Activation (VISTA). Mellman et al. (2011) *Nature* 480:480; Pardoll (2012) *Nat. Rev. Cancer* 12: 252; Baitsch et al. (2012) *PloS One* 7:e30852.

Anti-PD-1 antibodies OPDIVO® (nivolumab) and KEYTRUDA® (pembrolizumab), as well as anti-PD-L1 antibody TECENTRIQ® (atezolizumab), have been approved for use in treating cancer, and may be combined with the activatable anti-CLTA-4 antibodies of the present invention, e.g. activatable ipilimumab. These receptors and their ligands provide targets for therapeutics designed to stimulate, or prevent the suppression, of an immune response so as to thereby attack tumor cells. Weber (2010) *Semin. Oncol.* 37:430; Flies et al. (2011) Yale *J. Biol. Med.* 84:409; Mellman et al. (2011) *Nature* 480:480; Pardoll (2012) Nat. Rev. Cancer 12:252. Stimulatory receptors or receptor ligands are targeted by agonist agents, whereas inhibitory receptors or receptor ligands are targeted by blocking agents. Among the most promising approaches to enhancing immunotherapeutic anti-tumor activity is the blockade of so-called "immune checkpoints," which refer to the plethora of inhibitory signaling pathways that regulate the immune system and are crucial for maintaining self-tolerance and modulating the duration and amplitude of physiological immune responses in peripheral tissues in order to minimize collateral tissue damage. See e.g. Weber (2010) Semin. Oncol. 37:430; Pardoll (2012) Nat. Rev. Cancer 12:252. Because many of the immune checkpoints are initiated by ligand-receptor interactions, they can be readily blocked by antibodies or modulated by recombinant forms of ligands or receptors.

Anti-PD-1 Antibodies Useful for the Invention

Any anti-PD-1 antibody that is known in the art can be used in the presently described methods. In particular, various human monoclonal antibodies that bind specifically to PD-1 with high affinity have been disclosed in U.S. Pat. No. 8,008,449. Each of the anti-PD-1 humanized antibodies disclosed in U.S. Pat. No. 8,008,449 has been demonstrated to exhibit one or more of the following characteristics: (a) binds to human PD-1 with a $K_D$ of $1\times10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-7 production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates antibody responses; and (j) inhibits tumor cell growth in vivo. Anti-PD-1 antibodies usable in the present invention include monoclonal antibodies that bind specifically to human PD-1 and exhibit at least one, in some embodiments, at least five, of the preceding characteristics.

Other anti-PD-1 monoclonal antibodies have been described in, for example, U.S. Pat. Nos. 6,808,710, 7,488,802, 8,168,757 and 8,354,509, US Publication No. 2016/0272708, and PCT Publication Nos. WO 2012/145493, WO 2008/156712, WO 2015/112900, WO 2012/145493, WO 2015/112800, WO 2014/206107, WO 2015/35606, WO 2015/085847, WO 2014/179664, WO 2017/020291, WO 2017/020858, WO 2016/197367, WO 2017/024515, WO 2017/025051, WO 2017/123557, WO 2016/106159, WO 2014/194302, WO 2017/040790, WO 2017/133540, WO 2017/132827, WO 2017/024465, WO 2017/025016, WO 2017/106061, each of which is incorporated by reference in its entirety.

In some embodiments, the anti-PD-1 antibody is selected from the group consisting of nivolumab (also known as "OPDIVO®"; formerly designated 5C4, BMS-936558, MDX-1106, or ONO-4538), pembrolizumab (Merck, also known as "KEYTRUDA®", lambrolizumab, and MK-3475. See WO2008156712A1), PDR001 (Novartis; see WO 2015/112900), MEDI-0680 (AstraZeneca; AMP-514; see WO 2012/145493), REGN-2810 (Regeneron; see WO 2015/112800), JS001 (TAIZHOU JUNSHI PHARMA; see Si-Yang Liu et al., *J. Hematol. Oncol.* 10:136 (2017)), BGB-A317 (Beigene; see WO 2015/35606 and US 2015/0079109), INCSHR1210 (SHR-1210; Jiangsu Hengrui Medicine; see WO 2015/085847; Si-Yang Liu et al., *J Hematol. Oncol.* 10:136 (2017)), TSR-042 (ANB011; Tesaro Biopharmaceutical; see WO2014/179664), GLS-010 (WBP3055; Wuxi/Harbin Gloria Pharmaceuticals; see Si-Yang Liu et al., *J Hematol. Oncol.* 10:136 (2017)), AM-0001 (Armo), STI-1110 (Sorrento Therapeutics; see WO 2014/194302), AGEN2034 (Agenus; see WO 2017/040790), and MGD013 (Macrogenics).

In one embodiment, the anti-PD-1 antibody is nivolumab. Nivolumab is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9):846-56).

In another embodiment, the anti-PD-1 antibody is pembrolizumab. Pembrolizumab is a humanized monoclonal IgG4 antibody directed against human cell surface receptor PD-1 (programmed death-1 or programmed cell death-1). Pembrolizumab is described, for example, in U.S. Pat. Nos. 8,354,509 and 8,900,587; see also www.cancer.gov/drugdictionary?cdrid=695789 (last accessed: Dec. 14, 2014). Pembrolizumab has been approved by the FDA for the treatment of relapsed or refractory melanoma.

Anti-PD-1 antibodies usable in the disclosed methods also include isolated antibodies that bind specifically to human PD-1 and cross-compete for binding to human PD-1 with any anti-PD-1 antibody disclosed herein, e.g., nivolumab (see, e.g., U.S. Pat. Nos. 8,008,449 and 8,779,105; WO 2013/173223). In some embodiments, the anti-PD-1 antibody binds the same epitope as any of the anti-PD-1 antibodies described herein, e.g., nivolumab. The ability of antibodies to cross-compete for binding to an antigen indicates that these monoclonal antibodies bind to the same epitope region of the antigen and sterically hinder the binding of other cross-competing antibodies to that particular epitope region. These cross-competing antibodies are expected to have functional properties very similar those of the reference antibody, e.g., nivolumab, by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 antibody, nivolumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-1 antibodies usable in the methods of the disclosed invention also include antigen-binding portions of the above antibodies. It has been amply demonstrated that the antigen-binding function of an antibody can be performed by fragments of a full-length antibody.

Anti-PD-1 antibodies suitable for use in the disclosed methods or compositions are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and up-regulating the immune system. In certain embodiments, the anti-PD-1 antibody or antigen-binding portion thereof cross-competes with nivolumab for binding to human PD-1.

Anti-PD-L1 Antibodies Useful for the Invention

Any anti-PD-L1 antibody can be used in the methods of the present disclosure. Examples of anti-PD-L1 antibodies useful in the methods of the present disclosure include the antibodies disclosed in U.S. Pat. No. 9,580,507. Each of the anti-PD-L1 human monoclonal antibodies disclosed in U.S. Pat. No. 9,580,507 have been demonstrated to exhibit one or more of the following characteristics: (a) binds to human PD-L1 with a $K_D$ of $1\times10^{-7}$ M or less, as determined by surface plasmon resonance using a Biacore biosensor system; (b) increases T-cell proliferation in a Mixed Lymphocyte Reaction (MLR) assay; (c) increases interferon-7 production in an MLR assay; (d) increases IL-2 secretion in an MLR assay; (e) stimulates antibody responses; and (f) reverses the effect of T regulatory cells on T cell effector cells and/or dendritic cells. Anti-PD-L1 antibodies usable in the present invention include monoclonal antibodies that bind specifically to human PD-L1 and exhibit at least one, in some embodiments, at least five, of the preceding characteristics.

In certain embodiments, the anti-PD-L1 antibody is selected from the group consisting of BMS-936559 (formerly 12A4 or MDX-1105; see, e.g., U.S. Pat. No. 7,943,743 and WO 2013/173223), MPDL3280A (also known as RG7446, atezolizumab, and TECENTRIQ®; U.S. Pat. No. 8,217,149; see, also, Herbst et al. (2013) J Clin Oncol 31(suppl):3000), durvalumab (IVINZI™; MEDI-4736; AstraZeneca; see WO 2011/066389), avelumab (Pfizer; MSB-0010718C; BAVENCIO®; see WO 2013/079174), STI-1014 (Sorrento; see WO2013/181634), CX-072 (CytomX; see WO2016/149201), KN035 (3D Med/Alphamab; see Zhang et al., *Cell Discov.* 7:3 (March 2017), LY3300054 (Eli Lilly Co.; see, e.g., WO 2017/034916), and CK-301 (Checkpoint Therapeutics; see Gorelik et al., AACR:Abstract 4606 (April 2016)).

In certain embodiments, the PD-L1 antibody is atezolizumab (TECENTRIQ®). Atezolizumab is a fully humanized IgG1 monoclonal anti-PD-L1 antibody.

In certain embodiments, the PD-L1 antibody is durvalumab (IMIFINZI™) Durvalumab is a human IgG1 kappa monoclonal anti-PD-L1 antibody.

In certain embodiments, the PD-L1 antibody is avelumab (BAVENCIO®). Avelumab is a human IgG1 lambda monoclonal anti-PD-L1 antibody.

In other embodiments, the anti-PD-L1 monoclonal antibody is selected from the group consisting of 28-8, 28-1, 28-12, 29-8, 5H1, and any combination thereof.

Anti-PD-L1 antibodies usable in the disclosed methods also include isolated antibodies that bind specifically to human PD-L1 and cross-compete for binding to human PD-L1 with any anti-PD-L1 antibody disclosed herein, e.g., atezolizumab and/or avelumab. In some embodiments, the anti-PD-L1 antibody binds the same epitope as any of the anti-PD-L1 antibodies described herein, e.g., atezolizumab and/or avelumab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e.g., atezolizumab and/or avelumab, by virtue of their binding to the same epitope region of PD-L1. Cross-competing antibodies can be readily identified based on their ability to cross-compete with atezolizumab and/or avelumab in standard PD-L1 binding assays such as Biacore analysis, ELISA assays or flow cytometry (see, e.g., WO 2013/173223).

In certain embodiments, the antibodies that cross-compete for binding to human PD-L1 with, or bind to the same epitope region of human PD-L1 antibody as, atezolizumab and/or avelumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-L1 antibodies usable in the methods of the disclosed invention also include antigen-binding portions of the above antibodies. It has been amply demonstrated that the antigen-binding function of an antibody can be performed by fragments of a full-length antibody.

Anti-PD-L1 antibodies suitable for use in the disclosed methods or compositions are antibodies that bind to PD-L1 with high specificity and affinity, block the binding of PD-1, and inhibit the immunosuppressive effect of the PD-1 signaling pathway. In any of the compositions or methods disclosed herein, an anti-PD-L1 "antibody" includes an antigen-binding portion or fragment that binds to PD-L1 and exhibits the functional properties similar to those of whole antibodies in inhibiting receptor binding and up-regulating the immune system. In certain embodiments, the anti-PD-L1 antibody or antigen-binding portion thereof cross-competes with atezolizumab and/or avelumab for binding to human PD-L1.

Efficaciousness of prevention, amelioration or treatment is determined in association with any known method for diagnosing or treating the disease or disorder, including but not limited to, a disease or disorder associated with aberrant CTLA-4 expression and/or activity. Prolonging the survival of a subject or otherwise delaying the progression of the disease or disorder, including but not limited to, a disease or disorder associated with aberrant CTLA-4 expression and/or activity in a subject, indicates that the activatable antibody confers a clinical benefit.

It will be appreciated that therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™) DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol Pharmacol.* 32(2):210-8 (2000), Wang W. "Lyophilization and development of solid protein pharmaceuticals." *Int. J. Pharm.* 203(1-2):1-60 (2000), Charman W N "Lipids, lipophilic drugs, and oral drug delivery-some emerging concepts." *J Pharm Sci.* 89(8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists.

Activatable anti-CTLA-4 antibodies can be administered in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

In some embodiments, the activatable antibody contains a detectable label. An intact antibody, or a fragment thereof (e.g., Fab, scFv, or F(ab)2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. For example, the antibody can be labeled with a radioactive marker whose presence and location in a subject can be detected by standard imaging techniques.

III. Pharmaceutical Compositions

The activatable anti-CTLA-4 antibodies of the invention (also referred to herein as "active compounds"), and derivatives, fragments, analogs and homologs thereof, can be incorporated into pharmaceutical compositions suitable for administration. Such compositions typically comprise the activatable antibody and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringe ability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Activatable antibodies of the present invention may also be administered subcutaneously in conjunction with agents to facilitate injection of large volumes at a single site (insterstitial drug dispersion agents) such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

The compounds can also be prepared in the form of suppositories (e.g., with conventional suppository bases such as cocoa butter and other glycerides) or retention enemas for rectal delivery.

In some embodiments, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, may be practiced without departing from the scope of the present disclosure.

The invention will be further described in the following examples, which do not limit the scope of the invention described in the claims.

EXAMPLES

Example 1

Identification of Masking Moieties for the Activatable Anti-CTLA-4 Antibody

In order to identify masking moieties (MM) that reduce the binding of anti-CTLA-4 antibodies to their target protein, anti-CTLA-4 antibody (i.e., ipilimumab) was used to screen peptide libraries using methods similar to that described in PCT International Publication Nos. WO 2009/025846, WO 2010/081173, and WO 2016/149201, the contents of which are hereby incorporated by reference in their entireties. The screening consisted of two rounds of magnetic-activated cell sorting (MACS) purification followed by three rounds of fluorescence-activated cell sorting (FACS).

The initial MACS purification was done with protein-A Dynabeads® (Invitrogen) and anti-CTLA-4 antibody at a concentration of 100 nM. Approximately $10^{11}$ cells were screened for binding, and $6\times10^{6}$ cells were collected. The second MACS purification was done with streptavidin DYNABEADS® (Thermo Fisher Scientific) and biotinylated anti-CTLA-4 antibody at a concentration of 100 nM. The eluate from the initial MACS purification was expanded, approximately $10^{11}$ cells were screened for binding, and approximately $10^{7}$ cells were collected. The output of the previously described MACS purification was subjected to serial rounds of FACS sorting with decreasing concentrations of anti-CTLA-4 labeled with Alexa Fluor® 488 (Thermo Fisher Scientific). Labeled anti-CTLA4 antibody was used at concentrations of 10 nM, 1 nM, and 200 pM for the first, second, and third sorts, respectively. Individual peptide clones, from the third sort were identified by sequence analysis and subsequently verified for their ability to bind the anti-CTLA4 antibody. Two peptide consensus sequences were selected for affinity maturation: XXCXXXMYGYNLCPY (SEQ ID NO: 554) and XXXCXHSMYNVCLDP (SEQ ID NO: 555).

Affinity maturation libraries were built on these consensus sequences as described in Table 7. Rows 1 and 3 represent the consensus sequence and rows 2 and 4 represent the nucleotide sequences encoding the peptide libraries that were inserted into the display system using a method similar to that described in PCT International Publication Number WO 2010/081173, ibid.

TABLE 7

| Maturation Libraries | | | | | | | | | | | | | | | |
|---|---|---|---|---|---|---|---|---|---|---|---|---|---|---|---|
| 1 | X | X | C | X | X | X | M | Y | G | Y | N | L | C | P | Y |
| 2 | NNK | NNK | TGC | NNK | NNK | NNK | NTT | TWT | GGG | KWT | AAT | CTG | TGC | CCG | TAT |
| 3 | X | X | X | C | X | H | S | M | Y | N | V | C | L | D | P |
| 4 | NNK | NNK | NNK | TGC | NNK | NWT | AGT | NTT | TWT | AAT | NTT | TGC | CTT | GAT | CCT |

The maturation libraries were screened in a manner similar to that described for the naïve libraries described above. The screening consisted of one round of MACS and subsequent rounds of FACS sorting. The MACS was done with protein-A DYNABEADS® (Thermo Fisher Scientific) and the anti-CTLA-4 antibody at a concentration of 100 nM. For MACS, $10^{11}$ cells were screened for binding, and approximately $10^{8}$ cells were selected. The eluate from the MACS was expanded, and approximately $10^{11}$ cells were subjected to serial rounds of FACS sorting with decreasing concentrations of Alexa Fluor® 488-labeled anti-CTLA4 antibody. Labeled anti-CTLA4 antibody was used at concentrations of 100 nM, 20 nM, 5 nM, 1 nM, and 1 nM for the first, second, third, fourth and fifth sorts, respectively. Individual peptide clones from the fourth and fifth sorts were identified by sequence analysis and subsequently verified for their ability to bind the anti-CTLA4 antibody. The sequences of the anti-CTLA-4 masking moieties identified through the methods described above are provided in Tables 4 and 5. Four consensus sequences can be derived from the mask sequences listed in Tables 4 and 5:

```
Consensus 1
                                        (SEQ ID NO: 566)
C(L/M/V/T)Y(S/V/I)(F/L/M/A)(Y/F)N(V/I)CLDP.

Consensus 2
                                        (SEQ ID NO: 567)
CAQMYGYSMC(P/A)(H/R/A)T.

Consensus 3
                                        (SEQ ID NO: 568)
CX(M/I/Y/L/N/F)(Y/W/F/Q/T)(M/Y)YG(YN/F)
(N/D)LCP(Y/F).

Consensus 4
                                        (SEQ ID NO: 569)
(N/T)(S/T/M/A)CP(N/Y)HP(M/L)C(H/F/Y)D(Y/F/W).
```

Example 2

Construction and Characterization of Activatable Anti-muCTLA-4 Antibodies

In order to show a proof-of-concept that the activatable anti-CTLA-4 antibodies can be used to treat tumors, six activatable anti-mouse CTLA-4 antibodies (based on clone 9D9) were constructed using techniques similar to those disclosed in Examples 1 and 3 herein. These antibodies comprise either MY11 or MY03 as the masking moiety, and cleavable moiety "0003" having amino acid sequence TSTSGRSANPRG (SEQ ID NO: 320), "1004" having amino acid sequence AVGLLAPP (SEQ ID NO: 323), or "2001" having amino acid sequence ISSGLLSGRSDNH (SEQ ID NO: 297). The antibodies were all mouse IgG2a isotype. As controls, anti-mouse CTLA-4 monoclonal antibody (9D9) ("9D9 mg2a") and a human anti-diptheria toxin antibody with a mIgG2a isotype ("mg2a") were used.

On day 0, BALB/c mice were subcutaneously injected with $1\times10^{6}$ CT26 tumor cells. Administration of the different antibodies began on day 7 post tumor implantation. Prior to administration, tumor size was measured and the mice were randomized into different treatment groups, so as to have comparable mean tumor volumes (e.g., 39-44 $mm^3$). Tumors were measured with calipers two-dimensionally, and tumor volume was calculated as $L\times(W^2/2)$, L=length (the longer of the 2 measurements), W=width. The mice were then treated intraperitoneally (i.p.) with the designated antibody (e.g., 25 ag/dose). Tumor volume was measured twice weekly. At day 12 post tumor implantation, some of the mice from each group were sacrificed, and tumor and spleen were harvested for immunomonitoring to investigate the effects of the antibodies on the T cell populations. Some or all of the remaining mice from the different groups were used for subsequent pharmacokinetic (PK) and/or pharmacodynamics (PD) analysis.

As shown in FIG. 1A, mice that received the unrelated mouse IgG2a antibody (i.e., the human anti-diptheria toxin antibody) failed to control the tumor. In contrast, as shown in FIG. 1C, mice that received the activatable anti-mouse CTLA-4 antibody (comprising MY11 as the masking moiety and 2001 as the cleavable moiety) controlled tumor size almost as well as those mice that received the anti-mouse CTLA-4 mAb (9D9) (FIG. 1*i*). These data demonstrate that tumor-specific protease can cleave the cleavable moiety, resulting in the removal of the masking moiety and the binding of the released antibody to its target protein.

To determine whether or not activatable anti-mouse CTLA-4 antibodies are active in the periphery, proliferation and activity of Foxp3+ regulatory T cells were determined in the spleen, and regulatory T cell abundance was determined in tumor samples for comparison, as described in Example 5, infra. In agreement with the data from FIGS. 1B and 1C, all the activatable anti-CTLA-4 antibodies behaved similarly to the anti-mouse CTLA-4 mAb (9D9) in the tumor (FIG. 2A). In contrast, the activatable antibodies resembled the unrelated mouse IgG2a antibody in the spleen (FIGS. 2B and 2C). Such data suggest that the masking moiety-containing prodomain of the activatable anti-mouse CTLA-4 antibodies remains intact and attached to the antibody in the spleen, blocking the activity of the antibody, whereas the prodomain is cleaved off by tumor specific proteases to generate fully active anti-CTLA-4 antibody in the tumor.

Example 3

Construction of Activatable Anti-Human CTLA-4 Antibodies

Activatable anti-CTLA4 antibodies comprising an anti-CTLA4 masking moiety, a cleavable moiety, and an anti-CTLA4 antibody (e.g., ipilimumab) of the disclosure were produced according to methods similar to those described in PCT Publication Nos. WO 2009/025846 ibid. and WO 2010/081173 ibid, and WO 2016/118629, ibid. Activatable anti-CTLA4 antibodies were expressed in EXPI293™ cells (Thermo Fisher Scientific) and purified by protein A chromatography (MABSELECT SURE™ (protein A affinity resin), GE Healthcare) as per manufacturers' protocols. Quality control of the resultant activatable antibodies indicated that most comprise at least 95% monomer.

To assess the feasibility of using the activatable anti-CTLA-4 antibodies disclosed herein in a human setting, the antibodies were produced as human IgG1 (hIgG1) heavy chain (Hc) and human kappa (hK) light chain (Lc) format. The activatable antibodies all comprise the antibody or antigen binding domain thereof of ipilimumab. The cleavable moiety was selected from the group consisting of a cleavable moiety referred to herein as "2001" and comprising the sequence ISSGLLSGRSDNH (SEQ ID NO: 297) and derivatives thereof and a cleavable moiety referred to herein as "3001" and comprising the sequence AVGLLAPPGGLSGRSDNH (SEQ ID NO: 306) and derivatives thereof. In some embodiments, the cleavable moiety was selected from the group consisting of ISSGLLSGRSDNH (SEQ ID NO: 297), also referred to herein as "2001"; ISSGLLSGRSDDH (SEQ ID NO: 300), also referred to herein as "2006"; ISSGLLSGRSDIH (SEQ ID NO: 301), also referred to herein as "2007"; ISSGLLSGRSDQH (SEQ ID NO: 302), also referred to herein as "2008"; ISSGLLSGRSDTH (SEQ ID NO: 303), also referred to herein as "2009"; ISSGLLSGRSANP (SEQ ID NO: 305), also referred to herein as "2012"; ISSGLLSGRSDNP (SEQ ID NO: 304), also referred to herein as "2011"; ISSGLLSGRSANPRG (SEQ ID NO: 298), also referred to herein as "2003"; AVGLLAPPGGLSGRSDNH (SEQ ID NO: 306), also referred to herein as "3001"; AVGLLAPPGGLSGRSDDH (SEQ ID NO: 307), also referred to herein as "3006"; AVGLLAPPGGLSGRSDIH (SEQ ID NO: 308), also referred to herein as "3007"; AVGLLAPPGGLSGRSDQH (SEQ ID NO: 309), also referred to herein as "3008"; AVGLLAPPGGLSGRSDTH (SEQ ID NO: 310), also referred to herein as "3009"; AVGLLAPPGGLSGRSANP (SEQ ID NO: 312), also referred to herein as "3012"; AVGLLAPPGGLSGRSDNP (SEQ ID NO: 311), also referred to herein as "3011"; and AVGLLAPPSGRSANPRG (SEQ ID NO: 299), also referred to herein as "2005". The masking moiety was selected from the group of masking moieties provided in Tables 4 and 5. In some embodiments, the masking moiety was CRTQLYGYNLCPY (SEQ ID NO: 39), referred to herein as YV39. Some of the activatable anti-CTLA-4 antibodies also included spacer sequences and/or linker peptides.

Example 4

In Vitro Characterization of Activatable Anti-Human CTLA-4 Antibodies

In order to assess the ability of the activatable antibodies to bind to CTLA-4 in the absence of protease activity, an enzyme-linked immunosorbent assay (ELISA) was used to measure binding affinity. Briefly, Nunc MaxiSorp® plates were coated overnight at 40° C. with 100 μL/well of a 1 g/mL solution of human CTLA-4 protein (Sino Biological) in PBS, pH 7.4. Plates were then washed three times with PBST (PBS, pH 7.4, 0.05% TWEEN™ 20 (polysorbate 20)), and the wells were blocked with 200 μL/well, 10 mg/mL bovine serum albumin (BSA) in PBST for 2 hours at room temperature. Afterwards, the plates were washed three more times with PBST. The activatable antibodies were then serially diluted, as shown below in Table 8.

TABLE 8

Serial Dilution of Activatable Anti-CTLA-4 Antibodies for Binding Analysis

| | [Antibody] = nM Columns 1-3 | [activatable antibody 1] = nM Columns 4-6 | [activatable antibody 2] = nM Columns 7-9 | [activatable antibody 3] = nM Columns 10-12 |
|---|---|---|---|---|
| A | 10 | 1000 | 1000 | 1000 |
| B | 3.33 | 333 | 333 | 333 |
| C | 1.11 | 111 | 111 | 111 |
| D | 0.37 | 37 | 37 | 37 |
| E | 0.123 | 12.3 | 12.3 | 12.3 |
| F | 0.041 | 4.1 | 4.1 | 4.1 |
| G | 0.0137 | 1.34 | 1.34 | 1.34 |
| H | .0046 | 0.45 | 0.45 | Blank |

In the current Example, the highest concentration used for the parental antibody and the activatable antibodies were 10 nM and 100 nM, respectively. However, the concentrations can be increased or decreased to give full saturation binding curves for activatable antibodies with stronger or weaker masking.

The diluted antibodies were added to the plates and incubated for 1 hour at room temperature. Afterwards, the plates were washed three times with PBST. Then, 100 μL of goat-anti-human IgG (Fab specific, Sigma cat #A0293; diluted at 1:4,000 in 10 mg/mL BSA in PBST) was added to each well, and the plate was incubated for an additional 1 hour at room temperature. Next, the plates were developed with tetramethylbenzidine (TMB) and 1N HCl. Absorbance at 450 nm was then measured and reported as optical density (OD 450 nm).

As shown in FIGS. 3A to 3E, anti-CTLA-4 activatable antibodies typically had reduced binding to CTLA-4 as compared to ipilimumab ("YV1"). See also FIGS. 4A to 4D, FIGS. 5A to 5F, and FIGS. 6A to 6B. Such data demonstrate that the masking moieties effectively conceal the antigen binding domain on the anti-CTLA-4 activatable antibodies.

To further assess the binding ability, the activatable human anti-CTLA-4 antibodies were serially diluted (e.g., 60 μg/mL to 0.0003 μg/mL) and added to 58 α-β-CTLA-4/CD3ζ cells, which stably express human CTLA-4. After 30 minutes of incubation at 4° C., an allophycocyanin (APC)-labeled anti-human secondary antibody was added and binding of the activatable anti-human CTLA-4 antibodies to human CTLA-4 was assessed using a Canto flow cytometer. The geometric mean fluorescence intensity (GMFI) was determined using FlowJo® analysis software. Ipilimumab was used as a control. As shown in FIGS. 7A and 7B, the activatable human anti-CTLA-4 antibodies did not bind to human CTLA-4 as effectively as ipilimumab. These data further demonstrate that in the absence of specific proteases, the masking moiety of the activatable antibodies inhibits binding of such activatable antibodies to human CTLA-4.

To confirm that the reduced binding observed with the activatable anti-CTLA-4 antibodies was due to the masking moiety, studies were performed on mono-clippped, MMP fully-clipped and uPA fully-clipped forms of the activatable antibody comprising YV39 as the masking moiety and 2011 as the cleavable moiety. The mono-clipped form of the antibody was produced by expressing a construct producing one intact light chain (including the mask moiety) and a second light chain truncated at the same position as if it had been cleaved by MMP14. The MMP or uPA fully clipped forms were expressed from constructs with both light chains truncated as if they had been cleaved by MMP or μPA, respectively. As shown in FIGS. 7C and 7D, the mono-clipped activatable antibody had intermediate binding (EC50=2.8 nM) as compared to the non-clipped activatable antibody (EC50=22 nM) and ipilimumab (EC50=0.54 nM). In contrast, the MMP or uPA fully-clipped activatable antibodies behaved similarly to ipilimumab (MMP clipped: EC50=0.65 nM; μPA clipped: EC50=0.76). Such data confirm that the reduced binding observed with the activatable anti-CTLA-4 antibody is due to the masking moiety.

Next, to determine whether the observed reduced binding to CTLA-4 correlated with reduced activity, the activity of an activatable human anti-CTLA-4 antibody comprising YV39 as the masking moiety and 2011 as the cleavable moiety ("Ipi YV39 2011") was characterized in an in vitro functional assay using staphylococcal enterotoxin B (SEB). SEB is a superantigen that strongly activates T cells and stimulates cytokine secretion. Whole fresh peripheral blood mononuclear cells (PBMC) were isolated from healthy human donors using a standard FICOLL-PAQUE™ (density gradient medium) separation method. Serial dilution of the antibodies (e.g., 40 μg/mL to 0.01 μg/mL) were performed and plated in triplicate in a 96-well flat-bottom tissue culture plate. The antibodies used included (i) Ipi YV39 2011, (ii) ipilimumab, and (iii) an unrelated isotype control. Next, the isolated PBMC were resuspended in T-cell assay media (RPMI media+10% heat-inactivated fetal bovine serum (HI-FBS)+1% HEPES buffer+1% MEM non-essential amino acid+1% Na-pyruvate) and added to the plate at $1\times10^5$ cells/well. The cells were stimulated with a suboptimal concentration (e.g., 85 ng/mL—determined by titrating SEB and observing the stimulation on T-cell proliferation) of SEB. The cells were incubated at 37° C. for 3 days. Then, the IL-2 concentration in the supernatants was measured by homogeneous time-resolved fluorescence (HTRF). The HTRF data were analyzed using Softmax Pro and graphed using GRAPHPAD PRISM™.

As shown in FIG. 8, ipilimumab enhanced the SEB-mediated IL-2 production by the PBMC in a dose-dependent manner. In contrast, the Ipi YV39 2011 activatable antibody had activity similar to that of the isotype control, suggesting that the masking moiety (YV39) is effective in blocking the functional activity of ipilimumab. These data are in agreement with the binding data described above and demonstrate that in the absence of specific proteases, the activatable anti-human CTLA-4 antibodies exhibit reduced activity.

Example 5

In Vivo Characterization of Activatable Anti-Human CTLA-4 Antibodies

In order to characterize the antibodies disclosed herein in vivo, four activatable human anti-human CTLA-4 antibodies (based on ipilimumab) were prepared using mouse IgG2a. The antibodies comprise YV04, YV23, YV24, or YV39 as the masking moiety, and 2001 as the cleavable moiety ("Ipi YV04 2001", "Ipi YV23 2001", "Ipi YV24 2001", and "Ipi YV39 2001", respectively). As controls, ipilimumab ("Ipi mg2a") and an unrelated human anti-diphtheria toxin ("control mg2a") were used. The activity of these activatable anti-CTLA-4 antibodies was assessed using the MC38 tumor model as described below.

Briefly, on day 0, human CTLA-4 knock-in C57BL/6 mice were subcutaneously injected with $2\times10^6$ MC38 colon adenocarcinoma cells into their left lower abdominal quadrant. Tumors were measured with calipers two-dimensionally, and tumor volume was calculated as $L\times(W^2/2)$, L=length (the longer of the 2 measurements), W=width. Next, the mice were randomized into different groups, so as to have similar mean tumor volumes (e.g., 37 $mm^3$). Administration of the antibodies began on day 7 post tumor implantation with the mice receiving a single dose (e.g., 200 μg/mouse) of the relevant antibody via intraperitoneal (i.p.) injection. At day 12 post tumor implantation, several of the mice from each group were sacrificed, and tumor and spleen were harvested for immunomonitoring to investigate the effect of the antibodies on the T cell populations. Some or all of the remaining mice from the different groups were used for subsequent pharmacokinetic (PK) and/or pharmacodynamics (PD) analysis.

Immunomonitoring of T Cell Populations

The harvested tumor and spleen were processed on a gentleMACS Octo Dissociator™ (Miltenyi, San Diego, CA). Single cell suspensions were stained with the following T cell markers: CD4, CD8, CD19, ICOS, CD45, FoxP3, CTLA-4, CD3, Ki-67, PD-1, Granzyme B, and LIVE/DEAD®.

PK/PD Analysis

The mice were checked daily for postural, grooming, and respiratory changes, as well as lethargy. Tumors and group body weights were recorded twice a week until death, euthanasia, or end of the study period. The response to the treatments was measured as a function of tumor growth inhibition (TGI), which was calculated as follows: % TGI={1−[(Tt−To)/(Ct−Co)]}×100, Tt=tumor volume of the treatment group on a given day, To=initial tumor volume, Ct=tumor volume of the control group on a given day, Co=initial tumor volume of the control group. Animals were euthanized if the tumor reached a volume greater than approximately 2500 $mm^3$ or appeared ulcerated.

Statistical Analysis

Microsoft Excel was used to calculate the mean, standard deviation (SD), and median values of tumor volumes and body weights. The mean and median values were calculated when 100% and at least 60% of the study animals remained in each treatment group, respectively. GraphPad Prism® v.4 software was used to plot data.

Figures 9A, 9B, 9C, 9D, 9E, 9F:
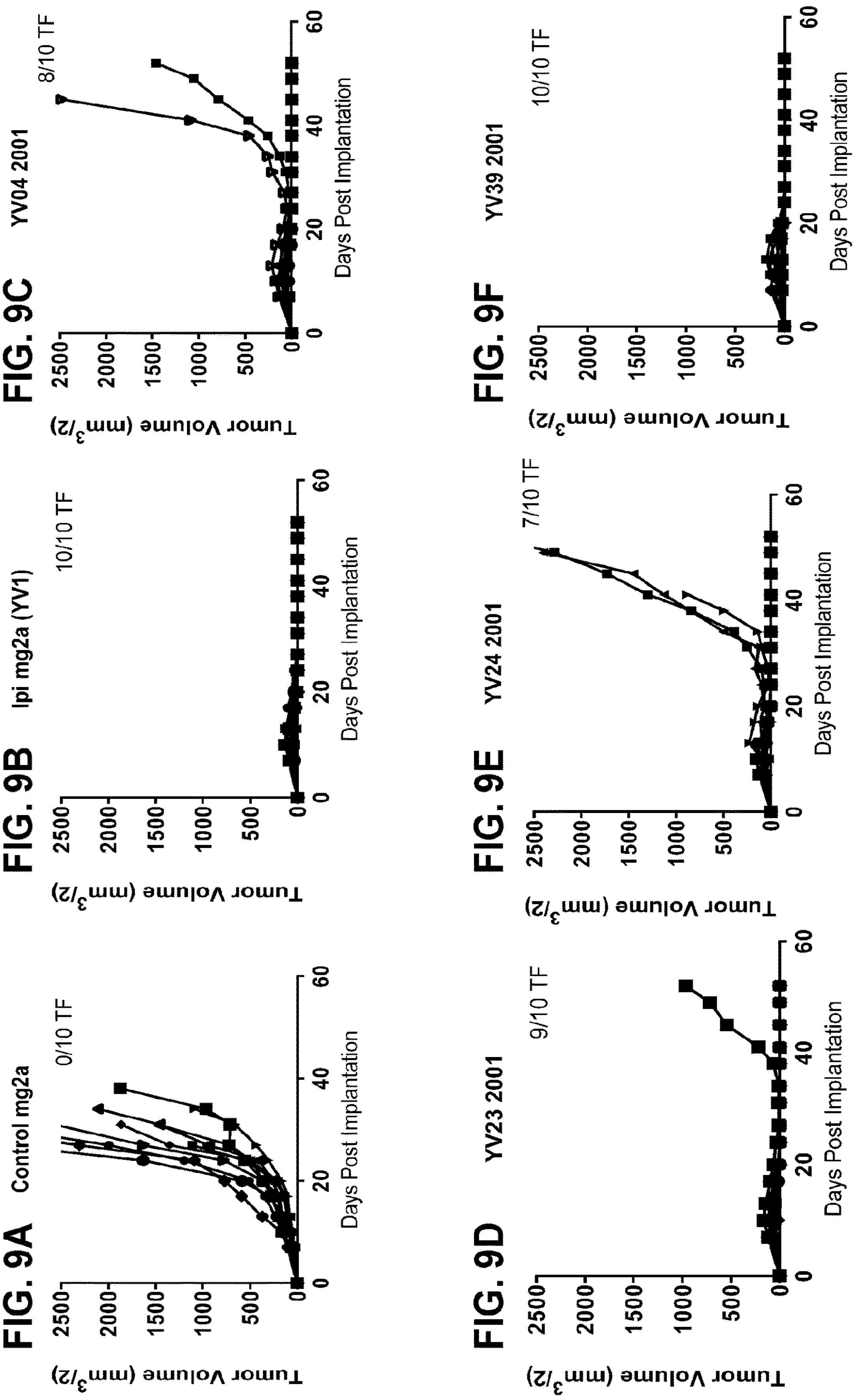

As expected, mice that received the unrelated control antibody failed to control tumor growth (FIG. 9A) whereas all the mice that received ipilimumab effectively controlled tumor growth (FIG. 9B). Mice that received the different activatable human anti-CTLA-4 antibodies controlled tumor growth comparably with ipilimumab (FIGS. 9C to 9F). Of the activatable antibodies, Ipi YV39 2001 most closely resembled the efficacy of ipilimumab in controlling tumor growth (FIG. 9F).

In regard to the frequency of regulatory T cells in the tumor and spleen of the treated mice, as observed earlier with the activatable anti-mouse CTLA-4 antibodies (see Example 2), activatable anti-human CTLA-4 antibodies (mouse IgG2a isotype) behaved similarly to ipilimumab in tumors (FIGS. 12A and 12B), but in the spleen, the activatable antibodies were more comparable to the unrelated control antibody (FIGS. 12C to 12F).

The data shown here collectively demonstrate that the activatable human anti-CTLA-4 antibodies disclosed herein can effectively control tumors like the traditional ipilimumab while exhibiting less risk of undesirable side effects.

Example 6

In Vivo Characterization of Activatable Anti-Human CTLA-4 Antibodies Comprising Modified Cleavable Moieties To address a possible deamidation site in certain cleavable moiety sequences (see Example 10), activatable human anti-CTLA4 antibodies were prepared using a human IgG1 and various CM sequences. The activatable antibodies comprise YV39 as the masking moiety and one of several variants of the 2001 cleavable moiety: WT (2001), ANP (2012), DNP (2011), or Q (2008) ("Ipi YV39 2001", "Ipi YV39 2012", "Ipi YV39 2011", and "Ipi YV39 2008", respectively). Ipilimumab and the unrelated human anti-diphtheria toxin were again used as controls.

To measure the activity of the activatable anti-CTLA-4 antibodies, the MC38 tumor model was used as described above in Example 5. For the dose titration study (FIGS. 11A to 11F), the mice were treated with ipilimumab or the activatable antibody comprising YV39 as the masking moiety and 2011 as the cleavable moiety ("Ipi YV39 2011") at doses of 200 μg/dose, 60 μg/dose, and 20 μg/dose.

Figure 10A:
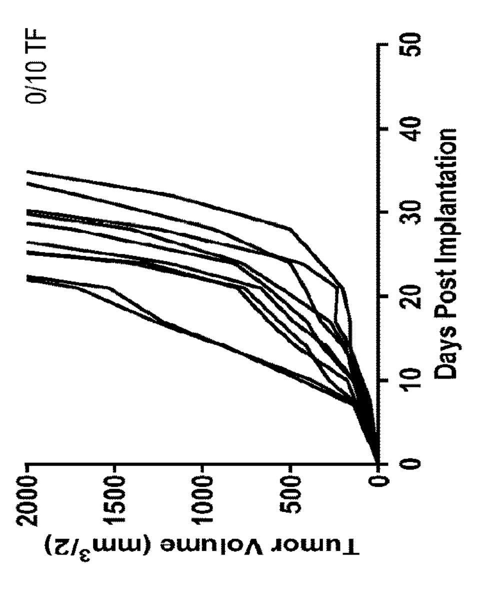
Figure 10B:
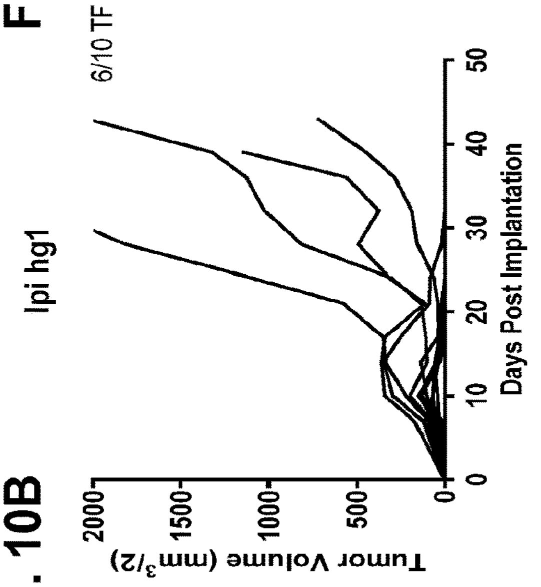
Figure 10C:
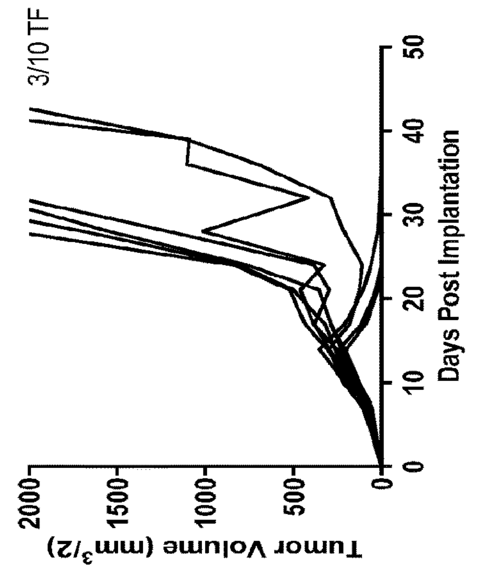
Figure 10D:
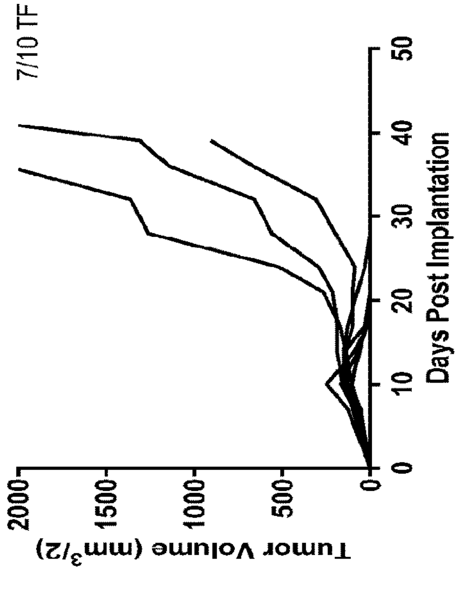
Figure 10E:
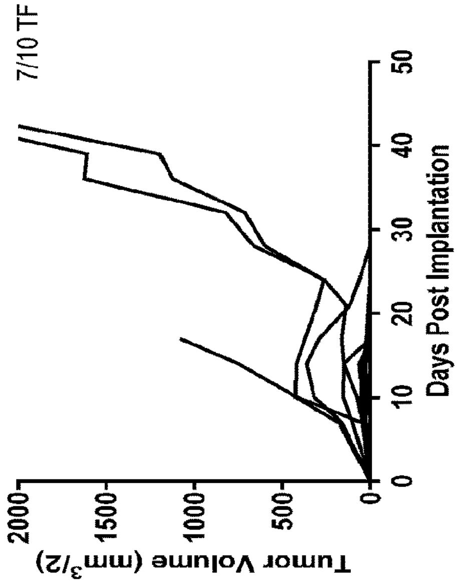
Figure 10F:
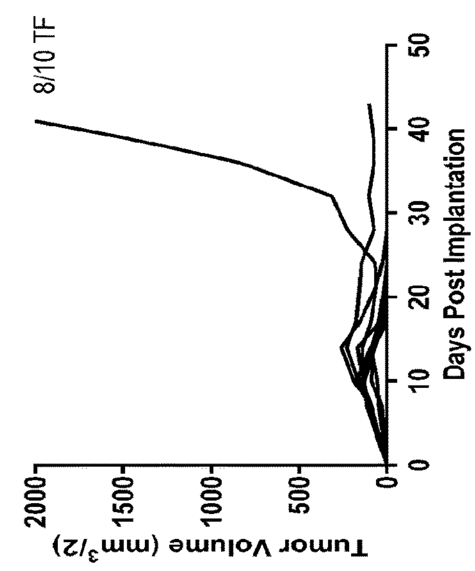

As shown in FIGS. 10A and 10B, mice treated with the control antibody failed to control the tumor, whereas 6 out of 10 mice treated with ipilimumab were tumor-free at the end of the experiment. Mice treated with the different activatable antibodies were able to control tumor as observed with the traditional ipilimumab (FIGS. 10C to 10F). See also FIGS. 11B-11G.

In regard to the frequency of regulatory T cells in the tumor and spleen of the treated mice, as observed earlier, tumor-specific protease was required to cleave the 2001 cleavable moiety variants. In the tumors, these activatable antibodies behaved like ipilimumab in reducing the frequency of Foxp3+ regulatory T cells (FIGS. 13A, 13B, 14A, and 14B). See also FIG. 15. In the spleen, the antibodies more closely mirrored the unrelated control antibody (FIGS. 13C to 13E, 14D to 14G, and 16A to 16B), demonstrating that the masking moiety remains coupled to the activatable antibody in the absence of the specific tumor-associated proteases.

Example 7

In Vivo Characterization of a Non-Fucosylated Version of Activatable Anti-Human CTLA-4 Antibodies As described above, the absence of core fucose residues can strongly enhance ADCC via improved binding of IgG to activating FcγRIIIA without altering antigen binding or CDC. Natsume et al. (2009) *Drug Des. Devel. Ther.* 3:7. Non-fucosylated forms of ipilimumab ("Ipi NF") and ipi YV39 2011 ("Ipi YV39 2011 NF") were prepared. Binding of Ipi and Ipi NF were determined for various mouse, human and cynomolgus monkey Fc receptors. Results are provided at FIG. 19. As expected, Ipi NF showed dramatically enhanced affinity (i.e., lower $K_d$) for activating receptors human CD16a (FcγRIIIa), cyno CD16 (FcγRIII) and mouse FcγRIV.

Ipi YV39 2011 NF and Ipi-NF were tested at various doses in the MC38 tumor model described in Example 5. Ipilimumab and an unrelated hIgG1 were used as controls. Results are provided at FIGS. 17A-D. Ipi NF was somewhat more effective at limiting or preventing tumor growth than ipilimumab (compare FIGS. 17B and 17C), and Ipi YV39 2011 NF was equivalent to Ipi NF (compare FIGS. 17C and 17D). In addition, FoxP3+ regulatory T cells were also similarly depleted in the tumors of mice treated with Ipi NF and Ipi YV39 2011 antibody (see FIG. 18). In both experiments, the Ipi YV39 2011 NF is shown to be fully activated in the tumor.

These results confirm that the methods of the present invention are equally applicable to non-fucosylated forms of ipilimumab, including non-fucosylated activatable CTLA-4 antibodies such as YV39 2011 NF.

Example 8

In Vivo Characterization of Activatable Anti-Human CTLA-4 Antibodies in Cynomolgus Monkeys To assess the anti-CTLA-4 antibodies in a primate, cynomolgous monkeys were administered activatable antibody comprising YV39 as the masking moiety and 2001 as the cleavable moiety. Vehicle and ipilimumab were used as controls. Each monkey received 10 mg of antibody or anti-CTLA-4 activatable antibody, and blood was collected on days 0, 4, 8, 15, 22, 36, and 43 post-antibody administration. As shown in FIG. 20, in monkeys that received ipilimumab, there was a spike in CD4+ T cell proliferation as measured by Ki67-staining at around days 8-15 post antibody administration. In contrast, activatable anti-CTLA-4 antibody behaved similarly to the vehicle control and did not induce CD4+ T cell proliferation in the monkeys. These data demonstrate that even in primates, the activatable anti-CTLA-4 antibody shows little if any activation, indicating the absence of specific proteases.

Collectively, the data presented at FIGS. 1-20 demonstrate that the activatable anti-CTLA-4 antibodies described herein offer an improvement over ipilimumab. The activatable antibodies control tumor growth just as effectively as ipilimumab while reducing the risk of serious adverse events often observed with ipilimumab treatment.

Example 9

$K_{App}$ and ME Values for Activatable CTLA-4 Antibodies

Table 9 provides the $K_{app}$ and masking efficiency (ME) values for activatable antibodies, disclosed herein, comprising a variety of masking moieties and cleavable moieties in a human IgG1 format. The values provided in this Table were calculated from the data depicted in the Figures. $K_{app}$ represents the binding affinity of the activatable antibody under the conditions of the measurement, in this example binding by ELISA; it is to be appreciated, however, that binding affinity can also be measured by binding to CTLA-4 expressed on primary or transfected cells or by other physical methods such as, but not limited to, surface plasmon resonance or equilibrium dialysis. Masking efficiency (ME) is calculated by dividing the $K_{app}$ of the activatable antibody by the $K_D$ of ipilimumab, measured under the same conditions.

TABLE 9

| | $K_{app}$ and ME Values | | | | | | | | | | | |
|---|---|---|---|---|---|---|---|---|---|---|---|---|
| | CM 2001 | | CM 3001 | | CM 2008 | | CM 2011 | | CM 2012 | | NSUB | |
| | $K_{app}$ nM | ME | $K_{app}$ nM | ME | $K_{app}$ nM | ME | $K_{app}$ nM | ME | $K_{app}$ nM | ME | $K_{app}$ nM | ME |
| YV04-YV1 | 17.8 | 57 | | | | | | | | | | |
| YV06-YV1 | 0.6 | 2 | | | | | | | | | | |
| YV09-YV1 | 33.6 | 112 | 44.4 | 126 | | | | | | | | |
| YV23-YV1 | 11.4 | 38 | 13.8 | 39 | | | | | | | | |
| YV24-YV1 | | | 9.0 | 29 | | | | | | | | |
| YV27-YV1 | 0.7 | 2.3 | 0.8 | 2.3 | | | | | | | | |
| YV29-YV1 | 0.7 | 2.3 | 0.8 | 2.3 | | | | | | | | |
| YV32-YV1 | 0.9 | 3.0 | 1.2 | 3.4 | | | | | | | | |
| YV33-YV1 | 1.3 | 4.3 | 1.9 | 5 | | | | | | | | |
| YV35-YV1 | 3.7 | 12.3 | 5.3 | 15 | | | | | | | | |
| YV39-YV1 | 16.9 | 56 | 14.3 | 41 | 31.4 | 135 | 13.2 | 57 | 14.9 | 64 | 31.8 | 137 |
| YV41-YV1 | 14.4 | 48 | 22.6 | 65 | | | | | | | | |
| YV51-YV1 | 4.4 | 15 | 4.9 | 14 | | | | | | | | |
| YV52-YV1 | 0.8 | 2.7 | 0.9 | 2.6 | | | | | | | | |
| YV53-YV1 | 4.1 | 14 | 5.3 | 15 | | | | | | | | |
| YV54-YV1 | 0.6 | 2 | 1.0 | 2.8 | | | | | | | | |
| YV55-YV1 | 4.8 | 16 | 6.0 | 18 | | | | | | | | |
| YV56-YV1 | 0.4 | 1.3 | 0.4 | 1 | | | | | | | | |
| YV57-YV1 | 0.4 | 1.3 | 1.6 | 4.6 | | | | | | | | |
| YV58-YV1 | 0.3 | 1 | 0.4 | 1 | | | | | | | | |

Table 10 provides the $K_{app}$ and ME values for the activatable antibodies disclosed herein, comprising a variety of masking moieties and cleavable moieties in a YV1 mouse Ig2a format. The values provided were calculated from the data depicted in the Figures.

TABLE 10

| | $K_{app}$ and ME values | | | | | | | | | |
|---|---|---|---|---|---|---|---|---|---|---|
| | CM 2001 | | CM 2006 | | CM 2007 | | CM 2008 | | CM 2009 | |
| | $K_{app}$ nM | ME | $K_{app}$ nM | ME | $K_{app}$ nM | ME | $K_{app}$ nM | ME | $K_{app}$ nM | ME |
| YV04-YV1 | 5.7 | 16.2 | 26.4 | 75 | 19.3 | 55 | 19.1 | 54 | 16.4 | 47 |
| YV23-YV1 | | | 12.5 | 36 | 7.8 | 22 | 2.7 | 8 | 9.4 | 27 |
| YV39-YV1 | 18.0 | 51 | 23.9 | 68 | | | 17.6 | 50 | 18.0 | 51 |

Table 11 provides $K_{app}$ and ME values for the activatable antibodies comprising masking moieties having higher ME values and the 2012 cleavable moiety in a YV1 mouse IgG2a format. The values provided were calculated from the data depicted in the Figures.

TABLE 11

| $K_{app}$ and ME values | | | | | | | | |
|---|---|---|---|---|---|---|---|---|
| | CM 2001 | | CM 2011 | | CM 2012 | | NSUB | |
| | $K_{app}$ nM | ME | $K_{app}$ nM | ME | $K_{app}$ nM | ME | $K_{app}$ nM | ME |
| YV39-YV1 | 18.0 | 51 | 18.0 | 51 | 12.9 | 144 | 29.8 | 85 |
| YV61-YV1 | | | | | 17.9 | 200 | | |
| YV62-YV1 | | | | | 15.5 | 173 | | |
| YV63-YV1 | | | | | 104 | 1170 | | |
| YV64-YV1 | | | | | 56.5 | 631 | | |
| YV65-YV1 | | | | | 12.3 | 156 | | |
| YV66-YV1 | | | | | 18.9 | 242 | | |
| YV01-YV1 | | | | | 38.6 | 493 | | |
| YV02-YV1 | | | | | 14.8 | 189 | | |

Example 10

Deamidation, Isomerization, and Stabilization Assessment for Activatable CTLA-4 Antibodies As suggested in Example 6, to address a possible deamidation site in certain cleavable moiety (CM) sequences in certain activatable human anti-CTLA-4 antibodies, such activatable antibodies were prepared using various CM sequences (i.e., 2001, 2011, 2012, and 2008). In the cleavable moieties 2011, 2012, and 2008, the DNH sequence found in the 2001 cleavable moiety was replaced with DNP, ANP, and DQH, respectively.

These activatable CTLA-4 antibodies were produced by transient transfection of the relevant constructs in HEK 293 cells, and subjected to peptide mapping liquid chromatography-mass spectroscopy (LC-MS) to detect potential breakdown products. The 2001 (DNH) cleavable moiety, which was initially selected for use in the activatable anti-CTLA-4 antibodies of the present invention, showed deamidation of the asparagine (N) residue (6.4%) after 7 days in PBS at 4° C. Forced stability studies showed an increase from 18.5% to 32.8% deamidation when stored at 25° C. for 4 weeks, and to 36.5% and 66.6% when stored at 40° C. for one week and four weeks, respectively.

Cleavable moieties 2008, 2011 and 2012 were selected to try to overcome the deamidation problem with 2001 in these activatable CTLA-4 antibodies. All of these had 0.1% or less deamidation when stored 40° C. for one week in PBS, compared with 6.4% deamidation of 2001. However, further stability analysis (also by LC-MS) showed that while these activatable CTLA-4 antibodies comprising the 2008 (DQH) cleavable moiety exhibited minimal deamidation, it showed significant aspartate isomerization at the aspartate residue under various conditions (see Table 12). In contrast, 2011 (DNP) exhibited minimal aspartate isomerization. Aspartate isomerization was not relevant for 2012 (ANP), in which the aspartate residue is replaced with alanine.

TABLE 12

| Isomerization values | | | | |
|---|---|---|---|---|
| | | Cleavable Moiety - Isomerization Values | | |
| Temperature | Time | 2011 (DNP) | 2012 (ANP) | 2008 (DQH) |
| −80° C. | 0 days ($T_0$) | 0.1% | N/A | 1.8% |
| 4° C. | 0 days ($T_0$) | 0.1% | N/A | 2.4% |
| 25° C. | 3 months | 0.2% | N/A | 8.2% |
| 40° C. | 3 months | 0.2% | N/A | 34.5% |

However, in vitro stability studies in mouse, rat, and cynomolgus monkey serum showed substantial clipping between asparagine and proline residues for 2012 (ANP) (see Table 13) in these activatable CTLA-4 antibodies. 2011 (DNP) remained as the cleavable moiety with acceptably low levels of deamidation, aspartate isomerization, and light chain clipping.

TABLE 13

| Degree of clipping observed between the asparagine and proline residues | | |
|---|---|---|
| | Cleavable Moiety - Clipping Between Asparagine and Proline Residues | |
| Serum | 2011 (DNP) | 2012 (ANP) |
| Mouse | − | ++ |
| Cyno | +/− | +++ |

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

What is claimed is:

1. An activatable anti-human CTLA-4 antibody comprising a heavy chain and a light chain, wherein:

(i) the heavy chain comprises a heavy chain variable domain (VH) comprising CDRH1: SYTMH (SEQ ID NO: 557); CDRH2: FISYDGNNKYYADSVKG (SEQ ID NO: 558); and CDRH3: TGWLGPFDY (SEQ ID NO: 559); and (ii) the light chain comprises:

(a) a light chain variable domain (VL) comprising CDRL1: RASQSVGSSYLA (SEQ ID NO: 560); CDRL2: GAFSRAT (SEQ ID NO: 561); and CDRL3: QQYGSSPWT (SEQ ID NO: 562);

(b) a cleavable moiety (CM); and (c) a masking moiety (MM), wherein the MM comprises the amino acid sequence selected from the group consisting of SEQ ID NO: 1, SEQ ID NO: 2, SEQ ID NO: 3, SEQ ID NO: 4, SEQ ID NO: 9, SEQ ID NO: 23, SEQ ID NO: 24, SEQ ID NO: 35, SEQ ID NO: 39, SEQ ID NO: 41, SEQ ID NO: 51, SEQ ID NO: 53, SEQ ID NO: 55, SEQ ID NO: 60, SEQ ID NO: 61, SEQ ID NO: 62, SEQ ID NO: 63, SEQ ID NO: 64, and SEQ ID NO: 65, wherein the light chain has the structural arrangement, from N-terminus to C-terminus, as follows: MM-CM-VL; and wherein the activatable anti-human CTLA-4 antibody is nonfucosylated.

2. The activatable anti-human CTLA-4 antibody of claim 1, wherein: the CM comprises the amino acid sequence selected from the group consisting of SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, and SEQ ID NO: 343.

3. The activatable anti-human CTLA-4 antibody of claim 2, wherein:

(i) the heavy chain further comprises a human IgG1 constant domain; and (ii) the light chain further comprises a human light chain kappa constant domain.

4. The activatable anti-human CTLA-4 antibody of claim 1, further comprising a first linker peptide (LP1) and a second linker peptide (LP2), and having the structural arrangement, from N-terminus to C-terminus, as follows: MM-LP1-CM-LP2-VL or MM-LP2-CM-LP1-VL.

5. The activatable anti-human CTLA-4 antibody of claim 1, further comprising a spacer, and having the structural arrangement, from N-terminus to C-terminus, as follows: spacer-MM-CM-VL.

6. A pharmaceutical composition comprising the activatable anti-human CTLA-4 antibody of claim 1 and a carrier.

7. A method of treating, alleviating a symptom of, or delaying the progression of a cancer in a subject in need thereof comprising administering a therapeutically effective amount of the pharmaceutical composition of claim 6 to the subject, wherein the pharmaceutical composition is administered alone or in combination with an immunomodulatory agent.

8. A method of selectively reducing the frequency of regulatory T cells ($T_{regs}$) as a percentage of total CD4+ T cells in a tumor of a subject in need thereof comprising administering a therapeutically effective amount of the pharmaceutical composition of claim 6, wherein the pharmaceutical composition is administered alone or in combination with an immunomodulatory agent, and wherein after the administration the frequency of $T_{regs}$ as a percentage of total CD4+ T cells in the tumor is reduced to a greater extent compared to the frequency of $T_{regs}$ as a percentage of total CD4+ T cells in a non-tumor tissue of the subject.

9. An isolated polypeptide comprising a masking moiety (MM), wherein the MM comprises an amino acid sequence selected from the group consisting of SEQ ID NO: 1, SEQ ID NO: 2, SEQ ID NO: 3, SEQ ID NO: 4, SEQ ID NO: 9, SEQ ID NO: 23, SEQ ID NO: 24, SEQ ID NO: 35, SEQ ID NO: 39, SEQ ID NO: 41, SEQ ID NO: 51, SEQ ID NO: 53, SEQ ID NO: 55, SEQ ID NO: 60, SEQ ID NO: 61, SEQ ID NO: 62, SEQ ID NO: 63, SEQ ID NO: 64, and SEQ ID NO: 65.

10. The isolated polypeptide of claim 9, which further comprises an anti-human CTLA-4 antibody, wherein the anti-human CTLA-4 antibody comprises a complete antibody, a Fab fragment, a $F(ab')_2$ fragment, a scFv, a scAb, or a combination thereof.

11. The isolated polypeptide of claim 10, which further comprises a cleavable moiety (CM).

12. The isolated polypeptide of claim 11, wherein the anti-human CTLA-4 antibody comprises a light chain variable domain (VL), and has the structural arrangement, from N-terminus to C-terminus, as follows: MM-CM-VL.

13. A pharmaceutical composition comprising the isolated polypeptide of claim 12 and a carrier.

14. A method of treating, alleviating a symptom of, or delaying the progression of a cancer in a subject in need thereof comprising administering a therapeutically effective amount of the pharmaceutical composition of claim 13 to the subject, wherein the pharmaceutical composition is administered alone or in combination with an immunomodulatory agent.

* * * * *

SEQUENCE LISTING

```
<160> NUMBER OF SEQ ID NOS: 570

<210> SEQ ID NO 1
<211> LENGTH: 15
<212> TYPE: PRT
<213> ORGANISM: Artificial Sequence
<220> FEATURE:
<223> OTHER INFORMATION: Masking Moiety - YV1

<400> SEQUENCE: 1

Asp Phe Ser Cys Leu His Ser Met Tyr Asn Val Cys Leu Asp Pro
1               5                   10                  15
```

<210> SEQ ID NO 2
<211> LENGTH: 15
<212> TYPE: PRT
<213> ORGANISM: Artificial Sequence
<220> FEATURE:
<223> OTHER INFORMATION: Masking Moiety - YV2

<400> SEQUENCE: 2

Gln Pro Cys Ala Gln Met Tyr Gly Tyr Ser Met Cys Pro His Thr
1 5 10 15

<210> SEQ ID NO 3
<211> LENGTH: 15
<212> TYPE: PRT
<213> ORGANISM: Artificial Sequence
<220> FEATURE:
<223> OTHER INFORMATION: Masking Moiety - YV3

<400> SEQUENCE: 3

Leu His Cys Arg Thr Gln Met Tyr Gly Tyr Asn Leu Cys Pro Tyr
1 5 10 15

<210> SEQ ID NO 4
<211> LENGTH: 15
<212> TYPE: PRT
<213> ORGANISM: Artificial Sequence
<220> FEATURE:
<223> OTHER INFORMATION: Masking Moiety - YV4

<400> SEQUENCE: 4

Leu His Cys Arg Thr Gln Leu Tyr Gly Tyr Asn Leu Cys Pro Tyr
1 5 10 15

<210> SEQ ID NO 5
<211> LENGTH: 9
<212> TYPE: PRT
<213> ORGANISM: Artificial Sequence
<220> FEATURE:
<223> OTHER INFORMATION: Masking Moiety - YV5

<400> SEQUENCE: 5

Cys Thr Tyr Ser Phe Phe Asn Val Cys
1 5

<210> SEQ ID NO 6
<211> LENGTH: 10
<212> TYPE: PRT
<213> ORGANISM: Artificial Sequence
<220> FEATURE:
<223> OTHER INFORMATION: Masking Moiety - YV6

<400> SEQUENCE: 6

Cys Ala Gln Met Tyr Gly Tyr Ser Met Cys
1 5 10

<210> SEQ ID NO 7
<211> LENGTH: 7
<212> TYPE: PRT
<213> ORGANISM: Artificial Sequence
<220> FEATURE:
<223> OTHER INFORMATION: Masking Moiety - YV7

<400> SEQUENCE: 7

Cys Pro Asn His Pro Met Cys
1 5

<210> SEQ ID NO 8

<211> LENGTH: 15
<212> TYPE: PRT
<213> ORGANISM: Artificial Sequence
<220> FEATURE:
<223> OTHER INFORMATION: Masking Moiety - YV8

<400> SEQUENCE: 8

Gly Thr Ala Cys Thr Tyr Ser Phe Phe Asn Val Cys Leu Asp Pro
1 5 10 15

<210> SEQ ID NO 9
<211> LENGTH: 15
<212> TYPE: PRT
<213> ORGANISM: Artificial Sequence
<220> FEATURE:
<223> OTHER INFORMATION: Masking Moiety - YV9

<400> SEQUENCE: 9

Phe Gly Thr Ala Cys Pro Asn His Pro Met Cys His Asp Trp Gln
1 5 10 15

<210> SEQ ID NO 10
<211> LENGTH: 15
<212> TYPE: PRT
<213> ORGANISM: Artificial Sequence
<220> FEATURE:
<223> OTHER INFORMATION: Masking Moiety - YV10

<400> SEQUENCE: 10

Ser Ala Cys Ala Tyr Trp Met Phe Gly Val Asn Leu Cys Pro Tyr
1 5 10 15

<210> SEQ ID NO 11
<211> LENGTH: 11
<212> TYPE: PRT
<213> ORGANISM: Artificial Sequence
<220> FEATURE:
<223> OTHER INFORMATION: Masking Moiety - YV11

<400> SEQUENCE: 11

Cys Arg Thr Gln Leu Tyr Gly Tyr Asn Leu Cys
1 5 10

<210> SEQ ID NO 12
<211> LENGTH: 11
<212> TYPE: PRT
<213> ORGANISM: Artificial Sequence
<220> FEATURE:
<223> OTHER INFORMATION: Masking Moiety - YV12

<400> SEQUENCE: 12

Cys Arg Thr Gln Ile Tyr Gly Tyr Asn Leu Cys
1 5 10

<210> SEQ ID NO 13
<211> LENGTH: 15
<212> TYPE: PRT
<213> ORGANISM: Artificial Sequence
<220> FEATURE:
<223> OTHER INFORMATION: Masking Moiety - YV13

<400> SEQUENCE: 13

Leu His Cys Arg Thr Gln Ile Tyr Gly Tyr Asn Leu Cys Pro Tyr
1 5 10 15

<210> SEQ ID NO 14
<211> LENGTH: 11

<212> TYPE: PRT
<213> ORGANISM: Artificial Sequence
<220> FEATURE:
<223> OTHER INFORMATION: Masking Moiety - YV14

<400> SEQUENCE: 14

Cys Pro Asn His Pro Met Cys His Asp Trp Gln
1 5 10

<210> SEQ ID NO 15
<211> LENGTH: 14
<212> TYPE: PRT
<213> ORGANISM: Artificial Sequence
<220> FEATURE:
<223> OTHER INFORMATION: Masking Moiety - YV15

<400> SEQUENCE: 15

Gly Thr Ala Cys Pro Asn His Pro Met Cys His Asp Trp Gln
1 5 10

<210> SEQ ID NO 16
<211> LENGTH: 13
<212> TYPE: PRT
<213> ORGANISM: Artificial Sequence
<220> FEATURE:
<223> OTHER INFORMATION: Masking Moiety - YV16

<400> SEQUENCE: 16

Cys Ala Tyr Trp Met Phe Gly Val Asn Leu Cys Pro Tyr
1 5 10

<210> SEQ ID NO 17
<211> LENGTH: 15
<212> TYPE: PRT
<213> ORGANISM: Artificial Sequence
<220> FEATURE:
<223> OTHER INFORMATION: Masking Moiety - YV17

<400> SEQUENCE: 17

Gln Glu Cys His Leu Tyr Met Tyr Gly Val Asn Leu Cys Pro Tyr
1 5 10 15

<210> SEQ ID NO 18
<211> LENGTH: 13
<212> TYPE: PRT
<213> ORGANISM: Artificial Sequence
<220> FEATURE:
<223> OTHER INFORMATION: Masking Moiety - YV18

<400> SEQUENCE: 18

Cys His Leu Tyr Met Tyr Gly Val Asn Leu Cys Pro Tyr
1 5 10

<210> SEQ ID NO 19
<211> LENGTH: 15
<212> TYPE: PRT
<213> ORGANISM: Artificial Sequence
<220> FEATURE:
<223> OTHER INFORMATION: Masking Moiety - YV19

<400> SEQUENCE: 19

Gly Gln Cys Gln Phe Tyr Met Phe Gly Tyr Asn Leu Cys Pro Tyr
1 5 10 15

<210> SEQ ID NO 20
<211> LENGTH: 15
<212> TYPE: PRT

<213> ORGANISM: Artificial Sequence
<220> FEATURE:
<223> OTHER INFORMATION: Masking Moiety - YV20

<400> SEQUENCE: 20

Leu Ser Thr Cys Met Tyr Ser Phe Phe Asn Val Cys Leu Asp Pro
1 5 10 15

<210> SEQ ID NO 21
<211> LENGTH: 12
<212> TYPE: PRT
<213> ORGANISM: Artificial Sequence
<220> FEATURE:
<223> OTHER INFORMATION: Masking Moiety - YV21

<400> SEQUENCE: 21

Cys Leu His Ser Met Tyr Asn Val Cys Leu Asp Pro
1 5 10

<210> SEQ ID NO 22
<211> LENGTH: 9
<212> TYPE: PRT
<213> ORGANISM: Artificial Sequence
<220> FEATURE:
<223> OTHER INFORMATION: Masking Moiety - YV22

<400> SEQUENCE: 22

Cys Leu His Ser Met Tyr Asn Val Cys
1 5

<210> SEQ ID NO 23
<211> LENGTH: 12
<212> TYPE: PRT
<213> ORGANISM: Artificial Sequence
<220> FEATURE:
<223> OTHER INFORMATION: Masking Moiety - YV23

<400> SEQUENCE: 23

Cys Leu His Ser Leu Tyr Asn Val Cys Leu Asp Pro
1 5 10

<210> SEQ ID NO 24
<211> LENGTH: 12
<212> TYPE: PRT
<213> ORGANISM: Artificial Sequence
<220> FEATURE:
<223> OTHER INFORMATION: Masking Moiety - YV24

<400> SEQUENCE: 24

Cys Leu His Ser Ala Tyr Asn Val Cys Leu Asp Pro
1 5 10

<210> SEQ ID NO 25
<211> LENGTH: 12
<212> TYPE: PRT
<213> ORGANISM: Artificial Sequence
<220> FEATURE:
<223> OTHER INFORMATION: Masking Moiety - YV25

<400> SEQUENCE: 25

Cys Met Tyr Ser Phe Phe Asn Val Cys Leu Asp Pro
1 5 10

<210> SEQ ID NO 26
<211> LENGTH: 9
<212> TYPE: PRT
<213> ORGANISM: Artificial Sequence
<220> FEATURE:
<223> OTHER INFORMATION: Masking Moiety - YV26

<400> SEQUENCE: 26

Cys Met Tyr Ser Phe Phe Asn Val Cys
1 5

<210> SEQ ID NO 27
<211> LENGTH: 12
<212> TYPE: PRT
<213> ORGANISM: Artificial Sequence
<220> FEATURE:
<223> OTHER INFORMATION: Masking Moiety - YV27

<400> SEQUENCE: 27

Gln Pro Cys Ala Gln Met Tyr Gly Tyr Ser Met Cys
1 5 10

<210> SEQ ID NO 28
<211> LENGTH: 13
<212> TYPE: PRT
<213> ORGANISM: Artificial Sequence
<220> FEATURE:
<223> OTHER INFORMATION: Masking Moiety - YV28

<400> SEQUENCE: 28

Cys Ala Gln Leu Tyr Gly Tyr Ser Met Cys Pro His Thr
1 5 10

<210> SEQ ID NO 29
<211> LENGTH: 13
<212> TYPE: PRT
<213> ORGANISM: Artificial Sequence
<220> FEATURE:
<223> OTHER INFORMATION: Masking Moiety - YV29

<400> SEQUENCE: 29

Cys Ala Gln Met Tyr Gly Tyr Ser Met Cys Ala His Thr
1 5 10

<210> SEQ ID NO 30
<211> LENGTH: 13
<212> TYPE: PRT
<213> ORGANISM: Artificial Sequence
<220> FEATURE:
<223> OTHER INFORMATION: Masking Moiety - YV30

<400> SEQUENCE: 30

Cys Ala Gln Met Tyr Gly Tyr Ser Met Cys Pro Ala Thr
1 5 10

<210> SEQ ID NO 31
<211> LENGTH: 13
<212> TYPE: PRT
<213> ORGANISM: Artificial Sequence
<220> FEATURE:
<223> OTHER INFORMATION: Masking Moiety - YV31

<400> SEQUENCE: 31

Cys Ala Gln Met Tyr Gly Tyr Ser Met Cys Pro His Thr
1 5 10

<210> SEQ ID NO 32
<211> LENGTH: 11
<212> TYPE: PRT
<213> ORGANISM: Artificial Sequence
<220> FEATURE:

<223> OTHER INFORMATION: Masking Moiety - YV32

<400> SEQUENCE: 32

Cys Pro Asn His Pro Leu Cys His Asp Trp Gln
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Masking Moiety - YV33

<400> SEQUENCE: 33

Cys Pro Asn His Pro Met Cys Ala Asp Trp Gln
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Masking Moiety - YV34

<400> SEQUENCE: 34

Cys Pro Asn His Pro Met Cys His Ala Trp Gln
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Masking Moiety - YV35

<400> SEQUENCE: 35

Cys Pro Asn His Pro Met Cys His Asp Ala Gln
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Masking Moiety - YV36

<400> SEQUENCE: 36

Cys Pro Asn His Pro Met Cys His Asp Trp Ala
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Masking Moiety - YV37

<400> SEQUENCE: 37

Gly Thr Ala Cys Pro Asn His Pro Met Cys
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Masking Moiety - YV38

<400> SEQUENCE: 38

Leu His Cys Arg Thr Gln Leu Tyr Gly Tyr Asn Leu Cys
1 5 10

<210> SEQ ID NO 39
<211> LENGTH: 13
<212> TYPE: PRT
<213> ORGANISM: Artificial Sequence
<220> FEATURE:
<223> OTHER INFORMATION: Masking Moiety - YV39

<400> SEQUENCE: 39

Cys Arg Thr Gln Leu Tyr Gly Tyr Asn Leu Cys Pro Tyr
1 5 10

<210> SEQ ID NO 40
<211> LENGTH: 13
<212> TYPE: PRT
<213> ORGANISM: Artificial Sequence
<220> FEATURE:
<223> OTHER INFORMATION: Masking Moiety - YV40

<400> SEQUENCE: 40

Cys Arg Thr Gln Leu Tyr Gly Tyr Asn Leu Cys Ala Tyr
1 5 10

<210> SEQ ID NO 41
<211> LENGTH: 13
<212> TYPE: PRT
<213> ORGANISM: Artificial Sequence
<220> FEATURE:
<223> OTHER INFORMATION: Masking Moiety - YV41

<400> SEQUENCE: 41

Cys Arg Thr Gln Leu Tyr Gly Tyr Asn Leu Cys Pro Ala
1 5 10

<210> SEQ ID NO 42
<211> LENGTH: 15
<212> TYPE: PRT
<213> ORGANISM: Artificial Sequence
<220> FEATURE:
<223> OTHER INFORMATION: Masking Moiety - YV42

<400> SEQUENCE: 42

Phe Gly Thr Ala Cys Pro Asn His Pro Leu Cys His Asp Trp Gln
1 5 10 15

<210> SEQ ID NO 43
<211> LENGTH: 11
<212> TYPE: PRT
<213> ORGANISM: Artificial Sequence
<220> FEATURE:
<223> OTHER INFORMATION: Masking Moiety - YV43

<400> SEQUENCE: 43

Cys Pro Asn His Pro Leu Cys His Asp Phe Gln
1 5 10

<210> SEQ ID NO 44
<211> LENGTH: 11
<212> TYPE: PRT
<213> ORGANISM: Artificial Sequence
<220> FEATURE:
<223> OTHER INFORMATION: Masking Moiety - YV44

<400> SEQUENCE: 44

Cys Pro Asn His Pro Leu Cys His Asp Tyr Gln
1 5 10

<210> SEQ ID NO 45
<211> LENGTH: 9
<212> TYPE: PRT
<213> ORGANISM: Artificial Sequence
<220> FEATURE:
<223> OTHER INFORMATION: Masking Moiety - YV45

<400> SEQUENCE: 45

Cys Pro Asn His Pro Leu Cys Pro Tyr
1 5

<210> SEQ ID NO 46
<211> LENGTH: 9
<212> TYPE: PRT
<213> ORGANISM: Artificial Sequence
<220> FEATURE:
<223> OTHER INFORMATION: Masking Moiety - YV46

<400> SEQUENCE: 46

Cys Pro Asn His Pro Leu Cys Pro Ala
1 5

<210> SEQ ID NO 47
<211> LENGTH: 11
<212> TYPE: PRT
<213> ORGANISM: Artificial Sequence
<220> FEATURE:
<223> OTHER INFORMATION: Masking Moiety - YV47

<400> SEQUENCE: 47

Cys Met Tyr Ser Phe Phe Asn Val Cys Tyr Pro
1 5 10

<210> SEQ ID NO 48
<211> LENGTH: 11
<212> TYPE: PRT
<213> ORGANISM: Artificial Sequence
<220> FEATURE:
<223> OTHER INFORMATION: Masking Moiety - YV48

<400> SEQUENCE: 48

Cys Met Tyr Ser Phe Phe Asn Val Cys Tyr Ala
1 5 10

<210> SEQ ID NO 49
<211> LENGTH: 11
<212> TYPE: PRT
<213> ORGANISM: Artificial Sequence
<220> FEATURE:
<223> OTHER INFORMATION: Masking Moiety - YV49

<400> SEQUENCE: 49

Cys Leu Tyr Ser Phe Phe Asn Val Cys Tyr Pro
1 5 10

<210> SEQ ID NO 50
<211> LENGTH: 11
<212> TYPE: PRT
<213> ORGANISM: Artificial Sequence
<220> FEATURE:
<223> OTHER INFORMATION: Masking Moiety - YV50

<400> SEQUENCE: 50

Cys Leu Tyr Ser Phe Phe Asn Val Cys Tyr Ala
1 5 10

<210> SEQ ID NO 51
<211> LENGTH: 15
<212> TYPE: PRT
<213> ORGANISM: Artificial Sequence
<220> FEATURE:
<223> OTHER INFORMATION: Masking Moiety - YV51

<400> SEQUENCE: 51

Phe Gly Ala Ala Cys Pro Asn His Pro Ile Cys His Asp Trp Gln
1 5 10 15

<210> SEQ ID NO 52
<211> LENGTH: 15
<212> TYPE: PRT
<213> ORGANISM: Artificial Sequence
<220> FEATURE:
<223> OTHER INFORMATION: Masking Moiety - YV52

<400> SEQUENCE: 52

Phe Gly Ala Ala Cys Pro Asn His Pro Leu Cys His Asp Trp Gln
1 5 10 15

<210> SEQ ID NO 53
<211> LENGTH: 15
<212> TYPE: PRT
<213> ORGANISM: Artificial Sequence
<220> FEATURE:
<223> OTHER INFORMATION: Masking Moiety - YV53

<400> SEQUENCE: 53

Phe Gly Ala Ala Cys Pro Asn His Pro Met Cys His Asp Ala Gln
1 5 10 15

<210> SEQ ID NO 54
<211> LENGTH: 12
<212> TYPE: PRT
<213> ORGANISM: Artificial Sequence
<220> FEATURE:
<223> OTHER INFORMATION: Masking Moiety - YV54

<400> SEQUENCE: 54

Cys Leu His Ser Ala Tyr Asn Ala Cys Leu Asp Pro
1 5 10

<210> SEQ ID NO 55
<211> LENGTH: 12
<212> TYPE: PRT
<213> ORGANISM: Artificial Sequence
<220> FEATURE:
<223> OTHER INFORMATION: Masking Moiety - YV55

<400> SEQUENCE: 55

Cys Ala His Ser Ala Tyr Asn Val Cys Leu Asp Pro
1 5 10

<210> SEQ ID NO 56
<211> LENGTH: 12
<212> TYPE: PRT
<213> ORGANISM: Artificial Sequence
<220> FEATURE:
<223> OTHER INFORMATION: Masking Moiety - YV56

<400> SEQUENCE: 56

Cys Leu His Ser Ala Tyr Asn Val Cys Ala Asp Pro
1 5 10

<210> SEQ ID NO 57
<211> LENGTH: 12
<212> TYPE: PRT
<213> ORGANISM: Artificial Sequence
<220> FEATURE:
<223> OTHER INFORMATION: Masking Moiety - YV57

<400> SEQUENCE: 57

Cys Leu His Ser Ala Tyr Asn Val Cys Leu Ala Pro
1 5 10

<210> SEQ ID NO 58
<211> LENGTH: 12
<212> TYPE: PRT
<213> ORGANISM: Artificial Sequence
<220> FEATURE:
<223> OTHER INFORMATION: Masking Moiety - YV58

<400> SEQUENCE: 58

Cys Leu His Ser Ala Tyr Asn Val Cys Leu Asp Ala
1 5 10

<210> SEQ ID NO 59
<211> LENGTH: 15
<212> TYPE: PRT
<213> ORGANISM: Artificial Sequence
<220> FEATURE:
<223> OTHER INFORMATION: Masking Moiety - YV60

<400> SEQUENCE: 59

Lys Asn Thr Cys Thr Tyr Val Met Tyr Asn Val Cys Leu Asp Pro
1 5 10 15

<210> SEQ ID NO 60
<211> LENGTH: 15
<212> TYPE: PRT
<213> ORGANISM: Artificial Sequence
<220> FEATURE:
<223> OTHER INFORMATION: Masking Moiety - YV61

<400> SEQUENCE: 60

Tyr Ile Ser Asp Cys Pro Tyr His Pro Met Cys His Asp Tyr Gln
1 5 10 15

<210> SEQ ID NO 61
<211> LENGTH: 15
<212> TYPE: PRT
<213> ORGANISM: Artificial Sequence
<220> FEATURE:
<223> OTHER INFORMATION: Masking Moiety - YV62

<400> SEQUENCE: 61

Phe Arg Asn Thr Cys Pro Tyr His Pro Met Cys His Asp Tyr Arg
1 5 10 15

<210> SEQ ID NO 62
<211> LENGTH: 15
<212> TYPE: PRT
<213> ORGANISM: Artificial Sequence
<220> FEATURE:
<223> OTHER INFORMATION: Masking Moiety - YV63

<400> SEQUENCE: 62

Arg Glu Cys His Met Trp Met Phe Gly Val Asn Leu Cys Pro Tyr 1 5 10 15

<210> SEQ ID NO 63
<211> LENGTH: 15
<212> TYPE: PRT
<213> ORGANISM: Artificial Sequence
<220> FEATURE:
<223> OTHER INFORMATION: Masking Moiety - YV64

<400> SEQUENCE: 63

Ala Val Cys His Met Tyr Met Tyr Gly Tyr Asn Leu Cys Pro Phe
1 5 10 15

<210> SEQ ID NO 64
<211> LENGTH: 15
<212> TYPE: PRT
<213> ORGANISM: Artificial Sequence
<220> FEATURE:
<223> OTHER INFORMATION: Masking Moiety - YV65

<400> SEQUENCE: 64

Arg Ser Cys Pro Gln Met Tyr Gly Tyr Ser Met Cys Pro His Thr
1 5 10 15

<210> SEQ ID NO 65
<211> LENGTH: 15
<212> TYPE: PRT
<213> ORGANISM: Artificial Sequence
<220> FEATURE:
<223> OTHER INFORMATION: Masking Moiety - YV66

<400> SEQUENCE: 65

Gln Pro Cys Ala Gln Met Phe Gly Tyr Ser Met Cys Pro His Thr
1 5 10 15

<210> SEQ ID NO 66
<211> LENGTH: 15
<212> TYPE: PRT
<213> ORGANISM: Artificial Sequence
<220> FEATURE:
<223> OTHER INFORMATION: Masking Moiety

<400> SEQUENCE: 66

Thr Ala Lys Cys Thr Tyr Ser Phe Phe Asn Val Cys Leu Asp Pro
1 5 10 15

<210> SEQ ID NO 67
<211> LENGTH: 15
<212> TYPE: PRT
<213> ORGANISM: Artificial Sequence
<220> FEATURE:
<223> OTHER INFORMATION: Masking Moiety

<400> SEQUENCE: 67

Asp Phe Ser Cys Leu Tyr Ser Met Tyr Asn Val Cys Leu Asp Pro
1 5 10 15

<210> SEQ ID NO 68
<211> LENGTH: 15
<212> TYPE: PRT
<213> ORGANISM: Artificial Sequence
<220> FEATURE:
<223> OTHER INFORMATION: Masking Moiety

<400> SEQUENCE: 68

Asp Val Ser Cys Met Tyr Met Met Tyr Asn Phe Cys Leu Asp Pro
1 5 10 15

<210> SEQ ID NO 69
<211> LENGTH: 7
<212> TYPE: PRT
<213> ORGANISM: Artificial Sequence
<220> FEATURE:
<223> OTHER INFORMATION: Masking Moiety

<400> SEQUENCE: 69

Cys Pro Asn His Pro Met Cys
1 5

<210> SEQ ID NO 70
<211> LENGTH: 11
<212> TYPE: PRT
<213> ORGANISM: Artificial Sequence
<220> FEATURE:
<223> OTHER INFORMATION: Masking Moiety

<400> SEQUENCE: 70

Cys Met Tyr Ser Phe Phe Asn Val Cys Pro Tyr
1 5 10

<210> SEQ ID NO 71
<211> LENGTH: 11
<212> TYPE: PRT
<213> ORGANISM: Artificial Sequence
<220> FEATURE:
<223> OTHER INFORMATION: Masking Moiety

<400> SEQUENCE: 71

Cys Met Tyr Ser Phe Phe Asn Val Cys Pro Ala
1 5 10

<210> SEQ ID NO 72
<211> LENGTH: 11
<212> TYPE: PRT
<213> ORGANISM: Artificial Sequence
<220> FEATURE:
<223> OTHER INFORMATION: Masking Moiety

<400> SEQUENCE: 72

Cys Thr Tyr Ser Phe Phe Asn Val Cys Pro Tyr
1 5 10

<210> SEQ ID NO 73
<211> LENGTH: 11
<212> TYPE: PRT
<213> ORGANISM: Artificial Sequence
<220> FEATURE:
<223> OTHER INFORMATION: Masking Moiety

<400> SEQUENCE: 73

Cys Thr Tyr Ser Phe Phe Asn Val Cys Pro Ala
1 5 10

<210> SEQ ID NO 74
<211> LENGTH: 15
<212> TYPE: PRT
<213> ORGANISM: Artificial Sequence
<220> FEATURE:
<223> OTHER INFORMATION: Masking Moiety

<400> SEQUENCE: 74

Gly Phe Pro Cys Met Tyr Ser Met Phe Asn Val Cys Leu Asp Pro
1 5 10 15

<210> SEQ ID NO 75
<211> LENGTH: 15
<212> TYPE: PRT
<213> ORGANISM: Artificial Sequence
<220> FEATURE:
<223> OTHER INFORMATION: Masking Moiety

<400> SEQUENCE: 75

Gly Leu Ser Cys Met Tyr Ser Met Tyr Gly Tyr Cys Leu Asp Pro
1 5 10 15

<210> SEQ ID NO 76
<211> LENGTH: 15
<212> TYPE: PRT
<213> ORGANISM: Artificial Sequence
<220> FEATURE:
<223> OTHER INFORMATION: Masking Moiety

<400> SEQUENCE: 76

Ile Pro Cys Asp Tyr Trp Met Phe Gly Val Asn Leu Cys Pro Tyr
1 5 10 15

<210> SEQ ID NO 77
<211> LENGTH: 15
<212> TYPE: PRT
<213> ORGANISM: Artificial Sequence
<220> FEATURE:
<223> OTHER INFORMATION: Masking Moiety

<400> SEQUENCE: 77

Gln Val Cys His Ala Tyr Met Tyr Gly Tyr Asn Leu Cys Pro Tyr
1 5 10 15

<210> SEQ ID NO 78
<211> LENGTH: 15
<212> TYPE: PRT
<213> ORGANISM: Artificial Sequence
<220> FEATURE:
<223> OTHER INFORMATION: Masking Moiety

<400> SEQUENCE: 78

Arg Met Tyr Cys Thr Tyr Ser Phe Tyr Asn Val Cys Leu Asp Pro
1 5 10 15

<210> SEQ ID NO 79
<211> LENGTH: 15
<212> TYPE: PRT
<213> ORGANISM: Artificial Sequence
<220> FEATURE:
<223> OTHER INFORMATION: Masking Moiety

<400> SEQUENCE: 79

Ala Leu Ser Cys Met Tyr Ile Met Tyr Asn Val Cys Leu Asp Pro
1 5 10 15

<210> SEQ ID NO 80
<211> LENGTH: 15
<212> TYPE: PRT
<213> ORGANISM: Artificial Sequence
<220> FEATURE:
<223> OTHER INFORMATION: Masking Moiety

<400> SEQUENCE: 80

Asp Phe Ser Cys Met Tyr Val Met Phe Asn Val Cys Leu Asp Pro
1 5 10 15

<210> SEQ ID NO 81
<211> LENGTH: 15
<212> TYPE: PRT
<213> ORGANISM: Artificial Sequence
<220> FEATURE:
<223> OTHER INFORMATION: Masking Moiety

<400> SEQUENCE: 81

Asp Phe Ser Cys Val Tyr Ser Met Phe Asn Val Cys Leu Asp Pro
1 5 10 15

<210> SEQ ID NO 82
<211> LENGTH: 15
<212> TYPE: PRT
<213> ORGANISM: Artificial Sequence
<220> FEATURE:
<223> OTHER INFORMATION: Masking Moiety

<400> SEQUENCE: 82

Asp Met Asn Thr Cys Pro Asn His Pro Met Cys Tyr Asp Tyr Arg
1 5 10 15

<210> SEQ ID NO 83
<211> LENGTH: 15
<212> TYPE: PRT
<213> ORGANISM: Artificial Sequence
<220> FEATURE:
<223> OTHER INFORMATION: Masking Moiety

<400> SEQUENCE: 83

Asp Met Asn Thr Cys Pro Arg His Pro Met Cys His Asp Tyr His
1 5 10 15

<210> SEQ ID NO 84
<211> LENGTH: 15
<212> TYPE: PRT
<213> ORGANISM: Artificial Sequence
<220> FEATURE:
<223> OTHER INFORMATION: Masking Moiety

<400> SEQUENCE: 84

Asp Ser Arg Cys Met Tyr Val Met Tyr Asn Val Cys Leu Asp Pro
1 5 10 15

<210> SEQ ID NO 85
<211> LENGTH: 15
<212> TYPE: PRT
<213> ORGANISM: Artificial Sequence
<220> FEATURE:
<223> OTHER INFORMATION: Masking Moiety

<400> SEQUENCE: 85

Glu His Leu Cys Thr Tyr Ser Phe Tyr Asn Val Cys Leu Asp Pro
1 5 10 15

<210> SEQ ID NO 86
<211> LENGTH: 15
<212> TYPE: PRT
<213> ORGANISM: Artificial Sequence
<220> FEATURE:
<223> OTHER INFORMATION: Masking Moiety

<400> SEQUENCE: 86

Glu Leu Ser Cys Val Tyr Ser Met Phe Gly Phe Cys Leu Asp Pro
1 5 10 15

<210> SEQ ID NO 87

```
<211> LENGTH: 15
<212> TYPE: PRT
<213> ORGANISM: Artificial Sequence
<220> FEATURE:
<223> OTHER INFORMATION: Masking Moiety

<400> SEQUENCE: 87

Phe Thr Asn Asn Cys Pro Tyr His Pro Met Cys His Asp Tyr Leu
1               5                   10                  15


<210> SEQ ID NO 88
<211> LENGTH: 15
<212> TYPE: PRT
<213> ORGANISM: Artificial Sequence
<220> FEATURE:
<223> OTHER INFORMATION: Masking Moiety

<400> SEQUENCE: 88

Gly Phe Ser Cys Thr Tyr Ile Met Tyr Asp Val Cys Leu Asp Pro
1               5                   10                  15


<210> SEQ ID NO 89
<211> LENGTH: 15
<212> TYPE: PRT
<213> ORGANISM: Artificial Sequence
<220> FEATURE:
<223> OTHER INFORMATION: Masking Moiety

<400> SEQUENCE: 89

Gly Ser Ser Cys Met Tyr Ser Met Tyr Asn Val Cys Leu Asp Pro
1               5                   10                  15


<210> SEQ ID NO 90
<211> LENGTH: 15
<212> TYPE: PRT
<213> ORGANISM: Artificial Sequence
<220> FEATURE:
<223> OTHER INFORMATION: Masking Moiety

<400> SEQUENCE: 90

His Phe Ser Cys Met Tyr Ile Met Tyr Asn Val Cys Leu Asp Pro
1               5                   10                  15


<210> SEQ ID NO 91
<211> LENGTH: 15
<212> TYPE: PRT
<213> ORGANISM: Artificial Sequence
<220> FEATURE:
<223> OTHER INFORMATION: Masking Moiety

<400> SEQUENCE: 91

Leu His Cys Gly Met Trp Met Phe Gly Val Asn Leu Cys Pro Lys
1               5                   10                  15


<210> SEQ ID NO 92
<211> LENGTH: 15
<212> TYPE: PRT
<213> ORGANISM: Artificial Sequence
<220> FEATURE:
<223> OTHER INFORMATION: Masking Moiety

<400> SEQUENCE: 92

Leu Pro Cys Gln Met Trp Met Phe Gly His Asn Leu Cys Pro His
1               5                   10                  15


<210> SEQ ID NO 93
<211> LENGTH: 15
```

<212> TYPE: PRT
<213> ORGANISM: Artificial Sequence
<220> FEATURE:
<223> OTHER INFORMATION: Masking Moiety

<400> SEQUENCE: 93

Leu Pro Cys Thr Met Tyr Met Tyr Gly Tyr Asn Leu Cys Pro Tyr
1 5 10 15

<210> SEQ ID NO 94
<211> LENGTH: 15
<212> TYPE: PRT
<213> ORGANISM: Artificial Sequence
<220> FEATURE:
<223> OTHER INFORMATION: Masking Moiety

<400> SEQUENCE: 94

Leu Thr Cys His His Trp Met Phe Gly Val Asn Leu Cys Pro Tyr
1 5 10 15

<210> SEQ ID NO 95
<211> LENGTH: 15
<212> TYPE: PRT
<213> ORGANISM: Artificial Sequence
<220> FEATURE:
<223> OTHER INFORMATION: Masking Moiety

<400> SEQUENCE: 95

Asn Phe Ser Cys Met Tyr Ser Met Phe Asn Val Cys Leu Asp Pro
1 5 10 15

<210> SEQ ID NO 96
<211> LENGTH: 15
<212> TYPE: PRT
<213> ORGANISM: Artificial Sequence
<220> FEATURE:
<223> OTHER INFORMATION: Masking Moiety

<400> SEQUENCE: 96

Asn Asn His Cys Met Tyr Ser Phe Phe Asn Ile Cys Leu Asp Pro
1 5 10 15

<210> SEQ ID NO 97
<211> LENGTH: 15
<212> TYPE: PRT
<213> ORGANISM: Artificial Sequence
<220> FEATURE:
<223> OTHER INFORMATION: Masking Moiety

<400> SEQUENCE: 97

Asn Arg Ser Cys Met Tyr Ile Met Tyr Asn Val Cys Leu Asp Pro
1 5 10 15

<210> SEQ ID NO 98
<211> LENGTH: 15
<212> TYPE: PRT
<213> ORGANISM: Artificial Sequence
<220> FEATURE:
<223> OTHER INFORMATION: Masking Moiety

<400> SEQUENCE: 98

Asn Ser Cys Thr Met Phe Met Phe Gly Val Asn Leu Cys Pro Tyr
1 5 10 15

<210> SEQ ID NO 99
<211> LENGTH: 15
<212> TYPE: PRT

<213> ORGANISM: Artificial Sequence
<220> FEATURE:
<223> OTHER INFORMATION: Masking Moiety

<400> SEQUENCE: 99

Asn Thr Cys Glu Leu Tyr Met Phe Gly Val Asn Leu Cys Pro Tyr
1 5 10 15

<210> SEQ ID NO 100
<211> LENGTH: 15
<212> TYPE: PRT
<213> ORGANISM: Artificial Sequence
<220> FEATURE:
<223> OTHER INFORMATION: Masking Moiety

<400> SEQUENCE: 100

Gln His Cys Asp Met Trp Met Phe Gly Tyr Asn Leu Cys Pro Tyr
1 5 10 15

<210> SEQ ID NO 101
<211> LENGTH: 15
<212> TYPE: PRT
<213> ORGANISM: Artificial Sequence
<220> FEATURE:
<223> OTHER INFORMATION: Masking Moiety

<400> SEQUENCE: 101

Gln His Cys Pro Met Tyr Met Phe Gly Tyr Asn Leu Cys Pro Phe
1 5 10 15

<210> SEQ ID NO 102
<211> LENGTH: 15
<212> TYPE: PRT
<213> ORGANISM: Artificial Sequence
<220> FEATURE:
<223> OTHER INFORMATION: Masking Moiety

<400> SEQUENCE: 102

Gln Val Cys His Ile Gln Met Tyr Gly Phe Asp Leu Cys Pro His
1 5 10 15

<210> SEQ ID NO 103
<211> LENGTH: 15
<212> TYPE: PRT
<213> ORGANISM: Artificial Sequence
<220> FEATURE:
<223> OTHER INFORMATION: Masking Moiety

<400> SEQUENCE: 103

Arg Ala Cys Asp Tyr Trp Met Tyr Gly Val Asn Leu Cys Pro Tyr
1 5 10 15

<210> SEQ ID NO 104
<211> LENGTH: 15
<212> TYPE: PRT
<213> ORGANISM: Artificial Sequence
<220> FEATURE:
<223> OTHER INFORMATION: Masking Moiety

<400> SEQUENCE: 104

Arg Gln Cys His Met Gln Met Phe Gly Tyr Asp Leu Cys Pro Phe
1 5 10 15

<210> SEQ ID NO 105
<211> LENGTH: 15
<212> TYPE: PRT
<213> ORGANISM: Artificial Sequence
<220> FEATURE:
<223> OTHER INFORMATION: Masking Moiety

<400> SEQUENCE: 105

Ser Gly Ser Cys Leu Tyr Ser Phe Tyr Asn Val Cys Leu Asp Pro
1 5 10 15

<210> SEQ ID NO 106
<211> LENGTH: 15
<212> TYPE: PRT
<213> ORGANISM: Artificial Sequence
<220> FEATURE:
<223> OTHER INFORMATION: Masking Moiety

<400> SEQUENCE: 106

Ser Asn Gly Cys Thr Tyr Ser Phe Phe Asn Val Cys Leu Asp Pro
1 5 10 15

<210> SEQ ID NO 107
<211> LENGTH: 14
<212> TYPE: PRT
<213> ORGANISM: Artificial Sequence
<220> FEATURE:
<223> OTHER INFORMATION: Masking Moiety

<400> SEQUENCE: 107

Ser Thr Cys Ala Gln Met Tyr Gly Tyr Ser Met Cys Pro His
1 5 10

<210> SEQ ID NO 108
<211> LENGTH: 15
<212> TYPE: PRT
<213> ORGANISM: Artificial Sequence
<220> FEATURE:
<223> OTHER INFORMATION: Masking Moiety

<400> SEQUENCE: 108

Ser Tyr Lys Cys Leu Tyr Ser Phe Tyr Asn Val Cys Leu Asp Pro
1 5 10 15

<210> SEQ ID NO 109
<211> LENGTH: 15
<212> TYPE: PRT
<213> ORGANISM: Artificial Sequence
<220> FEATURE:
<223> OTHER INFORMATION: Masking Moiety

<400> SEQUENCE: 109

Val Leu Tyr Cys Thr Tyr Val Met Tyr Asn Val Cys Leu Asp Pro
1 5 10 15

<210> SEQ ID NO 110
<211> LENGTH: 15
<212> TYPE: PRT
<213> ORGANISM: Artificial Sequence
<220> FEATURE:
<223> OTHER INFORMATION: Masking Moiety

<400> SEQUENCE: 110

Val Asn Cys Gly Met Trp Met Phe Gly Tyr Asn Leu Cys Pro Lys
1 5 10 15

<210> SEQ ID NO 111
<211> LENGTH: 15
<212> TYPE: PRT
<213> ORGANISM: Artificial Sequence
<220> FEATURE:

<223> OTHER INFORMATION: Masking Moiety

<400> SEQUENCE: 111

```
Tyr Gly Ser Cys Leu Tyr Ser Phe Tyr Asn Ile Cys Leu Asp Pro
1               5                   10                  15
```

<210> SEQ ID NO 112
<211> LENGTH: 15
<212> TYPE: PRT
<213> ORGANISM: Artificial Sequence
<220> FEATURE:
<223> OTHER INFORMATION: Masking Moiety

<400> SEQUENCE: 112

```
Tyr Pro Cys Ala Gln Met Tyr Gly Tyr Ser Met Cys Pro His Thr
1               5                   10                  15
```

<210> SEQ ID NO 113
<211> LENGTH: 15
<212> TYPE: PRT
<213> ORGANISM: Artificial Sequence
<220> FEATURE:
<223> OTHER INFORMATION: Masking Moiety

<400> SEQUENCE: 113

```
Ala Ala Cys Asp Leu Trp Met Phe Gly Val Asn Leu Cys Pro Tyr
1               5                   10                  15
```

<210> SEQ ID NO 114
<211> LENGTH: 15
<212> TYPE: PRT
<213> ORGANISM: Artificial Sequence
<220> FEATURE:
<223> OTHER INFORMATION: Masking Moiety

<400> SEQUENCE: 114

```
Ala Phe Cys Thr Leu Ala Pro Tyr Asn Gln Ala Cys Ile Ala Asn
1               5                   10                  15
```

<210> SEQ ID NO 115
<211> LENGTH: 15
<212> TYPE: PRT
<213> ORGANISM: Artificial Sequence
<220> FEATURE:
<223> OTHER INFORMATION: Masking Moiety

<400> SEQUENCE: 115

```
Ala Gly Ser Cys Leu Tyr Ser Met Tyr Asn Val Cys Leu Asp Pro
1               5                   10                  15
```

<210> SEQ ID NO 116
<211> LENGTH: 15
<212> TYPE: PRT
<213> ORGANISM: Artificial Sequence
<220> FEATURE:
<223> OTHER INFORMATION: Masking Moiety

<400> SEQUENCE: 116

```
Ala Leu Cys Glu Asn Thr Met Tyr Gly Tyr His Leu Cys Pro Trp
1               5                   10                  15
```

<210> SEQ ID NO 117
<211> LENGTH: 15
<212> TYPE: PRT
<213> ORGANISM: Artificial Sequence
<220> FEATURE:
<223> OTHER INFORMATION: Masking Moiety

<400> SEQUENCE: 117

Ala Leu Ser Cys Met Tyr Ile Met Tyr Gly Val Cys Leu Asp Pro
1 5 10 15

<210> SEQ ID NO 118
<211> LENGTH: 15
<212> TYPE: PRT
<213> ORGANISM: Artificial Sequence
<220> FEATURE:
<223> OTHER INFORMATION: Masking Moiety

<400> SEQUENCE: 118

Ala Pro Val Cys Asp Val Leu Met Phe Gly Phe Cys Met Gln Pro
1 5 10 15

<210> SEQ ID NO 119
<211> LENGTH: 15
<212> TYPE: PRT
<213> ORGANISM: Artificial Sequence
<220> FEATURE:
<223> OTHER INFORMATION: Masking Moiety

<400> SEQUENCE: 119

Ala Gln Val Cys Ser Ile Met Met Tyr Gly Thr Cys Leu Met Pro
1 5 10 15

<210> SEQ ID NO 120
<211> LENGTH: 15
<212> TYPE: PRT
<213> ORGANISM: Artificial Sequence
<220> FEATURE:
<223> OTHER INFORMATION: Masking Moiety

<400> SEQUENCE: 120

Ala Ser Thr Cys Met Tyr Ser Phe Tyr Asn Val Cys Leu Asp Pro
1 5 10 15

<210> SEQ ID NO 121
<211> LENGTH: 15
<212> TYPE: PRT
<213> ORGANISM: Artificial Sequence
<220> FEATURE:
<223> OTHER INFORMATION: Masking Moiety

<400> SEQUENCE: 121

Ala Val Cys Glu Phe Trp Met Phe Gly Phe Asn Leu Cys Pro Tyr
1 5 10 15

<210> SEQ ID NO 122
<211> LENGTH: 15
<212> TYPE: PRT
<213> ORGANISM: Artificial Sequence
<220> FEATURE:
<223> OTHER INFORMATION: Masking Moiety

<400> SEQUENCE: 122

Asp Ala Asn Thr Cys Pro Asn His Pro Met Cys Tyr Asp Tyr His
1 5 10 15

<210> SEQ ID NO 123
<211> LENGTH: 15
<212> TYPE: PRT
<213> ORGANISM: Artificial Sequence
<220> FEATURE:
<223> OTHER INFORMATION: Masking Moiety

<400> SEQUENCE: 123

Asp Phe Ser Cys Ile Tyr Ile Met Phe Asp Val Cys Leu Asp Pro
1 5 10 15

<210> SEQ ID NO 124
<211> LENGTH: 15
<212> TYPE: PRT
<213> ORGANISM: Artificial Sequence
<220> FEATURE:
<223> OTHER INFORMATION: Masking Moiety

<400> SEQUENCE: 124

Asp Phe Ser Cys Met Tyr Val Met Tyr Gly Phe Cys Leu Asp Pro
1 5 10 15

<210> SEQ ID NO 125
<211> LENGTH: 15
<212> TYPE: PRT
<213> ORGANISM: Artificial Sequence
<220> FEATURE:
<223> OTHER INFORMATION: Masking Moiety

<400> SEQUENCE: 125

Asp Phe Thr Cys Met Tyr Ser Met Tyr Asn Val Cys Leu Asp Pro
1 5 10 15

<210> SEQ ID NO 126
<211> LENGTH: 15
<212> TYPE: PRT
<213> ORGANISM: Artificial Sequence
<220> FEATURE:
<223> OTHER INFORMATION: Masking Moiety

<400> SEQUENCE: 126

Asp Phe Thr Cys Thr Tyr Ser Met Tyr Asn Val Cys Leu Asp Pro
1 5 10 15

<210> SEQ ID NO 127
<211> LENGTH: 15
<212> TYPE: PRT
<213> ORGANISM: Artificial Sequence
<220> FEATURE:
<223> OTHER INFORMATION: Masking Moiety

<400> SEQUENCE: 127

Asp His Tyr Cys Thr Tyr Ile Met Tyr Ser Ile Cys Leu Asp Pro
1 5 10 15

<210> SEQ ID NO 128
<211> LENGTH: 15
<212> TYPE: PRT
<213> ORGANISM: Artificial Sequence
<220> FEATURE:
<223> OTHER INFORMATION: Masking Moiety

<400> SEQUENCE: 128

Asp Ile Cys Thr Asn Phe Met Phe Gly Val Asn Leu Cys Pro Tyr
1 5 10 15

<210> SEQ ID NO 129
<211> LENGTH: 15
<212> TYPE: PRT
<213> ORGANISM: Artificial Sequence
<220> FEATURE:
<223> OTHER INFORMATION: Masking Moiety

<400> SEQUENCE: 129

Asp Ile Asn Thr Cys Pro Tyr His Pro Met Cys His Asp Tyr His
1 5 10 15

<210> SEQ ID NO 130
<211> LENGTH: 15
<212> TYPE: PRT
<213> ORGANISM: Artificial Sequence
<220> FEATURE:
<223> OTHER INFORMATION: Masking Moiety

<400> SEQUENCE: 130

Asp Lys Asn Thr Cys Pro Leu His Pro Met Cys His Asp Tyr Arg
1 5 10 15

<210> SEQ ID NO 131
<211> LENGTH: 15
<212> TYPE: PRT
<213> ORGANISM: Artificial Sequence
<220> FEATURE:
<223> OTHER INFORMATION: Masking Moiety

<400> SEQUENCE: 131

Asp Met Asn Met Cys Pro Asn His Pro Met Cys His Asp Trp His
1 5 10 15

<210> SEQ ID NO 132
<211> LENGTH: 15
<212> TYPE: PRT
<213> ORGANISM: Artificial Sequence
<220> FEATURE:
<223> OTHER INFORMATION: Masking Moiety

<400> SEQUENCE: 132

Asp Met Asn Ser Cys Pro Asn His Pro Met Cys His Asp Tyr His
1 5 10 15

<210> SEQ ID NO 133
<211> LENGTH: 15
<212> TYPE: PRT
<213> ORGANISM: Artificial Sequence
<220> FEATURE:
<223> OTHER INFORMATION: Masking Moiety

<400> SEQUENCE: 133

Asp Met Asn Ser Cys Pro Asn His Pro Met Cys Tyr Asp Tyr Arg
1 5 10 15

<210> SEQ ID NO 134
<211> LENGTH: 15
<212> TYPE: PRT
<213> ORGANISM: Artificial Sequence
<220> FEATURE:
<223> OTHER INFORMATION: Masking Moiety

<400> SEQUENCE: 134

Asp Met Asn Thr Cys Pro Asn His Pro Met Cys Phe Asp Tyr Arg
1 5 10 15

<210> SEQ ID NO 135
<211> LENGTH: 15
<212> TYPE: PRT
<213> ORGANISM: Artificial Sequence
<220> FEATURE:
<223> OTHER INFORMATION: Masking Moiety

<400> SEQUENCE: 135

Asp Met Asn Thr Cys Pro Asn His Pro Met Cys His Asp Phe Gln
1 5 10 15

<210> SEQ ID NO 136
<211> LENGTH: 15
<212> TYPE: PRT
<213> ORGANISM: Artificial Sequence
<220> FEATURE:
<223> OTHER INFORMATION: Masking Moiety

<400> SEQUENCE: 136

Asp Met Asn Thr Cys Pro Asn His Pro Met Cys His Asp Tyr Arg
1 5 10 15

<210> SEQ ID NO 137
<211> LENGTH: 15
<212> TYPE: PRT
<213> ORGANISM: Artificial Sequence
<220> FEATURE:
<223> OTHER INFORMATION: Masking Moiety

<400> SEQUENCE: 137

Asp Met Asn Thr Cys Pro Asn His Pro Met Cys Tyr Asp Tyr His
1 5 10 15

<210> SEQ ID NO 138
<211> LENGTH: 15
<212> TYPE: PRT
<213> ORGANISM: Artificial Sequence
<220> FEATURE:
<223> OTHER INFORMATION: Masking Moiety

<400> SEQUENCE: 138

Asp Met Asn Thr Cys Pro Asn His Pro Met Cys Tyr Asp Tyr Lys
1 5 10 15

<210> SEQ ID NO 139
<211> LENGTH: 15
<212> TYPE: PRT
<213> ORGANISM: Artificial Sequence
<220> FEATURE:
<223> OTHER INFORMATION: Masking Moiety

<400> SEQUENCE: 139

Asp Met Ser Thr Cys Pro Asn His Pro Met Cys His Asp Tyr Met
1 5 10 15

<210> SEQ ID NO 140
<211> LENGTH: 15
<212> TYPE: PRT
<213> ORGANISM: Artificial Sequence
<220> FEATURE:
<223> OTHER INFORMATION: Masking Moiety

<400> SEQUENCE: 140

Asp Arg Asn Met Cys Pro Tyr His Pro Met Cys Tyr Asp Tyr Arg
1 5 10 15

<210> SEQ ID NO 141
<211> LENGTH: 15
<212> TYPE: PRT
<213> ORGANISM: Artificial Sequence
<220> FEATURE:
<223> OTHER INFORMATION: Masking Moiety

<400> SEQUENCE: 141

Asp Ser Cys Ala Phe Met Met Phe Gly Val Asn Leu Cys Pro Tyr 1 5 10 15

<210> SEQ ID NO 142
<211> LENGTH: 15
<212> TYPE: PRT
<213> ORGANISM: Artificial Sequence
<220> FEATURE:
<223> OTHER INFORMATION: Masking Moiety

<400> SEQUENCE: 142

Asp Ser Cys Arg Ser Val Phe Asp Met Val Trp Asn Cys Trp Asn
1 5 10 15

<210> SEQ ID NO 143
<211> LENGTH: 15
<212> TYPE: PRT
<213> ORGANISM: Artificial Sequence
<220> FEATURE:
<223> OTHER INFORMATION: Masking Moiety

<400> SEQUENCE: 143

Asp Thr Pro Asn Cys Pro His His Pro Met Cys His Asn His Met
1 5 10 15

<210> SEQ ID NO 144
<211> LENGTH: 15
<212> TYPE: PRT
<213> ORGANISM: Artificial Sequence
<220> FEATURE:
<223> OTHER INFORMATION: Masking Moiety

<400> SEQUENCE: 144

Asp Val Ser Cys Leu Tyr Val Met Tyr Ser Val Cys Leu Asp Pro
1 5 10 15

<210> SEQ ID NO 145
<211> LENGTH: 15
<212> TYPE: PRT
<213> ORGANISM: Artificial Sequence
<220> FEATURE:
<223> OTHER INFORMATION: Masking Moiety

<400> SEQUENCE: 145

Asp Trp Cys Ala Ser Met Met Phe Gly Tyr Asn Leu Cys Pro Tyr
1 5 10 15

<210> SEQ ID NO 146
<211> LENGTH: 15
<212> TYPE: PRT
<213> ORGANISM: Artificial Sequence
<220> FEATURE:
<223> OTHER INFORMATION: Masking Moiety

<400> SEQUENCE: 146

Glu Phe Ser Cys Met Tyr Ser Met Phe Asn Val Cys Leu Asp Pro
1 5 10 15

<210> SEQ ID NO 147
<211> LENGTH: 15
<212> TYPE: PRT
<213> ORGANISM: Artificial Sequence
<220> FEATURE:
<223> OTHER INFORMATION: Masking Moiety

<400> SEQUENCE: 147

Glu His Cys Asp Val Trp Met Phe Gly Phe Asn Leu Cys Pro Tyr
1 5 10 15

<210> SEQ ID NO 148
<211> LENGTH: 15
<212> TYPE: PRT
<213> ORGANISM: Artificial Sequence
<220> FEATURE:
<223> OTHER INFORMATION: Masking Moiety

<400> SEQUENCE: 148

Glu Pro Cys Asp Tyr Trp Met Phe Gly Val Asn Leu Cys Pro Tyr
1 5 10 15

<210> SEQ ID NO 149
<211> LENGTH: 15
<212> TYPE: PRT
<213> ORGANISM: Artificial Sequence
<220> FEATURE:
<223> OTHER INFORMATION: Masking Moiety

<400> SEQUENCE: 149

Glu Gln Cys Thr Met Trp Met Tyr Gly Phe Asn Leu Cys Pro Tyr
1 5 10 15

<210> SEQ ID NO 150
<211> LENGTH: 15
<212> TYPE: PRT
<213> ORGANISM: Artificial Sequence
<220> FEATURE:
<223> OTHER INFORMATION: Masking Moiety

<400> SEQUENCE: 150

Glu Ser Ala Cys Ser Leu Arg Met Tyr Glu Val Cys Leu Gln Pro
1 5 10 15

<210> SEQ ID NO 151
<211> LENGTH: 15
<212> TYPE: PRT
<213> ORGANISM: Artificial Sequence
<220> FEATURE:
<223> OTHER INFORMATION: Masking Moiety

<400> SEQUENCE: 151

Glu Ser Cys Ala Ser Met Tyr Gly Tyr Ser Met Cys Pro Arg Thr
1 5 10 15

<210> SEQ ID NO 152
<211> LENGTH: 15
<212> TYPE: PRT
<213> ORGANISM: Artificial Sequence
<220> FEATURE:
<223> OTHER INFORMATION: Masking Moiety

<400> SEQUENCE: 152

Glu Ser Cys Ser Tyr Trp Met Phe Gly Tyr Asn Leu Cys Pro Tyr
1 5 10 15

<210> SEQ ID NO 153
<211> LENGTH: 15
<212> TYPE: PRT
<213> ORGANISM: Artificial Sequence
<220> FEATURE:
<223> OTHER INFORMATION: Masking Moiety

<400> SEQUENCE: 153

Phe Ser Asn Thr Cys Pro His His Pro Met Cys Tyr Asp Tyr Arg
1 5 10 15

<210> SEQ ID NO 154
<211> LENGTH: 15
<212> TYPE: PRT
<213> ORGANISM: Artificial Sequence
<220> FEATURE:
<223> OTHER INFORMATION: Masking Moiety

<400> SEQUENCE: 154

Phe Trp Asn Thr Cys Pro His His Pro Met Cys His Asp Tyr Lys
1 5 10 15

<210> SEQ ID NO 155
<211> LENGTH: 15
<212> TYPE: PRT
<213> ORGANISM: Artificial Sequence
<220> FEATURE:
<223> OTHER INFORMATION: Masking Moiety

<400> SEQUENCE: 155

Phe Tyr Gln Asn Cys Tyr Pro Pro Thr Trp Cys Ser Met Phe Ser
1 5 10 15

<210> SEQ ID NO 156
<211> LENGTH: 15
<212> TYPE: PRT
<213> ORGANISM: Artificial Sequence
<220> FEATURE:
<223> OTHER INFORMATION: Masking Moiety

<400> SEQUENCE: 156

Gly Glu Cys Ser Tyr Trp Met Phe Gly Tyr Asn Leu Cys Pro Tyr
1 5 10 15

<210> SEQ ID NO 157
<211> LENGTH: 15
<212> TYPE: PRT
<213> ORGANISM: Artificial Sequence
<220> FEATURE:
<223> OTHER INFORMATION: Masking Moiety

<400> SEQUENCE: 157

Gly Gly Ser Cys Met Tyr Ser Phe Phe Asn Ile Cys Leu Asp Pro
1 5 10 15

<210> SEQ ID NO 158
<211> LENGTH: 15
<212> TYPE: PRT
<213> ORGANISM: Artificial Sequence
<220> FEATURE:
<223> OTHER INFORMATION: Masking Moiety

<400> SEQUENCE: 158

Gly Gly Ser Cys Val Tyr Val Met Tyr Asn Val Cys Leu Asp Pro
1 5 10 15

<210> SEQ ID NO 159
<211> LENGTH: 15
<212> TYPE: PRT
<213> ORGANISM: Artificial Sequence
<220> FEATURE:
<223> OTHER INFORMATION: Masking Moiety

<400> SEQUENCE: 159

Gly His Cys Leu Met His Met Tyr Gly Tyr Asn Leu Cys Pro Lys
1 5 10 15

<210> SEQ ID NO 160
<211> LENGTH: 15
<212> TYPE: PRT
<213> ORGANISM: Artificial Sequence
<220> FEATURE:
<223> OTHER INFORMATION: Masking Moiety

<400> SEQUENCE: 160

Gly His Cys Arg Met Ser Met Tyr Glu Met Thr Leu Cys Pro Arg
1 5 10 15

<210> SEQ ID NO 161
<211> LENGTH: 15
<212> TYPE: PRT
<213> ORGANISM: Artificial Sequence
<220> FEATURE:
<223> OTHER INFORMATION: Masking Moiety

<400> SEQUENCE: 161

Gly Ile Ser Cys Val His Ile Met Phe Asn Phe Cys Leu Asp Pro
1 5 10 15

<210> SEQ ID NO 162
<211> LENGTH: 15
<212> TYPE: PRT
<213> ORGANISM: Artificial Sequence
<220> FEATURE:
<223> OTHER INFORMATION: Masking Moiety

<400> SEQUENCE: 162

Gly Leu Cys Val Met Tyr Met Phe Gly Val Asn Leu Cys Pro Tyr
1 5 10 15

<210> SEQ ID NO 163
<211> LENGTH: 15
<212> TYPE: PRT
<213> ORGANISM: Artificial Sequence
<220> FEATURE:
<223> OTHER INFORMATION: Masking Moiety

<400> SEQUENCE: 163

Gly Ser Cys Asp Tyr Trp Met Phe Gly Tyr Asn Leu Cys Pro Tyr
1 5 10 15

<210> SEQ ID NO 164
<211> LENGTH: 15
<212> TYPE: PRT
<213> ORGANISM: Artificial Sequence
<220> FEATURE:
<223> OTHER INFORMATION: Masking Moiety

<400> SEQUENCE: 164

Gly Ser Tyr Cys Met Tyr Val Met Tyr Asn Val Cys Leu Asp Pro
1 5 10 15

<210> SEQ ID NO 165
<211> LENGTH: 15
<212> TYPE: PRT
<213> ORGANISM: Artificial Sequence
<220> FEATURE:
<223> OTHER INFORMATION: Masking Moiety

<400> SEQUENCE: 165

Gly Thr Lys Cys Ile Tyr Ser Phe Tyr Asn Val Cys Leu Asp Pro
1 5 10 15

<210> SEQ ID NO 166

<211> LENGTH: 15
<212> TYPE: PRT
<213> ORGANISM: Artificial Sequence
<220> FEATURE:
<223> OTHER INFORMATION: Masking Moiety

<400> SEQUENCE: 166

Gly Thr Ser Thr Cys Pro Tyr His Pro Met Cys His Asp Tyr Arg
1 5 10 15

<210> SEQ ID NO 167
<211> LENGTH: 15
<212> TYPE: PRT
<213> ORGANISM: Artificial Sequence
<220> FEATURE:
<223> OTHER INFORMATION: Masking Moiety

<400> SEQUENCE: 167

Gly Thr Thr Cys Thr Tyr Ser Phe Phe Asn Val Cys Leu Asp Pro
1 5 10 15

<210> SEQ ID NO 168
<211> LENGTH: 15
<212> TYPE: PRT
<213> ORGANISM: Artificial Sequence
<220> FEATURE:
<223> OTHER INFORMATION: Masking Moiety

<400> SEQUENCE: 168

Gly Val Cys His Phe Phe Met Tyr Gly Val Ser Met Cys Pro Ala
1 5 10 15

<210> SEQ ID NO 169
<211> LENGTH: 15
<212> TYPE: PRT
<213> ORGANISM: Artificial Sequence
<220> FEATURE:
<223> OTHER INFORMATION: Masking Moiety

<400> SEQUENCE: 169

Gly Val Pro Cys Trp Tyr Ser Met Tyr Asn Val Cys Leu Asp Pro
1 5 10 15

<210> SEQ ID NO 170
<211> LENGTH: 15
<212> TYPE: PRT
<213> ORGANISM: Artificial Sequence
<220> FEATURE:
<223> OTHER INFORMATION: Masking Moiety

<400> SEQUENCE: 170

Gly Val Ser Cys Met Tyr Ser Met Phe Asn Ile Cys Leu Asp Pro
1 5 10 15

<210> SEQ ID NO 171
<211> LENGTH: 15
<212> TYPE: PRT
<213> ORGANISM: Artificial Sequence
<220> FEATURE:
<223> OTHER INFORMATION: Masking Moiety

<400> SEQUENCE: 171

His Ala Lys Cys Val Tyr Ser Phe Phe Asn Val Cys Leu Asp Pro
1 5 10 15

<210> SEQ ID NO 172
<211> LENGTH: 15

<212> TYPE: PRT
<213> ORGANISM: Artificial Sequence
<220> FEATURE:
<223> OTHER INFORMATION: Masking Moiety

<400> SEQUENCE: 172

His Asp Ser Cys Met Tyr Ser Met Tyr Asn Phe Cys Leu Asp Pro
1 5 10 15

<210> SEQ ID NO 173
<211> LENGTH: 15
<212> TYPE: PRT
<213> ORGANISM: Artificial Sequence
<220> FEATURE:
<223> OTHER INFORMATION: Masking Moiety

<400> SEQUENCE: 173

His Gly Asn Thr Cys Pro Asn His Pro Met Cys His Asp Tyr Gln
1 5 10 15

<210> SEQ ID NO 174
<211> LENGTH: 15
<212> TYPE: PRT
<213> ORGANISM: Artificial Sequence
<220> FEATURE:
<223> OTHER INFORMATION: Masking Moiety

<400> SEQUENCE: 174

His Lys Gly Cys Leu Tyr Ser Phe Tyr Asn Ile Cys Leu Asp Pro
1 5 10 15

<210> SEQ ID NO 175
<211> LENGTH: 15
<212> TYPE: PRT
<213> ORGANISM: Artificial Sequence
<220> FEATURE:
<223> OTHER INFORMATION: Masking Moiety

<400> SEQUENCE: 175

His Lys Gly Cys Leu Tyr Ser Phe Tyr Asn Val Cys Leu Asp Pro
1 5 10 15

<210> SEQ ID NO 176
<211> LENGTH: 15
<212> TYPE: PRT
<213> ORGANISM: Artificial Sequence
<220> FEATURE:
<223> OTHER INFORMATION: Masking Moiety

<400> SEQUENCE: 176

His Leu Ser Cys Met Tyr Ile Met Tyr Asn Val Cys Leu Asp Pro
1 5 10 15

<210> SEQ ID NO 177
<211> LENGTH: 15
<212> TYPE: PRT
<213> ORGANISM: Artificial Sequence
<220> FEATURE:
<223> OTHER INFORMATION: Masking Moiety

<400> SEQUENCE: 177

His Ser Ser Cys Ile Tyr Ser Met Phe Asn Val Cys Leu Asp Pro
1 5 10 15

<210> SEQ ID NO 178
<211> LENGTH: 15
<212> TYPE: PRT

<213> ORGANISM: Artificial Sequence
<220> FEATURE:
<223> OTHER INFORMATION: Masking Moiety

<400> SEQUENCE: 178

His Thr Asn Met Cys Pro Tyr His Pro Met Cys Tyr Asp Tyr Lys
1 5 10 15

<210> SEQ ID NO 179
<211> LENGTH: 15
<212> TYPE: PRT
<213> ORGANISM: Artificial Sequence
<220> FEATURE:
<223> OTHER INFORMATION: Masking Moiety

<400> SEQUENCE: 179

His Thr Pro Cys Thr Tyr Ser Phe Phe Asn Val Cys Leu Asp Pro
1 5 10 15

<210> SEQ ID NO 180
<211> LENGTH: 15
<212> TYPE: PRT
<213> ORGANISM: Artificial Sequence
<220> FEATURE:
<223> OTHER INFORMATION: Masking Moiety

<400> SEQUENCE: 180

Ile Met Asn Thr Cys Pro Tyr His Pro Met Cys His Asp Tyr Gln
1 5 10 15

<210> SEQ ID NO 181
<211> LENGTH: 15
<212> TYPE: PRT
<213> ORGANISM: Artificial Sequence
<220> FEATURE:
<223> OTHER INFORMATION: Masking Moiety

<400> SEQUENCE: 181

Ile Val Pro Cys Thr Tyr Met Met Phe Gly Val Cys Leu Gln Pro
1 5 10 15

<210> SEQ ID NO 182
<211> LENGTH: 15
<212> TYPE: PRT
<213> ORGANISM: Artificial Sequence
<220> FEATURE:
<223> OTHER INFORMATION: Masking Moiety

<400> SEQUENCE: 182

Lys Lys Cys Asp Tyr Trp Phe Tyr Gly Val Asn Leu Cys Pro Tyr
1 5 10 15

<210> SEQ ID NO 183
<211> LENGTH: 15
<212> TYPE: PRT
<213> ORGANISM: Artificial Sequence
<220> FEATURE:
<223> OTHER INFORMATION: Masking Moiety

<400> SEQUENCE: 183

Lys Asn Thr Cys Val Tyr Ser Phe Phe Asn Val Cys Leu Asp Pro
1 5 10 15

<210> SEQ ID NO 184
<211> LENGTH: 15
<212> TYPE: PRT
<213> ORGANISM: Artificial Sequence
<220> FEATURE:
<223> OTHER INFORMATION: Masking Moiety

<400> SEQUENCE: 184

Lys Pro Cys Ala Gln Met Tyr Gly Tyr Ser Met Cys Pro His Pro
1 5 10 15

<210> SEQ ID NO 185
<211> LENGTH: 15
<212> TYPE: PRT
<213> ORGANISM: Artificial Sequence
<220> FEATURE:
<223> OTHER INFORMATION: Masking Moiety

<400> SEQUENCE: 185

Lys Pro Ser Cys Met Tyr Ser Phe Phe Asn Val Cys Leu Asp Pro
1 5 10 15

<210> SEQ ID NO 186
<211> LENGTH: 15
<212> TYPE: PRT
<213> ORGANISM: Artificial Sequence
<220> FEATURE:
<223> OTHER INFORMATION: Masking Moiety

<400> SEQUENCE: 186

Lys Arg Pro Cys Met Tyr Ser Phe Tyr Asn Val Cys Leu Asp Pro
1 5 10 15

<210> SEQ ID NO 187
<211> LENGTH: 15
<212> TYPE: PRT
<213> ORGANISM: Artificial Sequence
<220> FEATURE:
<223> OTHER INFORMATION: Masking Moiety

<400> SEQUENCE: 187

Lys Thr Ser Cys Met Tyr Ser Phe Tyr Asn Ile Cys Leu Asp Pro
1 5 10 15

<210> SEQ ID NO 188
<211> LENGTH: 15
<212> TYPE: PRT
<213> ORGANISM: Artificial Sequence
<220> FEATURE:
<223> OTHER INFORMATION: Masking Moiety

<400> SEQUENCE: 188

Lys Thr Thr Cys Thr Tyr Ser Phe Phe Asn Val Cys Leu Asp Pro
1 5 10 15

<210> SEQ ID NO 189
<211> LENGTH: 15
<212> TYPE: PRT
<213> ORGANISM: Artificial Sequence
<220> FEATURE:
<223> OTHER INFORMATION: Masking Moiety

<400> SEQUENCE: 189

Leu Asp Cys Gln Met Tyr Trp Trp Phe Gly Ala Cys Gly Asp Met
1 5 10 15

<210> SEQ ID NO 190
<211> LENGTH: 15
<212> TYPE: PRT
<213> ORGANISM: Artificial Sequence
<220> FEATURE:

<223> OTHER INFORMATION: Masking Moiety

<400> SEQUENCE: 190

Leu His Cys Ala Ile Tyr Met Tyr Gly Tyr Asn Leu Cys Pro Phe
1 5 10 15

<210> SEQ ID NO 191
<211> LENGTH: 15
<212> TYPE: PRT
<213> ORGANISM: Artificial Sequence
<220> FEATURE:
<223> OTHER INFORMATION: Masking Moiety

<400> SEQUENCE: 191

Leu His Cys Pro Phe Gln Met Tyr Gly Tyr Asn Leu Cys Pro His
1 5 10 15

<210> SEQ ID NO 192
<211> LENGTH: 15
<212> TYPE: PRT
<213> ORGANISM: Artificial Sequence
<220> FEATURE:
<223> OTHER INFORMATION: Masking Moiety

<400> SEQUENCE: 192

Leu His Cys Ser Met Tyr Met Tyr Gly Phe Asn Leu Cys Pro Asn
1 5 10 15

<210> SEQ ID NO 193
<211> LENGTH: 15
<212> TYPE: PRT
<213> ORGANISM: Artificial Sequence
<220> FEATURE:
<223> OTHER INFORMATION: Masking Moiety

<400> SEQUENCE: 193

Arg Glu Cys Met Ala Tyr Met Tyr Gly Tyr Asn Leu Cys Pro Tyr
1 5 10 15

<210> SEQ ID NO 194
<211> LENGTH: 15
<212> TYPE: PRT
<213> ORGANISM: Artificial Sequence
<220> FEATURE:
<223> OTHER INFORMATION: Masking Moiety

<400> SEQUENCE: 194

Arg His Cys Gln Met His Met Phe Gly Tyr Asp Leu Cys Pro Tyr
1 5 10 15

<210> SEQ ID NO 195
<211> LENGTH: 15
<212> TYPE: PRT
<213> ORGANISM: Artificial Sequence
<220> FEATURE:
<223> OTHER INFORMATION: Masking Moiety

<400> SEQUENCE: 195

Leu Ile His Cys Arg Tyr Val Met Tyr Gly Met Cys Leu Glu Pro
1 5 10 15

<210> SEQ ID NO 196
<211> LENGTH: 15
<212> TYPE: PRT
<213> ORGANISM: Artificial Sequence
<220> FEATURE:
<223> OTHER INFORMATION: Masking Moiety

<400> SEQUENCE: 196

Leu Leu Pro Cys Glu Val Met Gly Pro Ser Arg Cys Lys His Asp
1 5 10 15

<210> SEQ ID NO 197
<211> LENGTH: 15
<212> TYPE: PRT
<213> ORGANISM: Artificial Sequence
<220> FEATURE:
<223> OTHER INFORMATION: Masking Moiety

<400> SEQUENCE: 197

Leu Pro Cys His Ala Tyr Met Tyr Gly Tyr Ser Leu Cys Pro Tyr
1 5 10 15

<210> SEQ ID NO 198
<211> LENGTH: 15
<212> TYPE: PRT
<213> ORGANISM: Artificial Sequence
<220> FEATURE:
<223> OTHER INFORMATION: Masking Moiety

<400> SEQUENCE: 198

Leu Pro Cys Leu Ala Tyr Met Tyr Gly Val Asn Leu Cys Pro Asn
1 5 10 15

<210> SEQ ID NO 199
<211> LENGTH: 15
<212> TYPE: PRT
<213> ORGANISM: Artificial Sequence
<220> FEATURE:
<223> OTHER INFORMATION: Masking Moiety

<400> SEQUENCE: 199

Leu Pro Cys Met Ala Tyr Met Phe Gly Phe Asn Leu Cys Pro His
1 5 10 15

<210> SEQ ID NO 200
<211> LENGTH: 15
<212> TYPE: PRT
<213> ORGANISM: Artificial Sequence
<220> FEATURE:
<223> OTHER INFORMATION: Masking Moiety

<400> SEQUENCE: 200

Leu Pro Cys Asn Phe His Met Phe Gly Phe Asn Leu Cys Pro Tyr
1 5 10 15

<210> SEQ ID NO 201
<211> LENGTH: 15
<212> TYPE: PRT
<213> ORGANISM: Artificial Sequence
<220> FEATURE:
<223> OTHER INFORMATION: Masking Moiety

<400> SEQUENCE: 201

Leu Gln Cys Ala Met Tyr Met Tyr Gly Tyr Asn Leu Cys Pro Tyr
1 5 10 15

<210> SEQ ID NO 202
<211> LENGTH: 15
<212> TYPE: PRT
<213> ORGANISM: Artificial Sequence
<220> FEATURE:
<223> OTHER INFORMATION: Masking Moiety

<400> SEQUENCE: 202

Leu Ser Ser Cys Thr Tyr Ser Phe Phe Asn Val Cys Leu Asp Pro
1 5 10 15

<210> SEQ ID NO 203
<211> LENGTH: 15
<212> TYPE: PRT
<213> ORGANISM: Artificial Sequence
<220> FEATURE:
<223> OTHER INFORMATION: Masking Moiety

<400> SEQUENCE: 203

Leu Thr Cys Pro Phe Gln Met Tyr Gly Tyr Asn Leu Cys Pro Tyr
1 5 10 15

<210> SEQ ID NO 204
<211> LENGTH: 15
<212> TYPE: PRT
<213> ORGANISM: Artificial Sequence
<220> FEATURE:
<223> OTHER INFORMATION: Masking Moiety

<400> SEQUENCE: 204

Leu Thr Ser Gln Cys Ser Pro Trp Tyr Trp Cys Gln Ile Tyr Asp
1 5 10 15

<210> SEQ ID NO 205
<211> LENGTH: 15
<212> TYPE: PRT
<213> ORGANISM: Artificial Sequence
<220> FEATURE:
<223> OTHER INFORMATION: Masking Moiety

<400> SEQUENCE: 205

Leu Tyr Cys Pro Tyr Met Met Tyr Gly Tyr Asn Leu Cys Pro Tyr
1 5 10 15

<210> SEQ ID NO 206
<211> LENGTH: 15
<212> TYPE: PRT
<213> ORGANISM: Artificial Sequence
<220> FEATURE:
<223> OTHER INFORMATION: Masking Moiety

<400> SEQUENCE: 206

Leu Tyr His Cys Thr Tyr Ser Phe Tyr Asn Val Cys Leu Asp Pro
1 5 10 15

<210> SEQ ID NO 207
<211> LENGTH: 15
<212> TYPE: PRT
<213> ORGANISM: Artificial Sequence
<220> FEATURE:
<223> OTHER INFORMATION: Masking Moiety

<400> SEQUENCE: 207

Leu Tyr Arg Cys Ile Tyr Ser Phe Tyr Asn Val Cys Leu Asp Pro
1 5 10 15

<210> SEQ ID NO 208
<211> LENGTH: 15
<212> TYPE: PRT
<213> ORGANISM: Artificial Sequence
<220> FEATURE:
<223> OTHER INFORMATION: Masking Moiety

<400> SEQUENCE: 208

```
Met Gly Cys Ser Met Arg Met Trp Gly Met Glu Leu Cys Pro Glu
1               5                   10                  15


<210> SEQ ID NO 209
<211> LENGTH: 15
<212> TYPE: PRT
<213> ORGANISM: Artificial Sequence
<220> FEATURE:
<223> OTHER INFORMATION: Masking Moiety

<400> SEQUENCE: 209

Met Lys Cys Asp Tyr Trp Leu Tyr Gly Tyr Asn Leu Cys Pro Tyr
1               5                   10                  15


<210> SEQ ID NO 210
<211> LENGTH: 15
<212> TYPE: PRT
<213> ORGANISM: Artificial Sequence
<220> FEATURE:
<223> OTHER INFORMATION: Masking Moiety

<400> SEQUENCE: 210

Met Asn His Cys Thr Leu His Met Tyr Asn Ile Cys Met Asp Pro
1               5                   10                  15


<210> SEQ ID NO 211
<211> LENGTH: 15
<212> TYPE: PRT
<213> ORGANISM: Artificial Sequence
<220> FEATURE:
<223> OTHER INFORMATION: Masking Moiety

<400> SEQUENCE: 211

Met Asn Pro Glu Cys Pro His His Pro Met Cys His Asn Ser Asn
1               5                   10                  15


<210> SEQ ID NO 212
<211> LENGTH: 15
<212> TYPE: PRT
<213> ORGANISM: Artificial Sequence
<220> FEATURE:
<223> OTHER INFORMATION: Masking Moiety

<400> SEQUENCE: 212

Met Pro Ala Cys Thr Tyr Ser Phe Phe Asn Ile Cys Leu Asp Pro
1               5                   10                  15


<210> SEQ ID NO 213
<211> LENGTH: 15
<212> TYPE: PRT
<213> ORGANISM: Artificial Sequence
<220> FEATURE:
<223> OTHER INFORMATION: Masking Moiety

<400> SEQUENCE: 213

Met Pro Gln Cys His Val Ile Met Tyr Asn Leu Cys Leu Asp Pro
1               5                   10                  15


<210> SEQ ID NO 214
<211> LENGTH: 15
<212> TYPE: PRT
<213> ORGANISM: Artificial Sequence
<220> FEATURE:
<223> OTHER INFORMATION: Masking Moiety

<400> SEQUENCE: 214
```

Met Ser Thr Cys Thr Tyr Ser Phe Phe Asn Val Cys Leu Asp Pro
1 5 10 15

<210> SEQ ID NO 215
<211> LENGTH: 15
<212> TYPE: PRT
<213> ORGANISM: Artificial Sequence
<220> FEATURE:
<223> OTHER INFORMATION: Masking Moiety

<400> SEQUENCE: 215

Met Thr Cys Asn Tyr Trp Phe Tyr Gly Val Asn Leu Cys Pro Tyr
1 5 10 15

<210> SEQ ID NO 216
<211> LENGTH: 15
<212> TYPE: PRT
<213> ORGANISM: Artificial Sequence
<220> FEATURE:
<223> OTHER INFORMATION: Masking Moiety

<400> SEQUENCE: 216

Met Tyr Cys His Gln Ser Met Phe Gly Phe Arg Met Cys Pro Asp
1 5 10 15

<210> SEQ ID NO 217
<211> LENGTH: 15
<212> TYPE: PRT
<213> ORGANISM: Artificial Sequence
<220> FEATURE:
<223> OTHER INFORMATION: Masking Moiety

<400> SEQUENCE: 217

Asn Ala Cys Ala Gln Met Tyr Gly Tyr Ser Met Cys Pro His Thr
1 5 10 15

<210> SEQ ID NO 218
<211> LENGTH: 15
<212> TYPE: PRT
<213> ORGANISM: Artificial Sequence
<220> FEATURE:
<223> OTHER INFORMATION: Masking Moiety

<400> SEQUENCE: 218

Asn Asp Cys Asp Ile Ser Met Phe Asp Gln Ser Leu Cys Pro Tyr
1 5 10 15

<210> SEQ ID NO 219
<211> LENGTH: 15
<212> TYPE: PRT
<213> ORGANISM: Artificial Sequence
<220> FEATURE:
<223> OTHER INFORMATION: Masking Moiety

<400> SEQUENCE: 219

Asn Phe Ser Cys Val Tyr Val Met Phe Asn Val Cys Leu Asp Pro
1 5 10 15

<210> SEQ ID NO 220
<211> LENGTH: 15
<212> TYPE: PRT
<213> ORGANISM: Artificial Sequence
<220> FEATURE:
<223> OTHER INFORMATION: Masking Moiety

<400> SEQUENCE: 220

Asn Phe Thr Cys Ala Leu Thr Met Tyr Glu Val Cys Leu Asp Pro 1 5 10 15

<210> SEQ ID NO 221
<211> LENGTH: 15
<212> TYPE: PRT
<213> ORGANISM: Artificial Sequence
<220> FEATURE:
<223> OTHER INFORMATION: Masking Moiety

<400> SEQUENCE: 221

Asn Leu Cys His Ala Phe Met Phe Gly Phe Asn Leu Cys Pro Tyr
1 5 10 15

<210> SEQ ID NO 222
<211> LENGTH: 15
<212> TYPE: PRT
<213> ORGANISM: Artificial Sequence
<220> FEATURE:
<223> OTHER INFORMATION: Masking Moiety

<400> SEQUENCE: 222

Asn Leu Asn Asn Cys Pro His His Pro Met Cys His Asp Tyr Gln
1 5 10 15

<210> SEQ ID NO 223
<211> LENGTH: 15
<212> TYPE: PRT
<213> ORGANISM: Artificial Sequence
<220> FEATURE:
<223> OTHER INFORMATION: Masking Moiety

<400> SEQUENCE: 223

Asn Pro Pro Cys Met Tyr Ser Phe Phe Asn Ile Cys Leu Asp Pro
1 5 10 15

<210> SEQ ID NO 224
<211> LENGTH: 15
<212> TYPE: PRT
<213> ORGANISM: Artificial Sequence
<220> FEATURE:
<223> OTHER INFORMATION: Masking Moiety

<400> SEQUENCE: 224

Asn Ser Ala Cys Thr Tyr Ser Phe Phe Asn Val Cys Leu Asp Pro
1 5 10 15

<210> SEQ ID NO 225
<211> LENGTH: 15
<212> TYPE: PRT
<213> ORGANISM: Artificial Sequence
<220> FEATURE:
<223> OTHER INFORMATION: Masking Moiety

<400> SEQUENCE: 225

Asn Val Cys Thr Val Ser Met Phe Gly Val Met Leu Cys Pro Ser
1 5 10 15

<210> SEQ ID NO 226
<211> LENGTH: 15
<212> TYPE: PRT
<213> ORGANISM: Artificial Sequence
<220> FEATURE:
<223> OTHER INFORMATION: Masking Moiety

<400> SEQUENCE: 226

Pro Ala Cys Ala Thr Leu Met Tyr Ser Val Pro Leu Cys Pro Ala
1 5 10 15

<210> SEQ ID NO 227
<211> LENGTH: 15
<212> TYPE: PRT
<213> ORGANISM: Artificial Sequence
<220> FEATURE:
<223> OTHER INFORMATION: Masking Moiety

<400> SEQUENCE: 227

Pro Ala Pro Cys Met Tyr Ser Phe Tyr Asn Val Cys Leu Asp Pro
1 5 10 15

<210> SEQ ID NO 228
<211> LENGTH: 15
<212> TYPE: PRT
<213> ORGANISM: Artificial Sequence
<220> FEATURE:
<223> OTHER INFORMATION: Masking Moiety

<400> SEQUENCE: 228

Pro Leu Cys Ala Glu Met Tyr Gly Tyr Ser Met Cys Pro His Asn
1 5 10 15

<210> SEQ ID NO 229
<211> LENGTH: 15
<212> TYPE: PRT
<213> ORGANISM: Artificial Sequence
<220> FEATURE:
<223> OTHER INFORMATION: Masking Moiety

<400> SEQUENCE: 229

Pro Gln Cys His Leu Tyr Met Tyr Gly Tyr Asn Leu Cys Pro Tyr
1 5 10 15

<210> SEQ ID NO 230
<211> LENGTH: 15
<212> TYPE: PRT
<213> ORGANISM: Artificial Sequence
<220> FEATURE:
<223> OTHER INFORMATION: Masking Moiety

<400> SEQUENCE: 230

Pro Arg Pro Cys Met Tyr Ser Phe Tyr Asn Val Cys Leu Asp Pro
1 5 10 15

<210> SEQ ID NO 231
<211> LENGTH: 15
<212> TYPE: PRT
<213> ORGANISM: Artificial Sequence
<220> FEATURE:
<223> OTHER INFORMATION: Masking Moiety

<400> SEQUENCE: 231

Gln His Cys Pro Phe Gln Met Tyr Gly Tyr Asn Leu Cys Pro Tyr
1 5 10 15

<210> SEQ ID NO 232
<211> LENGTH: 15
<212> TYPE: PRT
<213> ORGANISM: Artificial Sequence
<220> FEATURE:
<223> OTHER INFORMATION: Masking Moiety

<400> SEQUENCE: 232

Gln His Cys Gln Met His Met Phe Gly Tyr Asn Leu Cys Pro Tyr
1 5 10 15

<210> SEQ ID NO 233
<211> LENGTH: 15
<212> TYPE: PRT
<213> ORGANISM: Artificial Sequence
<220> FEATURE:
<223> OTHER INFORMATION: Masking Moiety

<400> SEQUENCE: 233

Gln His Ser Cys Met Tyr Ser Phe Phe Asn Val Cys Leu Asp Pro
1 5 10 15

<210> SEQ ID NO 234
<211> LENGTH: 15
<212> TYPE: PRT
<213> ORGANISM: Artificial Sequence
<220> FEATURE:
<223> OTHER INFORMATION: Masking Moiety

<400> SEQUENCE: 234

Gln Lys Cys His Ser Tyr Leu Tyr Gly Val Asn Leu Cys Pro Tyr
1 5 10 15

<210> SEQ ID NO 235
<211> LENGTH: 15
<212> TYPE: PRT
<213> ORGANISM: Artificial Sequence
<220> FEATURE:
<223> OTHER INFORMATION: Masking Moiety

<400> SEQUENCE: 235

Gln Lys Cys Asn Met Phe Met Phe Gly Tyr Asn Leu Cys Pro Tyr
1 5 10 15

<210> SEQ ID NO 236
<211> LENGTH: 15
<212> TYPE: PRT
<213> ORGANISM: Artificial Sequence
<220> FEATURE:
<223> OTHER INFORMATION: Masking Moiety

<400> SEQUENCE: 236

Gln Met Asn Asp Cys Pro Asn His Pro Met Cys His Asp Tyr His
1 5 10 15

<210> SEQ ID NO 237
<211> LENGTH: 15
<212> TYPE: PRT
<213> ORGANISM: Artificial Sequence
<220> FEATURE:
<223> OTHER INFORMATION: Masking Moiety

<400> SEQUENCE: 237

Gln Pro Cys Ala Gln Met Tyr Gly Tyr Ser Met Cys Pro Ala Thr
1 5 10 15

<210> SEQ ID NO 238
<211> LENGTH: 15
<212> TYPE: PRT
<213> ORGANISM: Artificial Sequence
<220> FEATURE:
<223> OTHER INFORMATION: Masking Moiety

<400> SEQUENCE: 238

Gln Pro Cys Ala Gln Met Tyr Gly Tyr Ser Met Cys Pro Arg Thr
1 5 10 15

<210> SEQ ID NO 239
<211> LENGTH: 15
<212> TYPE: PRT
<213> ORGANISM: Artificial Sequence
<220> FEATURE:
<223> OTHER INFORMATION: Masking Moiety

<400> SEQUENCE: 239

Arg Glu Cys His Phe Phe Phe Tyr Gly Val Asn Leu Cys Pro Tyr
1 5 10 15

<210> SEQ ID NO 240
<211> LENGTH: 15
<212> TYPE: PRT
<213> ORGANISM: Artificial Sequence
<220> FEATURE:
<223> OTHER INFORMATION: Masking Moiety

<400> SEQUENCE: 240

Leu Asn Cys Gly Met Phe Met Tyr Gly Tyr Asn Leu Cys Pro Tyr
1 5 10 15

<210> SEQ ID NO 241
<211> LENGTH: 15
<212> TYPE: PRT
<213> ORGANISM: Artificial Sequence
<220> FEATURE:
<223> OTHER INFORMATION: Masking Moiety

<400> SEQUENCE: 241

Arg Leu Cys Thr Ser Tyr Met Phe Gly Tyr Asn Leu Cys Pro Gln
1 5 10 15

<210> SEQ ID NO 242
<211> LENGTH: 15
<212> TYPE: PRT
<213> ORGANISM: Artificial Sequence
<220> FEATURE:
<223> OTHER INFORMATION: Masking Moiety

<400> SEQUENCE: 242

Arg Leu Ser Cys Met Tyr Ser Met Phe Asn Val Cys Leu Asp Pro
1 5 10 15

<210> SEQ ID NO 243
<211> LENGTH: 15
<212> TYPE: PRT
<213> ORGANISM: Artificial Sequence
<220> FEATURE:
<223> OTHER INFORMATION: Masking Moiety

<400> SEQUENCE: 243

Arg Asn Cys Pro Phe Val Met Phe Gly Val Asn Leu Cys Pro Tyr
1 5 10 15

<210> SEQ ID NO 244
<211> LENGTH: 15
<212> TYPE: PRT
<213> ORGANISM: Artificial Sequence
<220> FEATURE:
<223> OTHER INFORMATION: Masking Moiety

<400> SEQUENCE: 244

Arg Asn Gly Cys Met Tyr Ser Phe Phe Asn Val Cys Leu Asp Pro
1 5 10 15

<210> SEQ ID NO 245

<211> LENGTH: 15
<212> TYPE: PRT
<213> ORGANISM: Artificial Sequence
<220> FEATURE:
<223> OTHER INFORMATION: Masking Moiety

<400> SEQUENCE: 245

Arg Asn Gly Cys Val Tyr Ser Phe Phe Asn Val Cys Leu Asp Pro
1 5 10 15

<210> SEQ ID NO 246
<211> LENGTH: 15
<212> TYPE: PRT
<213> ORGANISM: Artificial Sequence
<220> FEATURE:
<223> OTHER INFORMATION: Masking Moiety

<400> SEQUENCE: 246

Arg Pro Cys His Leu Tyr Met Phe Gly Tyr Asn Leu Cys Pro Asp
1 5 10 15

<210> SEQ ID NO 247
<211> LENGTH: 15
<212> TYPE: PRT
<213> ORGANISM: Artificial Sequence
<220> FEATURE:
<223> OTHER INFORMATION: Masking Moiety

<400> SEQUENCE: 247

Arg Pro Cys His Ser Tyr Met Tyr Gly Ile Asn Leu Cys Pro Tyr
1 5 10 15

<210> SEQ ID NO 248
<211> LENGTH: 15
<212> TYPE: PRT
<213> ORGANISM: Artificial Sequence
<220> FEATURE:
<223> OTHER INFORMATION: Masking Moiety

<400> SEQUENCE: 248

Arg Ser Cys Asp Met Ile Met Phe Gly Phe Asn Leu Cys Pro Tyr
1 5 10 15

<210> SEQ ID NO 249
<211> LENGTH: 15
<212> TYPE: PRT
<213> ORGANISM: Artificial Sequence
<220> FEATURE:
<223> OTHER INFORMATION: Masking Moiety

<400> SEQUENCE: 249

Arg Ser Cys Pro Met Trp Phe Tyr Gly Val Asn Leu Cys Pro Tyr
1 5 10 15

<210> SEQ ID NO 250
<211> LENGTH: 15
<212> TYPE: PRT
<213> ORGANISM: Artificial Sequence
<220> FEATURE:
<223> OTHER INFORMATION: Masking Moiety

<400> SEQUENCE: 250

Arg Ser Thr Val Cys Phe Tyr Asp Phe Cys Gly Pro Trp Glu Arg
1 5 10 15

<210> SEQ ID NO 251
<211> LENGTH: 15

<212> TYPE: PRT
<213> ORGANISM: Artificial Sequence
<220> FEATURE:
<223> OTHER INFORMATION: Masking Moiety

<400> SEQUENCE: 251

Arg Thr Cys His Phe Tyr Met Tyr Gly Val Asn Leu Cys Pro Tyr
1 5 10 15

<210> SEQ ID NO 252
<211> LENGTH: 15
<212> TYPE: PRT
<213> ORGANISM: Artificial Sequence
<220> FEATURE:
<223> OTHER INFORMATION: Masking Moiety

<400> SEQUENCE: 252

Arg Thr Cys Ser Met Val Met Phe Gly Val Asn Leu Cys Pro Tyr
1 5 10 15

<210> SEQ ID NO 253
<211> LENGTH: 15
<212> TYPE: PRT
<213> ORGANISM: Artificial Sequence
<220> FEATURE:
<223> OTHER INFORMATION: Masking Moiety

<400> SEQUENCE: 253

Ser Gly Lys Cys Thr Tyr Ser Phe Phe Asn Val Cys Leu Asp Pro
1 5 10 15

<210> SEQ ID NO 254
<211> LENGTH: 15
<212> TYPE: PRT
<213> ORGANISM: Artificial Sequence
<220> FEATURE:
<223> OTHER INFORMATION: Masking Moiety

<400> SEQUENCE: 254

Ser Ile Val Cys Asp Leu Tyr Trp Glu Ala Thr Cys Leu Arg Pro
1 5 10 15

<210> SEQ ID NO 255
<211> LENGTH: 15
<212> TYPE: PRT
<213> ORGANISM: Artificial Sequence
<220> FEATURE:
<223> OTHER INFORMATION: Masking Moiety

<400> SEQUENCE: 255

Ser Leu Ser Cys Thr Tyr Ser Phe Phe Asn Ile Cys Leu Asp Pro
1 5 10 15

<210> SEQ ID NO 256
<211> LENGTH: 15
<212> TYPE: PRT
<213> ORGANISM: Artificial Sequence
<220> FEATURE:
<223> OTHER INFORMATION: Masking Moiety

<400> SEQUENCE: 256

Ser Met Asn Thr Cys Pro Tyr His Pro Met Cys Phe Asp Tyr Lys
1 5 10 15

<210> SEQ ID NO 257
<211> LENGTH: 15
<212> TYPE: PRT

<213> ORGANISM: Artificial Sequence
<220> FEATURE:
<223> OTHER INFORMATION: Masking Moiety

<400> SEQUENCE: 257

Ser Gln Cys Trp Met Trp Met Tyr Gly Tyr Asn Leu Cys Pro Lys
1 5 10 15

<210> SEQ ID NO 258
<211> LENGTH: 15
<212> TYPE: PRT
<213> ORGANISM: Artificial Sequence
<220> FEATURE:
<223> OTHER INFORMATION: Masking Moiety

<400> SEQUENCE: 258

Ser Ser Ser Cys Met Tyr Ser Phe Phe Asn Val Cys Leu Asp Pro
1 5 10 15

<210> SEQ ID NO 259
<211> LENGTH: 15
<212> TYPE: PRT
<213> ORGANISM: Artificial Sequence
<220> FEATURE:
<223> OTHER INFORMATION: Masking Moiety

<400> SEQUENCE: 259

Ser Thr Ala Cys Thr Tyr Ser Phe Tyr Asn Val Cys Leu Asp Pro
1 5 10 15

<210> SEQ ID NO 260
<211> LENGTH: 15
<212> TYPE: PRT
<213> ORGANISM: Artificial Sequence
<220> FEATURE:
<223> OTHER INFORMATION: Masking Moiety

<400> SEQUENCE: 260

Ser Thr Cys Ala Gln Met Tyr Gly Tyr Ser Met Cys Pro His Thr
1 5 10 15

<210> SEQ ID NO 261
<211> LENGTH: 15
<212> TYPE: PRT
<213> ORGANISM: Artificial Sequence
<220> FEATURE:
<223> OTHER INFORMATION: Masking Moiety

<400> SEQUENCE: 261

Ser Thr Arg Cys Val Tyr Ser Phe Tyr Asn Val Cys Leu Asp Pro
1 5 10 15

<210> SEQ ID NO 262
<211> LENGTH: 15
<212> TYPE: PRT
<213> ORGANISM: Artificial Sequence
<220> FEATURE:
<223> OTHER INFORMATION: Masking Moiety

<400> SEQUENCE: 262

Thr Ala Cys Gly Ala Trp Met Phe Gly Val Asn Leu Cys Pro Tyr
1 5 10 15

<210> SEQ ID NO 263
<211> LENGTH: 15
<212> TYPE: PRT
<213> ORGANISM: Artificial Sequence
<220> FEATURE:
<223> OTHER INFORMATION: Masking Moiety

<400> SEQUENCE: 263

Thr Gly Ala Cys Met Tyr Ser Phe Tyr Asn Val Cys Leu Asp Pro
1 5 10 15

<210> SEQ ID NO 264
<211> LENGTH: 15
<212> TYPE: PRT
<213> ORGANISM: Artificial Sequence
<220> FEATURE:
<223> OTHER INFORMATION: Masking Moiety

<400> SEQUENCE: 264

Thr Leu Ser Cys Met Tyr Ser Met Tyr Asn Val Cys Leu Asp Pro
1 5 10 15

<210> SEQ ID NO 265
<211> LENGTH: 15
<212> TYPE: PRT
<213> ORGANISM: Artificial Sequence
<220> FEATURE:
<223> OTHER INFORMATION: Masking Moiety

<400> SEQUENCE: 265

Thr Ser Cys Thr Val Thr Met Tyr Gln Ile Ser Met Cys Pro Tyr
1 5 10 15

<210> SEQ ID NO 266
<211> LENGTH: 15
<212> TYPE: PRT
<213> ORGANISM: Artificial Sequence
<220> FEATURE:
<223> OTHER INFORMATION: Masking Moiety

<400> SEQUENCE: 266

Val Gly Gly Cys Arg His Ser Phe Tyr Asn Val Cys Leu Asp Pro
1 5 10 15

<210> SEQ ID NO 267
<211> LENGTH: 15
<212> TYPE: PRT
<213> ORGANISM: Artificial Sequence
<220> FEATURE:
<223> OTHER INFORMATION: Masking Moiety

<400> SEQUENCE: 267

Val His Cys Gln Met Tyr Met Tyr Gly Tyr Asn Leu Cys Pro Tyr
1 5 10 15

<210> SEQ ID NO 268
<211> LENGTH: 15
<212> TYPE: PRT
<213> ORGANISM: Artificial Sequence
<220> FEATURE:
<223> OTHER INFORMATION: Masking Moiety

<400> SEQUENCE: 268

Val His Asn Cys Met Tyr Ser Phe Phe Asn Val Cys Leu Asp Pro
1 5 10 15

<210> SEQ ID NO 269
<211> LENGTH: 15
<212> TYPE: PRT
<213> ORGANISM: Artificial Sequence
<220> FEATURE:

<223> OTHER INFORMATION: Masking Moiety

<400> SEQUENCE: 269

Val Met Cys Lys Leu His Met Tyr Gly Ile Pro Val Cys Pro Lys
1 5 10 15

<210> SEQ ID NO 270
<211> LENGTH: 15
<212> TYPE: PRT
<213> ORGANISM: Artificial Sequence
<220> FEATURE:
<223> OTHER INFORMATION: Masking Moiety

<400> SEQUENCE: 270

Val Asn Phe Cys Asn Tyr Ser Met Tyr Gly Ile Cys Leu Leu Pro
1 5 10 15

<210> SEQ ID NO 271
<211> LENGTH: 15
<212> TYPE: PRT
<213> ORGANISM: Artificial Sequence
<220> FEATURE:
<223> OTHER INFORMATION: Masking Moiety

<400> SEQUENCE: 271

Val Asn Phe Cys Tyr Ala Cys Tyr Cys Met Ser Cys Val Phe Ser
1 5 10 15

<210> SEQ ID NO 272
<211> LENGTH: 15
<212> TYPE: PRT
<213> ORGANISM: Artificial Sequence
<220> FEATURE:
<223> OTHER INFORMATION: Masking Moiety

<400> SEQUENCE: 272

Val Asn Gln Cys Thr Tyr Ser Phe Phe Asn Val Cys Leu Asp Pro
1 5 10 15

<210> SEQ ID NO 273
<211> LENGTH: 15
<212> TYPE: PRT
<213> ORGANISM: Artificial Sequence
<220> FEATURE:
<223> OTHER INFORMATION: Masking Moiety

<400> SEQUENCE: 273

Val Pro Cys Pro Phe His Met Phe Gly Tyr Asn Leu Cys Pro Tyr
1 5 10 15

<210> SEQ ID NO 274
<211> LENGTH: 15
<212> TYPE: PRT
<213> ORGANISM: Artificial Sequence
<220> FEATURE:
<223> OTHER INFORMATION: Masking Moiety

<400> SEQUENCE: 274

Val Arg Cys Gln Met Trp Met Tyr Gly Phe Asn Leu Cys Pro His
1 5 10 15

<210> SEQ ID NO 275
<211> LENGTH: 15
<212> TYPE: PRT
<213> ORGANISM: Artificial Sequence
<220> FEATURE:
<223> OTHER INFORMATION: Masking Moiety

<400> SEQUENCE: 275

Val Arg Pro Cys Thr Tyr Ser Phe Phe Asn Val Cys Leu Asp Pro
1 5 10 15

<210> SEQ ID NO 276
<211> LENGTH: 15
<212> TYPE: PRT
<213> ORGANISM: Artificial Sequence
<220> FEATURE:
<223> OTHER INFORMATION: Masking Moiety

<400> SEQUENCE: 276

Val Ser Gly Cys Thr Tyr Ser Phe Phe Asn Ile Cys Leu Asp Pro
1 5 10 15

<210> SEQ ID NO 277
<211> LENGTH: 15
<212> TYPE: PRT
<213> ORGANISM: Artificial Sequence
<220> FEATURE:
<223> OTHER INFORMATION: Masking Moiety

<400> SEQUENCE: 277

Tyr Cys Ser Ser Trp Asp Thr Met Thr Ile Pro Ala Cys Asn Asn
1 5 10 15

<210> SEQ ID NO 278
<211> LENGTH: 15
<212> TYPE: PRT
<213> ORGANISM: Artificial Sequence
<220> FEATURE:
<223> OTHER INFORMATION: Masking Moiety

<400> SEQUENCE: 278

Tyr Asp Cys Asp Leu Ser Met Phe Gly Ile Glu Met Cys Pro Gln
1 5 10 15

<210> SEQ ID NO 279
<211> LENGTH: 15
<212> TYPE: PRT
<213> ORGANISM: Artificial Sequence
<220> FEATURE:
<223> OTHER INFORMATION: Masking Moiety

<400> SEQUENCE: 279

Tyr Gly Asn Thr Cys Pro Phe His Pro Met Cys His Asp Tyr Lys
1 5 10 15

<210> SEQ ID NO 280
<211> LENGTH: 15
<212> TYPE: PRT
<213> ORGANISM: Artificial Sequence
<220> FEATURE:
<223> OTHER INFORMATION: Masking Moiety

<400> SEQUENCE: 280

Tyr Gly Tyr Cys Met Tyr Ser Phe Phe Asn Val Cys Leu Asp Pro
1 5 10 15

<210> SEQ ID NO 281
<211> LENGTH: 15
<212> TYPE: PRT
<213> ORGANISM: Artificial Sequence
<220> FEATURE:
<223> OTHER INFORMATION: Masking Moiety

<400> SEQUENCE: 281

Tyr His Cys Thr Met His Met Phe Gly Tyr Asn Leu Cys Pro Phe
1 5 10 15

<210> SEQ ID NO 282
<211> LENGTH: 15
<212> TYPE: PRT
<213> ORGANISM: Artificial Sequence
<220> FEATURE:
<223> OTHER INFORMATION: Masking Moiety

<400> SEQUENCE: 282

Tyr Met Asn Thr Cys Pro Asn His Pro Met Cys Phe Asp Tyr Gln
1 5 10 15

<210> SEQ ID NO 283
<211> LENGTH: 15
<212> TYPE: PRT
<213> ORGANISM: Artificial Sequence
<220> FEATURE:
<223> OTHER INFORMATION: Masking Moiety

<400> SEQUENCE: 283

Tyr Met Asn Thr Cys Pro Tyr His Pro Met Cys His Asp Tyr Leu
1 5 10 15

<210> SEQ ID NO 284
<211> LENGTH: 15
<212> TYPE: PRT
<213> ORGANISM: Artificial Sequence
<220> FEATURE:
<223> OTHER INFORMATION: Masking Moiety

<400> SEQUENCE: 284

Tyr Met Asn Thr Cys Pro Tyr His Pro Met Cys His Asp Tyr Arg
1 5 10 15

<210> SEQ ID NO 285
<211> LENGTH: 15
<212> TYPE: PRT
<213> ORGANISM: Artificial Sequence
<220> FEATURE:
<223> OTHER INFORMATION: Masking Moiety

<400> SEQUENCE: 285

Tyr Asn Asn Cys Thr Tyr Ser Phe Phe Asn Val Cys Leu Asp Pro
1 5 10 15

<210> SEQ ID NO 286
<211> LENGTH: 15
<212> TYPE: PRT
<213> ORGANISM: Artificial Sequence
<220> FEATURE:
<223> OTHER INFORMATION: Masking Moiety

<400> SEQUENCE: 286

Tyr Pro Gly Cys Gln Tyr Ser Phe Phe Asn Val Cys Leu Asp Pro
1 5 10 15

<210> SEQ ID NO 287
<211> LENGTH: 15
<212> TYPE: PRT
<213> ORGANISM: Artificial Sequence
<220> FEATURE:
<223> OTHER INFORMATION: Masking Moiety

<400> SEQUENCE: 287

Tyr Arg Ser Cys Thr His Ile Met Tyr Asn Val Cys Leu Asp Pro
1 5 10 15

<210> SEQ ID NO 288
<211> LENGTH: 15
<212> TYPE: PRT
<213> ORGANISM: Artificial Sequence
<220> FEATURE:
<223> OTHER INFORMATION: Masking Moiety

<400> SEQUENCE: 288

Tyr Ser Phe Cys Asp Met Leu Met Tyr Asp Val Cys Leu Val Pro
1 5 10 15

<210> SEQ ID NO 289
<211> LENGTH: 15
<212> TYPE: PRT
<213> ORGANISM: Artificial Sequence
<220> FEATURE:
<223> OTHER INFORMATION: Masking Moiety

<400> SEQUENCE: 289

Tyr Ser Ile Asp Cys Gly Leu Ser Trp Trp Cys Gly Gly Met Thr
1 5 10 15

<210> SEQ ID NO 290
<211> LENGTH: 15
<212> TYPE: PRT
<213> ORGANISM: Artificial Sequence
<220> FEATURE:
<223> OTHER INFORMATION: Masking Moiety

<400> SEQUENCE: 290

Tyr Ser Thr Thr Cys Pro Tyr His Pro Met Cys His Asp Tyr His
1 5 10 15

<210> SEQ ID NO 291
<211> LENGTH: 15
<212> TYPE: PRT
<213> ORGANISM: Artificial Sequence
<220> FEATURE:
<223> OTHER INFORMATION: Masking Moiety

<400> SEQUENCE: 291

Tyr Val Asn Thr Cys Pro His His Pro Met Cys His Asp Tyr His
1 5 10 15

<210> SEQ ID NO 292
<211> LENGTH: 15
<212> TYPE: PRT
<213> ORGANISM: Artificial Sequence
<220> FEATURE:
<223> OTHER INFORMATION: Masking Moiety

<400> SEQUENCE: 292

Tyr Val Asn Thr Cys Pro Tyr His Pro Met Cys His Asp Tyr Asn
1 5 10 15

<210> SEQ ID NO 293
<211> LENGTH: 15
<212> TYPE: PRT
<213> ORGANISM: Artificial Sequence
<220> FEATURE:
<223> OTHER INFORMATION: Masking Moiety - MY03

<400> SEQUENCE: 293

Met Cys Leu Pro Pro Leu Phe Glu Leu Ala Ser Thr Cys Pro Tyr
1 5 10 15

<210> SEQ ID NO 294
<211> LENGTH: 15
<212> TYPE: PRT
<213> ORGANISM: Artificial Sequence
<220> FEATURE:
<223> OTHER INFORMATION: Masking Moiety - MY11

<400> SEQUENCE: 294

Leu Pro Asp Cys Gly Met Trp Gly Ile Ser Cys Gly Gly Thr Val
1 5 10 15

<210> SEQ ID NO 295
<211> LENGTH: 15
<212> TYPE: PRT
<213> ORGANISM: Artificial Sequence
<220> FEATURE:
<223> OTHER INFORMATION: Masking Moiety - MY16

<400> SEQUENCE: 295

Arg Asp His Thr Cys Asn Pro Arg Asn Cys His Pro Asn Met Phe
1 5 10 15

<210> SEQ ID NO 296
<211> LENGTH: 15
<212> TYPE: PRT
<213> ORGANISM: Artificial Sequence
<220> FEATURE:
<223> OTHER INFORMATION: Masking Moiety - MY04

<400> SEQUENCE: 296

Trp Arg Cys Met Pro Pro Thr Trp Glu Thr Thr Gln Cys His Thr
1 5 10 15

<210> SEQ ID NO 297
<211> LENGTH: 13
<212> TYPE: PRT
<213> ORGANISM: Artificial Sequence
<220> FEATURE:
<223> OTHER INFORMATION: Cleavable Moiety - 2001

<400> SEQUENCE: 297

Ile Ser Ser Gly Leu Leu Ser Gly Arg Ser Asp Asn His
1 5 10

<210> SEQ ID NO 298
<211> LENGTH: 15
<212> TYPE: PRT
<213> ORGANISM: Artificial Sequence
<220> FEATURE:
<223> OTHER INFORMATION: Cleavable Moiety - 2003

<400> SEQUENCE: 298

Ile Ser Ser Gly Leu Leu Ser Gly Arg Ser Ala Asn Pro Arg Gly
1 5 10 15

<210> SEQ ID NO 299
<211> LENGTH: 17
<212> TYPE: PRT
<213> ORGANISM: Artificial Sequence
<220> FEATURE:
<223> OTHER INFORMATION: Cleavable Moiety - 2005

<400> SEQUENCE: 299

Ala Val Gly Leu Leu Ala Pro Pro Ser Gly Arg Ser Ala Asn Pro Arg 1 5 10 15

Gly

<210> SEQ ID NO 300
<211> LENGTH: 13
<212> TYPE: PRT
<213> ORGANISM: Artificial Sequence
<220> FEATURE:
<223> OTHER INFORMATION: Cleavable Moiety - 2006

<400> SEQUENCE: 300

Ile Ser Ser Gly Leu Leu Ser Gly Arg Ser Asp Asp His
1 5 10

<210> SEQ ID NO 301
<211> LENGTH: 13
<212> TYPE: PRT
<213> ORGANISM: Artificial Sequence
<220> FEATURE:
<223> OTHER INFORMATION: Cleavable Moiety - 2007

<400> SEQUENCE: 301

Ile Ser Ser Gly Leu Leu Ser Gly Arg Ser Asp Ile His
1 5 10

<210> SEQ ID NO 302
<211> LENGTH: 13
<212> TYPE: PRT
<213> ORGANISM: Artificial Sequence
<220> FEATURE:
<223> OTHER INFORMATION: Cleavable Moiety - 2008

<400> SEQUENCE: 302

Ile Ser Ser Gly Leu Leu Ser Gly Arg Ser Asp Gln His
1 5 10

<210> SEQ ID NO 303
<211> LENGTH: 13
<212> TYPE: PRT
<213> ORGANISM: Artificial Sequence
<220> FEATURE:
<223> OTHER INFORMATION: Cleavable Moiety - 2009

<400> SEQUENCE: 303

Ile Ser Ser Gly Leu Leu Ser Gly Arg Ser Asp Thr His
1 5 10

<210> SEQ ID NO 304
<211> LENGTH: 13
<212> TYPE: PRT
<213> ORGANISM: Artificial Sequence
<220> FEATURE:
<223> OTHER INFORMATION: Cleavable Moiety - 2011

<400> SEQUENCE: 304

Ile Ser Ser Gly Leu Leu Ser Gly Arg Ser Asp Asn Pro
1 5 10

<210> SEQ ID NO 305
<211> LENGTH: 13
<212> TYPE: PRT
<213> ORGANISM: Artificial Sequence
<220> FEATURE:
<223> OTHER INFORMATION: Cleavable Moiety - 2012

<400> SEQUENCE: 305

Ile Ser Ser Gly Leu Leu Ser Gly Arg Ser Ala Asn Pro
1 5 10

<210> SEQ ID NO 306
<211> LENGTH: 18
<212> TYPE: PRT
<213> ORGANISM: Artificial Sequence
<220> FEATURE:
<223> OTHER INFORMATION: Cleavable Moiety - 3001

<400> SEQUENCE: 306

Ala Val Gly Leu Leu Ala Pro Pro Gly Gly Leu Ser Gly Arg Ser Asp
1 5 10 15

Asn His

<210> SEQ ID NO 307
<211> LENGTH: 18
<212> TYPE: PRT
<213> ORGANISM: Artificial Sequence
<220> FEATURE:
<223> OTHER INFORMATION: Cleavable Moiety - 3006

<400> SEQUENCE: 307

Ala Val Gly Leu Leu Ala Pro Pro Gly Gly Leu Ser Gly Arg Ser Asp
1 5 10 15

Asp His

<210> SEQ ID NO 308
<211> LENGTH: 18
<212> TYPE: PRT
<213> ORGANISM: Artificial Sequence
<220> FEATURE:
<223> OTHER INFORMATION: Cleavable Moiety - 3007

<400> SEQUENCE: 308

Ala Val Gly Leu Leu Ala Pro Pro Gly Gly Leu Ser Gly Arg Ser Asp
1 5 10 15

Ile His

<210> SEQ ID NO 309
<211> LENGTH: 18
<212> TYPE: PRT
<213> ORGANISM: Artificial Sequence
<220> FEATURE:
<223> OTHER INFORMATION: Cleavable Moiety - 3008

<400> SEQUENCE: 309

Ala Val Gly Leu Leu Ala Pro Pro Gly Gly Leu Ser Gly Arg Ser Asp
1 5 10 15

Gln His

<210> SEQ ID NO 310
<211> LENGTH: 18
<212> TYPE: PRT
<213> ORGANISM: Artificial Sequence
<220> FEATURE:
<223> OTHER INFORMATION: Cleavable Moiety - 3009

<400> SEQUENCE: 310

Ala Val Gly Leu Leu Ala Pro Pro Gly Gly Leu Ser Gly Arg Ser Asp
1 5 10 15

Thr His

<210> SEQ ID NO 311
<211> LENGTH: 18
<212> TYPE: PRT
<213> ORGANISM: Artificial Sequence
<220> FEATURE:
<223> OTHER INFORMATION: Cleavable Moiety - 3011

<400> SEQUENCE: 311

Ala Val Gly Leu Leu Ala Pro Pro Gly Gly Leu Ser Gly Arg Ser Asp
1 5 10 15

Asn Pro

<210> SEQ ID NO 312
<211> LENGTH: 18
<212> TYPE: PRT
<213> ORGANISM: Artificial Sequence
<220> FEATURE:
<223> OTHER INFORMATION: Cleavable Moiety - 3012

<400> SEQUENCE: 312

Ala Val Gly Leu Leu Ala Pro Pro Gly Gly Leu Ser Gly Arg Ser Ala
1 5 10 15

Asn Pro

<210> SEQ ID NO 313
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 313

Leu Ser Gly Arg Ser Asp Asn His
1 5

<210> SEQ ID NO 314
<211> LENGTH: 10
<212> TYPE: PRT
<213> ORGANISM: Artificial Sequence
<220> FEATURE:
<223> OTHER INFORMATION: Cleavable Moiety

<400> SEQUENCE: 314

Leu Ser Gly Arg Ser Ala Asn Pro Arg Gly
1 5 10

<210> SEQ ID NO 315
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 315

Thr Gly Arg Gly Pro Ser Trp Val
1 5

<210> SEQ ID NO 316
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 316

Pro Leu Thr Gly Arg Ser Gly Gly 1 5

<210> SEQ ID NO 317
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 317

Thr Ala Arg Gly Pro Ser Phe Lys
1 5

<210> SEQ ID NO 318
<211> LENGTH: 12
<212> TYPE: PRT
<213> ORGANISM: Artificial Sequence
<220> FEATURE:
<223> OTHER INFORMATION: Cleavable Moiety

<400> SEQUENCE: 318

Asn Thr Leu Ser Gly Arg Ser Glu Asn His Ser Gly
1 5 10

<210> SEQ ID NO 319
<211> LENGTH: 12
<212> TYPE: PRT
<213> ORGANISM: Artificial Sequence
<220> FEATURE:
<223> OTHER INFORMATION: Cleavable Moiety

<400> SEQUENCE: 319

Asn Thr Leu Ser Gly Arg Ser Gly Asn His Gly Ser
1 5 10

<210> SEQ ID NO 320
<211> LENGTH: 12
<212> TYPE: PRT
<213> ORGANISM: Artificial Sequence
<220> FEATURE:
<223> OTHER INFORMATION: Cleavable Moiety

<400> SEQUENCE: 320

Thr Ser Thr Ser Gly Arg Ser Ala Asn Pro Arg Gly
1 5 10

<210> SEQ ID NO 321
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 321

Thr Ser Gly Arg Ser Ala Asn Pro
1 5

<210> SEQ ID NO 322
<211> LENGTH: 10
<212> TYPE: PRT
<213> ORGANISM: Artificial Sequence
<220> FEATURE:
<223> OTHER INFORMATION: Cleavable Moiety

<400> SEQUENCE: 322

Val His Met Pro Leu Gly Phe Leu Gly Pro
1 5 10

<210> SEQ ID NO 323
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 323

Ala Val Gly Leu Leu Ala Pro Pro
1               5

<210> SEQ ID NO 324
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 324

Ala Gln Asn Leu Leu Gly Met Val
1               5

<210> SEQ ID NO 325
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 325

Gln Asn Gln Ala Leu Arg Met Ala
1               5

<210> SEQ ID NO 326
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 326

Leu Ala Ala Pro Leu Gly Leu Leu
1               5

<210> SEQ ID NO 327
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 327

Ser Thr Phe Pro Phe Gly Met Phe
1               5

<210> SEQ ID NO 328
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 328

Ile Ser Ser Gly Leu Leu Ser Ser
1               5

<210> SEQ ID NO 329
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 329

Pro Ala Gly Leu Trp Leu Asp Pro
1 5

<210> SEQ ID NO 330
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 330

Val Ala Gly Arg Ser Met Arg Pro
1 5

<210> SEQ ID NO 331
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 331

Val Val Pro Glu Gly Arg Arg Ser
1 5

<210> SEQ ID NO 332
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 332

Ile Leu Pro Arg Ser Pro Ala Phe
1 5

<210> SEQ ID NO 333
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 333

Met Val Leu Gly Arg Ser Leu Leu
1 5

<210> SEQ ID NO 334
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 334

Val Ala Gly Arg Ser Met Arg Pro
1 5

<210> SEQ ID NO 335
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 335

Gln Gly Arg Ala Ile Thr Phe Ile
1               5

<210> SEQ ID NO 336
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 336

Ser Pro Arg Ser Ile Met Leu Ala
1               5

<210> SEQ ID NO 337
<211> LENGTH: 8
<212> TYPE: PRT
<213> ORGANISM: Artificial Sequence
<220> FEATURE:
<223> OTHER INFORMATION: Cleavable Moiety

<400> SEQUENCE: 337

Ser Met Leu Arg Ser Met Pro Leu
1               5

<210> SEQ ID NO 338
<211> LENGTH: 18
<212> TYPE: PRT
<213> ORGANISM: Artificial Sequence
<220> FEATURE:
<223> OTHER INFORMATION: Cleavable Moiety

<400> SEQUENCE: 338

Ala Val Gly Leu Leu Ala Pro Pro Gly Gly Leu Ser Gly Arg Ser Asp
1               5                   10                  15

Tyr His

<210> SEQ ID NO 339
<211> LENGTH: 18
<212> TYPE: PRT
<213> ORGANISM: Artificial Sequence
<220> FEATURE:
<223> OTHER INFORMATION: Cleavable Moiety

<400> SEQUENCE: 339

Ala Val Gly Leu Leu Ala Pro Pro Gly Gly Leu Ser Gly Arg Ser Ala
1               5                   10                  15

Asn Ile

<210> SEQ ID NO 340
<211> LENGTH: 18
<212> TYPE: PRT
<213> ORGANISM: Artificial Sequence
<220> FEATURE:
<223> OTHER INFORMATION: Cleavable Moiety

<400> SEQUENCE: 340

Ala Val Gly Leu Leu Ala Pro Pro Gly Gly Leu Ser Gly Arg Ser Asp 1 5 10 15

Asn Ile

<210> SEQ ID NO 341
<211> LENGTH: 13
<212> TYPE: PRT
<213> ORGANISM: Artificial Sequence
<220> FEATURE:
<223> OTHER INFORMATION: Cleavable Moiety

<400> SEQUENCE: 341

Ile Ser Ser Gly Leu Leu Ser Gly Arg Ser Asp Tyr His
1 5 10

<210> SEQ ID NO 342
<211> LENGTH: 13
<212> TYPE: PRT
<213> ORGANISM: Artificial Sequence
<220> FEATURE:
<223> OTHER INFORMATION: Cleavable Moiety

<400> SEQUENCE: 342

Ile Ser Ser Gly Leu Leu Ser Gly Arg Ser Ala Asn Ile
1 5 10

<210> SEQ ID NO 343
<211> LENGTH: 13
<212> TYPE: PRT
<213> ORGANISM: Artificial Sequence
<220> FEATURE:
<223> OTHER INFORMATION: Cleavable Moiety

<400> SEQUENCE: 343

Ile Ser Ser Gly Leu Leu Ser Gly Arg Ser Asp Asn Ile
1 5 10

<210> SEQ ID NO 344
<211> LENGTH: 108
<212> TYPE: PRT
<213> ORGANISM: Artificial Sequence
<220> FEATURE:
<223> OTHER INFORMATION: Ipilimumab-VL

<400> SEQUENCE: 344

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Gly Ser Ser
20 25 30

Tyr Leu Ala Trp Tyr Gln Gln Lys Pro Gly Gln Ala Pro Arg Leu Leu
35 40 45

Ile Tyr Gly Ala Phe Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Trp Thr Phe Gly Gln Gly Thr Lys Val Glu Ile Lys
100 105

<210> SEQ ID NO 345
<211> LENGTH: 118
<212> TYPE: PRT
<213> ORGANISM: Artificial Sequence
<220> FEATURE:
<223> OTHER INFORMATION: Ipilimumab-VH

<400> SEQUENCE: 345

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115
```

<210> SEQ ID NO 346
<211> LENGTH: 107
<212> TYPE: PRT
<213> ORGANISM: Artificial Sequence
<220> FEATURE:
<223> OTHER INFORMATION: Human Kappa constant LC

<400> SEQUENCE: 346

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 347
<211> LENGTH: 107
<212> TYPE: PRT
<213> ORGANISM: Artificial Sequence
<220> FEATURE:
<223> OTHER INFORMATION: Mouse Kappa constant LC

<400> SEQUENCE: 347

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45
```

```
Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105


<210> SEQ ID NO 348
<211> LENGTH: 215
<212> TYPE: PRT
<213> ORGANISM: Artificial Sequence
<220> FEATURE:
<223> OTHER INFORMATION: Ipilimumab-Human Kappa LC

<400> SEQUENCE: 348

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 349
<211> LENGTH: 215
<212> TYPE: PRT
<213> ORGANISM: Artificial Sequence
<220> FEATURE:
<223> OTHER INFORMATION: Ipilimumab-Mouse Kappa LC

<400> SEQUENCE: 349

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30
```

```
Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215


<210> SEQ ID NO 350
<211> LENGTH: 329
<212> TYPE: PRT
<213> ORGANISM: Artificial Sequence
<220> FEATURE:
<223> OTHER INFORMATION: Human IgG1 constant HC

<400> SEQUENCE: 350

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 351
<211> LENGTH: 329
<212> TYPE: PRT
<213> ORGANISM: Artificial Sequence
<220> FEATURE:
<223> OTHER INFORMATION: Mouse IgG1 constant HC

<400> SEQUENCE: 351

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 352
<211> LENGTH: 330
<212> TYPE: PRT
<213> ORGANISM: Artificial Sequence
<220> FEATURE:
<223> OTHER INFORMATION: Mouse IgG2a constant HC

<400> SEQUENCE: 352

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

```
Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330


<210> SEQ ID NO 353
<211> LENGTH: 447
<212> TYPE: PRT
<213> ORGANISM: Artificial Sequence
<220> FEATURE:
<223> OTHER INFORMATION: Ipilimumab-VH-Human IgG1 constant HC

<400> SEQUENCE: 353

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 354
<211> LENGTH: 447
<212> TYPE: PRT
<213> ORGANISM: Artificial Sequence
<220> FEATURE:
<223> OTHER INFORMATION: Ipilimumab-VH-Mouse IgG1 constant HC

<400> SEQUENCE: 354

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

```
Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 355
<211> LENGTH: 448
<212> TYPE: PRT
<213> ORGANISM: Artificial Sequence
<220> FEATURE:
<223> OTHER INFORMATION: Ipilimumab-VH-Mouse IgG2a constant HC

<400> SEQUENCE: 355

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110
```

```
Leu Val Thr Val Ser Ser Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
        435                 440                 445
```

```
<210> SEQ ID NO 356
<211> LENGTH: 262
<212> TYPE: PRT
<213> ORGANISM: Artificial Sequence
<220> FEATURE:
<223> OTHER INFORMATION: Spacer - YV01-2001  LC

<400> SEQUENCE: 356

Gln Gly Gln Ser Gly Gln Gly Asp Phe Ser Cys Leu His Ser Met Tyr
1               5                   10                  15

Asn Val Cys Leu Asp Pro Gly Gly Gly Ser Ser Gly Gly Ser Ile Ser
            20                  25                  30
```

```
Ser Gly Leu Leu Ser Gly Arg Ser Asp Asn His Gly Gly Gly Ser Glu
        35                  40                  45

Ile Val Leu Thr Gln Ser Pro Gly Thr Leu Ser Leu Ser Pro Gly Glu
    50                  55                  60

Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
            260


<210> SEQ ID NO 357
<211> LENGTH: 255
<212> TYPE: PRT
<213> ORGANISM: Artificial Sequence
<220> FEATURE:
<223> OTHER INFORMATION: YV01-2001 LC

<400> SEQUENCE: 357

Asp Phe Ser Cys Leu His Ser Met Tyr Asn Val Cys Leu Asp Pro Gly
1               5                   10                  15

Gly Gly Ser Ser Gly Gly Ser Ile Ser Ser Gly Leu Leu Ser Gly Arg
            20                  25                  30

Ser Asp Asn His Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125
```

```
Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 358
<211> LENGTH: 262
<212> TYPE: PRT
<213> ORGANISM: Artificial Sequence
<220> FEATURE:
<223> OTHER INFORMATION: Spacer - YV02-2001 LC

<400> SEQUENCE: 358

Gln Gly Gln Ser Gly Gln Gly Gln Pro Cys Ala Gln Met Tyr Gly Tyr
1               5                   10                  15

Ser Met Cys Pro His Thr Gly Gly Gly Ser Ser Gly Gly Ser Ile Ser
            20                  25                  30

Ser Gly Leu Leu Ser Gly Arg Ser Asp Asn His Gly Gly Gly Ser Glu
        35                  40                  45

Ile Val Leu Thr Gln Ser Pro Gly Thr Leu Ser Leu Ser Pro Gly Glu
    50                  55                  60

Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240
```

```
Ala Cys Glu Val Thr His Gln Gly Leu Ser Ser Pro Val Thr Lys Ser
                245                 250                 255

Phe Asn Arg Gly Glu Cys
            260
```

<210> SEQ ID NO 359
<211> LENGTH: 255
<212> TYPE: PRT
<213> ORGANISM: Artificial Sequence
<220> FEATURE:
<223> OTHER INFORMATION: YV02-2001 LC

<400> SEQUENCE: 359

```
Gln Pro Cys Ala Gln Met Tyr Gly Tyr Ser Met Cys Pro His Thr Gly
1               5                   10                  15

Gly Gly Ser Ser Gly Gly Ser Ile Ser Ser Gly Leu Leu Ser Gly Arg
            20                  25                  30

Ser Asp Asn His Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255
```

<210> SEQ ID NO 360
<211> LENGTH: 262
<212> TYPE: PRT
<213> ORGANISM: Artificial Sequence
<220> FEATURE:
<223> OTHER INFORMATION: Spacer - YV03-2001 LC

<400> SEQUENCE: 360

```
Gln Gly Gln Ser Gly Gln Gly Leu His Cys Arg Thr Gln Met Tyr Gly
1               5                   10                  15

Tyr Asn Leu Cys Pro Tyr Gly Gly Gly Ser Ser Gly Gly Ser Ile Ser
```

```
            20                  25                  30

Ser Gly Leu Leu Ser Gly Arg Ser Asp Asn His Gly Gly Gly Ser Glu
        35                  40                  45

Ile Val Leu Thr Gln Ser Pro Gly Thr Leu Ser Leu Ser Pro Gly Glu
    50                  55                  60

Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
            260


<210> SEQ ID NO 361
<211> LENGTH: 255
<212> TYPE: PRT
<213> ORGANISM: Artificial Sequence
<220> FEATURE:
<223> OTHER INFORMATION: YV03-2001 LC

<400> SEQUENCE: 361

Leu His Cys Arg Thr Gln Met Tyr Gly Tyr Asn Leu Cys Pro Tyr Gly
1               5                   10                  15

Gly Gly Ser Ser Gly Gly Ser Ile Ser Ser Gly Leu Leu Ser Gly Arg
            20                  25                  30

Ser Asp Asn His Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
```

115 120 125

Cys Gln Gln Tyr Gly Ser Ser Pro Trp Thr Phe Gly Gln Gly Thr Lys
130 135 140

Val Glu Ile Lys Arg Thr Val Ala Ala Pro Ser Val Phe Ile Phe Pro
145 150 155 160

Pro Ser Asp Glu Gln Leu Lys Ser Gly Thr Ala Ser Val Val Cys Leu
165 170 175

Leu Asn Asn Phe Tyr Pro Arg Glu Ala Lys Val Gln Trp Lys Val Asp
180 185 190

Asn Ala Leu Gln Ser Gly Asn Ser Gln Glu Ser Val Thr Glu Gln Asp
195 200 205

Ser Lys Asp Ser Thr Tyr Ser Leu Ser Ser Thr Leu Thr Leu Ser Lys
210 215 220

Ala Asp Tyr Glu Lys His Lys Val Tyr Ala Cys Glu Val Thr His Gln
225 230 235 240

Gly Leu Ser Ser Pro Val Thr Lys Ser Phe Asn Arg Gly Glu Cys
245 250 255

<210> SEQ ID NO 362
<211> LENGTH: 261
<212> TYPE: PRT
<213> ORGANISM: Artificial Sequence
<220> FEATURE:
<223> OTHER INFORMATION: Spacer - YV04-2001 LC

<400> SEQUENCE: 362

Gln Gly Gln Ser Gly Ser Leu His Cys Arg Thr Gln Leu Tyr Gly Tyr
1 5 10 15

Asn Leu Cys Pro Tyr Gly Gly Gly Ser Ser Gly Gly Ser Ile Ser Ser
20 25 30

Gly Leu Leu Ser Gly Arg Ser Asp Asn His Gly Gly Gly Ser Glu Ile
35 40 45

Val Leu Thr Gln Ser Pro Gly Thr Leu Ser Leu Ser Pro Gly Glu Arg
50 55 60

Ala Thr Leu Ser Cys Arg Ala Ser Gln Ser Val Gly Ser Ser Tyr Leu
65 70 75 80

Ala Trp Tyr Gln Gln Lys Pro Gly Gln Ala Pro Arg Leu Leu Ile Tyr
85 90 95

Gly Ala Phe Ser Arg Ala Thr Gly Ile Pro Asp Arg Phe Ser Gly Ser
100 105 110

Gly Ser Gly Thr Asp Phe Thr Leu Thr Ile Ser Arg Leu Glu Pro Glu
115 120 125

Asp Phe Ala Val Tyr Tyr Cys Gln Gln Tyr Gly Ser Ser Pro Trp Thr
130 135 140

Phe Gly Gln Gly Thr Lys Val Glu Ile Lys Arg Thr Val Ala Ala Pro
145 150 155 160

Ser Val Phe Ile Phe Pro Pro Ser Asp Glu Gln Leu Lys Ser Gly Thr
165 170 175

Ala Ser Val Val Cys Leu Leu Asn Asn Phe Tyr Pro Arg Glu Ala Lys
180 185 190

Val Gln Trp Lys Val Asp Asn Ala Leu Gln Ser Gly Asn Ser Gln Glu
195 200 205

Ser Val Thr Glu Gln Asp Ser Lys Asp Ser Thr Tyr Ser Leu Ser Ser
210 215 220

Thr Leu Thr Leu Ser Lys Ala Asp Tyr Glu Lys His Lys Val Tyr Ala 225 230 235 240

Cys Glu Val Thr His Gln Gly Leu Ser Ser Pro Val Thr Lys Ser Phe
245 250 255

Asn Arg Gly Glu Cys
260

<210> SEQ ID NO 363
<211> LENGTH: 255
<212> TYPE: PRT
<213> ORGANISM: Artificial Sequence
<220> FEATURE:
<223> OTHER INFORMATION: YV04-2001 LC

<400> SEQUENCE: 363

Leu His Cys Arg Thr Gln Leu Tyr Gly Tyr Asn Leu Cys Pro Tyr Gly
1 5 10 15

Gly Gly Ser Ser Gly Gly Ser Ile Ser Ser Gly Leu Leu Ser Gly Arg
20 25 30

Ser Asp Asn His Gly Gly Gly Ser Glu Ile Val Leu Thr Gln Ser Pro
35 40 45

Gly Thr Leu Ser Leu Ser Pro Gly Glu Arg Ala Thr Leu Ser Cys Arg
50 55 60

Ala Ser Gln Ser Val Gly Ser Ser Tyr Leu Ala Trp Tyr Gln Gln Lys
65 70 75 80

Pro Gly Gln Ala Pro Arg Leu Leu Ile Tyr Gly Ala Phe Ser Arg Ala
85 90 95

Thr Gly Ile Pro Asp Arg Phe Ser Gly Ser Gly Ser Gly Thr Asp Phe
100 105 110

Thr Leu Thr Ile Ser Arg Leu Glu Pro Glu Asp Phe Ala Val Tyr Tyr
115 120 125

Cys Gln Gln Tyr Gly Ser Ser Pro Trp Thr Phe Gly Gln Gly Thr Lys
130 135 140

Val Glu Ile Lys Arg Thr Val Ala Ala Pro Ser Val Phe Ile Phe Pro
145 150 155 160

Pro Ser Asp Glu Gln Leu Lys Ser Gly Thr Ala Ser Val Val Cys Leu
165 170 175

Leu Asn Asn Phe Tyr Pro Arg Glu Ala Lys Val Gln Trp Lys Val Asp
180 185 190

Asn Ala Leu Gln Ser Gly Asn Ser Gln Glu Ser Val Thr Glu Gln Asp
195 200 205

Ser Lys Asp Ser Thr Tyr Ser Leu Ser Ser Thr Leu Thr Leu Ser Lys
210 215 220

Ala Asp Tyr Glu Lys His Lys Val Tyr Ala Cys Glu Val Thr His Gln
225 230 235 240

Gly Leu Ser Ser Pro Val Thr Lys Ser Phe Asn Arg Gly Glu Cys
245 250 255

<210> SEQ ID NO 364
<211> LENGTH: 256
<212> TYPE: PRT
<213> ORGANISM: Artificial Sequence
<220> FEATURE:
<223> OTHER INFORMATION: Spacer - YV06-2001 LC

<400> SEQUENCE: 364

Gln Gly Gln Ser Gly Ser Cys Ala Gln Met Tyr Gly Tyr Ser Met Cys
1 5 10 15

```
Gly Gly Gly Ser Ser Gly Gly Ser Ile Ser Ser Gly Leu Leu Ser Gly
            20                  25                  30

Arg Ser Asp Asn His Gly Gly Gly Ser Glu Ile Val Leu Thr Gln Ser
        35                  40                  45

Pro Gly Thr Leu Ser Leu Ser Pro Gly Glu Arg Ala Thr Leu Ser Cys
    50                  55                  60

Arg Ala Ser Gln Ser Val Gly Ser Ser Tyr Leu Ala Trp Tyr Gln Gln
65                  70                  75                  80

Lys Pro Gly Gln Ala Pro Arg Leu Leu Ile Tyr Gly Ala Phe Ser Arg
                85                  90                  95

Ala Thr Gly Ile Pro Asp Arg Phe Ser Gly Ser Gly Ser Gly Thr Asp
            100                 105                 110

Phe Thr Leu Thr Ile Ser Arg Leu Glu Pro Glu Asp Phe Ala Val Tyr
        115                 120                 125

Tyr Cys Gln Gln Tyr Gly Ser Ser Pro Trp Thr Phe Gly Gln Gly Thr
    130                 135                 140

Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Ser Thr Leu Thr Leu Ser
    210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255
```

<210> SEQ ID NO 365
<211> LENGTH: 252
<212> TYPE: PRT
<213> ORGANISM: Artificial Sequence
<220> FEATURE:
<223> OTHER INFORMATION: YV06-2001 LC

<400> SEQUENCE: 365

```
Cys Ala Gln Met Tyr Gly Tyr Ser Met Cys Gly Gly Gly Ser Ser Gly
1               5                   10                  15

Gly Ser Ile Ser Ser Gly Leu Leu Ser Gly Arg Ser Asp Asn His Gly
            20                  25                  30

Gly Gly Ser Glu Ile Val Leu Thr Gln Ser Pro Gly Thr Leu Ser Leu
        35                  40                  45

Ser Pro Gly Glu Arg Ala Thr Leu Ser Cys Arg Ala Ser Gln Ser Val
    50                  55                  60

Gly Ser Ser Tyr Leu Ala Trp Tyr Gln Gln Lys Pro Gly Gln Ala Pro
65                  70                  75                  80

Arg Leu Leu Ile Tyr Gly Ala Phe Ser Arg Ala Thr Gly Ile Pro Asp
                85                  90                  95

Arg Phe Ser Gly Ser Gly Tyr Val Ser Gly Thr Asp Phe Thr Leu Thr
            100                 105                 110

Ile Ser Arg Leu Glu Pro Glu Asp Phe Ala Val Tyr Tyr Cys Gln Gln
        115                 120                 125
```

Tyr Gly Ser Ser Pro Trp Thr Phe Gly Gln Gly Thr Lys Val Glu Ile
130 135 140

Lys Arg Thr Val Ala Ala Pro Ser Val Phe Ile Phe Pro Pro Ser Asp
145 150 155 160

Glu Gln Leu Lys Ser Gly Thr Ala Ser Val Val Cys Leu Leu Asn Asn
165 170 175

Phe Tyr Pro Arg Glu Ala Lys Val Gln Trp Lys Val Asp Asn Ala Leu
180 185 190

Gln Ser Gly Asn Ser Gln Glu Ser Val Thr Glu Gln Asp Ser Lys Asp
195 200 205

Ser Thr Tyr Ser Leu Ser Ser Thr Leu Thr Leu Ser Lys Ala Asp Tyr
210 215 220

Glu Lys His Lys Val Tyr Ala Cys Glu Val Thr His Gln Gly Leu Ser
225 230 235 240

Ser Pro Val Thr Lys Ser Phe Asn Arg Gly Glu Cys
245 250

<210> SEQ ID NO 366
<211> LENGTH: 263
<212> TYPE: PRT
<213> ORGANISM: Artificial Sequence
<220> FEATURE:
<223> OTHER INFORMATION: Spacer - YV09-2001 LC

<400> SEQUENCE: 366

Gln Gly Gln Ser Gly Ser Phe Gly Tyr Val Thr Ala Cys Pro Asn His
1 5 10 15

Pro Met Cys His Asp Trp Gln Gly Gly Gly Ser Ser Gly Gly Ser Ile
20 25 30

Ser Ser Gly Leu Leu Ser Gly Arg Ser Asp Asn His Gly Gly Gly Ser
35 40 45

Glu Ile Val Leu Thr Gln Ser Pro Gly Thr Leu Ser Leu Ser Pro Gly
50 55 60

Glu Arg Ala Thr Leu Ser Cys Arg Ala Ser Gln Ser Val Gly Ser Ser
65 70 75 80

Tyr Leu Ala Trp Tyr Gln Gln Lys Pro Gly Gln Ala Pro Arg Leu Leu
85 90 95

Ile Tyr Gly Ala Phe Ser Arg Ala Thr Gly Ile Pro Asp Arg Phe Ser
100 105 110

Gly Ser Gly Ser Gly Thr Asp Phe Thr Leu Thr Ile Ser Arg Leu Glu
115 120 125

Pro Glu Asp Phe Ala Val Tyr Tyr Cys Gln Gln Tyr Gly Ser Ser Pro
130 135 140

Trp Thr Phe Gly Gln Gly Thr Lys Val Glu Ile Lys Arg Thr Val Ala
145 150 155 160

Ala Pro Ser Val Phe Ile Phe Pro Pro Ser Asp Glu Gln Leu Lys Ser
165 170 175

Gly Thr Ala Ser Val Val Cys Leu Leu Asn Asn Phe Tyr Pro Arg Glu
180 185 190

Ala Lys Val Gln Trp Lys Val Asp Asn Ala Leu Gln Ser Gly Asn Ser
195 200 205

Gln Glu Ser Val Thr Glu Gln Asp Ser Lys Asp Ser Thr Tyr Ser Leu
210 215 220

Ser Ser Thr Leu Thr Leu Ser Lys Ala Asp Tyr Glu Lys His Lys Val
225 230 235 240

Tyr Ala Cys Glu Val Thr His Gln Gly Leu Ser Ser Pro Val Thr Lys
245 250 255

Ser Phe Asn Arg Gly Glu Cys
260

<210> SEQ ID NO 367
<211> LENGTH: 255
<212> TYPE: PRT
<213> ORGANISM: Artificial Sequence
<220> FEATURE:
<223> OTHER INFORMATION: YV09-2001 LC

<400> SEQUENCE: 367

Phe Gly Thr Ala Cys Pro Asn His Pro Met Cys His Asp Trp Gln Gly
1 5 10 15

Gly Gly Ser Ser Gly Gly Ser Ile Ser Ser Gly Leu Leu Ser Gly Arg
20 25 30

Ser Asp Asn His Gly Gly Gly Ser Glu Ile Val Leu Thr Gln Ser Pro
35 40 45

Gly Thr Leu Ser Leu Ser Pro Gly Glu Arg Ala Thr Leu Ser Cys Arg
50 55 60

Ala Ser Gln Ser Val Gly Ser Ser Tyr Leu Ala Trp Tyr Gln Gln Lys
65 70 75 80

Pro Gly Gln Ala Pro Arg Leu Leu Ile Tyr Gly Ala Phe Ser Arg Ala
85 90 95

Thr Gly Ile Pro Asp Arg Phe Ser Gly Ser Gly Ser Gly Thr Asp Phe
100 105 110

Thr Leu Thr Ile Ser Arg Leu Glu Pro Glu Asp Phe Ala Val Tyr Tyr
115 120 125

Cys Gln Gln Tyr Gly Ser Ser Pro Trp Thr Phe Gly Gln Gly Thr Lys
130 135 140

Val Glu Ile Lys Arg Thr Val Ala Ala Pro Ser Val Phe Ile Phe Pro
145 150 155 160

Pro Ser Asp Glu Gln Leu Lys Ser Gly Thr Ala Ser Val Val Cys Leu
165 170 175

Leu Asn Asn Phe Tyr Pro Arg Glu Ala Lys Val Gln Trp Lys Val Asp
180 185 190

Asn Ala Leu Gln Ser Gly Asn Ser Gln Glu Ser Val Thr Glu Gln Asp
195 200 205

Ser Lys Asp Ser Thr Tyr Ser Leu Ser Ser Thr Leu Thr Leu Ser Lys
210 215 220

Ala Asp Tyr Glu Lys His Lys Val Tyr Ala Cys Glu Val Thr His Gln
225 230 235 240

Gly Leu Ser Ser Pro Val Thr Lys Ser Phe Asn Arg Gly Glu Cys
245 250 255

<210> SEQ ID NO 368
<211> LENGTH: 258
<212> TYPE: PRT
<213> ORGANISM: Artificial Sequence
<220> FEATURE:
<223> OTHER INFORMATION: Spacer - YV23-2001 LC

<400> SEQUENCE: 368

Gln Gly Gln Ser Gly Ser Cys Leu His Ser Leu Tyr Asn Val Cys Leu
1 5 10 15

Asp Pro Gly Gly Gly Ser Ser Gly Gly Ser Ile Ser Ser Gly Leu Leu
20 25 30

```
Ser Gly Arg Ser Asp Asn His Gly Gly Gly Ser Glu Ile Val Leu Thr
        35                  40                  45

Gln Ser Pro Gly Thr Leu Ser Leu Ser Pro Gly Glu Arg Ala Thr Leu
    50                  55                  60

Ser Cys Arg Ala Ser Gln Ser Val Gly Ser Ser Tyr Leu Ala Trp Tyr
65                  70                  75                  80

Gln Gln Lys Pro Gly Gln Ala Pro Arg Leu Leu Ile Tyr Gly Ala Phe
                85                  90                  95

Ser Arg Ala Thr Gly Ile Pro Asp Arg Phe Ser Gly Ser Gly Ser Gly
            100                 105                 110

Thr Asp Phe Thr Leu Thr Ile Ser Arg Leu Glu Pro Glu Asp Phe Ala
        115                 120                 125

Val Tyr Tyr Cys Gln Gln Tyr Gly Ser Ser Pro Trp Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys


<210> SEQ ID NO 369
<211> LENGTH: 252
<212> TYPE: PRT
<213> ORGANISM: Artificial Sequence
<220> FEATURE:
<223> OTHER INFORMATION: YV23-2001 LC

<400> SEQUENCE: 369

Cys Leu His Ser Leu Tyr Asn Val Cys Leu Asp Pro Gly Gly Gly Ser
1               5                   10                  15

Ser Gly Gly Ser Ile Ser Ser Gly Leu Leu Ser Gly Arg Ser Asp Asn
            20                  25                  30

His Gly Gly Gly Ser Glu Ile Val Leu Thr Gln Ser Pro Gly Thr Leu
        35                  40                  45

Ser Leu Ser Pro Gly Glu Arg Ala Thr Leu Ser Cys Arg Ala Ser Gln
    50                  55                  60

Ser Val Gly Ser Ser Tyr Leu Ala Trp Tyr Gln Gln Lys Pro Gly Gln
65                  70                  75                  80

Ala Pro Arg Leu Leu Ile Tyr Gly Ala Phe Ser Arg Ala Thr Gly Ile
                85                  90                  95

Pro Asp Arg Phe Ser Gly Ser Gly Ser Gly Thr Asp Phe Thr Leu Thr
            100                 105                 110

Ile Ser Arg Leu Glu Pro Glu Asp Phe Ala Val Tyr Tyr Cys Gln Gln
        115                 120                 125
```

```
Tyr Gly Ser Ser Pro Trp Thr Phe Gly Gln Gly Thr Lys Val Glu Ile
    130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250


<210> SEQ ID NO 370
<211> LENGTH: 258
<212> TYPE: PRT
<213> ORGANISM: Artificial Sequence
<220> FEATURE:
<223> OTHER INFORMATION: Spacer - YV24-2001 LC

<400> SEQUENCE: 370

Gln Gly Gln Ser Gly Ser Cys Leu His Ser Ala Tyr Asn Val Cys Leu
1               5                   10                  15

Asp Pro Gly Gly Gly Ser Ser Gly Gly Ser Ile Ser Ser Gly Leu Leu
            20                  25                  30

Ser Gly Arg Ser Asp Asn His Gly Gly Gly Ser Glu Ile Val Leu Thr
        35                  40                  45

Gln Ser Pro Gly Thr Leu Ser Leu Ser Pro Gly Glu Arg Ala Thr Leu
    50                  55                  60

Ser Cys Arg Ala Ser Gln Ser Val Gly Ser Ser Tyr Leu Ala Trp Tyr
65                  70                  75                  80

Gln Gln Lys Pro Gly Gln Ala Pro Arg Leu Leu Ile Tyr Gly Ala Phe
                85                  90                  95

Ser Arg Ala Thr Gly Ile Pro Asp Arg Phe Ser Gly Ser Gly Ser Gly
            100                 105                 110

Thr Asp Phe Thr Leu Thr Ile Ser Arg Leu Glu Pro Glu Asp Phe Ala
        115                 120                 125

Val Tyr Tyr Cys Gln Gln Tyr Gly Ser Ser Pro Trp Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240
```

```
Thr His Gln Gly Leu Ser Ser Pro Val Thr Lys Ser Phe Asn Arg Gly
                245                 250                 255

Glu Cys
```

<210> SEQ ID NO 371
<211> LENGTH: 252
<212> TYPE: PRT
<213> ORGANISM: Artificial Sequence
<220> FEATURE:
<223> OTHER INFORMATION: YV24-2001 LC

<400> SEQUENCE: 371

```
Cys Leu His Ser Ala Tyr Asn Val Cys Leu Asp Pro Gly Gly Gly Ser
1               5                   10                  15

Ser Gly Gly Ser Ile Ser Ser Gly Leu Leu Ser Gly Arg Ser Asp Asn
            20                  25                  30

His Gly Gly Gly Ser Glu Ile Val Leu Thr Gln Ser Pro Gly Thr Leu
        35                  40                  45

Ser Leu Ser Pro Gly Glu Arg Ala Thr Leu Ser Cys Arg Ala Ser Gln
    50                  55                  60

Ser Val Gly Ser Ser Tyr Leu Ala Trp Tyr Gln Gln Lys Pro Gly Gln
65                  70                  75                  80

Ala Pro Arg Leu Leu Ile Tyr Gly Ala Phe Ser Arg Ala Thr Gly Ile
                85                  90                  95

Pro Asp Arg Phe Ser Gly Ser Gly Ser Gly Thr Asp Phe Thr Leu Thr
            100                 105                 110

Ile Ser Arg Leu Glu Pro Glu Asp Phe Ala Val Tyr Tyr Cys Gln Gln
        115                 120                 125

Tyr Gly Ser Ser Pro Trp Thr Phe Gly Gln Gly Thr Lys Val Glu Ile
    130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250
```

<210> SEQ ID NO 372
<211> LENGTH: 258
<212> TYPE: PRT
<213> ORGANISM: Artificial Sequence
<220> FEATURE:
<223> OTHER INFORMATION: Spacer - YV27-2001 LC

<400> SEQUENCE: 372

```
Gln Gly Gln Ser Gly Ser Gln Pro Cys Ala Gln Met Tyr Gly Tyr Ser
1               5                   10                  15

Met Cys Gly Gly Gly Ser Ser Gly Gly Ser Ile Ser Ser Gly Leu Leu
            20                  25                  30
```

Ser Gly Arg Ser Asp Asn His Gly Gly Gly Ser Glu Ile Val Leu Thr
        35                  40                  45

Gln Ser Pro Gly Thr Leu Ser Leu Ser Pro Gly Glu Arg Ala Thr Leu
    50                  55                  60

Ser Cys Arg Ala Ser Gln Ser Val Gly Ser Ser Tyr Leu Ala Trp Tyr
65                  70                  75                  80

Gln Gln Lys Pro Gly Gln Ala Pro Arg Leu Leu Ile Tyr Gly Ala Phe
                85                  90                  95

Ser Arg Ala Thr Gly Ile Pro Asp Arg Phe Ser Gly Ser Gly Ser Gly
            100                 105                 110

Thr Asp Phe Thr Leu Thr Ile Ser Arg Leu Glu Pro Glu Asp Phe Ala
        115                 120                 125

Val Tyr Tyr Cys Gln Gln Tyr Gly Ser Ser Pro Trp Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 373
<211> LENGTH: 252
<212> TYPE: PRT
<213> ORGANISM: Artificial Sequence
<220> FEATURE:
<223> OTHER INFORMATION: YV27-2001 LC

<400> SEQUENCE: 373

Gln Pro Cys Ala Gln Met Tyr Gly Tyr Ser Met Cys Gly Gly Gly Ser
1               5                   10                  15

Ser Gly Gly Ser Ile Ser Ser Gly Leu Leu Ser Gly Arg Ser Asp Asn
            20                  25                  30

His Gly Gly Gly Ser Glu Ile Val Leu Thr Gln Ser Pro Gly Thr Leu
        35                  40                  45

Ser Leu Ser Pro Gly Glu Arg Ala Thr Leu Ser Cys Arg Ala Ser Gln
    50                  55                  60

Ser Val Gly Ser Ser Tyr Leu Ala Trp Tyr Gln Gln Lys Pro Gly Gln
65                  70                  75                  80

Ala Pro Arg Leu Leu Ile Tyr Gly Ala Phe Ser Arg Ala Thr Gly Ile
                85                  90                  95

Pro Asp Arg Phe Ser Gly Ser Gly Ser Gly Thr Asp Phe Thr Leu Thr
            100                 105                 110

Ile Ser Arg Leu Glu Pro Glu Asp Phe Ala Val Tyr Tyr Cys Gln Gln
        115                 120                 125

Tyr Gly Ser Ser Pro Trp Thr Phe Gly Gln Gly Thr Lys Val Glu Ile

```
    130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250


<210> SEQ ID NO 374
<211> LENGTH: 259
<212> TYPE: PRT
<213> ORGANISM: Artificial Sequence
<220> FEATURE:
<223> OTHER INFORMATION: Spacer - YV29-2001 LC

<400> SEQUENCE: 374

Gln Gly Gln Ser Gly Ser Cys Ala Gln Met Tyr Gly Tyr Ser Met Cys
1               5                   10                  15

Ala His Thr Gly Gly Gly Ser Ser Gly Gly Ser Ile Ser Ser Gly Leu
            20                  25                  30

Leu Ser Gly Arg Ser Asp Asn His Gly Gly Gly Ser Glu Ile Val Leu
        35                  40                  45

Thr Gln Ser Pro Gly Thr Leu Ser Leu Ser Pro Gly Glu Arg Ala Thr
    50                  55                  60

Leu Ser Cys Arg Ala Ser Gln Ser Val Gly Ser Ser Tyr Leu Ala Trp
65                  70                  75                  80

Tyr Gln Gln Lys Pro Gly Gln Ala Pro Arg Leu Leu Ile Tyr Gly Ala
                85                  90                  95

Phe Ser Arg Ala Thr Gly Ile Pro Asp Arg Phe Ser Gly Ser Gly Ser
            100                 105                 110

Gly Thr Asp Phe Thr Leu Thr Ile Ser Arg Leu Glu Pro Glu Asp Phe
        115                 120                 125

Ala Val Tyr Tyr Cys Gln Gln Tyr Gly Ser Ser Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
```

245 250 255

Gly Glu Cys

<210> SEQ ID NO 375
<211> LENGTH: 253
<212> TYPE: PRT
<213> ORGANISM: Artificial Sequence
<220> FEATURE:
<223> OTHER INFORMATION: YV29-2001 LC

<400> SEQUENCE: 375

Cys Ala Gln Met Tyr Gly Tyr Ser Met Cys Ala His Thr Gly Gly Gly
1 5 10 15

Ser Ser Gly Gly Ser Ile Ser Ser Gly Leu Leu Ser Gly Arg Ser Asp
20 25 30

Asn His Gly Gly Gly Ser Glu Ile Val Leu Thr Gln Ser Pro Gly Thr
35 40 45

Leu Ser Leu Ser Pro Gly Glu Arg Ala Thr Leu Ser Cys Arg Ala Ser
50 55 60

Gln Ser Val Gly Ser Ser Tyr Leu Ala Trp Tyr Gln Gln Lys Pro Gly
65 70 75 80

Gln Ala Pro Arg Leu Leu Ile Tyr Gly Ala Phe Ser Arg Ala Thr Gly
85 90 95

Ile Pro Asp Arg Phe Ser Gly Ser Gly Ser Gly Thr Asp Phe Thr Leu
100 105 110

Thr Ile Ser Arg Leu Glu Pro Glu Asp Phe Ala Val Tyr Tyr Cys Gln
115 120 125

Gln Tyr Gly Ser Ser Pro Trp Thr Phe Gly Gln Gly Thr Lys Val Glu
130 135 140

Ile Lys Arg Thr Val Ala Ala Pro Ser Val Phe Ile Phe Pro Pro Ser
145 150 155 160

Asp Glu Gln Leu Lys Ser Gly Thr Ala Ser Val Val Cys Leu Leu Asn
165 170 175

Asn Phe Tyr Pro Arg Glu Ala Lys Val Gln Trp Lys Val Asp Asn Ala
180 185 190

Leu Gln Ser Gly Asn Ser Gln Glu Ser Val Thr Glu Gln Asp Ser Lys
195 200 205

Asp Ser Thr Tyr Ser Leu Ser Ser Thr Leu Thr Leu Ser Lys Ala Asp
210 215 220

Tyr Glu Lys His Lys Val Tyr Ala Cys Glu Val Thr His Gln Gly Leu
225 230 235 240

Ser Ser Pro Val Thr Lys Ser Phe Asn Arg Gly Glu Cys
245 250

<210> SEQ ID NO 376
<211> LENGTH: 257
<212> TYPE: PRT
<213> ORGANISM: Artificial Sequence
<220> FEATURE:
<223> OTHER INFORMATION: Spacer - YV32-2001 LC

<400> SEQUENCE: 376

Gln Gly Gln Ser Gly Ser Cys Pro Asn His Pro Leu Cys His Asp Trp
1 5 10 15

Gln Gly Gly Gly Ser Ser Gly Gly Ser Ile Ser Ser Gly Leu Leu Ser
20 25 30

Gly Arg Ser Asp Asn His Gly Gly Gly Ser Glu Ile Val Leu Thr Gln 35 40 45

Ser Pro Gly Thr Leu Ser Leu Ser Pro Gly Glu Arg Ala Thr Leu Ser
50 55 60

Cys Arg Ala Ser Gln Ser Val Gly Ser Ser Tyr Leu Ala Trp Tyr Gln
65 70 75 80

Gln Lys Pro Gly Gln Ala Pro Arg Leu Leu Ile Tyr Gly Ala Phe Ser
85 90 95

Arg Ala Thr Gly Ile Pro Asp Arg Phe Ser Gly Ser Gly Ser Gly Thr
100 105 110

Asp Phe Thr Leu Thr Ile Ser Arg Leu Glu Pro Glu Asp Phe Ala Val
115 120 125

Tyr Tyr Cys Gln Gln Tyr Gly Ser Ser Pro Trp Thr Phe Gly Gln Gly
130 135 140

Thr Lys Val Glu Ile Lys Arg Thr Val Ala Ala Pro Ser Val Phe Ile
145 150 155 160

Phe Pro Pro Ser Asp Glu Gln Leu Lys Ser Gly Thr Ala Ser Val Val
165 170 175

Cys Leu Leu Asn Asn Phe Tyr Pro Arg Glu Ala Lys Val Gln Trp Lys
180 185 190

Val Asp Asn Ala Leu Gln Ser Gly Asn Ser Gln Glu Ser Val Thr Glu
195 200 205

Gln Asp Ser Lys Asp Ser Thr Tyr Ser Leu Ser Ser Thr Leu Thr Leu
210 215 220

Ser Lys Ala Asp Tyr Glu Lys His Lys Val Tyr Ala Cys Glu Val Thr
225 230 235 240

His Gln Gly Leu Ser Ser Pro Val Thr Lys Ser Phe Asn Arg Gly Glu
245 250 255

Cys

<210> SEQ ID NO 377
<211> LENGTH: 251
<212> TYPE: PRT
<213> ORGANISM: Artificial Sequence
<220> FEATURE:
<223> OTHER INFORMATION: YV32-2001 LC

<400> SEQUENCE: 377

Cys Pro Asn His Pro Leu Cys His Asp Trp Gln Gly Gly Gly Ser Ser
1 5 10 15

Gly Gly Ser Ile Ser Ser Gly Leu Leu Ser Gly Arg Ser Asp Asn His
20 25 30

Gly Gly Gly Ser Glu Ile Val Leu Thr Gln Ser Pro Gly Thr Leu Ser
35 40 45

Leu Ser Pro Gly Glu Arg Ala Thr Leu Ser Cys Arg Ala Ser Gln Ser
50 55 60

Val Gly Ser Ser Tyr Leu Ala Trp Tyr Gln Gln Lys Pro Gly Gln Ala
65 70 75 80

Pro Arg Leu Leu Ile Tyr Gly Ala Phe Ser Arg Ala Thr Gly Ile Pro
85 90 95

Asp Arg Phe Ser Gly Ser Gly Ser Gly Thr Asp Phe Thr Leu Thr Ile
100 105 110

Ser Arg Leu Glu Pro Glu Asp Phe Ala Val Tyr Tyr Cys Gln Gln Tyr
115 120 125

Gly Ser Ser Pro Trp Thr Phe Gly Gln Gly Thr Lys Val Glu Ile Lys
130 135 140

```
Arg Thr Val Ala Ala Pro Ser Val Phe Ile Phe Pro Pro Ser Asp Glu
145                 150                 155                 160

Gln Leu Lys Ser Gly Thr Ala Ser Val Val Cys Leu Leu Asn Asn Phe
                165                 170                 175

Tyr Pro Arg Glu Ala Lys Val Gln Trp Lys Val Asp Asn Ala Leu Gln
            180                 185                 190

Ser Gly Asn Ser Gln Glu Ser Val Thr Glu Gln Asp Ser Lys Asp Ser
        195                 200                 205

Thr Tyr Ser Leu Ser Ser Thr Leu Thr Leu Ser Lys Ala Asp Tyr Glu
    210                 215                 220

Lys His Lys Val Tyr Ala Cys Glu Val Thr His Gln Gly Leu Ser Ser
225                 230                 235                 240

Pro Val Thr Lys Ser Phe Asn Arg Gly Glu Cys
                245                 250


<210> SEQ ID NO 378
<211> LENGTH: 257
<212> TYPE: PRT
<213> ORGANISM: Artificial Sequence
<220> FEATURE:
<223> OTHER INFORMATION: Spacer - YV33-2001 LC

<400> SEQUENCE: 378

Gln Gly Gln Ser Gly Ser Cys Pro Asn His Pro Met Cys Ala Asp Trp
1               5                   10                  15

Gln Gly Gly Gly Ser Ser Gly Gly Ser Ile Ser Ser Gly Leu Leu Ser
            20                  25                  30

Gly Arg Ser Asp Asn His Gly Gly Gly Ser Glu Ile Val Leu Thr Gln
        35                  40                  45

Ser Pro Gly Thr Leu Ser Leu Ser Pro Gly Glu Arg Ala Thr Leu Ser
    50                  55                  60

Cys Arg Ala Ser Gln Ser Val Gly Ser Ser Tyr Leu Ala Trp Tyr Gln
65                  70                  75                  80

Gln Lys Pro Gly Gln Ala Pro Arg Leu Leu Ile Tyr Gly Ala Phe Ser
                85                  90                  95

Arg Ala Thr Gly Ile Pro Asp Arg Phe Ser Gly Ser Gly Ser Gly Thr
            100                 105                 110

Asp Phe Thr Leu Thr Ile Ser Arg Leu Glu Pro Glu Asp Phe Ala Val
        115                 120                 125

Tyr Tyr Cys Gln Gln Tyr Gly Ser Ser Pro Trp Thr Phe Gly Gln Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255
```

Cys

<210> SEQ ID NO 379
<211> LENGTH: 251
<212> TYPE: PRT
<213> ORGANISM: Artificial Sequence
<220> FEATURE:
<223> OTHER INFORMATION: YV33-2001 LC

<400> SEQUENCE: 379

Cys Pro Asn His Pro Met Cys Ala Asp Trp Gln Gly Gly Gly Ser Ser
1               5                   10                  15

Gly Gly Ser Ile Ser Ser Gly Leu Leu Ser Gly Arg Ser Asp Asn His
            20                  25                  30

Gly Gly Gly Ser Glu Ile Val Leu Thr Gln Ser Pro Gly Thr Leu Ser
        35                  40                  45

Leu Ser Pro Gly Glu Arg Ala Thr Leu Ser Cys Arg Ala Ser Gln Ser
    50                  55                  60

Val Gly Ser Ser Tyr Leu Ala Trp Tyr Gln Gln Lys Pro Gly Gln Ala
65                  70                  75                  80

Pro Arg Leu Leu Ile Tyr Gly Ala Phe Ser Arg Ala Thr Gly Ile Pro
                85                  90                  95

Asp Arg Phe Ser Gly Ser Gly Ser Gly Thr Asp Phe Thr Leu Thr Ile
            100                 105                 110

Ser Arg Leu Glu Pro Glu Asp Phe Ala Val Tyr Tyr Cys Gln Gln Tyr
        115                 120                 125

Gly Ser Ser Pro Trp Thr Phe Gly Gln Gly Thr Lys Val Glu Ile Lys
    130                 135                 140

Arg Thr Val Ala Ala Pro Ser Val Phe Ile Phe Pro Pro Ser Asp Glu
145                 150                 155                 160

Gln Leu Lys Ser Gly Thr Ala Ser Val Val Cys Leu Leu Asn Asn Phe
                165                 170                 175

Tyr Pro Arg Glu Ala Lys Val Gln Trp Lys Val Asp Asn Ala Leu Gln
            180                 185                 190

Ser Gly Asn Ser Gln Glu Ser Val Thr Glu Gln Asp Ser Lys Asp Ser
        195                 200                 205

Thr Tyr Ser Leu Ser Ser Thr Leu Thr Leu Ser Lys Ala Asp Tyr Glu
    210                 215                 220

Lys His Lys Val Tyr Ala Cys Glu Val Thr His Gln Gly Leu Ser Ser
225                 230                 235                 240

Pro Val Thr Lys Ser Phe Asn Arg Gly Glu Cys
                245                 250

<210> SEQ ID NO 380
<211> LENGTH: 257
<212> TYPE: PRT
<213> ORGANISM: Artificial Sequence
<220> FEATURE:
<223> OTHER INFORMATION: Spacer - YV35-2001 LC

<400> SEQUENCE: 380

Gln Gly Gln Ser Gly Ser Cys Pro Asn His Pro Met Cys His Asp Ala
1               5                   10                  15

Gln Gly Gly Gly Ser Ser Gly Gly Ser Ile Ser Ser Gly Leu Leu Ser
            20                  25                  30

Gly Arg Ser Asp Asn His Gly Gly Gly Ser Glu Ile Val Leu Thr Gln
        35                  40                  45

```
Ser Pro Gly Thr Leu Ser Leu Ser Pro Gly Glu Arg Ala Thr Leu Ser
    50                  55                  60

Cys Arg Ala Ser Gln Ser Val Gly Ser Ser Tyr Leu Ala Trp Tyr Gln
65                  70                  75                  80

Gln Lys Pro Gly Gln Ala Pro Arg Leu Leu Ile Tyr Gly Ala Phe Ser
                85                  90                  95

Arg Ala Thr Gly Ile Pro Asp Arg Phe Ser Gly Ser Gly Ser Gly Thr
            100                 105                 110

Asp Phe Thr Leu Thr Ile Ser Arg Leu Glu Pro Glu Asp Phe Ala Val
        115                 120                 125

Tyr Tyr Cys Gln Gln Tyr Gly Ser Ser Pro Trp Thr Phe Gly Gln Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys


<210> SEQ ID NO 381
<211> LENGTH: 251
<212> TYPE: PRT
<213> ORGANISM: Artificial Sequence
<220> FEATURE:
<223> OTHER INFORMATION: YV35-2001 LC

<400> SEQUENCE: 381

Cys Pro Asn His Pro Met Cys His Asp Ala Gln Gly Gly Gly Ser Ser
1               5                   10                  15

Gly Gly Ser Ile Ser Ser Gly Leu Leu Ser Gly Arg Ser Asp Asn His
            20                  25                  30

Gly Gly Gly Ser Glu Ile Val Leu Thr Gln Ser Pro Gly Thr Leu Ser
        35                  40                  45

Leu Ser Pro Gly Glu Arg Ala Thr Leu Ser Cys Arg Ala Ser Gln Ser
    50                  55                  60

Val Gly Ser Ser Tyr Leu Ala Trp Tyr Gln Gln Lys Pro Gly Gln Ala
65                  70                  75                  80

Pro Arg Leu Leu Ile Tyr Gly Ala Phe Ser Arg Ala Thr Gly Ile Pro
                85                  90                  95

Asp Arg Phe Ser Gly Ser Gly Ser Gly Thr Asp Phe Thr Leu Thr Ile
            100                 105                 110

Ser Arg Leu Glu Pro Glu Asp Phe Ala Val Tyr Tyr Cys Gln Gln Tyr
        115                 120                 125

Gly Ser Ser Pro Trp Thr Phe Gly Gln Gly Thr Lys Val Glu Ile Lys
    130                 135                 140
```

```
Arg Thr Val Ala Ala Pro Ser Val Phe Ile Phe Pro Pro Ser Asp Glu
145                 150                 155                 160

Gln Leu Lys Ser Gly Thr Ala Ser Val Val Cys Leu Leu Asn Asn Phe
                165                 170                 175

Tyr Pro Arg Glu Ala Lys Val Gln Trp Lys Val Asp Asn Ala Leu Gln
            180                 185                 190

Ser Gly Asn Ser Gln Glu Ser Val Thr Glu Gln Asp Ser Lys Asp Ser
        195                 200                 205

Thr Tyr Ser Leu Ser Ser Thr Leu Thr Leu Ser Lys Ala Asp Tyr Glu
    210                 215                 220

Lys His Lys Val Tyr Ala Cys Glu Val Thr His Gln Gly Leu Ser Ser
225                 230                 235                 240

Pro Val Thr Lys Ser Phe Asn Arg Gly Glu Cys
                245                 250


<210> SEQ ID NO 382
<211> LENGTH: 259
<212> TYPE: PRT
<213> ORGANISM: Artificial Sequence
<220> FEATURE:
<223> OTHER INFORMATION: Spacer - YV39-2001 LC

<400> SEQUENCE: 382

Gln Gly Gln Ser Gly Ser Cys Arg Thr Gln Leu Tyr Gly Tyr Asn Leu
1               5                   10                  15

Cys Pro Tyr Gly Gly Gly Ser Ser Gly Gly Ser Ile Ser Ser Gly Leu
            20                  25                  30

Leu Ser Gly Arg Ser Asp Asn His Gly Gly Gly Ser Glu Ile Val Leu
        35                  40                  45

Thr Gln Ser Pro Gly Thr Leu Ser Leu Ser Pro Gly Glu Arg Ala Thr
    50                  55                  60

Leu Ser Cys Arg Ala Ser Gln Ser Val Gly Ser Ser Tyr Leu Ala Trp
65                  70                  75                  80

Tyr Gln Gln Lys Pro Gly Gln Ala Pro Arg Leu Leu Ile Tyr Gly Ala
                85                  90                  95

Phe Ser Arg Ala Thr Gly Ile Pro Asp Arg Phe Ser Gly Ser Gly Ser
            100                 105                 110

Gly Thr Asp Phe Thr Leu Thr Ile Ser Arg Leu Glu Pro Glu Asp Phe
        115                 120                 125

Ala Val Tyr Tyr Cys Gln Gln Tyr Gly Ser Ser Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255
```

Gly Glu Cys

<210> SEQ ID NO 383
<211> LENGTH: 253
<212> TYPE: PRT
<213> ORGANISM: Artificial Sequence
<220> FEATURE:
<223> OTHER INFORMATION: YV39-2001 LC

<400> SEQUENCE: 383

Cys Arg Thr Gln Leu Tyr Gly Tyr Asn Leu Cys Pro Tyr Gly Gly Gly
1 5 10 15

Ser Ser Gly Gly Ser Ile Ser Ser Gly Leu Leu Ser Gly Arg Ser Asp
20 25 30

Asn His Gly Gly Gly Ser Glu Ile Val Leu Thr Gln Ser Pro Gly Thr
35 40 45

Leu Ser Leu Ser Pro Gly Glu Arg Ala Thr Leu Ser Cys Arg Ala Ser
50 55 60

Gln Ser Val Gly Ser Ser Tyr Leu Ala Trp Tyr Gln Gln Lys Pro Gly
65 70 75 80

Gln Ala Pro Arg Leu Leu Ile Tyr Gly Ala Phe Ser Arg Ala Thr Gly
85 90 95

Ile Pro Asp Arg Phe Ser Gly Ser Gly Ser Gly Thr Asp Phe Thr Leu
100 105 110

Thr Ile Ser Arg Leu Glu Pro Glu Asp Phe Ala Val Tyr Tyr Cys Gln
115 120 125

Gln Tyr Gly Ser Ser Pro Trp Thr Phe Gly Gln Gly Thr Lys Val Glu
130 135 140

Ile Lys Arg Thr Val Ala Ala Pro Ser Val Phe Ile Phe Pro Pro Ser
145 150 155 160

Asp Glu Gln Leu Lys Ser Gly Thr Ala Ser Val Val Cys Leu Leu Asn
165 170 175

Asn Phe Tyr Pro Arg Glu Ala Lys Val Gln Trp Lys Val Asp Asn Ala
180 185 190

Leu Gln Ser Gly Asn Ser Gln Glu Ser Val Thr Glu Gln Asp Ser Lys
195 200 205

Asp Ser Thr Tyr Ser Leu Ser Ser Thr Leu Thr Leu Ser Lys Ala Asp
210 215 220

Tyr Glu Lys His Lys Val Tyr Ala Cys Glu Val Thr His Gln Gly Leu
225 230 235 240

Ser Ser Pro Val Thr Lys Ser Phe Asn Arg Gly Glu Cys
245 250

<210> SEQ ID NO 384
<211> LENGTH: 259
<212> TYPE: PRT
<213> ORGANISM: Artificial Sequence
<220> FEATURE:
<223> OTHER INFORMATION: Spacer - YV41-2001 LC

<400> SEQUENCE: 384

Gln Gly Gln Ser Gly Ser Cys Arg Thr Gln Leu Tyr Gly Tyr Asn Leu
1 5 10 15

Cys Pro Ala Gly Gly Gly Ser Ser Gly Gly Ser Ile Ser Ser Gly Leu
20 25 30

Leu Ser Gly Arg Ser Asp Asn His Gly Gly Gly Ser Glu Ile Val Leu
35 40 45

```
Thr Gln Ser Pro Gly Thr Leu Ser Leu Ser Pro Gly Glu Arg Ala Thr
    50                  55                  60

Leu Ser Cys Arg Ala Ser Gln Ser Val Gly Ser Ser Tyr Leu Ala Trp
65                  70                  75                  80

Tyr Gln Gln Lys Pro Gly Gln Ala Pro Arg Leu Leu Ile Tyr Gly Ala
                85                  90                  95

Phe Ser Arg Ala Thr Gly Ile Pro Asp Arg Phe Ser Gly Ser Gly Ser
            100                 105                 110

Gly Thr Asp Phe Thr Leu Thr Ile Ser Arg Leu Glu Pro Glu Asp Phe
        115                 120                 125

Ala Val Tyr Tyr Cys Gln Gln Tyr Gly Ser Ser Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys


<210> SEQ ID NO 385
<211> LENGTH: 253
<212> TYPE: PRT
<213> ORGANISM: Artificial Sequence
<220> FEATURE:
<223> OTHER INFORMATION: YV41-2001 LC

<400> SEQUENCE: 385

Cys Arg Thr Gln Leu Tyr Gly Tyr Asn Leu Cys Pro Ala Gly Gly Gly
1               5                   10                  15

Ser Ser Gly Gly Ser Ile Ser Ser Gly Leu Leu Ser Gly Arg Ser Asp
            20                  25                  30

Asn His Gly Gly Gly Ser Glu Ile Val Leu Thr Gln Ser Pro Gly Thr
        35                  40                  45

Leu Ser Leu Ser Pro Gly Glu Arg Ala Thr Leu Ser Cys Arg Ala Ser
    50                  55                  60

Gln Ser Val Gly Ser Ser Tyr Leu Ala Trp Tyr Gln Gln Lys Pro Gly
65                  70                  75                  80

Gln Ala Pro Arg Leu Leu Ile Tyr Gly Ala Phe Ser Arg Ala Thr Gly
                85                  90                  95

Ile Pro Asp Arg Phe Ser Gly Ser Gly Ser Gly Thr Asp Phe Thr Leu
            100                 105                 110

Thr Ile Ser Arg Leu Glu Pro Glu Asp Phe Ala Val Tyr Tyr Cys Gln
        115                 120                 125

Gln Tyr Gly Ser Ser Pro Trp Thr Phe Gly Gln Gly Thr Lys Val Glu
    130                 135                 140

Ile Lys Arg Thr Val Ala Ala Pro Ser Val Phe Ile Phe Pro Pro Ser
```

```
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250


<210> SEQ ID NO 386
<211> LENGTH: 261
<212> TYPE: PRT
<213> ORGANISM: Artificial Sequence
<220> FEATURE:
<223> OTHER INFORMATION: Spacer - YV51-2001 LC

<400> SEQUENCE: 386

Gln Gly Gln Ser Gly Ser Phe Gly Ala Ala Cys Pro Asn His Pro Ile
1               5                   10                  15

Cys His Asp Trp Gln Gly Gly Gly Ser Ser Gly Gly Ser Ile Ser Ser
            20                  25                  30

Gly Leu Leu Ser Gly Arg Ser Asp Asn His Gly Gly Gly Ser Glu Ile
        35                  40                  45

Val Leu Thr Gln Ser Pro Gly Thr Leu Ser Leu Ser Pro Gly Glu Arg
    50                  55                  60

Ala Thr Leu Ser Cys Arg Ala Ser Gln Ser Val Gly Ser Ser Tyr Leu
65                  70                  75                  80

Ala Trp Tyr Gln Gln Lys Pro Gly Gln Ala Pro Arg Leu Leu Ile Tyr
                85                  90                  95

Gly Ala Phe Ser Arg Ala Thr Gly Ile Pro Asp Arg Phe Ser Gly Ser
            100                 105                 110

Gly Ser Gly Thr Asp Phe Thr Leu Thr Ile Ser Arg Leu Glu Pro Glu
        115                 120                 125

Asp Phe Ala Val Tyr Tyr Cys Gln Gln Tyr Gly Ser Ser Pro Trp Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
```

260

<210> SEQ ID NO 387
<211> LENGTH: 255
<212> TYPE: PRT
<213> ORGANISM: Artificial Sequence
<220> FEATURE:
<223> OTHER INFORMATION: YV51-2001 LC

<400> SEQUENCE: 387

Phe Gly Ala Ala Cys Pro Asn His Pro Ile Cys His Asp Trp Gln Gly
1 5 10 15

Gly Gly Ser Ser Gly Gly Ser Ile Ser Ser Gly Leu Leu Ser Gly Arg
20 25 30

Ser Asp Asn His Gly Gly Gly Ser Glu Ile Val Leu Thr Gln Ser Pro
35 40 45

Gly Thr Leu Ser Leu Ser Pro Gly Glu Arg Ala Thr Leu Ser Cys Arg
50 55 60

Ala Ser Gln Ser Val Gly Ser Ser Tyr Leu Ala Trp Tyr Gln Gln Lys
65 70 75 80

Pro Gly Gln Ala Pro Arg Leu Leu Ile Tyr Gly Ala Phe Ser Arg Ala
85 90 95

Thr Gly Ile Pro Asp Arg Phe Ser Gly Ser Gly Ser Gly Thr Asp Phe
100 105 110

Thr Leu Thr Ile Ser Arg Leu Glu Pro Glu Asp Phe Ala Val Tyr Tyr
115 120 125

Cys Gln Gln Tyr Gly Ser Ser Pro Trp Thr Phe Gly Gln Gly Thr Lys
130 135 140

Val Glu Ile Lys Arg Thr Val Ala Ala Pro Ser Val Phe Ile Phe Pro
145 150 155 160

Pro Ser Asp Glu Gln Leu Lys Ser Gly Thr Ala Ser Val Val Cys Leu
165 170 175

Leu Asn Asn Phe Tyr Pro Arg Glu Ala Lys Val Gln Trp Lys Val Asp
180 185 190

Asn Ala Leu Gln Ser Gly Asn Ser Gln Glu Ser Val Thr Glu Gln Asp
195 200 205

Ser Lys Asp Ser Thr Tyr Ser Leu Ser Ser Thr Leu Thr Leu Ser Lys
210 215 220

Ala Asp Tyr Glu Lys His Lys Val Tyr Ala Cys Glu Val Thr His Gln
225 230 235 240

Gly Leu Ser Ser Pro Val Thr Lys Ser Phe Asn Arg Gly Glu Cys
245 250 255

<210> SEQ ID NO 388
<211> LENGTH: 261
<212> TYPE: PRT
<213> ORGANISM: Artificial Sequence
<220> FEATURE:
<223> OTHER INFORMATION: Spacer - YV52-2001 LC

<400> SEQUENCE: 388

Gln Gly Gln Ser Gly Ser Phe Gly Ala Ala Cys Pro Asn His Pro Leu
1 5 10 15

Cys His Asp Trp Gln Gly Gly Gly Ser Ser Gly Gly Ser Ile Ser Ser
20 25 30

Gly Leu Leu Ser Gly Arg Ser Asp Asn His Gly Gly Gly Ser Glu Ile
35 40 45

```
Val Leu Thr Gln Ser Pro Gly Thr Leu Ser Leu Ser Pro Gly Glu Arg
    50                  55                  60

Ala Thr Leu Ser Cys Arg Ala Ser Gln Ser Val Gly Ser Ser Tyr Leu
65                  70                  75                  80

Ala Trp Tyr Gln Gln Lys Pro Gly Gln Ala Pro Arg Leu Leu Ile Tyr
                85                  90                  95

Gly Ala Phe Ser Arg Ala Thr Gly Ile Pro Asp Arg Phe Ser Gly Ser
            100                 105                 110

Gly Ser Gly Thr Asp Phe Thr Leu Thr Ile Ser Arg Leu Glu Pro Glu
        115                 120                 125

Asp Phe Ala Val Tyr Tyr Cys Gln Gln Tyr Gly Ser Ser Pro Trp Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260


<210> SEQ ID NO 389
<211> LENGTH: 255
<212> TYPE: PRT
<213> ORGANISM: Artificial Sequence
<220> FEATURE:
<223> OTHER INFORMATION: YV52-2001 LC

<400> SEQUENCE: 389

Phe Gly Ala Ala Cys Pro Asn His Pro Leu Cys His Asp Trp Gln Gly
1               5                   10                  15

Gly Gly Ser Ser Gly Gly Ser Ile Ser Ser Gly Leu Leu Ser Gly Arg
            20                  25                  30

Ser Asp Asn His Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140
```

```
Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 390
<211> LENGTH: 261
<212> TYPE: PRT
<213> ORGANISM: Artificial Sequence
<220> FEATURE:
<223> OTHER INFORMATION: Spacer - YV53-2001 LC

<400> SEQUENCE: 390

Gln Gly Gln Ser Gly Ser Phe Gly Ala Ala Cys Pro Asn His Pro Met
1               5                   10                  15

Cys His Asp Ala Gln Gly Gly Gly Ser Ser Gly Gly Ser Ile Ser Ser
            20                  25                  30

Gly Leu Leu Ser Gly Arg Ser Asp Asn His Gly Gly Gly Ser Glu Ile
        35                  40                  45

Val Leu Thr Gln Ser Pro Gly Thr Leu Ser Leu Ser Pro Gly Glu Arg
    50                  55                  60

Ala Thr Leu Ser Cys Arg Ala Ser Gln Ser Val Gly Ser Ser Tyr Leu
65                  70                  75                  80

Ala Trp Tyr Gln Gln Lys Pro Gly Gln Ala Pro Arg Leu Leu Ile Tyr
                85                  90                  95

Gly Ala Phe Ser Arg Ala Thr Gly Ile Pro Asp Arg Phe Ser Gly Ser
            100                 105                 110

Gly Ser Gly Thr Asp Phe Thr Leu Thr Ile Ser Arg Leu Glu Pro Glu
        115                 120                 125

Asp Phe Ala Val Tyr Tyr Cys Gln Gln Tyr Gly Ser Ser Pro Trp Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255
```

```
Asn Arg Gly Glu Cys
            260


<210> SEQ ID NO 391
<211> LENGTH: 255
<212> TYPE: PRT
<213> ORGANISM: Artificial Sequence
<220> FEATURE:
<223> OTHER INFORMATION: YV53-2001 LC

<400> SEQUENCE: 391

Phe Gly Ala Ala Cys Pro Asn His Pro Met Cys His Asp Ala Gln Gly
1               5                   10                  15

Gly Gly Ser Ser Gly Gly Ser Ile Ser Ser Gly Leu Leu Ser Gly Arg
            20                  25                  30

Ser Asp Asn His Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 392
<211> LENGTH: 258
<212> TYPE: PRT
<213> ORGANISM: Artificial Sequence
<220> FEATURE:
<223> OTHER INFORMATION: Spacer - YV54-2001 LC

<400> SEQUENCE: 392

Gln Gly Gln Ser Gly Ser Cys Leu His Ser Ala Tyr Asn Ala Cys Leu
1               5                   10                  15

Asp Pro Gly Gly Gly Ser Ser Gly Gly Ser Ile Ser Ser Gly Leu Leu
            20                  25                  30

Ser Gly Arg Ser Asp Asn His Gly Gly Gly Ser Glu Ile Val Leu Thr
        35                  40                  45
```

```
Gln Ser Pro Gly Thr Leu Ser Leu Ser Pro Gly Glu Arg Ala Thr Leu
    50                  55                  60

Ser Cys Arg Ala Ser Gln Ser Val Gly Ser Ser Tyr Leu Ala Trp Tyr
65                  70                  75                  80

Gln Gln Lys Pro Gly Gln Ala Pro Arg Leu Leu Ile Tyr Gly Ala Phe
                85                  90                  95

Ser Arg Ala Thr Gly Ile Pro Asp Arg Phe Ser Gly Ser Gly Ser Gly
            100                 105                 110

Thr Asp Phe Thr Leu Thr Ile Ser Arg Leu Glu Pro Glu Asp Phe Ala
        115                 120                 125

Val Tyr Tyr Cys Gln Gln Tyr Gly Ser Ser Pro Trp Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys


<210> SEQ ID NO 393
<211> LENGTH: 252
<212> TYPE: PRT
<213> ORGANISM: Artificial Sequence
<220> FEATURE:
<223> OTHER INFORMATION: YV54-2001 LC

<400> SEQUENCE: 393

Cys Leu His Ser Ala Tyr Asn Ala Cys Leu Asp Pro Gly Gly Gly Ser
1               5                   10                  15

Ser Gly Gly Ser Ile Ser Ser Gly Leu Leu Ser Gly Arg Ser Asp Asn
            20                  25                  30

His Gly Gly Gly Ser Glu Ile Val Leu Thr Gln Ser Pro Gly Thr Leu
        35                  40                  45

Ser Leu Ser Pro Gly Glu Arg Ala Thr Leu Ser Cys Arg Ala Ser Gln
    50                  55                  60

Ser Val Gly Ser Ser Tyr Leu Ala Trp Tyr Gln Gln Lys Pro Gly Gln
65                  70                  75                  80

Ala Pro Arg Leu Leu Ile Tyr Gly Ala Phe Ser Arg Ala Thr Gly Ile
                85                  90                  95

Pro Asp Arg Phe Ser Gly Ser Gly Ser Gly Thr Asp Phe Thr Leu Thr
            100                 105                 110

Ile Ser Arg Leu Glu Pro Glu Asp Phe Ala Val Tyr Tyr Cys Gln Gln
        115                 120                 125

Tyr Gly Ser Ser Pro Trp Thr Phe Gly Gln Gly Thr Lys Val Glu Ile
    130                 135                 140
```

```
Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250


<210> SEQ ID NO 394
<211> LENGTH: 258
<212> TYPE: PRT
<213> ORGANISM: Artificial Sequence
<220> FEATURE:
<223> OTHER INFORMATION: Spacer - YV55-2001 LC

<400> SEQUENCE: 394

Gln Gly Gln Ser Gly Ser Cys Ala His Ser Ala Tyr Asn Val Cys Leu
1               5                   10                  15

Asp Pro Gly Gly Gly Ser Ser Gly Gly Ser Ile Ser Ser Gly Leu Leu
            20                  25                  30

Ser Gly Arg Ser Asp Asn His Gly Gly Gly Ser Glu Ile Val Leu Thr
        35                  40                  45

Gln Ser Pro Gly Thr Leu Ser Leu Ser Pro Gly Glu Arg Ala Thr Leu
    50                  55                  60

Ser Cys Arg Ala Ser Gln Ser Val Gly Ser Ser Tyr Leu Ala Trp Tyr
65                  70                  75                  80

Gln Gln Lys Pro Gly Gln Ala Pro Arg Leu Leu Ile Tyr Gly Ala Phe
                85                  90                  95

Ser Arg Ala Thr Gly Ile Pro Asp Arg Phe Ser Gly Ser Gly Ser Gly
            100                 105                 110

Thr Asp Phe Thr Leu Thr Ile Ser Arg Leu Glu Pro Glu Asp Phe Ala
        115                 120                 125

Val Tyr Tyr Cys Gln Gln Tyr Gly Ser Ser Pro Trp Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255
```

Glu Cys

<210> SEQ ID NO 395
<211> LENGTH: 252
<212> TYPE: PRT
<213> ORGANISM: Artificial Sequence
<220> FEATURE:
<223> OTHER INFORMATION: YV55-2001 LC

<400> SEQUENCE: 395

```
Cys Ala His Ser Ala Tyr Asn Val Cys Leu Asp Pro Gly Gly Gly Ser
1               5                   10                  15

Ser Gly Gly Ser Ile Ser Ser Gly Leu Leu Ser Gly Arg Ser Asp Asn
            20                  25                  30

His Gly Gly Gly Ser Glu Ile Val Leu Thr Gln Ser Pro Gly Thr Leu
        35                  40                  45

Ser Leu Ser Pro Gly Glu Arg Ala Thr Leu Ser Cys Arg Ala Ser Gln
    50                  55                  60

Ser Val Gly Ser Ser Tyr Leu Ala Trp Tyr Gln Gln Lys Pro Gly Gln
65                  70                  75                  80

Ala Pro Arg Leu Leu Ile Tyr Gly Ala Phe Ser Arg Ala Thr Gly Ile
                85                  90                  95

Pro Asp Arg Phe Ser Gly Ser Gly Ser Gly Thr Asp Phe Thr Leu Thr
            100                 105                 110

Ile Ser Arg Leu Glu Pro Glu Asp Phe Ala Val Tyr Tyr Cys Gln Gln
        115                 120                 125

Tyr Gly Ser Ser Pro Trp Thr Phe Gly Gln Gly Thr Lys Val Glu Ile
    130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250
```

<210> SEQ ID NO 396
<211> LENGTH: 258
<212> TYPE: PRT
<213> ORGANISM: Artificial Sequence
<220> FEATURE:
<223> OTHER INFORMATION: Spacer - YV56-2001 LC

<400> SEQUENCE: 396

```
Gln Gly Gln Ser Gly Ser Cys Leu His Ser Ala Tyr Asn Val Cys Ala
1               5                   10                  15

Asp Pro Gly Gly Gly Ser Ser Gly Gly Ser Ile Ser Ser Gly Leu Leu
            20                  25                  30

Ser Gly Arg Ser Asp Asn His Gly Gly Gly Ser Glu Ile Val Leu Thr
        35                  40                  45
```

Gln Ser Pro Gly Thr Leu Ser Leu Ser Pro Gly Glu Arg Ala Thr Leu
50 55 60

Ser Cys Arg Ala Ser Gln Ser Val Gly Ser Ser Tyr Leu Ala Trp Tyr
65 70 75 80

Gln Gln Lys Pro Gly Gln Ala Pro Arg Leu Leu Ile Tyr Gly Ala Phe
85 90 95

Ser Arg Ala Thr Gly Ile Pro Asp Arg Phe Ser Gly Ser Gly Ser Gly
100 105 110

Thr Asp Phe Thr Leu Thr Ile Ser Arg Leu Glu Pro Glu Asp Phe Ala
115 120 125

Val Tyr Tyr Cys Gln Gln Tyr Gly Ser Ser Pro Trp Thr Phe Gly Gln
130 135 140

Gly Thr Lys Val Glu Ile Lys Arg Thr Val Ala Ala Pro Ser Val Phe
145 150 155 160

Ile Phe Pro Pro Ser Asp Glu Gln Leu Lys Ser Gly Thr Ala Ser Val
165 170 175

Val Cys Leu Leu Asn Asn Phe Tyr Pro Arg Glu Ala Lys Val Gln Trp
180 185 190

Lys Val Asp Asn Ala Leu Gln Ser Gly Asn Ser Gln Glu Ser Val Thr
195 200 205

Glu Gln Asp Ser Lys Asp Ser Thr Tyr Ser Leu Ser Ser Thr Leu Thr
210 215 220

Leu Ser Lys Ala Asp Tyr Glu Lys His Lys Val Tyr Ala Cys Glu Val
225 230 235 240

Thr His Gln Gly Leu Ser Ser Pro Val Thr Lys Ser Phe Asn Arg Gly
245 250 255

Glu Cys

<210> SEQ ID NO 397
<211> LENGTH: 252
<212> TYPE: PRT
<213> ORGANISM: Artificial Sequence
<220> FEATURE:
<223> OTHER INFORMATION: YV56-2001 LC

<400> SEQUENCE: 397

Cys Leu His Ser Ala Tyr Asn Val Cys Ala Asp Pro Gly Gly Gly Ser
1 5 10 15

Ser Gly Gly Ser Ile Ser Ser Gly Leu Leu Ser Gly Arg Ser Asp Asn
20 25 30

His Gly Gly Gly Ser Glu Ile Val Leu Thr Gln Ser Pro Gly Thr Leu
35 40 45

Ser Leu Ser Pro Gly Glu Arg Ala Thr Leu Ser Cys Arg Ala Ser Gln
50 55 60

Ser Val Gly Ser Ser Tyr Leu Ala Trp Tyr Gln Gln Lys Pro Gly Gln
65 70 75 80

Ala Pro Arg Leu Leu Ile Tyr Gly Ala Phe Ser Arg Ala Thr Gly Ile
85 90 95

Pro Asp Arg Phe Ser Gly Ser Gly Ser Gly Thr Asp Phe Thr Leu Thr
100 105 110

Ile Ser Arg Leu Glu Pro Glu Asp Phe Ala Val Tyr Tyr Cys Gln Gln
115 120 125

Tyr Gly Ser Ser Pro Trp Thr Phe Gly Gln Gly Thr Lys Val Glu Ile
130 135 140

Lys Arg Thr Val Ala Ala Pro Ser Val Phe Ile Phe Pro Pro Ser Asp

```
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250


<210> SEQ ID NO 398
<211> LENGTH: 258
<212> TYPE: PRT
<213> ORGANISM: Artificial Sequence
<220> FEATURE:
<223> OTHER INFORMATION: Spacer - YV57-2001 LC

<400> SEQUENCE: 398

Gln Gly Gln Ser Gly Ser Cys Leu His Ser Ala Tyr Asn Val Cys Leu
1               5                   10                  15

Ala Pro Gly Gly Gly Ser Ser Gly Gly Ser Ile Ser Ser Gly Leu Leu
            20                  25                  30

Ser Gly Arg Ser Asp Asn His Gly Gly Gly Ser Glu Ile Val Leu Thr
        35                  40                  45

Gln Ser Pro Gly Thr Leu Ser Leu Ser Pro Gly Glu Arg Ala Thr Leu
    50                  55                  60

Ser Cys Arg Ala Ser Gln Ser Val Gly Ser Ser Tyr Leu Ala Trp Tyr
65                  70                  75                  80

Gln Gln Lys Pro Gly Gln Ala Pro Arg Leu Leu Ile Tyr Gly Ala Phe
                85                  90                  95

Ser Arg Ala Thr Gly Ile Pro Asp Arg Phe Ser Gly Ser Gly Ser Gly
            100                 105                 110

Thr Asp Phe Thr Leu Thr Ile Ser Arg Leu Glu Pro Glu Asp Phe Ala
        115                 120                 125

Val Tyr Tyr Cys Gln Gln Tyr Gly Ser Ser Pro Trp Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys
```

<210> SEQ ID NO 399
<211> LENGTH: 252
<212> TYPE: PRT
<213> ORGANISM: Artificial Sequence
<220> FEATURE:
<223> OTHER INFORMATION: YV57-2001 LC

<400> SEQUENCE: 399

Cys Leu His Ser Ala Tyr Asn Val Cys Leu Ala Pro Gly Gly Gly Ser
1 5 10 15

Ser Gly Gly Ser Ile Ser Ser Gly Leu Leu Ser Gly Arg Ser Asp Asn
20 25 30

His Gly Gly Gly Ser Glu Ile Val Leu Thr Gln Ser Pro Gly Thr Leu
35 40 45

Ser Leu Ser Pro Gly Glu Arg Ala Thr Leu Ser Cys Arg Ala Ser Gln
50 55 60

Ser Val Gly Ser Ser Tyr Leu Ala Trp Tyr Gln Gln Lys Pro Gly Gln
65 70 75 80

Ala Pro Arg Leu Leu Ile Tyr Gly Ala Phe Ser Arg Ala Thr Gly Ile
85 90 95

Pro Asp Arg Phe Ser Gly Ser Gly Ser Gly Thr Asp Phe Thr Leu Thr
100 105 110

Ile Ser Arg Leu Glu Pro Glu Asp Phe Ala Val Tyr Tyr Cys Gln Gln
115 120 125

Tyr Gly Ser Ser Pro Trp Thr Phe Gly Gln Gly Thr Lys Val Glu Ile
130 135 140

Lys Arg Thr Val Ala Ala Pro Ser Val Phe Ile Phe Pro Pro Ser Asp
145 150 155 160

Glu Gln Leu Lys Ser Gly Thr Ala Ser Val Val Cys Leu Leu Asn Asn
165 170 175

Phe Tyr Pro Arg Glu Ala Lys Val Gln Trp Lys Val Asp Asn Ala Leu
180 185 190

Gln Ser Gly Asn Ser Gln Glu Ser Val Thr Glu Gln Asp Ser Lys Asp
195 200 205

Ser Thr Tyr Ser Leu Ser Ser Thr Leu Thr Leu Ser Lys Ala Asp Tyr
210 215 220

Glu Lys His Lys Val Tyr Ala Cys Glu Val Thr His Gln Gly Leu Ser
225 230 235 240

Ser Pro Val Thr Lys Ser Phe Asn Arg Gly Glu Cys
245 250

<210> SEQ ID NO 400
<211> LENGTH: 258
<212> TYPE: PRT
<213> ORGANISM: Artificial Sequence
<220> FEATURE:
<223> OTHER INFORMATION: Spacer - YV58-2001 LC

<400> SEQUENCE: 400

Gln Gly Gln Ser Gly Ser Cys Leu His Ser Ala Tyr Asn Val Cys Leu
1 5 10 15

Asp Ala Gly Gly Gly Ser Ser Gly Gly Ser Ile Ser Ser Gly Leu Leu
20 25 30

Ser Gly Arg Ser Asp Asn His Gly Gly Gly Ser Glu Ile Val Leu Thr
35 40 45

Gln Ser Pro Gly Thr Leu Ser Leu Ser Pro Gly Glu Arg Ala Thr Leu

```
    50                  55                  60

Ser Cys Arg Ala Ser Gln Ser Val Gly Ser Ser Tyr Leu Ala Trp Tyr
65                  70                  75                  80

Gln Gln Lys Pro Gly Gln Ala Pro Arg Leu Leu Ile Tyr Gly Ala Phe
                85                  90                  95

Ser Arg Ala Thr Gly Ile Pro Asp Arg Phe Ser Gly Ser Gly Ser Gly
            100                 105                 110

Thr Asp Phe Thr Leu Thr Ile Ser Arg Leu Glu Pro Glu Asp Phe Ala
        115                 120                 125

Val Tyr Tyr Cys Gln Gln Tyr Gly Ser Ser Pro Trp Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys


<210> SEQ ID NO 401
<211> LENGTH: 252
<212> TYPE: PRT
<213> ORGANISM: Artificial Sequence
<220> FEATURE:
<223> OTHER INFORMATION: YV58-2001 LC

<400> SEQUENCE: 401

Cys Leu His Ser Ala Tyr Asn Val Cys Leu Asp Ala Gly Gly Gly Ser
1               5                   10                  15

Ser Gly Gly Ser Ile Ser Ser Gly Leu Leu Ser Gly Arg Ser Asp Asn
            20                  25                  30

His Gly Gly Gly Ser Glu Ile Val Leu Thr Gln Ser Pro Gly Thr Leu
        35                  40                  45

Ser Leu Ser Pro Gly Glu Arg Ala Thr Leu Ser Cys Arg Ala Ser Gln
    50                  55                  60

Ser Val Gly Ser Ser Tyr Leu Ala Trp Tyr Gln Gln Lys Pro Gly Gln
65                  70                  75                  80

Ala Pro Arg Leu Leu Ile Tyr Gly Ala Phe Ser Arg Ala Thr Gly Ile
                85                  90                  95

Pro Asp Arg Phe Ser Gly Ser Gly Ser Gly Thr Asp Phe Thr Leu Thr
            100                 105                 110

Ile Ser Arg Leu Glu Pro Glu Asp Phe Ala Val Tyr Tyr Cys Gln Gln
        115                 120                 125

Tyr Gly Ser Ser Pro Trp Thr Phe Gly Gln Gly Thr Lys Val Glu Ile
    130                 135                 140

Lys Arg Thr Val Ala Ala Pro Ser Val Phe Ile Phe Pro Pro Ser Asp
145                 150                 155                 160
```

Glu Gln Leu Lys Ser Gly Thr Ala Ser Val Val Cys Leu Leu Asn Asn
165 170 175

Phe Tyr Pro Arg Glu Ala Lys Val Gln Trp Lys Val Asp Asn Ala Leu
180 185 190

Gln Ser Gly Asn Ser Gln Glu Ser Val Thr Glu Gln Asp Ser Lys Asp
195 200 205

Ser Thr Tyr Ser Leu Ser Ser Thr Leu Thr Leu Ser Lys Ala Asp Tyr
210 215 220

Glu Lys His Lys Val Tyr Ala Cys Glu Val Thr His Gln Gly Leu Ser
225 230 235 240

Ser Pro Val Thr Lys Ser Phe Asn Arg Gly Glu Cys
245 250

<210> SEQ ID NO 402
<211> LENGTH: 261
<212> TYPE: PRT
<213> ORGANISM: Artificial Sequence
<220> FEATURE:
<223> OTHER INFORMATION: Spacer - YV61-2001 LC

<400> SEQUENCE: 402

Gln Gly Gln Ser Gly Ser Tyr Ile Ser Asp Cys Pro Tyr His Pro Met
1 5 10 15

Cys His Asp Tyr Gln Gly Gly Gly Ser Ser Gly Gly Ser Ile Ser Ser
20 25 30

Gly Leu Leu Ser Gly Arg Ser Asp Asn His Gly Gly Ser Glu Ile
35 40 45

Val Leu Thr Gln Ser Pro Gly Thr Leu Ser Leu Ser Pro Gly Glu Arg
50 55 60

Ala Thr Leu Ser Cys Arg Ala Ser Gln Ser Val Gly Ser Ser Tyr Leu
65 70 75 80

Ala Trp Tyr Gln Gln Lys Pro Gly Gln Ala Pro Arg Leu Leu Ile Tyr
85 90 95

Gly Ala Phe Ser Arg Ala Thr Gly Ile Pro Asp Arg Phe Ser Gly Ser
100 105 110

Gly Ser Gly Thr Asp Phe Thr Leu Thr Ile Ser Arg Leu Glu Pro Glu
115 120 125

Asp Phe Ala Val Tyr Tyr Cys Gln Gln Tyr Gly Ser Ser Pro Trp Thr
130 135 140

Phe Gly Gln Gly Thr Lys Val Glu Ile Lys Arg Thr Val Ala Ala Pro
145 150 155 160

Ser Val Phe Ile Phe Pro Pro Ser Asp Glu Gln Leu Lys Ser Gly Thr
165 170 175

Ala Ser Val Val Cys Leu Leu Asn Asn Phe Tyr Pro Arg Glu Ala Lys
180 185 190

Val Gln Trp Lys Val Asp Asn Ala Leu Gln Ser Gly Asn Ser Gln Glu
195 200 205

Ser Val Thr Glu Gln Asp Ser Lys Asp Ser Thr Tyr Ser Leu Ser Ser
210 215 220

Thr Leu Thr Leu Ser Lys Ala Asp Tyr Glu Lys His Lys Val Tyr Ala
225 230 235 240

Cys Glu Val Thr His Gln Gly Leu Ser Ser Pro Val Thr Lys Ser Phe
245 250 255

Asn Arg Gly Glu Cys
260

<210> SEQ ID NO 403
<211> LENGTH: 255
<212> TYPE: PRT
<213> ORGANISM: Artificial Sequence
<220> FEATURE:
<223> OTHER INFORMATION: YV61-2001 LC

<400> SEQUENCE: 403

Tyr Ile Ser Asp Cys Pro Tyr His Pro Met Cys His Asp Tyr Gln Gly
1 5 10 15

Gly Gly Ser Ser Gly Gly Ser Ile Ser Ser Gly Leu Leu Ser Gly Arg
20 25 30

Ser Asp Asn His Gly Gly Gly Ser Glu Ile Val Leu Thr Gln Ser Pro
35 40 45

Gly Thr Leu Ser Leu Ser Pro Gly Glu Arg Ala Thr Leu Ser Cys Arg
50 55 60

Ala Ser Gln Ser Val Gly Ser Ser Tyr Leu Ala Trp Tyr Gln Gln Lys
65 70 75 80

Pro Gly Gln Ala Pro Arg Leu Leu Ile Tyr Gly Ala Phe Ser Arg Ala
85 90 95

Thr Gly Ile Pro Asp Arg Phe Ser Gly Ser Gly Ser Gly Thr Asp Phe
100 105 110

Thr Leu Thr Ile Ser Arg Leu Glu Pro Glu Asp Phe Ala Val Tyr Tyr
115 120 125

Cys Gln Gln Tyr Gly Ser Ser Pro Trp Thr Phe Gly Gln Gly Thr Lys
130 135 140

Val Glu Ile Lys Arg Thr Val Ala Ala Pro Ser Val Phe Ile Phe Pro
145 150 155 160

Pro Ser Asp Glu Gln Leu Lys Ser Gly Thr Ala Ser Val Val Cys Leu
165 170 175

Leu Asn Asn Phe Tyr Pro Arg Glu Ala Lys Val Gln Trp Lys Val Asp
180 185 190

Asn Ala Leu Gln Ser Gly Asn Ser Gln Glu Ser Val Thr Glu Gln Asp
195 200 205

Ser Lys Asp Ser Thr Tyr Ser Leu Ser Ser Thr Leu Thr Leu Ser Lys
210 215 220

Ala Asp Tyr Glu Lys His Lys Val Tyr Ala Cys Glu Val Thr His Gln
225 230 235 240

Gly Leu Ser Ser Pro Val Thr Lys Ser Phe Asn Arg Gly Glu Cys
245 250 255

<210> SEQ ID NO 404
<211> LENGTH: 261
<212> TYPE: PRT
<213> ORGANISM: Artificial Sequence
<220> FEATURE:
<223> OTHER INFORMATION: Spacer - YV62-2001 LC

<400> SEQUENCE: 404

Gln Gly Gln Ser Gly Ser Phe Arg Asn Thr Cys Pro Tyr His Pro Met
1 5 10 15

Cys His Asp Tyr Arg Gly Gly Gly Ser Ser Gly Gly Ser Ile Ser Ser
20 25 30

Gly Leu Leu Ser Gly Arg Ser Asp Asn His Gly Gly Gly Ser Glu Ile
35 40 45

Val Leu Thr Gln Ser Pro Gly Thr Leu Ser Leu Ser Pro Gly Glu Arg

```
    50                  55                  60

Ala Thr Leu Ser Cys Arg Ala Ser Gln Ser Val Gly Ser Ser Tyr Leu
65                  70                  75                  80

Ala Trp Tyr Gln Gln Lys Pro Gly Gln Ala Pro Arg Leu Leu Ile Tyr
                85                  90                  95

Gly Ala Phe Ser Arg Ala Thr Gly Ile Pro Asp Arg Phe Ser Gly Ser
            100                 105                 110

Gly Ser Gly Thr Asp Phe Thr Leu Thr Ile Ser Arg Leu Glu Pro Glu
        115                 120                 125

Asp Phe Ala Val Tyr Tyr Cys Gln Gln Tyr Gly Ser Ser Pro Trp Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260
```

<210> SEQ ID NO 405
<211> LENGTH: 255
<212> TYPE: PRT
<213> ORGANISM: Artificial Sequence
<220> FEATURE:
<223> OTHER INFORMATION: YV62-2001 LC

<400> SEQUENCE: 405

```
Phe Arg Asn Thr Cys Pro Tyr His Pro Met Cys His Asp Tyr Arg Gly
1               5                   10                  15

Gly Gly Ser Ser Gly Gly Ser Ile Ser Ser Gly Leu Leu Ser Gly Arg
            20                  25                  30

Ser Asp Asn His Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
```

```
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 406
<211> LENGTH: 261
<212> TYPE: PRT
<213> ORGANISM: Artificial Sequence
<220> FEATURE:
<223> OTHER INFORMATION: Spacer - YV63-2001 LC

<400> SEQUENCE: 406

Gln Gly Gln Ser Gly Ser Arg Glu Cys His Met Trp Met Phe Gly Val
1               5                   10                  15

Asn Leu Cys Pro Tyr Gly Gly Gly Ser Ser Gly Gly Ser Ile Ser Ser
            20                  25                  30

Gly Leu Leu Ser Gly Arg Ser Asp Asn His Gly Gly Gly Ser Glu Ile
        35                  40                  45

Val Leu Thr Gln Ser Pro Gly Thr Leu Ser Leu Ser Pro Gly Glu Arg
    50                  55                  60

Ala Thr Leu Ser Cys Arg Ala Ser Gln Ser Val Gly Ser Ser Tyr Leu
65                  70                  75                  80

Ala Trp Tyr Gln Gln Lys Pro Gly Gln Ala Pro Arg Leu Leu Ile Tyr
                85                  90                  95

Gly Ala Phe Ser Arg Ala Thr Gly Ile Pro Asp Arg Phe Ser Gly Ser
            100                 105                 110

Gly Ser Gly Thr Asp Phe Thr Leu Thr Ile Ser Arg Leu Glu Pro Glu
        115                 120                 125

Asp Phe Ala Val Tyr Tyr Cys Gln Gln Tyr Gly Ser Ser Pro Trp Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
```

260

<210> SEQ ID NO 407
<211> LENGTH: 255
<212> TYPE: PRT
<213> ORGANISM: Artificial Sequence
<220> FEATURE:
<223> OTHER INFORMATION: YV63-2001 LC

<400> SEQUENCE: 407

Arg Glu Cys His Met Trp Met Phe Gly Val Asn Leu Cys Pro Tyr Gly
1 5 10 15

Gly Gly Ser Ser Gly Gly Ser Ile Ser Ser Gly Leu Leu Ser Gly Arg
20 25 30

Ser Asp Asn His Gly Gly Gly Ser Glu Ile Val Leu Thr Gln Ser Pro
35 40 45

Gly Thr Leu Ser Leu Ser Pro Gly Glu Arg Ala Thr Leu Ser Cys Arg
50 55 60

Ala Ser Gln Ser Val Gly Ser Ser Tyr Leu Ala Trp Tyr Gln Gln Lys
65 70 75 80

Pro Gly Gln Ala Pro Arg Leu Leu Ile Tyr Gly Ala Phe Ser Arg Ala
85 90 95

Thr Gly Ile Pro Asp Arg Phe Ser Gly Ser Gly Ser Gly Thr Asp Phe
100 105 110

Thr Leu Thr Ile Ser Arg Leu Glu Pro Glu Asp Phe Ala Val Tyr Tyr
115 120 125

Cys Gln Gln Tyr Gly Ser Ser Pro Trp Thr Phe Gly Gln Gly Thr Lys
130 135 140

Val Glu Ile Lys Arg Thr Val Ala Ala Pro Ser Val Phe Ile Phe Pro
145 150 155 160

Pro Ser Asp Glu Gln Leu Lys Ser Gly Thr Ala Ser Val Val Cys Leu
165 170 175

Leu Asn Asn Phe Tyr Pro Arg Glu Ala Lys Val Gln Trp Lys Val Asp
180 185 190

Asn Ala Leu Gln Ser Gly Asn Ser Gln Glu Ser Val Thr Glu Gln Asp
195 200 205

Ser Lys Asp Ser Thr Tyr Ser Leu Ser Ser Thr Leu Thr Leu Ser Lys
210 215 220

Ala Asp Tyr Glu Lys His Lys Val Tyr Ala Cys Glu Val Thr His Gln
225 230 235 240

Gly Leu Ser Ser Pro Val Thr Lys Ser Phe Asn Arg Gly Glu Cys
245 250 255

<210> SEQ ID NO 408
<211> LENGTH: 261
<212> TYPE: PRT
<213> ORGANISM: Artificial Sequence
<220> FEATURE:
<223> OTHER INFORMATION: Spacer - YV64-2001 LC

<400> SEQUENCE: 408

Gln Gly Gln Ser Gly Ser Ala Val Cys His Met Tyr Met Tyr Gly Tyr
1 5 10 15

Asn Leu Cys Pro Phe Gly Gly Gly Ser Ser Gly Gly Ser Ile Ser Ser
20 25 30

Gly Leu Leu Ser Gly Arg Ser Asp Asn His Gly Gly Gly Ser Glu Ile
35 40 45

Val Leu Thr Gln Ser Pro Gly Thr Leu Ser Leu Ser Pro Gly Glu Arg
50 55 60

Ala Thr Leu Ser Cys Arg Ala Ser Gln Ser Val Gly Ser Ser Tyr Leu
65 70 75 80

Ala Trp Tyr Gln Gln Lys Pro Gly Gln Ala Pro Arg Leu Leu Ile Tyr
85 90 95

Gly Ala Phe Ser Arg Ala Thr Gly Ile Pro Asp Arg Phe Ser Gly Ser
100 105 110

Gly Ser Gly Thr Asp Phe Thr Leu Thr Ile Ser Arg Leu Glu Pro Glu
115 120 125

Asp Phe Ala Val Tyr Tyr Cys Gln Gln Tyr Gly Ser Ser Pro Trp Thr
130 135 140

Phe Gly Gln Gly Thr Lys Val Glu Ile Lys Arg Thr Val Ala Ala Pro
145 150 155 160

Ser Val Phe Ile Phe Pro Pro Ser Asp Glu Gln Leu Lys Ser Gly Thr
165 170 175

Ala Ser Val Val Cys Leu Leu Asn Asn Phe Tyr Pro Arg Glu Ala Lys
180 185 190

Val Gln Trp Lys Val Asp Asn Ala Leu Gln Ser Gly Asn Ser Gln Glu
195 200 205

Ser Val Thr Glu Gln Asp Ser Lys Asp Ser Thr Tyr Ser Leu Ser Ser
210 215 220

Thr Leu Thr Leu Ser Lys Ala Asp Tyr Glu Lys His Lys Val Tyr Ala
225 230 235 240

Cys Glu Val Thr His Gln Gly Leu Ser Ser Pro Val Thr Lys Ser Phe
245 250 255

Asn Arg Gly Glu Cys
260

<210> SEQ ID NO 409
<211> LENGTH: 255
<212> TYPE: PRT
<213> ORGANISM: Artificial Sequence
<220> FEATURE:
<223> OTHER INFORMATION: YV64-2001 LC

<400> SEQUENCE: 409

Ala Val Cys His Met Tyr Met Tyr Gly Tyr Asn Leu Cys Pro Phe Gly
1 5 10 15

Gly Gly Ser Ser Gly Gly Ser Ile Ser Ser Gly Leu Leu Ser Gly Arg
20 25 30

Ser Asp Asn His Gly Gly Gly Ser Glu Ile Val Leu Thr Gln Ser Pro
35 40 45

Gly Thr Leu Ser Leu Ser Pro Gly Glu Arg Ala Thr Leu Ser Cys Arg
50 55 60

Ala Ser Gln Ser Val Gly Ser Ser Tyr Leu Ala Trp Tyr Gln Gln Lys
65 70 75 80

Pro Gly Gln Ala Pro Arg Leu Leu Ile Tyr Gly Ala Phe Ser Arg Ala
85 90 95

Thr Gly Ile Pro Asp Arg Phe Ser Gly Ser Gly Ser Gly Thr Asp Phe
100 105 110

Thr Leu Thr Ile Ser Arg Leu Glu Pro Glu Asp Phe Ala Val Tyr Tyr
115 120 125

Cys Gln Gln Tyr Gly Ser Ser Pro Trp Thr Phe Gly Gln Gly Thr Lys
130 135 140

Val Glu Ile Lys Arg Thr Val Ala Ala Pro Ser Val Phe Ile Phe Pro
145 150 155 160

Pro Ser Asp Glu Gln Leu Lys Ser Gly Thr Ala Ser Val Val Cys Leu
165 170 175

Leu Asn Asn Phe Tyr Pro Arg Glu Ala Lys Val Gln Trp Lys Val Asp
180 185 190

Asn Ala Leu Gln Ser Gly Asn Ser Gln Glu Ser Val Thr Glu Gln Asp
195 200 205

Ser Lys Asp Ser Thr Tyr Ser Leu Ser Ser Thr Leu Thr Leu Ser Lys
210 215 220

Ala Asp Tyr Glu Lys His Lys Val Tyr Ala Cys Glu Val Thr His Gln
225 230 235 240

Gly Leu Ser Ser Pro Val Thr Lys Ser Phe Asn Arg Gly Glu Cys
245 250 255

<210> SEQ ID NO 410
<211> LENGTH: 262
<212> TYPE: PRT
<213> ORGANISM: Artificial Sequence
<220> FEATURE:
<223> OTHER INFORMATION: Spacer - YV65-2001 LC

<400> SEQUENCE: 410

Gln Gly Gln Ser Gly Gln Gly Arg Ser Cys Pro Gln Met Tyr Gly Tyr
1 5 10 15

Ser Met Cys Pro His Thr Gly Gly Gly Ser Ser Gly Gly Ser Ile Ser
20 25 30

Ser Gly Leu Leu Ser Gly Arg Ser Asp Asn His Gly Gly Gly Ser Glu
35 40 45

Ile Val Leu Thr Gln Ser Pro Gly Thr Leu Ser Leu Ser Pro Gly Glu
50 55 60

Arg Ala Thr Leu Ser Cys Arg Ala Ser Gln Ser Val Gly Ser Ser Tyr
65 70 75 80

Leu Ala Trp Tyr Gln Gln Lys Pro Gly Gln Ala Pro Arg Leu Leu Ile
85 90 95

Tyr Gly Ala Phe Ser Arg Ala Thr Gly Ile Pro Asp Arg Phe Ser Gly
100 105 110

Ser Gly Ser Gly Thr Asp Phe Thr Leu Thr Ile Ser Arg Leu Glu Pro
115 120 125

Glu Asp Phe Ala Val Tyr Tyr Cys Gln Gln Tyr Gly Ser Ser Pro Trp
130 135 140

Thr Phe Gly Gln Gly Thr Lys Val Glu Ile Lys Arg Thr Val Ala Ala
145 150 155 160

Pro Ser Val Phe Ile Phe Pro Pro Ser Asp Glu Gln Leu Lys Ser Gly
165 170 175

Thr Ala Ser Val Val Cys Leu Leu Asn Asn Phe Tyr Pro Arg Glu Ala
180 185 190

Lys Val Gln Trp Lys Val Asp Asn Ala Leu Gln Ser Gly Asn Ser Gln
195 200 205

Glu Ser Val Thr Glu Gln Asp Ser Lys Asp Ser Thr Tyr Ser Leu Ser
210 215 220

Ser Thr Leu Thr Leu Ser Lys Ala Asp Tyr Glu Lys His Lys Val Tyr
225 230 235 240

Ala Cys Glu Val Thr His Gln Gly Leu Ser Ser Pro Val Thr Lys Ser
245 250 255

Phe Asn Arg Gly Glu Cys
260

<210> SEQ ID NO 411
<211> LENGTH: 255
<212> TYPE: PRT
<213> ORGANISM: Artificial Sequence
<220> FEATURE:
<223> OTHER INFORMATION: YV65-2001 LC

<400> SEQUENCE: 411

Arg Ser Cys Pro Gln Met Tyr Gly Tyr Ser Met Cys Pro His Thr Gly
1 5 10 15

Gly Gly Ser Ser Gly Gly Ser Ile Ser Ser Gly Leu Leu Ser Gly Arg
20 25 30

Ser Asp Asn His Gly Gly Gly Ser Glu Ile Val Leu Thr Gln Ser Pro
35 40 45

Gly Thr Leu Ser Leu Ser Pro Gly Glu Arg Ala Thr Leu Ser Cys Arg
50 55 60

Ala Ser Gln Ser Val Gly Ser Ser Tyr Leu Ala Trp Tyr Gln Gln Lys
65 70 75 80

Pro Gly Gln Ala Pro Arg Leu Leu Ile Tyr Gly Ala Phe Ser Arg Ala
85 90 95

Thr Gly Ile Pro Asp Arg Phe Ser Gly Ser Gly Ser Gly Thr Asp Phe
100 105 110

Thr Leu Thr Ile Ser Arg Leu Glu Pro Glu Asp Phe Ala Val Tyr Tyr
115 120 125

Cys Gln Gln Tyr Gly Ser Ser Pro Trp Thr Phe Gly Gln Gly Thr Lys
130 135 140

Val Glu Ile Lys Arg Thr Val Ala Ala Pro Ser Val Phe Ile Phe Pro
145 150 155 160

Pro Ser Asp Glu Gln Leu Lys Ser Gly Thr Ala Ser Val Val Cys Leu
165 170 175

Leu Asn Asn Phe Tyr Pro Arg Glu Ala Lys Val Gln Trp Lys Val Asp
180 185 190

Asn Ala Leu Gln Ser Gly Asn Ser Gln Glu Ser Val Thr Glu Gln Asp
195 200 205

Ser Lys Asp Ser Thr Tyr Ser Leu Ser Ser Thr Leu Thr Leu Ser Lys
210 215 220

Ala Asp Tyr Glu Lys His Lys Val Tyr Ala Cys Glu Val Thr His Gln
225 230 235 240

Gly Leu Ser Ser Pro Val Thr Lys Ser Phe Asn Arg Gly Glu Cys
245 250 255

<210> SEQ ID NO 412
<211> LENGTH: 262
<212> TYPE: PRT
<213> ORGANISM: Artificial Sequence
<220> FEATURE:
<223> OTHER INFORMATION: Spacer - YV66-2001 LC

<400> SEQUENCE: 412

Gln Gly Gln Ser Gly Gln Gly Gln Pro Cys Ala Gln Met Phe Gly Tyr
1 5 10 15

Ser Met Cys Pro His Thr Gly Gly Gly Ser Ser Gly Gly Ser Ile Ser
20 25 30

Ser Gly Leu Leu Ser Gly Arg Ser Asp Asn His Gly Gly Gly Ser Glu
35 40 45

```
Ile Val Leu Thr Gln Ser Pro Gly Thr Leu Ser Leu Ser Pro Gly Glu
    50                  55                  60

Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
            260


<210> SEQ ID NO 413
<211> LENGTH: 255
<212> TYPE: PRT
<213> ORGANISM: Artificial Sequence
<220> FEATURE:
<223> OTHER INFORMATION: YV66-2001 LC

<400> SEQUENCE: 413

Gln Pro Cys Ala Gln Met Phe Gly Tyr Ser Met Cys Pro His Thr Gly
1               5                   10                  15

Gly Gly Ser Ser Gly Gly Ser Ile Ser Ser Gly Leu Leu Ser Gly Arg
            20                  25                  30

Ser Asp Asn His Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140
```

```
Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 414
<211> LENGTH: 262
<212> TYPE: PRT
<213> ORGANISM: Artificial Sequence
<220> FEATURE:
<223> OTHER INFORMATION: Spacer - YV04-2006 LC

<400> SEQUENCE: 414

Gln Gly Gln Ser Gly Ser Leu His Cys Arg Thr Gln Leu Tyr Gly Tyr
1               5                   10                  15

Asn Leu Cys Pro Tyr Gly Gly Gly Ser Ser Gly Gly Ser Ile Ser Ser
            20                  25                  30

Gly Leu Leu Ser Gly Arg Ser Asp Asp His Gly Gly Gly Ser Glu Ile
        35                  40                  45

Val Leu Thr Gln Ser Pro Gly Thr Leu Ser Leu Ser Pro Gly Glu Arg
    50                  55                  60

Ala Thr Leu Ser Cys Arg Ala Ser Gln Ser Val Gly Ser Ser Tyr Leu
65                  70                  75                  80

Ala Trp Tyr Gln Gln Lys Pro Gly Gln Ala Pro Arg Leu Leu Ile Tyr
                85                  90                  95

Gly Ala Phe Ser Arg Ala Thr Gly Ile Pro Asp Arg Phe Ser Gly Ser
            100                 105                 110

Gly Ser Gly Thr Asp Phe Thr Leu Thr Ile Ser Arg Leu Glu Pro Glu
        115                 120                 125

Asp Phe Ala Val Tyr Tyr Cys Gln Gln Tyr Gly Ser Ser Pro Trp Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255
```

```
Asn Arg Gly Glu Cys Cys
            260


<210> SEQ ID NO 415
<211> LENGTH: 255
<212> TYPE: PRT
<213> ORGANISM: Artificial Sequence
<220> FEATURE:
<223> OTHER INFORMATION: YV04-2006 LC

<400> SEQUENCE: 415

Leu His Cys Arg Thr Gln Leu Tyr Gly Tyr Asn Leu Cys Pro Tyr Gly
1               5                   10                  15

Gly Gly Ser Ser Gly Gly Ser Ile Ser Ser Gly Leu Leu Ser Gly Arg
            20                  25                  30

Ser Asp Asp His Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 416
<211> LENGTH: 258
<212> TYPE: PRT
<213> ORGANISM: Artificial Sequence
<220> FEATURE:
<223> OTHER INFORMATION: Spacer - YV23-2006 LC

<400> SEQUENCE: 416

Gln Gly Gln Ser Gly Ser Cys Leu His Ser Leu Tyr Asn Val Cys Leu
1               5                   10                  15

Asp Pro Gly Gly Gly Ser Ser Gly Gly Ser Ile Ser Ser Gly Leu Leu
            20                  25                  30

Ser Gly Arg Ser Asp Asp His Gly Gly Gly Ser Glu Ile Val Leu Thr
```

```
        35                  40                  45

Gln Ser Pro Gly Thr Leu Ser Leu Ser Pro Gly Glu Arg Ala Thr Leu
    50                  55                  60

Ser Cys Arg Ala Ser Gln Ser Val Gly Ser Ser Tyr Leu Ala Trp Tyr
65                  70                  75                  80

Gln Gln Lys Pro Gly Gln Ala Pro Arg Leu Leu Ile Tyr Gly Ala Phe
                85                  90                  95

Ser Arg Ala Thr Gly Ile Pro Asp Arg Phe Ser Gly Ser Gly Ser Gly
            100                 105                 110

Thr Asp Phe Thr Leu Thr Ile Ser Arg Leu Glu Pro Glu Asp Phe Ala
        115                 120                 125

Val Tyr Tyr Cys Gln Gln Tyr Gly Ser Ser Pro Trp Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys


<210> SEQ ID NO 417
<211> LENGTH: 252
<212> TYPE: PRT
<213> ORGANISM: Artificial Sequence
<220> FEATURE:
<223> OTHER INFORMATION: YV23-2006 LC

<400> SEQUENCE: 417

Cys Leu His Ser Leu Tyr Asn Val Cys Leu Asp Pro Gly Gly Gly Ser
1               5                   10                  15

Ser Gly Gly Ser Ile Ser Ser Gly Leu Leu Ser Gly Arg Ser Asp Asp
            20                  25                  30

His Gly Gly Gly Ser Glu Ile Val Leu Thr Gln Ser Pro Gly Thr Leu
        35                  40                  45

Ser Leu Ser Pro Gly Glu Arg Ala Thr Leu Ser Cys Arg Ala Ser Gln
    50                  55                  60

Ser Val Gly Ser Ser Tyr Leu Ala Trp Tyr Gln Gln Lys Pro Gly Gln
65                  70                  75                  80

Ala Pro Arg Leu Leu Ile Tyr Gly Ala Phe Ser Arg Ala Thr Gly Ile
                85                  90                  95

Pro Asp Arg Phe Ser Gly Ser Gly Ser Gly Thr Asp Phe Thr Leu Thr
            100                 105                 110

Ile Ser Arg Leu Glu Pro Glu Asp Phe Ala Val Tyr Tyr Cys Gln Gln
        115                 120                 125

Tyr Gly Ser Ser Pro Trp Thr Phe Gly Gln Gly Thr Lys Val Glu Ile
    130                 135                 140
```

```
Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250


<210> SEQ ID NO 418
<211> LENGTH: 259
<212> TYPE: PRT
<213> ORGANISM: Artificial Sequence
<220> FEATURE:
<223> OTHER INFORMATION: Spacer - YV39-2006 LC

<400> SEQUENCE: 418

Gln Gly Gln Ser Gly Ser Cys Arg Thr Gln Leu Tyr Gly Tyr Asn Leu
1               5                   10                  15

Cys Pro Tyr Gly Gly Gly Ser Ser Gly Gly Ser Ile Ser Ser Gly Leu
            20                  25                  30

Leu Ser Gly Arg Ser Asp Asp His Gly Gly Gly Ser Glu Ile Val Leu
        35                  40                  45

Thr Gln Ser Pro Gly Thr Leu Ser Leu Ser Pro Gly Glu Arg Ala Thr
    50                  55                  60

Leu Ser Cys Arg Ala Ser Gln Ser Val Gly Ser Ser Tyr Leu Ala Trp
65                  70                  75                  80

Tyr Gln Gln Lys Pro Gly Gln Ala Pro Arg Leu Leu Ile Tyr Gly Ala
                85                  90                  95

Phe Ser Arg Ala Thr Gly Ile Pro Asp Arg Phe Ser Gly Ser Gly Ser
            100                 105                 110

Gly Thr Asp Phe Thr Leu Thr Ile Ser Arg Leu Glu Pro Glu Asp Phe
        115                 120                 125

Ala Val Tyr Tyr Cys Gln Gln Tyr Gly Ser Ser Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255
```

Gly Glu Cys

<210> SEQ ID NO 419
<211> LENGTH: 253
<212> TYPE: PRT
<213> ORGANISM: Artificial Sequence
<220> FEATURE:
<223> OTHER INFORMATION: YV39-2006 LC

<400> SEQUENCE: 419

Cys Arg Thr Gln Leu Tyr Gly Tyr Asn Leu Cys Pro Tyr Gly Gly Gly
1 5 10 15

Ser Ser Gly Gly Ser Ile Ser Ser Gly Leu Leu Ser Gly Arg Ser Asp
20 25 30

Asp His Gly Gly Gly Ser Glu Ile Val Leu Thr Gln Ser Pro Gly Thr
35 40 45

Leu Ser Leu Ser Pro Gly Glu Arg Ala Thr Leu Ser Cys Arg Ala Ser
50 55 60

Gln Ser Val Gly Ser Ser Tyr Leu Ala Trp Tyr Gln Gln Lys Pro Gly
65 70 75 80

Gln Ala Pro Arg Leu Leu Ile Tyr Gly Ala Phe Ser Arg Ala Thr Gly
85 90 95

Ile Pro Asp Arg Phe Ser Gly Ser Gly Ser Gly Thr Asp Phe Thr Leu
100 105 110

Thr Ile Ser Arg Leu Glu Pro Glu Asp Phe Ala Val Tyr Tyr Cys Gln
115 120 125

Gln Tyr Gly Ser Ser Pro Trp Thr Phe Gly Gln Gly Thr Lys Val Glu
130 135 140

Ile Lys Arg Thr Val Ala Ala Pro Ser Val Phe Ile Phe Pro Pro Ser
145 150 155 160

Asp Glu Gln Leu Lys Ser Gly Thr Ala Ser Val Val Cys Leu Leu Asn
165 170 175

Asn Phe Tyr Pro Arg Glu Ala Lys Val Gln Trp Lys Val Asp Asn Ala
180 185 190

Leu Gln Ser Gly Asn Ser Gln Glu Ser Val Thr Glu Gln Asp Ser Lys
195 200 205

Asp Ser Thr Tyr Ser Leu Ser Ser Thr Leu Thr Leu Ser Lys Ala Asp
210 215 220

Tyr Glu Lys His Lys Val Tyr Ala Cys Glu Val Thr His Gln Gly Leu
225 230 235 240

Ser Ser Pro Val Thr Lys Ser Phe Asn Arg Gly Glu Cys
245 250

<210> SEQ ID NO 420
<211> LENGTH: 261
<212> TYPE: PRT
<213> ORGANISM: Artificial Sequence
<220> FEATURE:
<223> OTHER INFORMATION: Spacer - YV04-2007 LC

<400> SEQUENCE: 420

Gln Gly Gln Ser Gly Ser Leu His Cys Arg Thr Gln Leu Tyr Gly Tyr
1 5 10 15

Asn Leu Cys Pro Tyr Gly Gly Gly Ser Ser Gly Gly Ser Ile Ser Ser
20 25 30

Gly Leu Leu Ser Gly Arg Ser Asp Ile His Gly Gly Gly Ser Glu Ile
35 40 45

```
Val Leu Thr Gln Ser Pro Gly Thr Leu Ser Leu Ser Pro Gly Glu Arg
    50                  55                  60

Ala Thr Leu Ser Cys Arg Ala Ser Gln Ser Val Gly Ser Ser Tyr Leu
65                  70                  75                  80

Ala Trp Tyr Gln Gln Lys Pro Gly Gln Ala Pro Arg Leu Leu Ile Tyr
                85                  90                  95

Gly Ala Phe Ser Arg Ala Thr Gly Ile Pro Asp Arg Phe Ser Gly Ser
            100                 105                 110

Gly Ser Gly Thr Asp Phe Thr Leu Thr Ile Ser Arg Leu Glu Pro Glu
        115                 120                 125

Asp Phe Ala Val Tyr Tyr Cys Gln Gln Tyr Gly Ser Ser Pro Trp Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260


<210> SEQ ID NO 421
<211> LENGTH: 255
<212> TYPE: PRT
<213> ORGANISM: Artificial Sequence
<220> FEATURE:
<223> OTHER INFORMATION: YV04-2007 LC

<400> SEQUENCE: 421

Leu His Cys Arg Thr Gln Leu Tyr Gly Tyr Asn Leu Cys Pro Tyr Gly
1               5                   10                  15

Gly Gly Ser Ser Gly Gly Ser Ile Ser Ser Gly Leu Leu Ser Gly Arg
            20                  25                  30

Ser Asp Ile His Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140
```

Val Glu Ile Lys Arg Thr Val Ala Ala Pro Ser Val Phe Ile Phe Pro
145 150 155 160

Pro Ser Asp Glu Gln Leu Lys Ser Gly Thr Ala Ser Val Val Cys Leu
165 170 175

Leu Asn Asn Phe Tyr Pro Arg Glu Ala Lys Val Gln Trp Lys Val Asp
180 185 190

Asn Ala Leu Gln Ser Gly Asn Ser Gln Glu Ser Val Thr Glu Gln Asp
195 200 205

Ser Lys Asp Ser Thr Tyr Ser Leu Ser Ser Thr Leu Thr Leu Ser Lys
210 215 220

Ala Asp Tyr Glu Lys His Lys Val Tyr Ala Cys Glu Val Thr His Gln
225 230 235 240

Gly Leu Ser Ser Pro Val Thr Lys Ser Phe Asn Arg Gly Glu Cys
245 250 255

<210> SEQ ID NO 422
<211> LENGTH: 258
<212> TYPE: PRT
<213> ORGANISM: Artificial Sequence
<220> FEATURE:
<223> OTHER INFORMATION: Spacer - YV23-2007 LC

<400> SEQUENCE: 422

Gln Gly Gln Ser Gly Ser Cys Leu His Ser Leu Tyr Asn Val Cys Leu
1 5 10 15

Asp Pro Gly Gly Gly Ser Ser Gly Gly Ser Ile Ser Ser Gly Leu Leu
20 25 30

Ser Gly Arg Ser Asp Ile His Gly Gly Gly Ser Glu Ile Val Leu Thr
35 40 45

Gln Ser Pro Gly Thr Leu Ser Leu Ser Pro Gly Glu Arg Ala Thr Leu
50 55 60

Ser Cys Arg Ala Ser Gln Ser Val Gly Ser Ser Tyr Leu Ala Trp Tyr
65 70 75 80

Gln Gln Lys Pro Gly Gln Ala Pro Arg Leu Leu Ile Tyr Gly Ala Phe
85 90 95

Ser Arg Ala Thr Gly Ile Pro Asp Arg Phe Ser Gly Ser Gly Ser Gly
100 105 110

Thr Asp Phe Thr Leu Thr Ile Ser Arg Leu Glu Pro Glu Asp Phe Ala
115 120 125

Val Tyr Tyr Cys Gln Gln Tyr Gly Ser Ser Pro Trp Thr Phe Gly Gln
130 135 140

Gly Thr Lys Val Glu Ile Lys Arg Thr Val Ala Ala Pro Ser Val Phe
145 150 155 160

Ile Phe Pro Pro Ser Asp Glu Gln Leu Lys Ser Gly Thr Ala Ser Val
165 170 175

Val Cys Leu Leu Asn Asn Phe Tyr Pro Arg Glu Ala Lys Val Gln Trp
180 185 190

Lys Val Asp Asn Ala Leu Gln Ser Gly Asn Ser Gln Glu Ser Val Thr
195 200 205

Glu Gln Asp Ser Lys Asp Ser Thr Tyr Ser Leu Ser Ser Thr Leu Thr
210 215 220

Leu Ser Lys Ala Asp Tyr Glu Lys His Lys Val Tyr Ala Cys Glu Val
225 230 235 240

Thr His Gln Gly Leu Ser Ser Pro Val Thr Lys Ser Phe Asn Arg Gly
245 250 255

Glu Cys

<210> SEQ ID NO 423
<211> LENGTH: 252
<212> TYPE: PRT
<213> ORGANISM: Artificial Sequence
<220> FEATURE:
<223> OTHER INFORMATION: YV23-2007 LC

<400> SEQUENCE: 423

```
Cys Leu His Ser Leu Tyr Asn Val Cys Leu Asp Pro Gly Gly Gly Ser
1               5                   10                  15

Ser Gly Gly Ser Ile Ser Ser Gly Leu Leu Ser Gly Arg Ser Asp Ile
            20                  25                  30

His Gly Gly Gly Ser Glu Ile Val Leu Thr Gln Ser Pro Gly Thr Leu
        35                  40                  45

Ser Leu Ser Pro Gly Glu Arg Ala Thr Leu Ser Cys Arg Ala Ser Gln
    50                  55                  60

Ser Val Gly Ser Ser Tyr Leu Ala Trp Tyr Gln Gln Lys Pro Gly Gln
65                  70                  75                  80

Ala Pro Arg Leu Leu Ile Tyr Gly Ala Phe Ser Arg Ala Thr Gly Ile
                85                  90                  95

Pro Asp Arg Phe Ser Gly Ser Gly Ser Gly Thr Asp Phe Thr Leu Thr
            100                 105                 110

Ile Ser Arg Leu Glu Pro Glu Asp Phe Ala Val Tyr Tyr Cys Gln Gln
        115                 120                 125

Tyr Gly Ser Ser Pro Trp Thr Phe Gly Gln Gly Thr Lys Val Glu Ile
    130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250
```

<210> SEQ ID NO 424
<211> LENGTH: 259
<212> TYPE: PRT
<213> ORGANISM: Artificial Sequence
<220> FEATURE:
<223> OTHER INFORMATION: Spacer - YV39-2007 LC

<400> SEQUENCE: 424

```
Gln Gly Gln Ser Gly Ser Cys Arg Thr Gln Leu Tyr Gly Tyr Asn Leu
1               5                   10                  15

Cys Pro Tyr Gly Gly Gly Ser Ser Gly Gly Ser Ile Ser Ser Gly Leu
            20                  25                  30

Leu Ser Gly Arg Ser Asp Ile His Gly Gly Gly Ser Glu Ile Val Leu
        35                  40                  45
```

```
Thr Gln Ser Pro Gly Thr Leu Ser Leu Ser Pro Gly Glu Arg Ala Thr
    50                  55                  60

Leu Ser Cys Arg Ala Ser Gln Ser Val Gly Ser Ser Tyr Leu Ala Trp
65                  70                  75                  80

Tyr Gln Gln Lys Pro Gly Gln Ala Pro Arg Leu Leu Ile Tyr Gly Ala
                85                  90                  95

Phe Ser Arg Ala Thr Gly Ile Pro Asp Arg Phe Ser Gly Ser Gly Ser
            100                 105                 110

Gly Thr Asp Phe Thr Leu Thr Ile Ser Arg Leu Glu Pro Glu Asp Phe
        115                 120                 125

Ala Val Tyr Tyr Cys Gln Gln Tyr Gly Ser Ser Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys


<210> SEQ ID NO 425
<211> LENGTH: 253
<212> TYPE: PRT
<213> ORGANISM: Artificial Sequence
<220> FEATURE:
<223> OTHER INFORMATION: YV39-2007 LC

<400> SEQUENCE: 425

Cys Arg Thr Gln Leu Tyr Gly Tyr Asn Leu Cys Pro Tyr Gly Gly Gly
1               5                   10                  15

Ser Ser Gly Gly Ser Ile Ser Ser Gly Leu Leu Ser Gly Arg Ser Asp
            20                  25                  30

Ile His Gly Gly Gly Ser Glu Ile Val Leu Thr Gln Ser Pro Gly Thr
        35                  40                  45

Leu Ser Leu Ser Pro Gly Glu Arg Ala Thr Leu Ser Cys Arg Ala Ser
    50                  55                  60

Gln Ser Val Gly Ser Ser Tyr Leu Ala Trp Tyr Gln Gln Lys Pro Gly
65                  70                  75                  80

Gln Ala Pro Arg Leu Leu Ile Tyr Gly Ala Phe Ser Arg Ala Thr Gly
                85                  90                  95

Ile Pro Asp Arg Phe Ser Gly Ser Gly Ser Gly Thr Asp Phe Thr Leu
            100                 105                 110

Thr Ile Ser Arg Leu Glu Pro Glu Asp Phe Ala Val Tyr Tyr Cys Gln
        115                 120                 125

Gln Tyr Gly Ser Ser Pro Trp Thr Phe Gly Gln Gly Thr Lys Val Glu
    130                 135                 140
```

```
Ile Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250


<210> SEQ ID NO 426
<211> LENGTH: 261
<212> TYPE: PRT
<213> ORGANISM: Artificial Sequence
<220> FEATURE:
<223> OTHER INFORMATION: Spacer - YV04-2008 LC

<400> SEQUENCE: 426

Gln Gly Gln Ser Gly Ser Leu His Cys Arg Thr Gln Leu Tyr Gly Tyr
1               5                   10                  15

Asn Leu Cys Pro Tyr Gly Gly Gly Ser Ser Gly Gly Ser Ile Ser Ser
            20                  25                  30

Gly Leu Leu Ser Gly Arg Ser Asp Gln His Gly Gly Gly Ser Glu Ile
        35                  40                  45

Val Leu Thr Gln Ser Pro Gly Thr Leu Ser Leu Ser Pro Gly Glu Arg
    50                  55                  60

Ala Thr Leu Ser Cys Arg Ala Ser Gln Ser Val Gly Ser Ser Tyr Leu
65                  70                  75                  80

Ala Trp Tyr Gln Gln Lys Pro Gly Gln Ala Pro Arg Leu Leu Ile Tyr
                85                  90                  95

Gly Ala Phe Ser Arg Ala Thr Gly Ile Pro Asp Arg Phe Ser Gly Ser
            100                 105                 110

Gly Ser Gly Thr Asp Phe Thr Leu Thr Ile Ser Arg Leu Glu Pro Glu
        115                 120                 125

Asp Phe Ala Val Tyr Tyr Cys Gln Gln Tyr Gly Ser Ser Pro Trp Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255
```

```
Asn Arg Gly Glu Cys
            260


<210> SEQ ID NO 427
<211> LENGTH: 255
<212> TYPE: PRT
<213> ORGANISM: Artificial Sequence
<220> FEATURE:
<223> OTHER INFORMATION: YV04-2008 LC

<400> SEQUENCE: 427

Leu His Cys Arg Thr Gln Leu Tyr Gly Tyr Asn Leu Cys Pro Tyr Gly
1               5                   10                  15

Gly Gly Ser Ser Gly Gly Ser Ile Ser Ser Gly Leu Leu Ser Gly Arg
            20                  25                  30

Ser Asp Gln His Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 428
<211> LENGTH: 258
<212> TYPE: PRT
<213> ORGANISM: Artificial Sequence
<220> FEATURE:
<223> OTHER INFORMATION: Spacer - YV23-2008 LC

<400> SEQUENCE: 428

Gln Gly Gln Ser Gly Ser Cys Leu His Ser Leu Tyr Asn Val Cys Leu
1               5                   10                  15

Asp Pro Gly Gly Gly Ser Ser Gly Gly Ser Ile Ser Ser Gly Leu Leu
            20                  25                  30

Ser Gly Arg Ser Asp Gln His Gly Gly Gly Ser Glu Ile Val Leu Thr
        35                  40                  45
```

```
Gln Ser Pro Gly Thr Leu Ser Leu Ser Pro Gly Glu Arg Ala Thr Leu
    50                  55                  60

Ser Cys Arg Ala Ser Gln Ser Val Gly Ser Ser Tyr Leu Ala Trp Tyr
65                  70                  75                  80

Gln Gln Lys Pro Gly Gln Ala Pro Arg Leu Leu Ile Tyr Gly Ala Phe
                85                  90                  95

Ser Arg Ala Thr Gly Ile Pro Asp Arg Phe Ser Gly Ser Gly Ser Gly
            100                 105                 110

Thr Asp Phe Thr Leu Thr Ile Ser Arg Leu Glu Pro Glu Asp Phe Ala
        115                 120                 125

Val Tyr Tyr Cys Gln Gln Tyr Gly Ser Ser Pro Trp Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys


<210> SEQ ID NO 429
<211> LENGTH: 252
<212> TYPE: PRT
<213> ORGANISM: Artificial Sequence
<220> FEATURE:
<223> OTHER INFORMATION: YV23-2008 LC

<400> SEQUENCE: 429

Cys Leu His Ser Leu Tyr Asn Val Cys Leu Asp Pro Gly Gly Gly Ser
1               5                   10                  15

Ser Gly Gly Ser Ile Ser Ser Gly Leu Leu Ser Gly Arg Ser Asp Gln
            20                  25                  30

His Gly Gly Gly Ser Glu Ile Val Leu Thr Gln Ser Pro Gly Thr Leu
        35                  40                  45

Ser Leu Ser Pro Gly Glu Arg Ala Thr Leu Ser Cys Arg Ala Ser Gln
    50                  55                  60

Ser Val Gly Ser Ser Tyr Leu Ala Trp Tyr Gln Gln Lys Pro Gly Gln
65                  70                  75                  80

Ala Pro Arg Leu Leu Ile Tyr Gly Ala Phe Ser Arg Ala Thr Gly Ile
                85                  90                  95

Pro Asp Arg Phe Ser Gly Ser Gly Ser Gly Thr Asp Phe Thr Leu Thr
            100                 105                 110

Ile Ser Arg Leu Glu Pro Glu Asp Phe Ala Val Tyr Tyr Cys Gln Gln
        115                 120                 125

Tyr Gly Ser Ser Pro Trp Thr Phe Gly Gln Gly Thr Lys Val Glu Ile
    130                 135                 140
```

```
Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250


<210> SEQ ID NO 430
<211> LENGTH: 259
<212> TYPE: PRT
<213> ORGANISM: Artificial Sequence
<220> FEATURE:
<223> OTHER INFORMATION: Spacer - YV39-2008 LC

<400> SEQUENCE: 430

Gln Gly Gln Ser Gly Ser Cys Arg Thr Gln Leu Tyr Gly Tyr Asn Leu
1               5                   10                  15

Cys Pro Tyr Gly Gly Gly Ser Ser Gly Gly Ser Ile Ser Ser Gly Leu
            20                  25                  30

Leu Ser Gly Arg Ser Asp Gln His Gly Gly Gly Ser Glu Ile Val Leu
        35                  40                  45

Thr Gln Ser Pro Gly Thr Leu Ser Leu Ser Pro Gly Glu Arg Ala Thr
    50                  55                  60

Leu Ser Cys Arg Ala Ser Gln Ser Val Gly Ser Ser Tyr Leu Ala Trp
65                  70                  75                  80

Tyr Gln Gln Lys Pro Gly Gln Ala Pro Arg Leu Leu Ile Tyr Gly Ala
                85                  90                  95

Phe Ser Arg Ala Thr Gly Ile Pro Asp Arg Phe Ser Gly Ser Gly Ser
            100                 105                 110

Gly Thr Asp Phe Thr Leu Thr Ile Ser Arg Leu Glu Pro Glu Asp Phe
        115                 120                 125

Ala Val Tyr Tyr Cys Gln Gln Tyr Gly Ser Ser Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255
```

Gly Glu Cys

<210> SEQ ID NO 431
<211> LENGTH: 253
<212> TYPE: PRT
<213> ORGANISM: Artificial Sequence
<220> FEATURE:
<223> OTHER INFORMATION: YV39-2008 LC

<400> SEQUENCE: 431

```
Cys Arg Thr Gln Leu Tyr Gly Tyr Asn Leu Cys Pro Tyr Gly Gly Gly
1               5                   10                  15

Ser Ser Gly Gly Ser Ile Ser Ser Gly Leu Leu Ser Gly Arg Ser Asp
            20                  25                  30

Gln His Gly Gly Gly Ser Glu Ile Val Leu Thr Gln Ser Pro Gly Thr
        35                  40                  45

Leu Ser Leu Ser Pro Gly Glu Arg Ala Thr Leu Ser Cys Arg Ala Ser
    50                  55                  60

Gln Ser Val Gly Ser Ser Tyr Leu Ala Trp Tyr Gln Gln Lys Pro Gly
65                  70                  75                  80

Gln Ala Pro Arg Leu Leu Ile Tyr Gly Ala Phe Ser Arg Ala Thr Gly
                85                  90                  95

Ile Pro Asp Arg Phe Ser Gly Ser Gly Ser Gly Thr Asp Phe Thr Leu
            100                 105                 110

Thr Ile Ser Arg Leu Glu Pro Glu Asp Phe Ala Val Tyr Tyr Cys Gln
        115                 120                 125

Gln Tyr Gly Ser Ser Pro Trp Thr Phe Gly Gln Gly Thr Lys Val Glu
    130                 135                 140

Ile Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250
```

<210> SEQ ID NO 432
<211> LENGTH: 259
<212> TYPE: PRT
<213> ORGANISM: Artificial Sequence
<220> FEATURE:
<223> OTHER INFORMATION: Spacer - YV04-2009 LC

<400> SEQUENCE: 432

```
Gln Gly Gln Ser Gly Ser Leu His Cys Arg Thr Gln Leu Tyr Gly Tyr
1               5                   10                  15

Asn Leu Cys Pro Tyr Gly Ser Ser Gly Gly Ser Ile Ser Ser Gly Leu
            20                  25                  30

Leu Ser Gly Arg Ser Asp Thr His Gly Gly Gly Ser Glu Ile Val Leu
        35                  40                  45
```

Thr Gln Ser Pro Gly Thr Leu Ser Leu Ser Pro Gly Glu Arg Ala Thr
50 55 60

Leu Ser Cys Arg Ala Ser Gln Ser Val Gly Ser Ser Tyr Leu Ala Trp
65 70 75 80

Tyr Gln Gln Lys Pro Gly Gln Ala Pro Arg Leu Leu Ile Tyr Gly Ala
85 90 95

Phe Ser Arg Ala Thr Gly Ile Pro Asp Arg Phe Ser Gly Ser Gly Ser
100 105 110

Gly Thr Asp Phe Thr Leu Thr Ile Ser Arg Leu Glu Pro Glu Asp Phe
115 120 125

Ala Val Tyr Tyr Cys Gln Gln Tyr Gly Ser Ser Pro Trp Thr Phe Gly
130 135 140

Gln Gly Thr Lys Val Glu Ile Lys Arg Thr Val Ala Ala Pro Ser Val
145 150 155 160

Phe Ile Phe Pro Pro Ser Asp Glu Gln Leu Lys Ser Gly Thr Ala Ser
165 170 175

Val Val Cys Leu Leu Asn Asn Phe Tyr Pro Arg Glu Ala Lys Val Gln
180 185 190

Trp Lys Val Asp Asn Ala Leu Gln Ser Gly Asn Ser Gln Glu Ser Val
195 200 205

Thr Glu Gln Asp Ser Lys Asp Ser Thr Tyr Ser Leu Ser Ser Thr Leu
210 215 220

Thr Leu Ser Lys Ala Asp Tyr Glu Lys His Lys Val Tyr Ala Cys Glu
225 230 235 240

Val Thr His Gln Gly Leu Ser Ser Pro Val Thr Lys Ser Phe Asn Arg
245 250 255

Gly Glu Cys

<210> SEQ ID NO 433
<211> LENGTH: 253
<212> TYPE: PRT
<213> ORGANISM: Artificial Sequence
<220> FEATURE:
<223> OTHER INFORMATION: YV04-2009 LC

<400> SEQUENCE: 433

Leu His Cys Arg Thr Gln Leu Tyr Gly Tyr Asn Leu Cys Pro Tyr Gly
1 5 10 15

Ser Ser Gly Gly Ser Ile Ser Ser Gly Leu Leu Ser Gly Arg Ser Asp
20 25 30

Thr His Gly Gly Gly Ser Glu Ile Val Leu Thr Gln Ser Pro Gly Thr
35 40 45

Leu Ser Leu Ser Pro Gly Glu Arg Ala Thr Leu Ser Cys Arg Ala Ser
50 55 60

Gln Ser Val Gly Ser Ser Tyr Leu Ala Trp Tyr Gln Gln Lys Pro Gly
65 70 75 80

Gln Ala Pro Arg Leu Leu Ile Tyr Gly Ala Phe Ser Arg Ala Thr Gly
85 90 95

Ile Pro Asp Arg Phe Ser Gly Ser Gly Ser Gly Thr Asp Phe Thr Leu
100 105 110

Thr Ile Ser Arg Leu Glu Pro Glu Asp Phe Ala Val Tyr Tyr Cys Gln
115 120 125

Gln Tyr Gly Ser Ser Pro Trp Thr Phe Gly Gln Gly Thr Lys Val Glu
130 135 140

Ile Lys Arg Thr Val Ala Ala Pro Ser Val Phe Ile Phe Pro Pro Ser

```
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250


<210> SEQ ID NO 434
<211> LENGTH: 256
<212> TYPE: PRT
<213> ORGANISM: Artificial Sequence
<220> FEATURE:
<223> OTHER INFORMATION: Spacer - YV23-2009 LC

<400> SEQUENCE: 434

Gln Gly Gln Ser Gly Ser Cys Leu His Ser Leu Tyr Asn Val Cys Leu
1               5                   10                  15

Asp Pro Gly Ser Ser Gly Gly Ser Ile Ser Ser Gly Leu Leu Ser Gly
            20                  25                  30

Arg Ser Asp Thr His Gly Gly Gly Ser Glu Ile Val Leu Thr Gln Ser
        35                  40                  45

Pro Gly Thr Leu Ser Leu Ser Pro Gly Glu Arg Ala Thr Leu Ser Cys
    50                  55                  60

Arg Ala Ser Gln Ser Val Gly Ser Ser Tyr Leu Ala Trp Tyr Gln Gln
65                  70                  75                  80

Lys Pro Gly Gln Ala Pro Arg Leu Leu Ile Tyr Gly Ala Phe Ser Arg
                85                  90                  95

Ala Thr Gly Ile Pro Asp Arg Phe Ser Gly Ser Gly Ser Gly Thr Asp
            100                 105                 110

Phe Thr Leu Thr Ile Ser Arg Leu Glu Pro Glu Asp Phe Ala Val Tyr
        115                 120                 125

Tyr Cys Gln Gln Tyr Gly Ser Ser Pro Trp Thr Phe Gly Gln Gly Thr
    130                 135                 140

Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Ser Thr Leu Thr Leu Ser
    210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255
```

<210> SEQ ID NO 435
<211> LENGTH: 250
<212> TYPE: PRT
<213> ORGANISM: Artificial Sequence
<220> FEATURE:
<223> OTHER INFORMATION: YV23-2009 LC

<400> SEQUENCE: 435

```
Cys Leu His Ser Leu Tyr Asn Val Cys Leu Asp Pro Gly Ser Ser Gly
1               5                   10                  15

Gly Ser Ile Ser Ser Gly Leu Leu Ser Gly Arg Ser Asp Thr His Gly
            20                  25                  30

Gly Gly Ser Glu Ile Val Leu Thr Gln Ser Pro Gly Thr Leu Ser Leu
        35                  40                  45

Ser Pro Gly Glu Arg Ala Thr Leu Ser Cys Arg Ala Ser Gln Ser Val
    50                  55                  60

Gly Ser Ser Tyr Leu Ala Trp Tyr Gln Gln Lys Pro Gly Gln Ala Pro
65                  70                  75                  80

Arg Leu Leu Ile Tyr Gly Ala Phe Ser Arg Ala Thr Gly Ile Pro Asp
                85                  90                  95

Arg Phe Ser Gly Ser Gly Ser Gly Thr Asp Phe Thr Leu Thr Ile Ser
            100                 105                 110

Arg Leu Glu Pro Glu Asp Phe Ala Val Tyr Tyr Cys Gln Gln Tyr Gly
        115                 120                 125

Ser Ser Pro Trp Thr Phe Gly Gln Gly Thr Lys Val Glu Ile Lys Arg
    130                 135                 140

Thr Val Ala Ala Pro Ser Val Phe Ile Phe Pro Pro Ser Asp Glu Gln
145                 150                 155                 160

Leu Lys Ser Gly Thr Ala Ser Val Val Cys Leu Leu Asn Asn Phe Tyr
                165                 170                 175

Pro Arg Glu Ala Lys Val Gln Trp Lys Val Asp Asn Ala Leu Gln Ser
            180                 185                 190

Gly Asn Ser Gln Glu Ser Val Thr Glu Gln Asp Ser Lys Asp Ser Thr
        195                 200                 205

Tyr Ser Leu Ser Ser Thr Leu Thr Leu Ser Lys Ala Asp Tyr Glu Lys
    210                 215                 220

His Lys Val Tyr Ala Cys Glu Val Thr His Gln Gly Leu Ser Ser Pro
225                 230                 235                 240

Val Thr Lys Ser Phe Asn Arg Gly Glu Cys
                245                 250
```

<210> SEQ ID NO 436
<211> LENGTH: 259
<212> TYPE: PRT
<213> ORGANISM: Artificial Sequence
<220> FEATURE:
<223> OTHER INFORMATION: Spacer - YV39-2009 LC

<400> SEQUENCE: 436

```
Gln Gly Gln Ser Gly Ser Cys Arg Thr Gln Leu Tyr Gly Tyr Asn Leu
1               5                   10                  15

Cys Pro Tyr Gly Gly Gly Ser Ser Gly Gly Ser Ile Ser Ser Gly Leu
            20                  25                  30

Leu Ser Gly Arg Ser Asp Thr His Gly Gly Gly Ser Glu Ile Val Leu
        35                  40                  45

Thr Gln Ser Pro Gly Thr Leu Ser Leu Ser Pro Gly Glu Arg Ala Thr
    50                  55                  60
```

```
Leu Ser Cys Arg Ala Ser Gln Ser Val Gly Ser Ser Tyr Leu Ala Trp
65                  70                  75                  80

Tyr Gln Gln Lys Pro Gly Gln Ala Pro Arg Leu Leu Ile Tyr Gly Ala
                85                  90                  95

Phe Ser Arg Ala Thr Gly Ile Pro Asp Arg Phe Ser Gly Ser Gly Ser
            100                 105                 110

Gly Thr Asp Phe Thr Leu Thr Ile Ser Arg Leu Glu Pro Glu Asp Phe
        115                 120                 125

Ala Val Tyr Tyr Cys Gln Gln Tyr Gly Ser Ser Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys


<210> SEQ ID NO 437
<211> LENGTH: 253
<212> TYPE: PRT
<213> ORGANISM: Artificial Sequence
<220> FEATURE:
<223> OTHER INFORMATION: YV39-2009 LC

<400> SEQUENCE: 437

Cys Arg Thr Gln Leu Tyr Gly Tyr Asn Leu Cys Pro Tyr Gly Gly Gly
1               5                   10                  15

Ser Ser Gly Gly Ser Ile Ser Ser Gly Leu Leu Ser Gly Arg Ser Asp
            20                  25                  30

Thr His Gly Gly Gly Ser Glu Ile Val Leu Thr Gln Ser Pro Gly Thr
        35                  40                  45

Leu Ser Leu Ser Pro Gly Glu Arg Ala Thr Leu Ser Cys Arg Ala Ser
    50                  55                  60

Gln Ser Val Gly Ser Ser Tyr Leu Ala Trp Tyr Gln Gln Lys Pro Gly
65                  70                  75                  80

Gln Ala Pro Arg Leu Leu Ile Tyr Gly Ala Phe Ser Arg Ala Thr Gly
                85                  90                  95

Ile Pro Asp Arg Phe Ser Gly Ser Gly Ser Gly Thr Asp Phe Thr Leu
            100                 105                 110

Thr Ile Ser Arg Leu Glu Pro Glu Asp Phe Ala Val Tyr Tyr Cys Gln
        115                 120                 125

Gln Tyr Gly Ser Ser Pro Trp Thr Phe Gly Gln Gly Thr Lys Val Glu
    130                 135                 140

Ile Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
```

```
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250


<210> SEQ ID NO 438
<211> LENGTH: 263
<212> TYPE: PRT
<213> ORGANISM: Artificial Sequence
<220> FEATURE:
<223> OTHER INFORMATION: Spacer - YV01-2011 LC

<400> SEQUENCE: 438

Gln Gly Gln Ser Gly Gln Gly Asp Phe Ser Cys Leu His Ser Met Tyr
1               5                   10                  15

Asn Val Cys Leu Asp Pro Gly Gly Gly Ser Ser Gly Gly Ser Ile Ser
            20                  25                  30

Ser Gly Leu Leu Ser Gly Arg Ser Asp Asn Pro Gly Gly Gly Ser Glu
        35                  40                  45

Ile Val Leu Thr Gln Ser Pro Gly Thr Leu Ser Leu Ser Pro Gly Glu
    50                  55                  60

Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys Cys
            260
```

<210> SEQ ID NO 439
<211> LENGTH: 255
<212> TYPE: PRT
<213> ORGANISM: Artificial Sequence
<220> FEATURE:
<223> OTHER INFORMATION: YV01-2011 LC

<400> SEQUENCE: 439

Asp Phe Ser Cys Leu His Ser Met Tyr Asn Val Cys Leu Asp Pro Gly
1 5 10 15

Gly Gly Ser Ser Gly Gly Ser Ile Ser Ser Gly Leu Leu Ser Gly Arg
20 25 30

Ser Asp Asn Pro Gly Gly Gly Ser Glu Ile Val Leu Thr Gln Ser Pro
35 40 45

Gly Thr Leu Ser Leu Ser Pro Gly Glu Arg Ala Thr Leu Ser Cys Arg
50 55 60

Ala Ser Gln Ser Val Gly Ser Ser Tyr Leu Ala Trp Tyr Gln Gln Lys
65 70 75 80

Pro Gly Gln Ala Pro Arg Leu Leu Ile Tyr Gly Ala Phe Ser Arg Ala
85 90 95

Thr Gly Ile Pro Asp Arg Phe Ser Gly Ser Gly Ser Gly Thr Asp Phe
100 105 110

Thr Leu Thr Ile Ser Arg Leu Glu Pro Glu Asp Phe Ala Val Tyr Tyr
115 120 125

Cys Gln Gln Tyr Gly Ser Ser Pro Trp Thr Phe Gly Gln Gly Thr Lys
130 135 140

Val Glu Ile Lys Arg Thr Val Ala Ala Pro Ser Val Phe Ile Phe Pro
145 150 155 160

Pro Ser Asp Glu Gln Leu Lys Ser Gly Thr Ala Ser Val Val Cys Leu
165 170 175

Leu Asn Asn Phe Tyr Pro Arg Glu Ala Lys Val Gln Trp Lys Val Asp
180 185 190

Asn Ala Leu Gln Ser Gly Asn Ser Gln Glu Ser Val Thr Glu Gln Asp
195 200 205

Ser Lys Asp Ser Thr Tyr Ser Leu Ser Ser Thr Leu Thr Leu Ser Lys
210 215 220

Ala Asp Tyr Glu Lys His Lys Val Tyr Ala Cys Glu Val Thr His Gln
225 230 235 240

Gly Leu Ser Ser Pro Val Thr Lys Ser Phe Asn Arg Gly Glu Cys
245 250 255

<210> SEQ ID NO 440
<211> LENGTH: 262
<212> TYPE: PRT
<213> ORGANISM: Artificial Sequence
<220> FEATURE:
<223> OTHER INFORMATION: Spacer - YV02-2011 LC

<400> SEQUENCE: 440

Gln Gly Gln Ser Gly Gln Gly Gln Pro Cys Ala Gln Met Tyr Gly Tyr
1 5 10 15

Ser Met Cys Pro His Thr Gly Gly Gly Ser Ser Gly Gly Ser Ile Ser
20 25 30

Ser Gly Leu Leu Ser Gly Arg Ser Asp Asn Pro Gly Gly Gly Ser Glu
35 40 45

Ile Val Leu Thr Gln Ser Pro Gly Thr Leu Ser Leu Ser Pro Gly Glu
50 55 60

```
Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
            260


<210> SEQ ID NO 441
<211> LENGTH: 255
<212> TYPE: PRT
<213> ORGANISM: Artificial Sequence
<220> FEATURE:
<223> OTHER INFORMATION: YV02-2011 LC

<400> SEQUENCE: 441

Gln Pro Cys Ala Gln Met Tyr Gly Tyr Ser Met Cys Pro His Thr Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160
```

```
Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 442
<211> LENGTH: 262
<212> TYPE: PRT
<213> ORGANISM: Artificial Sequence
<220> FEATURE:
<223> OTHER INFORMATION: Spacer - YV03-2011 LC

<400> SEQUENCE: 442

Gln Gly Gln Ser Gly Gln Gly Leu His Cys Arg Thr Gln Met Tyr Gly
1               5                   10                  15

Tyr Asn Leu Cys Pro Tyr Gly Gly Gly Ser Ser Gly Gly Ser Ile Ser
            20                  25                  30

Ser Gly Leu Leu Ser Gly Arg Ser Asp Asn Pro Gly Gly Gly Ser Glu
        35                  40                  45

Ile Val Leu Thr Gln Ser Pro Gly Thr Leu Ser Leu Ser Pro Gly Glu
    50                  55                  60

Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
            260
```

<210> SEQ ID NO 443
<211> LENGTH: 255
<212> TYPE: PRT
<213> ORGANISM: Artificial Sequence
<220> FEATURE:
<223> OTHER INFORMATION: YV03-2011 LC

<400> SEQUENCE: 443

Leu His Cys Arg Thr Gln Met Tyr Gly Tyr Asn Leu Cys Pro Tyr Gly
1 5 10 15

Gly Gly Ser Ser Gly Gly Ser Ile Ser Ser Gly Leu Leu Ser Gly Arg
20 25 30

Ser Asp Asn Pro Gly Gly Gly Ser Glu Ile Val Leu Thr Gln Ser Pro
35 40 45

Gly Thr Leu Ser Leu Ser Pro Gly Glu Arg Ala Thr Leu Ser Cys Arg
50 55 60

Ala Ser Gln Ser Val Gly Ser Ser Tyr Leu Ala Trp Tyr Gln Gln Lys
65 70 75 80

Pro Gly Gln Ala Pro Arg Leu Leu Ile Tyr Gly Ala Phe Ser Arg Ala
85 90 95

Thr Gly Ile Pro Asp Arg Phe Ser Gly Ser Gly Ser Gly Thr Asp Phe
100 105 110

Thr Leu Thr Ile Ser Arg Leu Glu Pro Glu Asp Phe Ala Val Tyr Tyr
115 120 125

Cys Gln Gln Tyr Gly Ser Ser Pro Trp Thr Phe Gly Gln Gly Thr Lys
130 135 140

Val Glu Ile Lys Arg Thr Val Ala Ala Pro Ser Val Phe Ile Phe Pro
145 150 155 160

Pro Ser Asp Glu Gln Leu Lys Ser Gly Thr Ala Ser Val Val Cys Leu
165 170 175

Leu Asn Asn Phe Tyr Pro Arg Glu Ala Lys Val Gln Trp Lys Val Asp
180 185 190

Asn Ala Leu Gln Ser Gly Asn Ser Gln Glu Ser Val Thr Glu Gln Asp
195 200 205

Ser Lys Asp Ser Thr Tyr Ser Leu Ser Ser Thr Leu Thr Leu Ser Lys
210 215 220

Ala Asp Tyr Glu Lys His Lys Val Tyr Ala Cys Glu Val Thr His Gln
225 230 235 240

Gly Leu Ser Ser Pro Val Thr Lys Ser Phe Asn Arg Gly Glu Cys
245 250 255

<210> SEQ ID NO 444
<211> LENGTH: 261
<212> TYPE: PRT
<213> ORGANISM: Artificial Sequence
<220> FEATURE:
<223> OTHER INFORMATION: Spacer - YV04-2011 LC

<400> SEQUENCE: 444

Gln Gly Gln Ser Gly Ser Leu His Cys Arg Thr Gln Leu Tyr Gly Tyr
1 5 10 15

Asn Leu Cys Pro Tyr Gly Gly Gly Ser Ser Gly Gly Ser Ile Ser Ser
20 25 30

Gly Leu Leu Ser Gly Arg Ser Asp Asn Pro Gly Gly Gly Ser Glu Ile
35 40 45

Val Leu Thr Gln Ser Pro Gly Thr Leu Ser Leu Ser Pro Gly Glu Arg
50 55 60

```
Ala Thr Leu Ser Cys Arg Ala Ser Gln Ser Val Gly Ser Ser Tyr Leu
65                  70                  75                  80

Ala Trp Tyr Gln Gln Lys Pro Gly Gln Ala Pro Arg Leu Leu Ile Tyr
                85                  90                  95

Gly Ala Phe Ser Arg Ala Thr Gly Ile Pro Asp Arg Phe Ser Gly Ser
            100                 105                 110

Gly Ser Gly Thr Asp Phe Thr Leu Thr Ile Ser Arg Leu Glu Pro Glu
        115                 120                 125

Asp Phe Ala Val Tyr Tyr Cys Gln Gln Tyr Gly Ser Ser Pro Trp Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260


<210> SEQ ID NO 445
<211> LENGTH: 255
<212> TYPE: PRT
<213> ORGANISM: Artificial Sequence
<220> FEATURE:
<223> OTHER INFORMATION: YV04-2011 LC

<400> SEQUENCE: 445

Leu His Cys Arg Thr Gln Leu Tyr Gly Tyr Asn Leu Cys Pro Tyr Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160
```

```
Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 446
<211> LENGTH: 258
<212> TYPE: PRT
<213> ORGANISM: Artificial Sequence
<220> FEATURE:
<223> OTHER INFORMATION: Spacer - YV23-2011 LC

<400> SEQUENCE: 446

Gln Gly Gln Ser Gly Ser Cys Leu His Ser Leu Tyr Asn Val Cys Leu
1               5                   10                  15

Asp Pro Gly Gly Gly Ser Ser Gly Gly Ser Ile Ser Ser Gly Leu Leu
            20                  25                  30

Ser Gly Arg Ser Asp Asn Pro Gly Gly Gly Ser Glu Ile Val Leu Thr
        35                  40                  45

Gln Ser Pro Gly Thr Leu Ser Leu Ser Pro Gly Glu Arg Ala Thr Leu
    50                  55                  60

Ser Cys Arg Ala Ser Gln Ser Val Gly Ser Ser Tyr Leu Ala Trp Tyr
65                  70                  75                  80

Gln Gln Lys Pro Gly Gln Ala Pro Arg Leu Leu Ile Tyr Gly Ala Phe
                85                  90                  95

Ser Arg Ala Thr Gly Ile Pro Asp Arg Phe Ser Gly Ser Gly Ser Gly
            100                 105                 110

Thr Asp Phe Thr Leu Thr Ile Ser Arg Leu Glu Pro Glu Asp Phe Ala
        115                 120                 125

Val Tyr Tyr Cys Gln Gln Tyr Gly Ser Ser Pro Trp Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys
```

<210> SEQ ID NO 447
<211> LENGTH: 252
<212> TYPE: PRT
<213> ORGANISM: Artificial Sequence
<220> FEATURE:
<223> OTHER INFORMATION: YV23-2011 LC

<400> SEQUENCE: 447

```
Cys Leu His Ser Leu Tyr Asn Val Cys Leu Asp Pro Gly Gly Gly Ser
1               5                   10                  15

Ser Gly Gly Ser Ile Ser Ser Gly Leu Leu Ser Gly Arg Ser Asp Asn
            20                  25                  30

Pro Gly Gly Gly Ser Glu Ile Val Leu Thr Gln Ser Pro Gly Thr Leu
        35                  40                  45

Ser Leu Ser Pro Gly Glu Arg Ala Thr Leu Ser Cys Arg Ala Ser Gln
    50                  55                  60

Ser Val Gly Ser Ser Tyr Leu Ala Trp Tyr Gln Gln Lys Pro Gly Gln
65                  70                  75                  80

Ala Pro Arg Leu Leu Ile Tyr Gly Ala Phe Ser Arg Ala Thr Gly Ile
                85                  90                  95

Pro Asp Arg Phe Ser Gly Ser Gly Ser Gly Thr Asp Phe Thr Leu Thr
            100                 105                 110

Ile Ser Arg Leu Glu Pro Glu Asp Phe Ala Val Tyr Tyr Cys Gln Gln
        115                 120                 125

Tyr Gly Ser Ser Pro Trp Thr Phe Gly Gln Gly Thr Lys Val Glu Ile
    130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250
```

<210> SEQ ID NO 448
<211> LENGTH: 259
<212> TYPE: PRT
<213> ORGANISM: Artificial Sequence
<220> FEATURE:
<223> OTHER INFORMATION: Spacer - YV39-2011 LC

<400> SEQUENCE: 448

```
Gln Gly Gln Ser Gly Ser Cys Arg Thr Gln Leu Tyr Gly Tyr Asn Leu
1               5                   10                  15

Cys Pro Tyr Gly Gly Gly Ser Ser Gly Gly Ser Ile Ser Ser Gly Leu
            20                  25                  30

Leu Ser Gly Arg Ser Asp Asn Pro Gly Gly Gly Ser Glu Ile Val Leu
        35                  40                  45

Thr Gln Ser Pro Gly Thr Leu Ser Leu Ser Pro Gly Glu Arg Ala Thr
    50                  55                  60
```

```
Leu Ser Cys Arg Ala Ser Gln Ser Val Gly Ser Ser Tyr Leu Ala Trp
65                  70                  75                  80

Tyr Gln Gln Lys Pro Gly Gln Ala Pro Arg Leu Leu Ile Tyr Gly Ala
                85                  90                  95

Phe Ser Arg Ala Thr Gly Ile Pro Asp Arg Phe Ser Gly Ser Gly Ser
            100                 105                 110

Gly Thr Asp Phe Thr Leu Thr Ile Ser Arg Leu Glu Pro Glu Asp Phe
        115                 120                 125

Ala Val Tyr Tyr Cys Gln Gln Tyr Gly Ser Ser Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys


<210> SEQ ID NO 449
<211> LENGTH: 253
<212> TYPE: PRT
<213> ORGANISM: Artificial Sequence
<220> FEATURE:
<223> OTHER INFORMATION: YV39-2011 LC

<400> SEQUENCE: 449

Cys Arg Thr Gln Leu Tyr Gly Tyr Asn Leu Cys Pro Tyr Gly Gly Gly
1               5                   10                  15

Ser Ser Gly Gly Ser Ile Ser Ser Gly Leu Leu Ser Gly Arg Ser Asp
            20                  25                  30

Asn Pro Gly Gly Gly Ser Glu Ile Val Leu Thr Gln Ser Pro Gly Thr
        35                  40                  45

Leu Ser Leu Ser Pro Gly Glu Arg Ala Thr Leu Ser Cys Arg Ala Ser
    50                  55                  60

Gln Ser Val Gly Ser Ser Tyr Leu Ala Trp Tyr Gln Gln Lys Pro Gly
65                  70                  75                  80

Gln Ala Pro Arg Leu Leu Ile Tyr Gly Ala Phe Ser Arg Ala Thr Gly
                85                  90                  95

Ile Pro Asp Arg Phe Ser Gly Ser Gly Ser Gly Thr Asp Phe Thr Leu
            100                 105                 110

Thr Ile Ser Arg Leu Glu Pro Glu Asp Phe Ala Val Tyr Tyr Cys Gln
        115                 120                 125

Gln Tyr Gly Ser Ser Pro Trp Thr Phe Gly Gln Gly Thr Lys Val Glu
    130                 135                 140

Ile Lys Arg Thr Val Ala Ala Pro Ser Val Phe Ile Phe Pro Pro Ser
145                 150                 155                 160
```

```
Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250


<210> SEQ ID NO 450
<211> LENGTH: 261
<212> TYPE: PRT
<213> ORGANISM: Artificial Sequence
<220> FEATURE:
<223> OTHER INFORMATION: Spacer - YV61-2011 LC

<400> SEQUENCE: 450

Gln Gly Gln Ser Gly Ser Tyr Ile Ser Asp Cys Pro Tyr His Pro Met
1               5                   10                  15

Cys His Asp Tyr Gln Gly Gly Gly Ser Ser Gly Gly Ser Ile Ser Ser
            20                  25                  30

Gly Leu Leu Ser Gly Arg Ser Asp Asn Pro Gly Gly Gly Ser Glu Ile
        35                  40                  45

Val Leu Thr Gln Ser Pro Gly Thr Leu Ser Leu Ser Pro Gly Glu Arg
    50                  55                  60

Ala Thr Leu Ser Cys Arg Ala Ser Gln Ser Val Gly Ser Ser Tyr Leu
65                  70                  75                  80

Ala Trp Tyr Gln Gln Lys Pro Gly Gln Ala Pro Arg Leu Leu Ile Tyr
                85                  90                  95

Gly Ala Phe Ser Arg Ala Thr Gly Ile Pro Asp Arg Phe Ser Gly Ser
            100                 105                 110

Gly Ser Gly Thr Asp Phe Thr Leu Thr Ile Ser Arg Leu Glu Pro Glu
        115                 120                 125

Asp Phe Ala Val Tyr Tyr Cys Gln Gln Tyr Gly Ser Ser Pro Trp Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260
```

<210> SEQ ID NO 451
<211> LENGTH: 255
<212> TYPE: PRT
<213> ORGANISM: Artificial Sequence
<220> FEATURE:
<223> OTHER INFORMATION: YV61-2011 LC

<400> SEQUENCE: 451

```
Tyr Ile Ser Asp Cys Pro Tyr His Pro Met Cys His Asp Tyr Gln Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255
```

<210> SEQ ID NO 452
<211> LENGTH: 261
<212> TYPE: PRT
<213> ORGANISM: Artificial Sequence
<220> FEATURE:
<223> OTHER INFORMATION: Spacer - YV62-2011 LC

<400> SEQUENCE: 452

```
Gln Gly Gln Ser Gly Ser Phe Arg Asn Thr Cys Pro Tyr His Pro Met
1               5                   10                  15

Cys His Asp Tyr Arg Gly Gly Gly Ser Ser Gly Gly Ser Ile Ser Ser
            20                  25                  30

Gly Leu Leu Ser Gly Arg Ser Asp Asn Pro Gly Gly Gly Ser Glu Ile
        35                  40                  45

Val Leu Thr Gln Ser Pro Gly Thr Leu Ser Leu Ser Pro Gly Glu Arg
    50                  55                  60
```

Ala Thr Leu Ser Cys Arg Ala Ser Gln Ser Val Gly Ser Ser Tyr Leu
65 70 75 80

Ala Trp Tyr Gln Gln Lys Pro Gly Gln Ala Pro Arg Leu Leu Ile Tyr
85 90 95

Gly Ala Phe Ser Arg Ala Thr Gly Ile Pro Asp Arg Phe Ser Gly Ser
100 105 110

Gly Ser Gly Thr Asp Phe Thr Leu Thr Ile Ser Arg Leu Glu Pro Glu
115 120 125

Asp Phe Ala Val Tyr Tyr Cys Gln Gln Tyr Gly Ser Ser Pro Trp Thr
130 135 140

Phe Gly Gln Gly Thr Lys Val Glu Ile Lys Arg Thr Val Ala Ala Pro
145 150 155 160

Ser Val Phe Ile Phe Pro Pro Ser Asp Glu Gln Leu Lys Ser Gly Thr
165 170 175

Ala Ser Val Val Cys Leu Leu Asn Asn Phe Tyr Pro Arg Glu Ala Lys
180 185 190

Val Gln Trp Lys Val Asp Asn Ala Leu Gln Ser Gly Asn Ser Gln Glu
195 200 205

Ser Val Thr Glu Gln Asp Ser Lys Asp Ser Thr Tyr Ser Leu Ser Ser
210 215 220

Thr Leu Thr Leu Ser Lys Ala Asp Tyr Glu Lys His Lys Val Tyr Ala
225 230 235 240

Cys Glu Val Thr His Gln Gly Leu Ser Ser Pro Val Thr Lys Ser Phe
245 250 255

Asn Arg Gly Glu Cys
260

<210> SEQ ID NO 453
<211> LENGTH: 255
<212> TYPE: PRT
<213> ORGANISM: Artificial Sequence
<220> FEATURE:
<223> OTHER INFORMATION: YV62-2011 LC

<400> SEQUENCE: 453

Phe Arg Asn Thr Cys Pro Tyr His Pro Met Cys His Asp Tyr Arg Gly
1 5 10 15

Gly Gly Ser Ser Gly Gly Ser Ile Ser Ser Gly Leu Leu Ser Gly Arg
20 25 30

Ser Asp Asn Pro Gly Gly Gly Ser Glu Ile Val Leu Thr Gln Ser Pro
35 40 45

Gly Thr Leu Ser Leu Ser Pro Gly Glu Arg Ala Thr Leu Ser Cys Arg
50 55 60

Ala Ser Gln Ser Val Gly Ser Ser Tyr Leu Ala Trp Tyr Gln Gln Lys
65 70 75 80

Pro Gly Gln Ala Pro Arg Leu Leu Ile Tyr Gly Ala Phe Ser Arg Ala
85 90 95

Thr Gly Ile Pro Asp Arg Phe Ser Gly Ser Gly Ser Gly Thr Asp Phe
100 105 110

Thr Leu Thr Ile Ser Arg Leu Glu Pro Glu Asp Phe Ala Val Tyr Tyr
115 120 125

Cys Gln Gln Tyr Gly Ser Ser Pro Trp Thr Phe Gly Gln Gly Thr Lys
130 135 140

Val Glu Ile Lys Arg Thr Val Ala Ala Pro Ser Val Phe Ile Phe Pro
145 150 155 160

```
Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 454
<211> LENGTH: 261
<212> TYPE: PRT
<213> ORGANISM: Artificial Sequence
<220> FEATURE:
<223> OTHER INFORMATION: Spacer - YV63-2011 LC

<400> SEQUENCE: 454

Gln Gly Gln Ser Gly Ser Arg Glu Cys His Met Trp Met Phe Gly Val
1               5                   10                  15

Asn Leu Cys Pro Tyr Gly Gly Gly Ser Ser Gly Gly Ser Ile Ser Ser
            20                  25                  30

Gly Leu Leu Ser Gly Arg Ser Asp Asn Pro Gly Gly Gly Ser Glu Ile
        35                  40                  45

Val Leu Thr Gln Ser Pro Gly Thr Leu Ser Leu Ser Pro Gly Glu Arg
    50                  55                  60

Ala Thr Leu Ser Cys Arg Ala Ser Gln Ser Val Gly Ser Ser Tyr Leu
65                  70                  75                  80

Ala Trp Tyr Gln Gln Lys Pro Gly Gln Ala Pro Arg Leu Leu Ile Tyr
                85                  90                  95

Gly Ala Phe Ser Arg Ala Thr Gly Ile Pro Asp Arg Phe Ser Gly Ser
            100                 105                 110

Gly Ser Gly Thr Asp Phe Thr Leu Thr Ile Ser Arg Leu Glu Pro Glu
        115                 120                 125

Asp Phe Ala Val Tyr Tyr Cys Gln Gln Tyr Gly Ser Ser Pro Trp Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260
```

<210> SEQ ID NO 455
<211> LENGTH: 255
<212> TYPE: PRT
<213> ORGANISM: Artificial Sequence
<220> FEATURE:
<223> OTHER INFORMATION: YV63-2011 LC

<400> SEQUENCE: 455

Arg Glu Cys His Met Trp Met Phe Gly Val Asn Leu Cys Pro Tyr Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255

<210> SEQ ID NO 456
<211> LENGTH: 262
<212> TYPE: PRT
<213> ORGANISM: Artificial Sequence
<220> FEATURE:
<223> OTHER INFORMATION: Spacer - YV64-2011 LC

<400> SEQUENCE: 456

Gln Gly Gln Ser Gly Ser Ala Val Cys His Met Tyr Met Tyr Gly Tyr
1               5                   10                  15

Asn Leu Cys Pro Phe Gly Gly Gly Ser Ser Gly Gly Ser Ile Ser Ser
            20                  25                  30

Gly Leu Leu Ser Gly Arg Ser Asp Asn Pro Gly Gly Gly Ser Glu Ile
        35                  40                  45

Val Leu Thr Gln Ser Pro Gly Thr Leu Ser Leu Ser Pro Gly Glu Arg

```
    50                  55                  60

Ala Thr Leu Ser Cys Arg Ala Ser Gln Ser Val Gly Ser Ser Tyr Leu
65                  70                  75                  80

Ala Trp Tyr Gln Gln Lys Pro Gly Gln Ala Pro Arg Leu Leu Ile Tyr
                85                  90                  95

Gly Ala Phe Ser Arg Ala Thr Gly Ile Pro Asp Arg Phe Ser Gly Ser
            100                 105                 110

Gly Ser Gly Thr Asp Phe Thr Leu Thr Ile Ser Arg Leu Glu Pro Glu
        115                 120                 125

Asp Phe Ala Val Tyr Tyr Cys Gln Gln Tyr Gly Ser Ser Pro Trp Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys Cys
            260


<210> SEQ ID NO 457
<211> LENGTH: 255
<212> TYPE: PRT
<213> ORGANISM: Artificial Sequence
<220> FEATURE:
<223> OTHER INFORMATION: YV64-2011 LC

<400> SEQUENCE: 457

Ala Val Cys His Met Tyr Met Tyr Gly Tyr Asn Leu Cys Pro Phe Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
```

```
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 458
<211> LENGTH: 262
<212> TYPE: PRT
<213> ORGANISM: Artificial Sequence
<220> FEATURE:
<223> OTHER INFORMATION: Spacer - YV65-2011 LC

<400> SEQUENCE: 458

Gln Gly Gln Ser Gly Gln Gly Arg Ser Cys Pro Gln Met Tyr Gly Tyr
1               5                   10                  15

Ser Met Cys Pro His Thr Gly Gly Gly Ser Ser Gly Gly Ser Ile Ser
            20                  25                  30

Ser Gly Leu Leu Ser Gly Arg Ser Asp Asn Pro Gly Gly Gly Ser Glu
        35                  40                  45

Ile Val Leu Thr Gln Ser Pro Gly Thr Leu Ser Leu Ser Pro Gly Glu
    50                  55                  60

Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
```

260

<210> SEQ ID NO 459
<211> LENGTH: 255
<212> TYPE: PRT
<213> ORGANISM: Artificial Sequence
<220> FEATURE:
<223> OTHER INFORMATION: YV65-2011 LC

<400> SEQUENCE: 459

```
Arg Ser Cys Pro Gln Met Tyr Gly Tyr Ser Met Cys Pro His Thr Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255
```

<210> SEQ ID NO 460
<211> LENGTH: 262
<212> TYPE: PRT
<213> ORGANISM: Artificial Sequence
<220> FEATURE:
<223> OTHER INFORMATION: Spacer - YV66-2011 LC

<400> SEQUENCE: 460

```
Gln Gly Gln Ser Gly Gln Gly Gln Pro Cys Ala Gln Met Phe Gly Tyr
1               5                   10                  15

Ser Met Cys Pro His Thr Gly Gly Gly Ser Ser Gly Gly Ser Ile Ser
            20                  25                  30

Ser Gly Leu Leu Ser Gly Arg Ser Asp Asn Pro Gly Gly Gly Ser Glu
        35                  40                  45
```

```
Ile Val Leu Thr Gln Ser Pro Gly Thr Leu Ser Leu Ser Pro Gly Glu
    50                  55                  60

Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
            260
```

```
<210> SEQ ID NO 461
<211> LENGTH: 255
<212> TYPE: PRT
<213> ORGANISM: Artificial Sequence
<220> FEATURE:
<223> OTHER INFORMATION: YV66-2011 LC

<400> SEQUENCE: 461

Gln Pro Cys Ala Gln Met Phe Gly Tyr Ser Met Cys Pro His Thr Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140
```

```
Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 462
<211> LENGTH: 262
<212> TYPE: PRT
<213> ORGANISM: Artificial Sequence
<220> FEATURE:
<223> OTHER INFORMATION: Spacer - YV01-2012 LC

<400> SEQUENCE: 462

Gln Gly Gln Ser Gly Gln Gly Asp Phe Ser Cys Leu His Ser Met Tyr
1               5                   10                  15

Asn Val Cys Leu Asp Pro Gly Gly Gly Ser Ser Gly Gly Ser Ile Ser
            20                  25                  30

Ser Gly Leu Leu Ser Gly Arg Ser Ala Asn Pro Gly Gly Gly Ser Glu
        35                  40                  45

Ile Val Leu Thr Gln Ser Pro Gly Thr Leu Ser Leu Ser Pro Gly Glu
    50                  55                  60

Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255
```

Phe Asn Arg Gly Glu Cys
260

<210> SEQ ID NO 463
<211> LENGTH: 255
<212> TYPE: PRT
<213> ORGANISM: Artificial Sequence
<220> FEATURE:
<223> OTHER INFORMATION: YV01-2012 LC

<400> SEQUENCE: 463

Asp Phe Ser Cys Leu His Ser Met Tyr Asn Val Cys Leu Asp Pro Gly
1 5 10 15

Gly Gly Ser Ser Gly Gly Ser Ile Ser Ser Gly Leu Leu Ser Gly Arg
20 25 30

Ser Ala Asn Pro Gly Gly Gly Ser Glu Ile Val Leu Thr Gln Ser Pro
35 40 45

Gly Thr Leu Ser Leu Ser Pro Gly Glu Arg Ala Thr Leu Ser Cys Arg
50 55 60

Ala Ser Gln Ser Val Gly Ser Ser Tyr Leu Ala Trp Tyr Gln Gln Lys
65 70 75 80

Pro Gly Gln Ala Pro Arg Leu Leu Ile Tyr Gly Ala Phe Ser Arg Ala
85 90 95

Thr Gly Ile Pro Asp Arg Phe Ser Gly Ser Gly Ser Gly Thr Asp Phe
100 105 110

Thr Leu Thr Ile Ser Arg Leu Glu Pro Glu Asp Phe Ala Val Tyr Tyr
115 120 125

Cys Gln Gln Tyr Gly Ser Ser Pro Trp Thr Phe Gly Gln Gly Thr Lys
130 135 140

Val Glu Ile Lys Arg Thr Val Ala Ala Pro Ser Val Phe Ile Phe Pro
145 150 155 160

Pro Ser Asp Glu Gln Leu Lys Ser Gly Thr Ala Ser Val Val Cys Leu
165 170 175

Leu Asn Asn Phe Tyr Pro Arg Glu Ala Lys Val Gln Trp Lys Val Asp
180 185 190

Asn Ala Leu Gln Ser Gly Asn Ser Gln Glu Ser Val Thr Glu Gln Asp
195 200 205

Ser Lys Asp Ser Thr Tyr Ser Leu Ser Ser Thr Leu Thr Leu Ser Lys
210 215 220

Ala Asp Tyr Glu Lys His Lys Val Tyr Ala Cys Glu Val Thr His Gln
225 230 235 240

Gly Leu Ser Ser Pro Val Thr Lys Ser Phe Asn Arg Gly Glu Cys
245 250 255

<210> SEQ ID NO 464
<211> LENGTH: 262
<212> TYPE: PRT
<213> ORGANISM: Artificial Sequence
<220> FEATURE:
<223> OTHER INFORMATION: Spacer - YV02-2012 LC

<400> SEQUENCE: 464

Gln Gly Gln Ser Gly Gln Gly Gln Pro Cys Ala Gln Met Tyr Gly Tyr
1 5 10 15

Ser Met Cys Pro His Thr Gly Gly Gly Ser Ser Gly Gly Ser Ile Ser
20 25 30

Ser Gly Leu Leu Ser Gly Arg Ser Ala Asn Pro Gly Gly Gly Ser Glu
35 40 45

```
Ile Val Leu Thr Gln Ser Pro Gly Thr Leu Ser Leu Ser Pro Gly Glu
    50                  55                  60

Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
            260


<210> SEQ ID NO 465
<211> LENGTH: 255
<212> TYPE: PRT
<213> ORGANISM: Artificial Sequence
<220> FEATURE:
<223> OTHER INFORMATION: YV02-2012 LC

<400> SEQUENCE: 465

Gln Pro Cys Ala Gln Met Tyr Gly Tyr Ser Met Cys Pro His Thr Gly
1               5                   10                  15

Gly Gly Ser Ser Gly Gly Ser Ile Ser Ser Gly Leu Leu Ser Gly Arg
            20                  25                  30

Ser Ala Asn Pro Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140
```

Val Glu Ile Lys Arg Thr Val Ala Ala Pro Ser Val Phe Ile Phe Pro
145 150 155 160

Pro Ser Asp Glu Gln Leu Lys Ser Gly Thr Ala Ser Val Val Cys Leu
165 170 175

Leu Asn Asn Phe Tyr Pro Arg Glu Ala Lys Val Gln Trp Lys Val Asp
180 185 190

Asn Ala Leu Gln Ser Gly Asn Ser Gln Glu Ser Val Thr Glu Gln Asp
195 200 205

Ser Lys Asp Ser Thr Tyr Ser Leu Ser Ser Thr Leu Thr Leu Ser Lys
210 215 220

Ala Asp Tyr Glu Lys His Lys Val Tyr Ala Cys Glu Val Thr His Gln
225 230 235 240

Gly Leu Ser Ser Pro Val Thr Lys Ser Phe Asn Arg Gly Glu Cys
245 250 255

<210> SEQ ID NO 466
<211> LENGTH: 262
<212> TYPE: PRT
<213> ORGANISM: Artificial Sequence
<220> FEATURE:
<223> OTHER INFORMATION: Spacer - YV03-2012 LC

<400> SEQUENCE: 466

Gln Gly Gln Ser Gly Gln Gly Leu His Cys Arg Thr Gln Met Tyr Gly
1 5 10 15

Tyr Asn Leu Cys Pro Tyr Gly Gly Gly Ser Ser Gly Gly Ser Ile Ser
20 25 30

Ser Gly Leu Leu Ser Gly Arg Ser Ala Asn Pro Gly Gly Gly Ser Glu
35 40 45

Ile Val Leu Thr Gln Ser Pro Gly Thr Leu Ser Leu Ser Pro Gly Glu
50 55 60

Arg Ala Thr Leu Ser Cys Arg Ala Ser Gln Ser Val Gly Ser Ser Tyr
65 70 75 80

Leu Ala Trp Tyr Gln Gln Lys Pro Gly Gln Ala Pro Arg Leu Leu Ile
85 90 95

Tyr Gly Ala Phe Ser Arg Ala Thr Gly Ile Pro Asp Arg Phe Ser Gly
100 105 110

Ser Gly Ser Gly Thr Asp Phe Thr Leu Thr Ile Ser Arg Leu Glu Pro
115 120 125

Glu Asp Phe Ala Val Tyr Tyr Cys Gln Gln Tyr Gly Ser Ser Pro Trp
130 135 140

Thr Phe Gly Gln Gly Thr Lys Val Glu Ile Lys Arg Thr Val Ala Ala
145 150 155 160

Pro Ser Val Phe Ile Phe Pro Pro Ser Asp Glu Gln Leu Lys Ser Gly
165 170 175

Thr Ala Ser Val Val Cys Leu Leu Asn Asn Phe Tyr Pro Arg Glu Ala
180 185 190

Lys Val Gln Trp Lys Val Asp Asn Ala Leu Gln Ser Gly Asn Ser Gln
195 200 205

Glu Ser Val Thr Glu Gln Asp Ser Lys Asp Ser Thr Tyr Ser Leu Ser
210 215 220

Ser Thr Leu Thr Leu Ser Lys Ala Asp Tyr Glu Lys His Lys Val Tyr
225 230 235 240

Ala Cys Glu Val Thr His Gln Gly Leu Ser Ser Pro Val Thr Lys Ser
245 250 255

Phe Asn Arg Gly Glu Cys
260

<210> SEQ ID NO 467
<211> LENGTH: 255
<212> TYPE: PRT
<213> ORGANISM: Artificial Sequence
<220> FEATURE:
<223> OTHER INFORMATION: YV03-2012 LC

<400> SEQUENCE: 467

Leu His Cys Arg Thr Gln Met Tyr Gly Tyr Asn Leu Cys Pro Tyr Gly
1 5 10 15

Gly Gly Ser Ser Gly Gly Ser Ile Ser Ser Gly Leu Leu Ser Gly Arg
20 25 30

Ser Ala Asn Pro Gly Gly Gly Ser Glu Ile Val Leu Thr Gln Ser Pro
35 40 45

Gly Thr Leu Ser Leu Ser Pro Gly Glu Arg Ala Thr Leu Ser Cys Arg
50 55 60

Ala Ser Gln Ser Val Gly Ser Ser Tyr Leu Ala Trp Tyr Gln Gln Lys
65 70 75 80

Pro Gly Gln Ala Pro Arg Leu Leu Ile Tyr Gly Ala Phe Ser Arg Ala
85 90 95

Thr Gly Ile Pro Asp Arg Phe Ser Gly Ser Gly Ser Gly Thr Asp Phe
100 105 110

Thr Leu Thr Ile Ser Arg Leu Glu Pro Glu Asp Phe Ala Val Tyr Tyr
115 120 125

Cys Gln Gln Tyr Gly Ser Ser Pro Trp Thr Phe Gly Gln Gly Thr Lys
130 135 140

Val Glu Ile Lys Arg Thr Val Ala Ala Pro Ser Val Phe Ile Phe Pro
145 150 155 160

Pro Ser Asp Glu Gln Leu Lys Ser Gly Thr Ala Ser Val Val Cys Leu
165 170 175

Leu Asn Asn Phe Tyr Pro Arg Glu Ala Lys Val Gln Trp Lys Val Asp
180 185 190

Asn Ala Leu Gln Ser Gly Asn Ser Gln Glu Ser Val Thr Glu Gln Asp
195 200 205

Ser Lys Asp Ser Thr Tyr Ser Leu Ser Ser Thr Leu Thr Leu Ser Lys
210 215 220

Ala Asp Tyr Glu Lys His Lys Val Tyr Ala Cys Glu Val Thr His Gln
225 230 235 240

Gly Leu Ser Ser Pro Val Thr Lys Ser Phe Asn Arg Gly Glu Cys
245 250 255

<210> SEQ ID NO 468
<211> LENGTH: 261
<212> TYPE: PRT
<213> ORGANISM: Artificial Sequence
<220> FEATURE:
<223> OTHER INFORMATION: Spacer - YV04-2012 LC

<400> SEQUENCE: 468

Gln Gly Gln Ser Gly Ser Leu His Cys Arg Thr Gln Leu Tyr Gly Tyr
1 5 10 15

Asn Leu Cys Pro Tyr Gly Gly Gly Ser Ser Gly Gly Ser Ile Ser Ser
20 25 30

Gly Leu Leu Ser Gly Arg Ser Ala Asn Pro Gly Gly Gly Ser Glu Ile

```
        35                  40                  45

Val Leu Thr Gln Ser Pro Gly Thr Leu Ser Leu Ser Pro Gly Glu Arg
    50                  55                  60

Ala Thr Leu Ser Cys Arg Ala Ser Gln Ser Val Gly Ser Ser Tyr Leu
65                  70                  75                  80

Ala Trp Tyr Gln Gln Lys Pro Gly Gln Ala Pro Arg Leu Leu Ile Tyr
                85                  90                  95

Gly Ala Phe Ser Arg Ala Thr Gly Ile Pro Asp Arg Phe Ser Gly Ser
            100                 105                 110

Gly Ser Gly Thr Asp Phe Thr Leu Thr Ile Ser Arg Leu Glu Pro Glu
        115                 120                 125

Asp Phe Ala Val Tyr Tyr Cys Gln Gln Tyr Gly Ser Ser Pro Trp Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260


<210> SEQ ID NO 469
<211> LENGTH: 255
<212> TYPE: PRT
<213> ORGANISM: Artificial Sequence
<220> FEATURE:
<223> OTHER INFORMATION: YV04-2012 LC

<400> SEQUENCE: 469

Leu His Cys Arg Thr Gln Leu Tyr Gly Tyr Asn Leu Cys Pro Tyr Gly
1               5                   10                  15

Gly Gly Ser Ser Gly Gly Ser Ile Ser Ser Gly Leu Leu Ser Gly Arg
            20                  25                  30

Ser Ala Asn Pro Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
```

```
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 470
<211> LENGTH: 258
<212> TYPE: PRT
<213> ORGANISM: Artificial Sequence
<220> FEATURE:
<223> OTHER INFORMATION: Spacer - YV23-2012 LC

<400> SEQUENCE: 470

Gln Gly Gln Ser Gly Ser Cys Leu His Ser Leu Tyr Asn Val Cys Leu
1               5                   10                  15

Asp Pro Gly Gly Gly Ser Ser Gly Gly Ser Ile Ser Ser Gly Leu Leu
            20                  25                  30

Ser Gly Arg Ser Ala Asn Pro Gly Gly Gly Ser Glu Ile Val Leu Thr
        35                  40                  45

Gln Ser Pro Gly Thr Leu Ser Leu Ser Pro Gly Glu Arg Ala Thr Leu
    50                  55                  60

Ser Cys Arg Ala Ser Gln Ser Val Gly Ser Ser Tyr Leu Ala Trp Tyr
65                  70                  75                  80

Gln Gln Lys Pro Gly Gln Ala Pro Arg Leu Leu Ile Tyr Gly Ala Phe
                85                  90                  95

Ser Arg Ala Thr Gly Ile Pro Asp Arg Phe Ser Gly Ser Gly Ser Gly
            100                 105                 110

Thr Asp Phe Thr Leu Thr Ile Ser Arg Leu Glu Pro Glu Asp Phe Ala
        115                 120                 125

Val Tyr Tyr Cys Gln Gln Tyr Gly Ser Ser Pro Trp Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
```

245 250 255

Glu Cys

<210> SEQ ID NO 471
<211> LENGTH: 252
<212> TYPE: PRT
<213> ORGANISM: Artificial Sequence
<220> FEATURE:
<223> OTHER INFORMATION: YV23-2012 LC

<400> SEQUENCE: 471

```
Cys Leu His Ser Leu Tyr Asn Val Cys Leu Asp Pro Gly Gly Gly Ser
1               5                   10                  15

Ser Gly Gly Ser Ile Ser Ser Gly Leu Leu Ser Gly Arg Ser Ala Asn
            20                  25                  30

Pro Gly Gly Gly Ser Glu Ile Val Leu Thr Gln Ser Pro Gly Thr Leu
        35                  40                  45

Ser Leu Ser Pro Gly Glu Arg Ala Thr Leu Ser Cys Arg Ala Ser Gln
    50                  55                  60

Ser Val Gly Ser Ser Tyr Leu Ala Trp Tyr Gln Gln Lys Pro Gly Gln
65                  70                  75                  80

Ala Pro Arg Leu Leu Ile Tyr Gly Ala Phe Ser Arg Ala Thr Gly Ile
                85                  90                  95

Pro Asp Arg Phe Ser Gly Ser Gly Ser Gly Thr Asp Phe Thr Leu Thr
            100                 105                 110

Ile Ser Arg Leu Glu Pro Glu Asp Phe Ala Val Tyr Tyr Cys Gln Gln
        115                 120                 125

Tyr Gly Ser Ser Pro Trp Thr Phe Gly Gln Gly Thr Lys Val Glu Ile
    130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250
```

<210> SEQ ID NO 472
<211> LENGTH: 259
<212> TYPE: PRT
<213> ORGANISM: Artificial Sequence
<220> FEATURE:
<223> OTHER INFORMATION: Spacer - YV39-2012 LC

<400> SEQUENCE: 472

```
Gln Gly Gln Ser Gly Ser Cys Arg Thr Gln Leu Tyr Gly Tyr Asn Leu
1               5                   10                  15

Cys Pro Tyr Gly Gly Gly Ser Ser Gly Gly Ser Ile Ser Ser Gly Leu
            20                  25                  30

Leu Ser Gly Arg Ser Ala Asn Pro Gly Gly Gly Ser Glu Ile Val Leu
```

```
        35                  40                  45

Thr Gln Ser Pro Gly Thr Leu Ser Leu Ser Pro Gly Glu Arg Ala Thr
    50                  55                  60

Leu Ser Cys Arg Ala Ser Gln Ser Val Gly Ser Ser Tyr Leu Ala Trp
65                  70                  75                  80

Tyr Gln Gln Lys Pro Gly Gln Ala Pro Arg Leu Leu Ile Tyr Gly Ala
                85                  90                  95

Phe Ser Arg Ala Thr Gly Ile Pro Asp Arg Phe Ser Gly Ser Gly Ser
            100                 105                 110

Gly Thr Asp Phe Thr Leu Thr Ile Ser Arg Leu Glu Pro Glu Asp Phe
        115                 120                 125

Ala Val Tyr Tyr Cys Gln Gln Tyr Gly Ser Ser Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys


<210> SEQ ID NO 473
<211> LENGTH: 253
<212> TYPE: PRT
<213> ORGANISM: Artificial Sequence
<220> FEATURE:
<223> OTHER INFORMATION: YV39-2012 LC

<400> SEQUENCE: 473

Cys Arg Thr Gln Leu Tyr Gly Tyr Asn Leu Cys Pro Tyr Gly Gly Gly
1               5                   10                  15

Ser Ser Gly Gly Ser Ile Ser Ser Gly Leu Leu Ser Gly Arg Ser Ala
            20                  25                  30

Asn Pro Gly Gly Gly Ser Glu Ile Val Leu Thr Gln Ser Pro Gly Thr
        35                  40                  45

Leu Ser Leu Ser Pro Gly Glu Arg Ala Thr Leu Ser Cys Arg Ala Ser
    50                  55                  60

Gln Ser Val Gly Ser Ser Tyr Leu Ala Trp Tyr Gln Gln Lys Pro Gly
65                  70                  75                  80

Gln Ala Pro Arg Leu Leu Ile Tyr Gly Ala Phe Ser Arg Ala Thr Gly
                85                  90                  95

Ile Pro Asp Arg Phe Ser Gly Ser Gly Ser Gly Thr Asp Phe Thr Leu
            100                 105                 110

Thr Ile Ser Arg Leu Glu Pro Glu Asp Phe Ala Val Tyr Tyr Cys Gln
        115                 120                 125

Gln Tyr Gly Ser Ser Pro Trp Thr Phe Gly Gln Gly Thr Lys Val Glu
    130                 135                 140
```

Ile Lys Arg Thr Val Ala Ala Pro Ser Val Phe Ile Phe Pro Pro Ser
145 150 155 160

Asp Glu Gln Leu Lys Ser Gly Thr Ala Ser Val Val Cys Leu Leu Asn
165 170 175

Asn Phe Tyr Pro Arg Glu Ala Lys Val Gln Trp Lys Val Asp Asn Ala
180 185 190

Leu Gln Ser Gly Asn Ser Gln Glu Ser Val Thr Glu Gln Asp Ser Lys
195 200 205

Asp Ser Thr Tyr Ser Leu Ser Ser Thr Leu Thr Leu Ser Lys Ala Asp
210 215 220

Tyr Glu Lys His Lys Val Tyr Ala Cys Glu Val Thr His Gln Gly Leu
225 230 235 240

Ser Ser Pro Val Thr Lys Ser Phe Asn Arg Gly Glu Cys
245 250

<210> SEQ ID NO 474
<211> LENGTH: 261
<212> TYPE: PRT
<213> ORGANISM: Artificial Sequence
<220> FEATURE:
<223> OTHER INFORMATION: Spacer - YV61-2012 LC

<400> SEQUENCE: 474

Gln Gly Gln Ser Gly Ser Tyr Ile Ser Asp Cys Pro Tyr His Pro Met
1 5 10 15

Cys His Asp Tyr Gln Gly Gly Gly Ser Ser Gly Gly Ser Ile Ser Ser
20 25 30

Gly Leu Leu Ser Gly Arg Ser Ala Asn Pro Gly Gly Gly Ser Glu Ile
35 40 45

Val Leu Thr Gln Ser Pro Gly Thr Leu Ser Leu Ser Pro Gly Glu Arg
50 55 60

Ala Thr Leu Ser Cys Arg Ala Ser Gln Ser Val Gly Ser Ser Tyr Leu
65 70 75 80

Ala Trp Tyr Gln Gln Lys Pro Gly Gln Ala Pro Arg Leu Leu Ile Tyr
85 90 95

Gly Ala Phe Ser Arg Ala Thr Gly Ile Pro Asp Arg Phe Ser Gly Ser
100 105 110

Gly Ser Gly Thr Asp Phe Thr Leu Thr Ile Ser Arg Leu Glu Pro Glu
115 120 125

Asp Phe Ala Val Tyr Tyr Cys Gln Gln Tyr Gly Ser Ser Pro Trp Thr
130 135 140

Phe Gly Gln Gly Thr Lys Val Glu Ile Lys Arg Thr Val Ala Ala Pro
145 150 155 160

Ser Val Phe Ile Phe Pro Pro Ser Asp Glu Gln Leu Lys Ser Gly Thr
165 170 175

Ala Ser Val Val Cys Leu Leu Asn Asn Phe Tyr Pro Arg Glu Ala Lys
180 185 190

Val Gln Trp Lys Val Asp Asn Ala Leu Gln Ser Gly Asn Ser Gln Glu
195 200 205

Ser Val Thr Glu Gln Asp Ser Lys Asp Ser Thr Tyr Ser Leu Ser Ser
210 215 220

Thr Leu Thr Leu Ser Lys Ala Asp Tyr Glu Lys His Lys Val Tyr Ala
225 230 235 240

Cys Glu Val Thr His Gln Gly Leu Ser Ser Pro Val Thr Lys Ser Phe
245 250 255

```
Asn Arg Gly Glu Cys
            260


<210> SEQ ID NO 475
<211> LENGTH: 255
<212> TYPE: PRT
<213> ORGANISM: Artificial Sequence
<220> FEATURE:
<223> OTHER INFORMATION: YV61-2012 LC

<400> SEQUENCE: 475

Tyr Ile Ser Asp Cys Pro Tyr His Pro Met Cys His Asp Tyr Gln Gly
1               5                   10                  15

Gly Gly Ser Ser Gly Gly Ser Ile Ser Ser Gly Leu Leu Ser Gly Arg
            20                  25                  30

Ser Ala Asn Pro Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 476
<211> LENGTH: 261
<212> TYPE: PRT
<213> ORGANISM: Artificial Sequence
<220> FEATURE:
<223> OTHER INFORMATION: Spacer - YV62-2012 LC

<400> SEQUENCE: 476

Gln Gly Gln Ser Gly Ser Phe Arg Asn Thr Cys Pro Tyr His Pro Met
1               5                   10                  15

Cys His Asp Tyr Arg Gly Gly Gly Ser Ser Gly Gly Ser Ile Ser Ser
            20                  25                  30

Gly Leu Leu Ser Gly Arg Ser Ala Asn Pro Gly Gly Gly Ser Glu Ile
```

```
        35                  40                  45

Val Leu Thr Gln Ser Pro Gly Thr Leu Ser Leu Ser Pro Gly Glu Arg
    50                  55                  60

Ala Thr Leu Ser Cys Arg Ala Ser Gln Ser Val Gly Ser Ser Tyr Leu
65                  70                  75                  80

Ala Trp Tyr Gln Gln Lys Pro Gly Gln Ala Pro Arg Leu Leu Ile Tyr
                85                  90                  95

Gly Ala Phe Ser Arg Ala Thr Gly Ile Pro Asp Arg Phe Ser Gly Ser
            100                 105                 110

Gly Ser Gly Thr Asp Phe Thr Leu Thr Ile Ser Arg Leu Glu Pro Glu
        115                 120                 125

Asp Phe Ala Val Tyr Tyr Cys Gln Gln Tyr Gly Ser Ser Pro Trp Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260


<210> SEQ ID NO 477
<211> LENGTH: 255
<212> TYPE: PRT
<213> ORGANISM: Artificial Sequence
<220> FEATURE:
<223> OTHER INFORMATION: YV62-2012 LC

<400> SEQUENCE: 477

Phe Arg Asn Thr Cys Pro Tyr His Pro Met Cys His Asp Tyr Arg Gly
1               5                   10                  15

Gly Gly Ser Ser Gly Gly Ser Ile Ser Ser Gly Leu Leu Ser Gly Arg
            20                  25                  30

Ser Ala Asn Pro Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
```

```
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 478
<211> LENGTH: 261
<212> TYPE: PRT
<213> ORGANISM: Artificial Sequence
<220> FEATURE:
<223> OTHER INFORMATION: Spacer - YV63-2012 LC

<400> SEQUENCE: 478

Gln Gly Gln Ser Gly Ser Arg Glu Cys His Met Trp Met Phe Gly Val
1               5                   10                  15

Asn Leu Cys Pro Tyr Gly Gly Gly Ser Ser Gly Gly Ser Ile Ser Ser
            20                  25                  30

Gly Leu Leu Ser Gly Arg Ser Ala Asn Pro Gly Gly Gly Ser Glu Ile
        35                  40                  45

Val Leu Thr Gln Ser Pro Gly Thr Leu Ser Leu Ser Pro Gly Glu Arg
    50                  55                  60

Ala Thr Leu Ser Cys Arg Ala Ser Gln Ser Val Gly Ser Ser Tyr Leu
65                  70                  75                  80

Ala Trp Tyr Gln Gln Lys Pro Gly Gln Ala Pro Arg Leu Leu Ile Tyr
                85                  90                  95

Gly Ala Phe Ser Arg Ala Thr Gly Ile Pro Asp Arg Phe Ser Gly Ser
            100                 105                 110

Gly Ser Gly Thr Asp Phe Thr Leu Thr Ile Ser Arg Leu Glu Pro Glu
        115                 120                 125

Asp Phe Ala Val Tyr Tyr Cys Gln Gln Tyr Gly Ser Ser Pro Trp Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
```

```
                245                 250                 255

Asn Arg Gly Glu Cys
            260


<210> SEQ ID NO 479
<211> LENGTH: 255
<212> TYPE: PRT
<213> ORGANISM: Artificial Sequence
<220> FEATURE:
<223> OTHER INFORMATION: YV63-2012 LC

<400> SEQUENCE: 479

Arg Glu Cys His Met Trp Met Phe Gly Val Asn Leu Cys Pro Tyr Gly
1               5                   10                  15

Gly Gly Ser Ser Gly Gly Ser Ile Ser Ser Gly Leu Leu Ser Gly Arg
            20                  25                  30

Ser Ala Asn Pro Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 480
<211> LENGTH: 261
<212> TYPE: PRT
<213> ORGANISM: Artificial Sequence
<220> FEATURE:
<223> OTHER INFORMATION: Spacer - YV64-2012 LC

<400> SEQUENCE: 480

Gln Gly Gln Ser Gly Ser Ala Val Cys His Met Tyr Met Tyr Gly Tyr
1               5                   10                  15

Asn Leu Cys Pro Phe Gly Gly Gly Ser Ser Gly Gly Ser Ile Ser Ser
            20                  25                  30
```

```
Gly Leu Leu Ser Gly Arg Ser Ala Asn Pro Gly Gly Gly Ser Glu Ile
        35                  40                  45

Val Leu Thr Gln Ser Pro Gly Thr Leu Ser Leu Ser Pro Gly Glu Arg
    50                  55                  60

Ala Thr Leu Ser Cys Arg Ala Ser Gln Ser Val Gly Ser Ser Tyr Leu
65                  70                  75                  80

Ala Trp Tyr Gln Gln Lys Pro Gly Gln Ala Pro Arg Leu Leu Ile Tyr
                85                  90                  95

Gly Ala Phe Ser Arg Ala Thr Gly Ile Pro Asp Arg Phe Ser Gly Ser
            100                 105                 110

Gly Ser Gly Thr Asp Phe Thr Leu Thr Ile Ser Arg Leu Glu Pro Glu
        115                 120                 125

Asp Phe Ala Val Tyr Tyr Cys Gln Gln Tyr Gly Ser Ser Pro Trp Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260


<210> SEQ ID NO 481
<211> LENGTH: 255
<212> TYPE: PRT
<213> ORGANISM: Artificial Sequence
<220> FEATURE:
<223> OTHER INFORMATION: YV64-2012 LC

<400> SEQUENCE: 481

Ala Val Cys His Met Tyr Met Tyr Gly Tyr Asn Leu Cys Pro Phe Gly
1               5                   10                  15

Gly Gly Ser Ser Gly Gly Ser Ile Ser Ser Gly Leu Leu Ser Gly Arg
            20                  25                  30

Ser Ala Asn Pro Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125
```

```
Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 482
<211> LENGTH: 262
<212> TYPE: PRT
<213> ORGANISM: Artificial Sequence
<220> FEATURE:
<223> OTHER INFORMATION: Spacer - YV65-2012 LC

<400> SEQUENCE: 482

Gln Gly Gln Ser Gly Gln Gly Arg Ser Cys Pro Gln Met Tyr Gly Tyr
1               5                   10                  15

Ser Met Cys Pro His Thr Gly Gly Gly Ser Ser Gly Gly Ser Ile Ser
            20                  25                  30

Ser Gly Leu Leu Ser Gly Arg Ser Ala Asn Pro Gly Gly Gly Ser Glu
        35                  40                  45

Ile Val Leu Thr Gln Ser Pro Gly Thr Leu Ser Leu Ser Pro Gly Glu
    50                  55                  60

Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240
```

```
Ala Cys Glu Val Thr His Gln Gly Leu Ser Ser Pro Val Thr Lys Ser
                245                 250                 255

Phe Asn Arg Gly Glu Cys
            260


<210> SEQ ID NO 483
<211> LENGTH: 255
<212> TYPE: PRT
<213> ORGANISM: Artificial Sequence
<220> FEATURE:
<223> OTHER INFORMATION: YV65-2012 LC

<400> SEQUENCE: 483

Arg Ser Cys Pro Gln Met Tyr Gly Tyr Ser Met Cys Pro His Thr Gly
1               5                   10                  15

Gly Gly Ser Ser Gly Gly Ser Ile Ser Ser Gly Leu Leu Ser Gly Arg
            20                  25                  30

Ser Ala Asn Pro Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 484
<211> LENGTH: 262
<212> TYPE: PRT
<213> ORGANISM: Artificial Sequence
<220> FEATURE:
<223> OTHER INFORMATION: Spacer - YV66-2012 LC

<400> SEQUENCE: 484

Gln Gly Gln Ser Gly Gln Gly Gln Pro Cys Ala Gln Met Phe Gly Tyr
1               5                   10                  15

Ser Met Cys Pro His Thr Gly Gly Gly Ser Ser Gly Gly Ser Ile Ser
            20                  25                  30
```

```
Ser Gly Leu Leu Ser Gly Arg Ser Ala Asn Pro Gly Gly Gly Ser Glu
        35                  40                  45

Ile Val Leu Thr Gln Ser Pro Gly Thr Leu Ser Leu Ser Pro Gly Glu
    50                  55                  60

Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
            260
```

<210> SEQ ID NO 485
<211> LENGTH: 255
<212> TYPE: PRT
<213> ORGANISM: Artificial Sequence
<220> FEATURE:
<223> OTHER INFORMATION: YV66-2012 LC

<400> SEQUENCE: 485

```
Gln Pro Cys Ala Gln Met Phe Gly Tyr Ser Met Cys Pro His Thr Gly
1               5                   10                  15

Gly Gly Ser Ser Gly Gly Ser Ile Ser Ser Gly Leu Leu Ser Gly Arg
            20                  25                  30

Ser Ala Asn Pro Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125
```

```
Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 486
<211> LENGTH: 267
<212> TYPE: PRT
<213> ORGANISM: Artificial Sequence
<220> FEATURE:
<223> OTHER INFORMATION: Spacer - YV01-3001 LC

<400> SEQUENCE: 486

Gln Gly Gln Ser Gly Gln Gly Asp Phe Ser Cys Leu His Ser Met Tyr
1               5                   10                  15

Asn Val Cys Leu Asp Pro Gly Gly Gly Ser Ser Gly Gly Ser Ala Val
            20                  25                  30

Gly Leu Leu Ala Pro Pro Gly Gly Leu Ser Gly Arg Ser Asp Asn His
        35                  40                  45

Gly Gly Gly Ser Glu Ile Val Leu Thr Gln Ser Pro Gly Thr Leu Ser
    50                  55                  60

Leu Ser Pro Gly Glu Arg Ala Thr Leu Ser Cys Arg Ala Ser Gln Ser
65                  70                  75                  80

Val Gly Ser Ser Tyr Leu Ala Trp Tyr Gln Gln Lys Pro Gly Gln Ala
                85                  90                  95

Pro Arg Leu Leu Ile Tyr Gly Ala Phe Ser Arg Ala Thr Gly Ile Pro
            100                 105                 110

Asp Arg Phe Ser Gly Ser Gly Ser Gly Thr Asp Phe Thr Leu Thr Ile
        115                 120                 125

Ser Arg Leu Glu Pro Glu Asp Phe Ala Val Tyr Tyr Cys Gln Gln Tyr
    130                 135                 140

Gly Ser Ser Pro Trp Thr Phe Gly Gln Gly Thr Lys Val Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240
```

```
Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265


<210> SEQ ID NO 487
<211> LENGTH: 260
<212> TYPE: PRT
<213> ORGANISM: Artificial Sequence
<220> FEATURE:
<223> OTHER INFORMATION: YV01-3001 LC

<400> SEQUENCE: 487

Asp Phe Ser Cys Leu His Ser Met Tyr Asn Val Cys Leu Asp Pro Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Asn His Gly Gly Gly Ser Glu Ile Val
        35                  40                  45

Leu Thr Gln Ser Pro Gly Thr Leu Ser Leu Ser Pro Gly Glu Arg Ala
    50                  55                  60

Thr Leu Ser Cys Arg Ala Ser Gln Ser Val Gly Ser Ser Tyr Leu Ala
65                  70                  75                  80

Trp Tyr Gln Gln Lys Pro Gly Gln Ala Pro Arg Leu Leu Ile Tyr Gly
                85                  90                  95

Ala Phe Ser Arg Ala Thr Gly Ile Pro Asp Arg Phe Ser Gly Ser Gly
            100                 105                 110

Ser Gly Thr Asp Phe Thr Leu Thr Ile Ser Arg Leu Glu Pro Glu Asp
        115                 120                 125

Phe Ala Val Tyr Tyr Cys Gln Gln Tyr Gly Ser Ser Pro Trp Thr Phe
    130                 135                 140

Gly Gln Gly Thr Lys Val Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260


<210> SEQ ID NO 488
<211> LENGTH: 267
<212> TYPE: PRT
<213> ORGANISM: Artificial Sequence
<220> FEATURE:
<223> OTHER INFORMATION: Spacer - YV02-3001 LC

<400> SEQUENCE: 488

Gln Gly Gln Ser Gly Gln Gly Gln Pro Cys Ala Gln Met Tyr Gly Tyr
```

```
1               5                   10                  15

Ser Met Cys Pro His Thr Gly Gly Gly Ser Ser Gly Gly Ser Ala Val
            20                  25                  30

Gly Leu Leu Ala Pro Pro Gly Gly Leu Ser Gly Arg Ser Asp Asn His
        35                  40                  45

Gly Gly Gly Ser Glu Ile Val Leu Thr Gln Ser Pro Gly Thr Leu Ser
    50                  55                  60

Leu Ser Pro Gly Glu Arg Ala Thr Leu Ser Cys Arg Ala Ser Gln Ser
65                  70                  75                  80

Val Gly Ser Ser Tyr Leu Ala Trp Tyr Gln Gln Lys Pro Gly Gln Ala
                85                  90                  95

Pro Arg Leu Leu Ile Tyr Gly Ala Phe Ser Arg Ala Thr Gly Ile Pro
            100                 105                 110

Asp Arg Phe Ser Gly Ser Gly Ser Gly Thr Asp Phe Thr Leu Thr Ile
        115                 120                 125

Ser Arg Leu Glu Pro Glu Asp Phe Ala Val Tyr Tyr Cys Gln Gln Tyr
    130                 135                 140

Gly Ser Ser Pro Trp Thr Phe Gly Gln Gly Thr Lys Val Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265


<210> SEQ ID NO 489
<211> LENGTH: 260
<212> TYPE: PRT
<213> ORGANISM: Artificial Sequence
<220> FEATURE:
<223> OTHER INFORMATION: YV02-3001 LC

<400> SEQUENCE: 489

Gln Pro Cys Ala Gln Met Tyr Gly Tyr Ser Met Cys Pro His Thr Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Asn His Gly Gly Gly Ser Glu Ile Val
        35                  40                  45

Leu Thr Gln Ser Pro Gly Thr Leu Ser Leu Ser Pro Gly Glu Arg Ala
    50                  55                  60

Thr Leu Ser Cys Arg Ala Ser Gln Ser Val Gly Ser Ser Tyr Leu Ala
65                  70                  75                  80

Trp Tyr Gln Gln Lys Pro Gly Gln Ala Pro Arg Leu Leu Ile Tyr Gly
                85                  90                  95

Ala Phe Ser Arg Ala Thr Gly Ile Pro Asp Arg Phe Ser Gly Ser Gly
```

```
            100                 105                 110

Ser Gly Thr Asp Phe Thr Leu Thr Ile Ser Arg Leu Glu Pro Glu Asp
        115                 120                 125

Phe Ala Val Tyr Tyr Cys Gln Gln Tyr Gly Ser Ser Pro Trp Thr Phe
    130                 135                 140

Gly Gln Gly Thr Lys Val Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260
```

<210> SEQ ID NO 490
<211> LENGTH: 267
<212> TYPE: PRT
<213> ORGANISM: Artificial Sequence
<220> FEATURE:
<223> OTHER INFORMATION: Spacer - YV03-3001 LC

<400> SEQUENCE: 490

```
Gln Gly Gln Ser Gly Gln Gly Leu His Cys Arg Thr Gln Met Tyr Gly
1               5                   10                  15

Tyr Asn Leu Cys Pro Tyr Gly Gly Gly Ser Ser Gly Gly Ser Ala Val
            20                  25                  30

Gly Leu Leu Ala Pro Pro Gly Gly Leu Ser Gly Arg Ser Asp Asn His
        35                  40                  45

Gly Gly Gly Ser Glu Ile Val Leu Thr Gln Ser Pro Gly Thr Leu Ser
    50                  55                  60

Leu Ser Pro Gly Glu Arg Ala Thr Leu Ser Cys Arg Ala Ser Gln Ser
65                  70                  75                  80

Val Gly Ser Ser Tyr Leu Ala Trp Tyr Gln Gln Lys Pro Gly Gln Ala
                85                  90                  95

Pro Arg Leu Leu Ile Tyr Gly Ala Phe Ser Arg Ala Thr Gly Ile Pro
            100                 105                 110

Asp Arg Phe Ser Gly Ser Gly Ser Gly Thr Asp Phe Thr Leu Thr Ile
        115                 120                 125

Ser Arg Leu Glu Pro Glu Asp Phe Ala Val Tyr Tyr Cys Gln Gln Tyr
    130                 135                 140

Gly Ser Ser Pro Trp Thr Phe Gly Gln Gly Thr Lys Val Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
```

```
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265


<210> SEQ ID NO 491
<211> LENGTH: 260
<212> TYPE: PRT
<213> ORGANISM: Artificial Sequence
<220> FEATURE:
<223> OTHER INFORMATION: YV03-3001 LC

<400> SEQUENCE: 491

Leu His Cys Arg Thr Gln Met Tyr Gly Tyr Asn Leu Cys Pro Tyr Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Asn His Gly Gly Gly Ser Glu Ile Val
        35                  40                  45

Leu Thr Gln Ser Pro Gly Thr Leu Ser Leu Ser Pro Gly Glu Arg Ala
    50                  55                  60

Thr Leu Ser Cys Arg Ala Ser Gln Ser Val Gly Ser Ser Tyr Leu Ala
65                  70                  75                  80

Trp Tyr Gln Gln Lys Pro Gly Gln Ala Pro Arg Leu Leu Ile Tyr Gly
                85                  90                  95

Ala Phe Ser Arg Ala Thr Gly Ile Pro Asp Arg Phe Ser Gly Ser Gly
            100                 105                 110

Ser Gly Thr Asp Phe Thr Leu Thr Ile Ser Arg Leu Glu Pro Glu Asp
        115                 120                 125

Phe Ala Val Tyr Tyr Cys Gln Gln Tyr Gly Ser Ser Pro Trp Thr Phe
    130                 135                 140

Gly Gln Gly Thr Lys Val Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260


<210> SEQ ID NO 492
<211> LENGTH: 265
<212> TYPE: PRT
```

<213> ORGANISM: Artificial Sequence
<220> FEATURE:
<223> OTHER INFORMATION: Spacer - YV04-3001 LC

<400> SEQUENCE: 492

```
Gln Gly Gln Ser Gly Ser Leu His Cys Arg Thr Gln Leu Tyr Gly Tyr
1               5                   10                  15

Asn Leu Cys Pro Tyr Gly Gly Gly Ser Ser Gly Gly Ala Val Gly Leu
            20                  25                  30

Leu Ala Pro Pro Gly Gly Leu Ser Gly Arg Ser Asp Asn His Gly Gly
        35                  40                  45

Gly Ser Glu Ile Val Leu Thr Gln Ser Pro Gly Thr Leu Ser Leu Ser
    50                  55                  60

Pro Gly Glu Arg Ala Thr Leu Ser Cys Arg Ala Ser Gln Ser Val Gly
65                  70                  75                  80

Ser Ser Tyr Leu Ala Trp Tyr Gln Gln Lys Pro Gly Gln Ala Pro Arg
                85                  90                  95

Leu Leu Ile Tyr Gly Ala Phe Ser Arg Ala Thr Gly Ile Pro Asp Arg
            100                 105                 110

Phe Ser Gly Ser Gly Ser Gly Thr Asp Phe Thr Leu Thr Ile Ser Arg
        115                 120                 125

Leu Glu Pro Glu Asp Phe Ala Val Tyr Tyr Cys Gln Gln Tyr Gly Ser
    130                 135                 140

Ser Pro Trp Thr Phe Gly Gln Gly Thr Lys Val Glu Ile Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265
```

<210> SEQ ID NO 493
<211> LENGTH: 259
<212> TYPE: PRT
<213> ORGANISM: Artificial Sequence
<220> FEATURE:
<223> OTHER INFORMATION: YV04-3001 LC

<400> SEQUENCE: 493

```
Leu His Cys Arg Thr Gln Leu Tyr Gly Tyr Asn Leu Cys Pro Tyr Gly
1               5                   10                  15

Gly Gly Ser Ser Gly Gly Ala Val Gly Leu Leu Ala Pro Pro Gly Gly
            20                  25                  30

Leu Ser Gly Arg Ser Asp Asn His Gly Gly Gly Ser Glu Ile Val Leu
        35                  40                  45

Thr Gln Ser Pro Gly Thr Leu Ser Leu Ser Pro Gly Glu Arg Ala Thr
    50                  55                  60
```

```
Leu Ser Cys Arg Ala Ser Gln Ser Val Gly Ser Ser Tyr Leu Ala Trp
65                  70                  75                  80

Tyr Gln Gln Lys Pro Gly Gln Ala Pro Arg Leu Leu Ile Tyr Gly Ala
                85                  90                  95

Phe Ser Arg Ala Thr Gly Ile Pro Asp Arg Phe Ser Gly Ser Gly Ser
            100                 105                 110

Gly Thr Asp Phe Thr Leu Thr Ile Ser Arg Leu Glu Pro Glu Asp Phe
        115                 120                 125

Ala Val Tyr Tyr Cys Gln Gln Tyr Gly Ser Ser Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys


<210> SEQ ID NO 494
<211> LENGTH: 260
<212> TYPE: PRT
<213> ORGANISM: Artificial Sequence
<220> FEATURE:
<223> OTHER INFORMATION: Spacer - YV06-3001 LC

<400> SEQUENCE: 494

Gln Gly Gln Ser Gly Ser Cys Ala Gln Met Tyr Gly Tyr Ser Met Cys
1               5                   10                  15

Gly Gly Gly Ser Ser Gly Gly Ala Val Gly Leu Leu Ala Pro Pro Gly
            20                  25                  30

Gly Leu Ser Gly Arg Ser Asp Asn His Gly Gly Gly Ser Glu Ile Val
        35                  40                  45

Leu Thr Gln Ser Pro Gly Thr Leu Ser Leu Ser Pro Gly Glu Arg Ala
    50                  55                  60

Thr Leu Ser Cys Arg Ala Ser Gln Ser Val Gly Ser Ser Tyr Leu Ala
65                  70                  75                  80

Trp Tyr Gln Gln Lys Pro Gly Gln Ala Pro Arg Leu Leu Ile Tyr Gly
                85                  90                  95

Ala Phe Ser Arg Ala Thr Gly Ile Pro Asp Arg Phe Ser Gly Ser Gly
            100                 105                 110

Ser Gly Thr Asp Phe Thr Leu Thr Ile Ser Arg Leu Glu Pro Glu Asp
        115                 120                 125

Phe Ala Val Tyr Tyr Cys Gln Gln Tyr Gly Ser Ser Pro Trp Thr Phe
    130                 135                 140

Gly Gln Gly Thr Lys Val Glu Ile Lys Arg Thr Val Ala Ala Pro Ser
145                 150                 155                 160

Val Phe Ile Phe Pro Pro Ser Asp Glu Gln Leu Lys Ser Gly Thr Ala
```

```
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260


<210> SEQ ID NO 495
<211> LENGTH: 254
<212> TYPE: PRT
<213> ORGANISM: Artificial Sequence
<220> FEATURE:
<223> OTHER INFORMATION: YV06-3001 LC

<400> SEQUENCE: 495

Cys Ala Gln Met Tyr Gly Tyr Ser Met Cys Gly Gly Gly Ser Ser Gly
1               5                   10                  15

Gly Ala Val Gly Leu Leu Ala Pro Pro Gly Gly Leu Ser Gly Arg Ser
            20                  25                  30

Asp Asn His Gly Gly Gly Ser Glu Ile Val Leu Thr Gln Ser Pro Gly
        35                  40                  45

Thr Leu Ser Leu Ser Pro Gly Glu Arg Ala Thr Leu Ser Cys Arg Ala
    50                  55                  60

Ser Gln Ser Val Gly Ser Ser Tyr Leu Ala Trp Tyr Gln Gln Lys Pro
65                  70                  75                  80

Gly Gln Ala Pro Arg Leu Leu Ile Tyr Gly Ala Phe Ser Arg Ala Thr
                85                  90                  95

Gly Ile Pro Asp Arg Phe Ser Gly Ser Gly Ser Gly Thr Asp Phe Thr
            100                 105                 110

Leu Thr Ile Ser Arg Leu Glu Pro Glu Asp Phe Ala Val Tyr Tyr Cys
        115                 120                 125

Gln Gln Tyr Gly Ser Ser Pro Trp Thr Phe Gly Gln Gly Thr Lys Val
    130                 135                 140

Glu Ile Lys Arg Thr Val Ala Ala Pro Ser Val Phe Ile Phe Pro Pro
145                 150                 155                 160

Ser Asp Glu Gln Leu Lys Ser Gly Thr Ala Ser Val Val Cys Leu Leu
                165                 170                 175

Asn Asn Phe Tyr Pro Arg Glu Ala Lys Val Gln Trp Lys Val Asp Asn
            180                 185                 190

Ala Leu Gln Ser Gly Asn Ser Gln Glu Ser Val Thr Glu Gln Asp Ser
        195                 200                 205

Lys Asp Ser Thr Tyr Ser Leu Ser Ser Thr Leu Thr Leu Ser Lys Ala
    210                 215                 220

Asp Tyr Glu Lys His Lys Val Tyr Ala Cys Glu Val Thr His Gln Gly
225                 230                 235                 240

Leu Ser Ser Pro Val Thr Lys Ser Phe Asn Arg Gly Glu Cys
                245                 250
```

<210> SEQ ID NO 496
<211> LENGTH: 265
<212> TYPE: PRT
<213> ORGANISM: Artificial Sequence
<220> FEATURE:
<223> OTHER INFORMATION: Spacer - YV09-3001 LC

<400> SEQUENCE: 496

Gln Gly Gln Ser Gly Ser Phe Gly Thr Ala Cys Pro Asn His Pro Met
1 5 10 15

Cys His Asp Trp Gln Gly Gly Gly Ser Ser Gly Gly Ala Val Gly Leu
20 25 30

Leu Ala Pro Pro Gly Gly Leu Ser Gly Arg Ser Asp Asn His Gly Gly
35 40 45

Gly Ser Glu Ile Val Leu Thr Gln Ser Pro Gly Thr Leu Ser Leu Ser
50 55 60

Pro Gly Glu Arg Ala Thr Leu Ser Cys Arg Ala Ser Gln Ser Val Gly
65 70 75 80

Ser Ser Tyr Leu Ala Trp Tyr Gln Gln Lys Pro Gly Gln Ala Pro Arg
85 90 95

Leu Leu Ile Tyr Gly Ala Phe Ser Arg Ala Thr Gly Ile Pro Asp Arg
100 105 110

Phe Ser Gly Ser Gly Ser Gly Thr Asp Phe Thr Leu Thr Ile Ser Arg
115 120 125

Leu Glu Pro Glu Asp Phe Ala Val Tyr Tyr Cys Gln Gln Tyr Gly Ser
130 135 140

Ser Pro Trp Thr Phe Gly Gln Gly Thr Lys Val Glu Ile Lys Arg Thr
145 150 155 160

Val Ala Ala Pro Ser Val Phe Ile Phe Pro Pro Ser Asp Glu Gln Leu
165 170 175

Lys Ser Gly Thr Ala Ser Val Val Cys Leu Leu Asn Asn Phe Tyr Pro
180 185 190

Arg Glu Ala Lys Val Gln Trp Lys Val Asp Asn Ala Leu Gln Ser Gly
195 200 205

Asn Ser Gln Glu Ser Val Thr Glu Gln Asp Ser Lys Asp Ser Thr Tyr
210 215 220

Ser Leu Ser Ser Thr Leu Thr Leu Ser Lys Ala Asp Tyr Glu Lys His
225 230 235 240

Lys Val Tyr Ala Cys Glu Val Thr His Gln Gly Leu Ser Ser Pro Val
245 250 255

Thr Lys Ser Phe Asn Arg Gly Glu Cys
260 265

<210> SEQ ID NO 497
<211> LENGTH: 259
<212> TYPE: PRT
<213> ORGANISM: Artificial Sequence
<220> FEATURE:
<223> OTHER INFORMATION: YV09-3001 LC

<400> SEQUENCE: 497

Phe Gly Thr Ala Cys Pro Asn His Pro Met Cys His Asp Trp Gln Gly
1 5 10 15

Gly Gly Ser Ser Gly Gly Ala Val Gly Leu Leu Ala Pro Pro Gly Gly
20 25 30

Leu Ser Gly Arg Ser Asp Asn His Gly Gly Gly Ser Glu Ile Val Leu
35 40 45

```
Thr Gln Ser Pro Gly Thr Leu Ser Leu Ser Pro Gly Glu Arg Ala Thr
    50                  55                  60

Leu Ser Cys Arg Ala Ser Gln Ser Val Gly Ser Ser Tyr Leu Ala Trp
65                  70                  75                  80

Tyr Gln Gln Lys Pro Gly Gln Ala Pro Arg Leu Leu Ile Tyr Gly Ala
                85                  90                  95

Phe Ser Arg Ala Thr Gly Ile Pro Asp Arg Phe Ser Gly Ser Gly Ser
            100                 105                 110

Gly Thr Asp Phe Thr Leu Thr Ile Ser Arg Leu Glu Pro Glu Asp Phe
        115                 120                 125

Ala Val Tyr Tyr Cys Gln Gln Tyr Gly Ser Ser Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys


<210> SEQ ID NO 498
<211> LENGTH: 262
<212> TYPE: PRT
<213> ORGANISM: Artificial Sequence
<220> FEATURE:
<223> OTHER INFORMATION: Spacer - YV23-3001 LC

<400> SEQUENCE: 498

Gln Gly Gln Ser Gly Ser Cys Leu His Ser Leu Tyr Asn Val Cys Leu
1               5                   10                  15

Asp Pro Gly Gly Gly Ser Ser Gly Gly Ala Val Gly Leu Leu Ala Pro
            20                  25                  30

Pro Gly Gly Leu Ser Gly Arg Ser Asp Asn His Gly Gly Gly Ser Glu
        35                  40                  45

Ile Val Leu Thr Gln Ser Pro Gly Thr Leu Ser Leu Ser Pro Gly Glu
    50                  55                  60

Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
```

145 150 155 160

Pro Ser Val Phe Ile Phe Pro Pro Ser Asp Glu Gln Leu Lys Ser Gly
165 170 175

Thr Ala Ser Val Val Cys Leu Leu Asn Asn Phe Tyr Pro Arg Glu Ala
180 185 190

Lys Val Gln Trp Lys Val Asp Asn Ala Leu Gln Ser Gly Asn Ser Gln
195 200 205

Glu Ser Val Thr Glu Gln Asp Ser Lys Asp Ser Thr Tyr Ser Leu Ser
210 215 220

Ser Thr Leu Thr Leu Ser Lys Ala Asp Tyr Glu Lys His Lys Val Tyr
225 230 235 240

Ala Cys Glu Val Thr His Gln Gly Leu Ser Ser Pro Val Thr Lys Ser
245 250 255

Phe Asn Arg Gly Glu Cys
260

<210> SEQ ID NO 499
<211> LENGTH: 256
<212> TYPE: PRT
<213> ORGANISM: Artificial Sequence
<220> FEATURE:
<223> OTHER INFORMATION: YV23-3001 LC

<400> SEQUENCE: 499

Cys Leu His Ser Leu Tyr Asn Val Cys Leu Asp Pro Gly Gly Gly Ser
1 5 10 15

Ser Gly Gly Ala Val Gly Leu Leu Ala Pro Pro Gly Gly Leu Ser Gly
20 25 30

Arg Ser Asp Asn His Gly Gly Gly Ser Glu Ile Val Leu Thr Gln Ser
35 40 45

Pro Gly Thr Leu Ser Leu Ser Pro Gly Glu Arg Ala Thr Leu Ser Cys
50 55 60

Arg Ala Ser Gln Ser Val Gly Ser Ser Tyr Leu Ala Trp Tyr Gln Gln
65 70 75 80

Lys Pro Gly Gln Ala Pro Arg Leu Leu Ile Tyr Gly Ala Phe Ser Arg
85 90 95

Ala Thr Gly Ile Pro Asp Arg Phe Ser Gly Ser Gly Ser Gly Thr Asp
100 105 110

Phe Thr Leu Thr Ile Ser Arg Leu Glu Pro Glu Asp Phe Ala Val Tyr
115 120 125

Tyr Cys Gln Gln Tyr Gly Ser Ser Pro Trp Thr Phe Gly Gln Gly Thr
130 135 140

Lys Val Glu Ile Lys Arg Thr Val Ala Ala Pro Ser Val Phe Ile Phe
145 150 155 160

Pro Pro Ser Asp Glu Gln Leu Lys Ser Gly Thr Ala Ser Val Val Cys
165 170 175

Leu Leu Asn Asn Phe Tyr Pro Arg Glu Ala Lys Val Gln Trp Lys Val
180 185 190

Asp Asn Ala Leu Gln Ser Gly Asn Ser Gln Glu Ser Val Thr Glu Gln
195 200 205

Asp Ser Lys Asp Ser Thr Tyr Ser Leu Ser Ser Thr Leu Thr Leu Ser
210 215 220

Lys Ala Asp Tyr Glu Lys His Lys Val Tyr Ala Cys Glu Val Thr His
225 230 235 240

Gln Gly Leu Ser Ser Pro Val Thr Lys Ser Phe Asn Arg Gly Glu Cys 245 250 255

<210> SEQ ID NO 500
<211> LENGTH: 262
<212> TYPE: PRT
<213> ORGANISM: Artificial Sequence
<220> FEATURE:
<223> OTHER INFORMATION: Spacer - YV27-3001 LC

<400> SEQUENCE: 500

Gln Gly Gln Ser Gly Ser Gln Pro Cys Ala Gln Met Tyr Gly Tyr Ser
1 5 10 15

Met Cys Gly Gly Gly Ser Ser Gly Gly Ala Val Gly Leu Leu Ala Pro
20 25 30

Pro Gly Gly Leu Ser Gly Arg Ser Asp Asn His Gly Gly Gly Ser Glu
35 40 45

Ile Val Leu Thr Gln Ser Pro Gly Thr Leu Ser Leu Ser Pro Gly Glu
50 55 60

Arg Ala Thr Leu Ser Cys Arg Ala Ser Gln Ser Val Gly Ser Ser Tyr
65 70 75 80

Leu Ala Trp Tyr Gln Gln Lys Pro Gly Gln Ala Pro Arg Leu Leu Ile
85 90 95

Tyr Gly Ala Phe Ser Arg Ala Thr Gly Ile Pro Asp Arg Phe Ser Gly
100 105 110

Ser Gly Ser Gly Thr Asp Phe Thr Leu Thr Ile Ser Arg Leu Glu Pro
115 120 125

Glu Asp Phe Ala Val Tyr Tyr Cys Gln Gln Tyr Gly Ser Ser Pro Trp
130 135 140

Thr Phe Gly Gln Gly Thr Lys Val Glu Ile Lys Arg Thr Val Ala Ala
145 150 155 160

Pro Ser Val Phe Ile Phe Pro Pro Ser Asp Glu Gln Leu Lys Ser Gly
165 170 175

Thr Ala Ser Val Val Cys Leu Leu Asn Asn Phe Tyr Pro Arg Glu Ala
180 185 190

Lys Val Gln Trp Lys Val Asp Asn Ala Leu Gln Ser Gly Asn Ser Gln
195 200 205

Glu Ser Val Thr Glu Gln Asp Ser Lys Asp Ser Thr Tyr Ser Leu Ser
210 215 220

Ser Thr Leu Thr Leu Ser Lys Ala Asp Tyr Glu Lys His Lys Val Tyr
225 230 235 240

Ala Cys Glu Val Thr His Gln Gly Leu Ser Ser Pro Val Thr Lys Ser
245 250 255

Phe Asn Arg Gly Glu Cys
260

<210> SEQ ID NO 501
<211> LENGTH: 256
<212> TYPE: PRT
<213> ORGANISM: Artificial Sequence
<220> FEATURE:
<223> OTHER INFORMATION: YV27-3001 LC

<400> SEQUENCE: 501

Gln Pro Cys Ala Gln Met Tyr Gly Tyr Ser Met Cys Gly Gly Gly Ser
1 5 10 15

Ser Gly Gly Ala Val Gly Leu Leu Ala Pro Pro Gly Gly Leu Ser Gly
20 25 30

```
Arg Ser Asp Asn His Gly Gly Gly Ser Glu Ile Val Leu Thr Gln Ser
        35                  40                  45

Pro Gly Thr Leu Ser Leu Ser Pro Gly Glu Arg Ala Thr Leu Ser Cys
    50                  55                  60

Arg Ala Ser Gln Ser Val Gly Ser Ser Tyr Leu Ala Trp Tyr Gln Gln
65                  70                  75                  80

Lys Pro Gly Gln Ala Pro Arg Leu Leu Ile Tyr Gly Ala Phe Ser Arg
                85                  90                  95

Ala Thr Gly Ile Pro Asp Arg Phe Ser Gly Ser Gly Ser Gly Thr Asp
            100                 105                 110

Phe Thr Leu Thr Ile Ser Arg Leu Glu Pro Glu Asp Phe Ala Val Tyr
        115                 120                 125

Tyr Cys Gln Gln Tyr Gly Ser Ser Pro Trp Thr Phe Gly Gln Gly Thr
    130                 135                 140

Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Ser Thr Leu Thr Leu Ser
    210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255


<210> SEQ ID NO 502
<211> LENGTH: 263
<212> TYPE: PRT
<213> ORGANISM: Artificial Sequence
<220> FEATURE:
<223> OTHER INFORMATION: Spacer - YV29-3001 LC

<400> SEQUENCE: 502

Gln Gly Gln Ser Gly Ser Cys Ala Gln Met Tyr Gly Tyr Ser Met Cys
1               5                   10                  15

Ala His Thr Gly Gly Gly Ser Ser Gly Gly Ala Val Gly Leu Leu Ala
            20                  25                  30

Pro Pro Gly Gly Leu Ser Gly Arg Ser Asp Asn His Gly Gly Gly Ser
        35                  40                  45

Glu Ile Val Leu Thr Gln Ser Pro Gly Thr Leu Ser Leu Ser Pro Gly
    50                  55                  60

Glu Arg Ala Thr Leu Ser Cys Arg Ala Ser Gln Ser Val Gly Ser Ser
65                  70                  75                  80

Tyr Leu Ala Trp Tyr Gln Gln Lys Pro Gly Gln Ala Pro Arg Leu Leu
                85                  90                  95

Ile Tyr Gly Ala Phe Ser Arg Ala Thr Gly Ile Pro Asp Arg Phe Ser
            100                 105                 110

Gly Ser Gly Ser Gly Thr Asp Phe Thr Leu Thr Ile Ser Arg Leu Glu
        115                 120                 125

Pro Glu Asp Phe Ala Val Tyr Tyr Cys Gln Gln Tyr Gly Ser Ser Pro
    130                 135                 140
```

```
Trp Thr Phe Gly Gln Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260


<210> SEQ ID NO 503
<211> LENGTH: 257
<212> TYPE: PRT
<213> ORGANISM: Artificial Sequence
<220> FEATURE:
<223> OTHER INFORMATION: YV29-3001 LC

<400> SEQUENCE: 503

Cys Ala Gln Met Tyr Gly Tyr Ser Met Cys Ala His Thr Gly Gly Gly
1               5                   10                  15

Ser Ser Gly Gly Ala Val Gly Leu Leu Ala Pro Pro Gly Gly Leu Ser
            20                  25                  30

Gly Arg Ser Asp Asn His Gly Gly Gly Ser Glu Ile Val Leu Thr Gln
        35                  40                  45

Ser Pro Gly Thr Leu Ser Leu Ser Pro Gly Glu Arg Ala Thr Leu Ser
    50                  55                  60

Cys Arg Ala Ser Gln Ser Val Gly Ser Ser Tyr Leu Ala Trp Tyr Gln
65                  70                  75                  80

Gln Lys Pro Gly Gln Ala Pro Arg Leu Leu Ile Tyr Gly Ala Phe Ser
                85                  90                  95

Arg Ala Thr Gly Ile Pro Asp Arg Phe Ser Gly Ser Gly Ser Gly Thr
            100                 105                 110

Asp Phe Thr Leu Thr Ile Ser Arg Leu Glu Pro Glu Asp Phe Ala Val
        115                 120                 125

Tyr Tyr Cys Gln Gln Tyr Gly Ser Ser Pro Trp Thr Phe Gly Gln Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240
```

His Gln Gly Leu Ser Ser Pro Val Thr Lys Ser Phe Asn Arg Gly Glu
245 250 255

Cys

<210> SEQ ID NO 504
<211> LENGTH: 261
<212> TYPE: PRT
<213> ORGANISM: Artificial Sequence
<220> FEATURE:
<223> OTHER INFORMATION: Spacer - YV32-3001 LC

<400> SEQUENCE: 504

Gln Gly Gln Ser Gly Ser Cys Pro Asn His Pro Leu Cys His Asp Trp
1 5 10 15

Gln Gly Gly Gly Ser Ser Gly Gly Ala Val Gly Leu Leu Ala Pro Pro
20 25 30

Gly Gly Leu Ser Gly Arg Ser Asp Asn His Gly Gly Ser Glu Ile
35 40 45

Val Leu Thr Gln Ser Pro Gly Thr Leu Ser Leu Ser Pro Gly Glu Arg
50 55 60

Ala Thr Leu Ser Cys Arg Ala Ser Gln Ser Val Gly Ser Ser Tyr Leu
65 70 75 80

Ala Trp Tyr Gln Gln Lys Pro Gly Gln Ala Pro Arg Leu Leu Ile Tyr
85 90 95

Gly Ala Phe Ser Arg Ala Thr Gly Ile Pro Asp Arg Phe Ser Gly Ser
100 105 110

Gly Ser Gly Thr Asp Phe Thr Leu Thr Ile Ser Arg Leu Glu Pro Glu
115 120 125

Asp Phe Ala Val Tyr Tyr Cys Gln Gln Tyr Gly Ser Ser Pro Trp Thr
130 135 140

Phe Gly Gln Gly Thr Lys Val Glu Ile Lys Arg Thr Val Ala Ala Pro
145 150 155 160

Ser Val Phe Ile Phe Pro Pro Ser Asp Glu Gln Leu Lys Ser Gly Thr
165 170 175

Ala Ser Val Val Cys Leu Leu Asn Asn Phe Tyr Pro Arg Glu Ala Lys
180 185 190

Val Gln Trp Lys Val Asp Asn Ala Leu Gln Ser Gly Asn Ser Gln Glu
195 200 205

Ser Val Thr Glu Gln Asp Ser Lys Asp Ser Thr Tyr Ser Leu Ser Ser
210 215 220

Thr Leu Thr Leu Ser Lys Ala Asp Tyr Glu Lys His Lys Val Tyr Ala
225 230 235 240

Cys Glu Val Thr His Gln Gly Leu Ser Ser Pro Val Thr Lys Ser Phe
245 250 255

Asn Arg Gly Glu Cys
260

<210> SEQ ID NO 505
<211> LENGTH: 255
<212> TYPE: PRT
<213> ORGANISM: Artificial Sequence
<220> FEATURE:
<223> OTHER INFORMATION: YV32-3001 LC

<400> SEQUENCE: 505

Cys Pro Asn His Pro Leu Cys His Asp Trp Gln Gly Gly Gly Ser Ser
1 5 10 15

```
Gly Gly Ala Val Gly Leu Leu Ala Pro Pro Gly Gly Leu Ser Gly Arg
            20                  25                  30

Ser Asp Asn His Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255
```

<210> SEQ ID NO 506
<211> LENGTH: 261
<212> TYPE: PRT
<213> ORGANISM: Artificial Sequence
<220> FEATURE:
<223> OTHER INFORMATION: Spacer - YV33-3001 LC

<400> SEQUENCE: 506

```
Gln Gly Gln Ser Gly Ser Cys Pro Asn His Pro Met Cys Ala Asp Trp
1               5                   10                  15

Gln Gly Gly Gly Ser Ser Gly Gly Ala Val Gly Leu Leu Ala Pro Pro
            20                  25                  30

Gly Gly Leu Ser Gly Arg Ser Asp Asn His Gly Gly Gly Ser Glu Ile
        35                  40                  45

Val Leu Thr Gln Ser Pro Gly Thr Leu Ser Leu Ser Pro Gly Glu Arg
    50                  55                  60

Ala Thr Leu Ser Cys Arg Ala Ser Gln Ser Val Gly Ser Ser Tyr Leu
65                  70                  75                  80

Ala Trp Tyr Gln Gln Lys Pro Gly Gln Ala Pro Arg Leu Leu Ile Tyr
                85                  90                  95

Gly Ala Phe Ser Arg Ala Thr Gly Ile Pro Asp Arg Phe Ser Gly Ser
            100                 105                 110

Gly Ser Gly Thr Asp Phe Thr Leu Thr Ile Ser Arg Leu Glu Pro Glu
        115                 120                 125
```

```
Asp Phe Ala Val Tyr Tyr Cys Gln Gln Tyr Gly Ser Ser Pro Trp Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260


<210> SEQ ID NO 507
<211> LENGTH: 255
<212> TYPE: PRT
<213> ORGANISM: Artificial Sequence
<220> FEATURE:
<223> OTHER INFORMATION: Spacer - YV33-3001 LC

<400> SEQUENCE: 507

Cys Pro Asn His Pro Met Cys Ala Asp Trp Gln Gly Gly Gly Ser Ser
1               5                   10                  15

Gly Gly Ala Val Gly Leu Leu Ala Pro Pro Gly Gly Leu Ser Gly Arg
            20                  25                  30

Ser Asp Asn His Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220
```

Ala Asp Tyr Glu Lys His Lys Val Tyr Ala Cys Glu Val Thr His Gln
225 230 235 240

Gly Leu Ser Ser Pro Val Thr Lys Ser Phe Asn Arg Gly Glu Cys
245 250 255

<210> SEQ ID NO 508
<211> LENGTH: 261
<212> TYPE: PRT
<213> ORGANISM: Artificial Sequence
<220> FEATURE:
<223> OTHER INFORMATION: Spacer - YV35-3001 LC

<400> SEQUENCE: 508

Gln Gly Gln Ser Gly Ser Cys Pro Asn His Pro Met Cys His Asp Ala
1 5 10 15

Gln Gly Gly Gly Ser Ser Gly Gly Ala Val Gly Leu Leu Ala Pro Pro
20 25 30

Gly Gly Leu Ser Gly Arg Ser Asp Asn His Gly Gly Gly Ser Glu Ile
35 40 45

Val Leu Thr Gln Ser Pro Gly Thr Leu Ser Leu Ser Pro Gly Glu Arg
50 55 60

Ala Thr Leu Ser Cys Arg Ala Ser Gln Ser Val Gly Ser Ser Tyr Leu
65 70 75 80

Ala Trp Tyr Gln Gln Lys Pro Gly Gln Ala Pro Arg Leu Leu Ile Tyr
85 90 95

Gly Ala Phe Ser Arg Ala Thr Gly Ile Pro Asp Arg Phe Ser Gly Ser
100 105 110

Gly Ser Gly Thr Asp Phe Thr Leu Thr Ile Ser Arg Leu Glu Pro Glu
115 120 125

Asp Phe Ala Val Tyr Tyr Cys Gln Gln Tyr Gly Ser Ser Pro Trp Thr
130 135 140

Phe Gly Gln Gly Thr Lys Val Glu Ile Lys Arg Thr Val Ala Ala Pro
145 150 155 160

Ser Val Phe Ile Phe Pro Pro Ser Asp Glu Gln Leu Lys Ser Gly Thr
165 170 175

Ala Ser Val Val Cys Leu Leu Asn Asn Phe Tyr Pro Arg Glu Ala Lys
180 185 190

Val Gln Trp Lys Val Asp Asn Ala Leu Gln Ser Gly Asn Ser Gln Glu
195 200 205

Ser Val Thr Glu Gln Asp Ser Lys Asp Ser Thr Tyr Ser Leu Ser Ser
210 215 220

Thr Leu Thr Leu Ser Lys Ala Asp Tyr Glu Lys His Lys Val Tyr Ala
225 230 235 240

Cys Glu Val Thr His Gln Gly Leu Ser Ser Pro Val Thr Lys Ser Phe
245 250 255

Asn Arg Gly Glu Cys
260

<210> SEQ ID NO 509
<211> LENGTH: 255
<212> TYPE: PRT
<213> ORGANISM: Artificial Sequence
<220> FEATURE:
<223> OTHER INFORMATION: YV35-3001 LC

<400> SEQUENCE: 509

Cys Pro Asn His Pro Met Cys His Asp Ala Gln Gly Gly Gly Ser Ser
1 5 10 15

```
Gly Gly Ala Val Gly Leu Leu Ala Pro Pro Gly Gly Leu Ser Gly Arg
            20                  25                  30

Ser Asp Asn His Gly Gly Gly Ser Glu Ile Val Leu Thr Gln Ser Pro
        35                  40                  45

Gly Thr Leu Ser Leu Ser Pro Gly Glu Arg Ala Thr Leu Ser Cys Arg
    50                  55                  60

Ala Ser Gln Ser Val Gly Ser Ser Tyr Leu Ala Trp Tyr Gln Gln Lys
65                  70                  75                  80

Pro Gly Gln Ala Pro Arg Leu Leu Ile Tyr Gly Ala Phe Ser Arg Ala
                85                  90                  95

Thr Gly Ile Pro Asp Arg Phe Ser Gly Ser Gly Ser Gly Thr Asp Phe
            100                 105                 110

Thr Leu Thr Ile Ser Arg Leu Glu Pro Glu Asp Phe Ala Val Tyr Tyr
        115                 120                 125

Cys Gln Gln Tyr Gly Ser Ser Pro Trp Thr Phe Gly Gln Gly Thr Lys
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 510
<211> LENGTH: 263
<212> TYPE: PRT
<213> ORGANISM: Artificial Sequence
<220> FEATURE:
<223> OTHER INFORMATION: Spacer - YV39-3001 LC

<400> SEQUENCE: 510

Gln Gly Gln Ser Gly Ser Cys Arg Thr Gln Leu Tyr Gly Tyr Asn Leu
1               5                   10                  15

Cys Pro Tyr Gly Gly Gly Ser Ser Gly Gly Ala Val Gly Leu Leu Ala
            20                  25                  30

Pro Pro Gly Gly Leu Ser Gly Arg Ser Asp Asn His Gly Gly Gly Ser
        35                  40                  45

Glu Ile Val Leu Thr Gln Ser Pro Gly Thr Leu Ser Leu Ser Pro Gly
    50                  55                  60

Glu Arg Ala Thr Leu Ser Cys Arg Ala Ser Gln Ser Val Gly Ser Ser
65                  70                  75                  80

Tyr Leu Ala Trp Tyr Gln Gln Lys Pro Gly Gln Ala Pro Arg Leu Leu
                85                  90                  95

Ile Tyr Gly Ala Phe Ser Arg Ala Thr Gly Ile Pro Asp Arg Phe Ser
            100                 105                 110

Gly Ser Gly Ser Gly Thr Asp Phe Thr Leu Thr Ile Ser Arg Leu Glu
        115                 120                 125
```

```
Pro Glu Asp Phe Ala Val Tyr Tyr Cys Gln Gln Tyr Gly Ser Ser Pro
    130                 135                 140

Trp Thr Phe Gly Gln Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260


<210> SEQ ID NO 511
<211> LENGTH: 257
<212> TYPE: PRT
<213> ORGANISM: Artificial Sequence
<220> FEATURE:
<223> OTHER INFORMATION: YV39-3001 LC

<400> SEQUENCE: 511

Cys Arg Thr Gln Leu Tyr Gly Tyr Asn Leu Cys Pro Tyr Gly Gly Gly
1               5                   10                  15

Ser Ser Gly Gly Ala Val Gly Leu Leu Ala Pro Pro Gly Gly Leu Ser
            20                  25                  30

Gly Arg Ser Asp Asn His Gly Gly Gly Ser Glu Ile Val Leu Thr Gln
        35                  40                  45

Ser Pro Gly Thr Leu Ser Leu Ser Pro Gly Glu Arg Ala Thr Leu Ser
    50                  55                  60

Cys Arg Ala Ser Gln Ser Val Gly Ser Ser Tyr Leu Ala Trp Tyr Gln
65                  70                  75                  80

Gln Lys Pro Gly Gln Ala Pro Arg Leu Leu Ile Tyr Gly Ala Phe Ser
                85                  90                  95

Arg Ala Thr Gly Ile Pro Asp Arg Phe Ser Gly Ser Gly Ser Gly Thr
            100                 105                 110

Asp Phe Thr Leu Thr Ile Ser Arg Leu Glu Pro Glu Asp Phe Ala Val
        115                 120                 125

Tyr Tyr Cys Gln Gln Tyr Gly Ser Ser Pro Trp Thr Phe Gly Gln Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220
```

Ser Lys Ala Asp Tyr Glu Lys His Lys Val Tyr Ala Cys Glu Val Thr
225 230 235 240

His Gln Gly Leu Ser Ser Pro Val Thr Lys Ser Phe Asn Arg Gly Glu
245 250 255

Cys

<210> SEQ ID NO 512
<211> LENGTH: 263
<212> TYPE: PRT
<213> ORGANISM: Artificial Sequence
<220> FEATURE:
<223> OTHER INFORMATION: Spacer - YV41-3001 LC

<400> SEQUENCE: 512

Gln Gly Gln Ser Gly Ser Cys Arg Thr Gln Leu Tyr Gly Tyr Asn Leu
1 5 10 15

Cys Pro Ala Gly Gly Gly Ser Ser Gly Gly Ala Val Gly Leu Leu Ala
20 25 30

Pro Pro Gly Gly Leu Ser Gly Arg Ser Asp Asn His Gly Gly Gly Ser
35 40 45

Glu Ile Val Leu Thr Gln Ser Pro Gly Thr Leu Ser Leu Ser Pro Gly
50 55 60

Glu Arg Ala Thr Leu Ser Cys Arg Ala Ser Gln Ser Val Gly Ser Ser
65 70 75 80

Tyr Leu Ala Trp Tyr Gln Gln Lys Pro Gly Gln Ala Pro Arg Leu Leu
85 90 95

Ile Tyr Gly Ala Phe Ser Arg Ala Thr Gly Ile Pro Asp Arg Phe Ser
100 105 110

Gly Ser Gly Ser Gly Thr Asp Phe Thr Leu Thr Ile Ser Arg Leu Glu
115 120 125

Pro Glu Asp Phe Ala Val Tyr Tyr Cys Gln Gln Tyr Gly Ser Ser Pro
130 135 140

Trp Thr Phe Gly Gln Gly Thr Lys Val Glu Ile Lys Arg Thr Val Ala
145 150 155 160

Ala Pro Ser Val Phe Ile Phe Pro Pro Ser Asp Glu Gln Leu Lys Ser
165 170 175

Gly Thr Ala Ser Val Val Cys Leu Leu Asn Asn Phe Tyr Pro Arg Glu
180 185 190

Ala Lys Val Gln Trp Lys Val Asp Asn Ala Leu Gln Ser Gly Asn Ser
195 200 205

Gln Glu Ser Val Thr Glu Gln Asp Ser Lys Asp Ser Thr Tyr Ser Leu
210 215 220

Ser Ser Thr Leu Thr Leu Ser Lys Ala Asp Tyr Glu Lys His Lys Val
225 230 235 240

Tyr Ala Cys Glu Val Thr His Gln Gly Leu Ser Ser Pro Val Thr Lys
245 250 255

Ser Phe Asn Arg Gly Glu Cys
260

<210> SEQ ID NO 513
<211> LENGTH: 257
<212> TYPE: PRT
<213> ORGANISM: Artificial Sequence
<220> FEATURE:
<223> OTHER INFORMATION: YV41-3001 LC

<400> SEQUENCE: 513

```
Cys Arg Thr Gln Leu Tyr Gly Tyr Asn Leu Cys Pro Ala Gly Gly Gly
1               5                   10                  15

Ser Ser Gly Gly Ala Val Gly Leu Leu Ala Pro Pro Gly Gly Leu Ser
            20                  25                  30

Gly Arg Ser Asp Asn His Gly Gly Gly Ser Glu Ile Val Leu Thr Gln
        35                  40                  45

Ser Pro Gly Thr Leu Ser Leu Ser Pro Gly Glu Arg Ala Thr Leu Ser
    50                  55                  60

Cys Arg Ala Ser Gln Ser Val Gly Ser Ser Tyr Leu Ala Trp Tyr Gln
65                  70                  75                  80

Gln Lys Pro Gly Gln Ala Pro Arg Leu Leu Ile Tyr Gly Ala Phe Ser
                85                  90                  95

Arg Ala Thr Gly Ile Pro Asp Arg Phe Ser Gly Ser Gly Ser Gly Thr
            100                 105                 110

Asp Phe Thr Leu Thr Ile Ser Arg Leu Glu Pro Glu Asp Phe Ala Val
        115                 120                 125

Tyr Tyr Cys Gln Gln Tyr Gly Ser Ser Pro Trp Thr Phe Gly Gln Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys


<210> SEQ ID NO 514
<211> LENGTH: 265
<212> TYPE: PRT
<213> ORGANISM: Artificial Sequence
<220> FEATURE:
<223> OTHER INFORMATION: Spacer - YV51-3001 LC

<400> SEQUENCE: 514

Gln Gly Gln Ser Gly Ser Phe Gly Ala Ala Cys Pro Asn His Pro Ile
1               5                   10                  15

Cys His Asp Trp Gln Gly Gly Gly Ser Ser Gly Gly Ala Val Gly Leu
            20                  25                  30

Leu Ala Pro Pro Gly Gly Leu Ser Gly Arg Ser Asp Asn His Gly Gly
        35                  40                  45

Gly Ser Glu Ile Val Leu Thr Gln Ser Pro Gly Thr Leu Ser Leu Ser
    50                  55                  60

Pro Gly Glu Arg Ala Thr Leu Ser Cys Arg Ala Ser Gln Ser Val Gly
65                  70                  75                  80

Ser Ser Tyr Leu Ala Trp Tyr Gln Gln Lys Pro Gly Gln Ala Pro Arg
                85                  90                  95
```

```
Leu Leu Ile Tyr Gly Ala Phe Ser Arg Ala Thr Gly Ile Pro Asp Arg
            100                 105                 110

Phe Ser Gly Ser Gly Ser Gly Thr Asp Phe Thr Leu Thr Ile Ser Arg
        115                 120                 125

Leu Glu Pro Glu Asp Phe Ala Val Tyr Tyr Cys Gln Gln Tyr Gly Ser
    130                 135                 140

Ser Pro Trp Thr Phe Gly Gln Gly Thr Lys Val Glu Ile Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265
```

<210> SEQ ID NO 515
<211> LENGTH: 259
<212> TYPE: PRT
<213> ORGANISM: Artificial Sequence
<220> FEATURE:
<223> OTHER INFORMATION: YV51-3001 LC

<400> SEQUENCE: 515

```
Phe Gly Ala Ala Cys Pro Asn His Pro Ile Cys His Asp Trp Gln Gly
1               5                   10                  15

Gly Gly Ser Ser Gly Gly Ala Val Gly Leu Leu Ala Pro Pro Gly Gly
            20                  25                  30

Leu Ser Gly Arg Ser Asp Asn His Gly Gly Gly Ser Glu Ile Val Leu
        35                  40                  45

Thr Gln Ser Pro Gly Thr Leu Ser Leu Ser Pro Gly Glu Arg Ala Thr
    50                  55                  60

Leu Ser Cys Arg Ala Ser Gln Ser Val Gly Ser Ser Tyr Leu Ala Trp
65                  70                  75                  80

Tyr Gln Gln Lys Pro Gly Gln Ala Pro Arg Leu Leu Ile Tyr Gly Ala
                85                  90                  95

Phe Ser Arg Ala Thr Gly Ile Pro Asp Arg Phe Ser Gly Ser Gly Ser
            100                 105                 110

Gly Thr Asp Phe Thr Leu Thr Ile Ser Arg Leu Glu Pro Glu Asp Phe
        115                 120                 125

Ala Val Tyr Tyr Cys Gln Gln Tyr Gly Ser Ser Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190
```

```
Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys


<210> SEQ ID NO 516
<211> LENGTH: 265
<212> TYPE: PRT
<213> ORGANISM: Artificial Sequence
<220> FEATURE:
<223> OTHER INFORMATION: Spacer - YV52-3001 LC

<400> SEQUENCE: 516

Gln Gly Gln Ser Gly Ser Phe Gly Ala Ala Cys Pro Asn His Pro Leu
1               5                   10                  15

Cys His Asp Trp Gln Gly Gly Gly Ser Ser Gly Gly Ala Val Gly Leu
            20                  25                  30

Leu Ala Pro Pro Gly Gly Leu Ser Gly Arg Ser Asp Asn His Gly Gly
        35                  40                  45

Gly Ser Glu Ile Val Leu Thr Gln Ser Pro Gly Thr Leu Ser Leu Ser
    50                  55                  60

Pro Gly Glu Arg Ala Thr Leu Ser Cys Arg Ala Ser Gln Ser Val Gly
65                  70                  75                  80

Ser Ser Tyr Leu Ala Trp Tyr Gln Gln Lys Pro Gly Gln Ala Pro Arg
                85                  90                  95

Leu Leu Ile Tyr Gly Ala Phe Ser Arg Ala Thr Gly Ile Pro Asp Arg
            100                 105                 110

Phe Ser Gly Ser Gly Ser Gly Thr Asp Phe Thr Leu Thr Ile Ser Arg
        115                 120                 125

Leu Glu Pro Glu Asp Phe Ala Val Tyr Tyr Cys Gln Gln Tyr Gly Ser
    130                 135                 140

Ser Pro Trp Thr Phe Gly Gln Gly Thr Lys Val Glu Ile Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265


<210> SEQ ID NO 517
<211> LENGTH: 259
<212> TYPE: PRT
```

<213> ORGANISM: Artificial Sequence
<220> FEATURE:
<223> OTHER INFORMATION: YV52-3001 LC

<400> SEQUENCE: 517

```
Phe Gly Ala Ala Cys Pro Asn His Pro Leu Cys His Asp Trp Gln Gly
1               5                   10                  15

Gly Gly Ser Ser Gly Gly Ala Val Gly Leu Leu Ala Pro Pro Gly Gly
            20                  25                  30

Leu Ser Gly Arg Ser Asp Asn His Gly Gly Gly Ser Glu Ile Val Leu
        35                  40                  45

Thr Gln Ser Pro Gly Thr Leu Ser Leu Ser Pro Gly Glu Arg Ala Thr
    50                  55                  60

Leu Ser Cys Arg Ala Ser Gln Ser Val Gly Ser Ser Tyr Leu Ala Trp
65                  70                  75                  80

Tyr Gln Gln Lys Pro Gly Gln Ala Pro Arg Leu Leu Ile Tyr Gly Ala
                85                  90                  95

Phe Ser Arg Ala Thr Gly Ile Pro Asp Arg Phe Ser Gly Ser Gly Ser
            100                 105                 110

Gly Thr Asp Phe Thr Leu Thr Ile Ser Arg Leu Glu Pro Glu Asp Phe
        115                 120                 125

Ala Val Tyr Tyr Cys Gln Gln Tyr Gly Ser Ser Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys
```

<210> SEQ ID NO 518
<211> LENGTH: 265
<212> TYPE: PRT
<213> ORGANISM: Artificial Sequence
<220> FEATURE:
<223> OTHER INFORMATION: Spacer - YV53-3001 LC

<400> SEQUENCE: 518

```
Gln Gly Gln Ser Gly Ser Phe Gly Ala Ala Cys Pro Asn His Pro Met
1               5                   10                  15

Cys His Asp Ala Gln Gly Gly Gly Ser Ser Gly Gly Ala Val Gly Leu
            20                  25                  30

Leu Ala Pro Pro Gly Gly Leu Ser Gly Arg Ser Asp Asn His Gly Gly
        35                  40                  45

Gly Ser Glu Ile Val Leu Thr Gln Ser Pro Gly Thr Leu Ser Leu Ser
    50                  55                  60

Pro Gly Glu Arg Ala Thr Leu Ser Cys Arg Ala Ser Gln Ser Val Gly
```

```
65                  70                  75                  80

Ser Ser Tyr Leu Ala Trp Tyr Gln Gln Lys Pro Gly Gln Ala Pro Arg
                85                  90                  95

Leu Leu Ile Tyr Gly Ala Phe Ser Arg Ala Thr Gly Ile Pro Asp Arg
            100                 105                 110

Phe Ser Gly Ser Gly Ser Gly Thr Asp Phe Thr Leu Thr Ile Ser Arg
        115                 120                 125

Leu Glu Pro Glu Asp Phe Ala Val Tyr Tyr Cys Gln Gln Tyr Gly Ser
    130                 135                 140

Ser Pro Trp Thr Phe Gly Gln Gly Thr Lys Val Glu Ile Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265


<210> SEQ ID NO 519
<211> LENGTH: 259
<212> TYPE: PRT
<213> ORGANISM: Artificial Sequence
<220> FEATURE:
<223> OTHER INFORMATION: YV53-3001 LC

<400> SEQUENCE: 519

Phe Gly Ala Ala Cys Pro Asn His Pro Met Cys His Asp Ala Gln Gly
1               5                   10                  15

Gly Gly Ser Ser Gly Gly Ala Val Gly Leu Leu Ala Pro Pro Gly Gly
            20                  25                  30

Leu Ser Gly Arg Ser Asp Asn His Gly Gly Gly Ser Glu Ile Val Leu
        35                  40                  45

Thr Gln Ser Pro Gly Thr Leu Ser Leu Ser Pro Gly Glu Arg Ala Thr
    50                  55                  60

Leu Ser Cys Arg Ala Ser Gln Ser Val Gly Ser Ser Tyr Leu Ala Trp
65                  70                  75                  80

Tyr Gln Gln Lys Pro Gly Gln Ala Pro Arg Leu Leu Ile Tyr Gly Ala
                85                  90                  95

Phe Ser Arg Ala Thr Gly Ile Pro Asp Arg Phe Ser Gly Ser Gly Ser
            100                 105                 110

Gly Thr Asp Phe Thr Leu Thr Ile Ser Arg Leu Glu Pro Glu Asp Phe
        115                 120                 125

Ala Val Tyr Tyr Cys Gln Gln Tyr Gly Ser Ser Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
```

```
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys


<210> SEQ ID NO 520
<211> LENGTH: 262
<212> TYPE: PRT
<213> ORGANISM: Artificial Sequence
<220> FEATURE:
<223> OTHER INFORMATION: Spacer - YV54-3001 LC

<400> SEQUENCE: 520

Gln Gly Gln Ser Gly Ser Cys Leu His Ser Ala Tyr Asn Ala Cys Leu
1               5                   10                  15

Asp Pro Gly Gly Gly Ser Ser Gly Gly Ala Val Gly Leu Leu Ala Pro
            20                  25                  30

Pro Gly Gly Leu Ser Gly Arg Ser Asp Asn His Gly Gly Ser Glu
        35                  40                  45

Ile Val Leu Thr Gln Ser Pro Gly Thr Leu Ser Leu Ser Pro Gly Glu
    50                  55                  60

Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
            260
```

<210> SEQ ID NO 521
<211> LENGTH: 256
<212> TYPE: PRT
<213> ORGANISM: Artificial Sequence
<220> FEATURE:
<223> OTHER INFORMATION: YV54-3001 LC

<400> SEQUENCE: 521

```
Cys Leu His Ser Ala Tyr Asn Ala Cys Leu Asp Pro Gly Gly Gly Ser
1               5                   10                  15

Ser Gly Gly Ala Val Gly Leu Leu Ala Pro Pro Gly Gly Leu Ser Gly
            20                  25                  30

Arg Ser Asp Asn His Gly Gly Gly Ser Glu Ile Val Leu Thr Gln Ser
        35                  40                  45

Pro Gly Thr Leu Ser Leu Ser Pro Gly Glu Arg Ala Thr Leu Ser Cys
    50                  55                  60

Arg Ala Ser Gln Ser Val Gly Ser Ser Tyr Leu Ala Trp Tyr Gln Gln
65                  70                  75                  80

Lys Pro Gly Gln Ala Pro Arg Leu Leu Ile Tyr Gly Ala Phe Ser Arg
                85                  90                  95

Ala Thr Gly Ile Pro Asp Arg Phe Ser Gly Ser Gly Ser Gly Thr Asp
            100                 105                 110

Phe Thr Leu Thr Ile Ser Arg Leu Glu Pro Glu Asp Phe Ala Val Tyr
        115                 120                 125

Tyr Cys Gln Gln Tyr Gly Ser Ser Pro Trp Thr Phe Gly Gln Gly Thr
    130                 135                 140

Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Ser Thr Leu Thr Leu Ser
    210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255
```

<210> SEQ ID NO 522
<211> LENGTH: 262
<212> TYPE: PRT
<213> ORGANISM: Artificial Sequence
<220> FEATURE:
<223> OTHER INFORMATION: Spacer - YV55-3001 LC

<400> SEQUENCE: 522

```
Gln Gly Gln Ser Gly Ser Cys Ala His Ser Ala Tyr Asn Val Cys Leu
1               5                   10                  15

Asp Pro Gly Gly Gly Ser Ser Gly Gly Ala Val Gly Leu Leu Ala Pro
            20                  25                  30

Pro Gly Gly Leu Ser Gly Arg Ser Asp Asn His Gly Gly Gly Ser Glu
        35                  40                  45

Ile Val Leu Thr Gln Ser Pro Gly Thr Leu Ser Leu Ser Pro Gly Glu
```

50 55 60

Arg Ala Thr Leu Ser Cys Arg Ala Ser Gln Ser Val Gly Ser Ser Tyr
65 70 75 80

Leu Ala Trp Tyr Gln Gln Lys Pro Gly Gln Ala Pro Arg Leu Leu Ile
85 90 95

Tyr Gly Ala Phe Ser Arg Ala Thr Gly Ile Pro Asp Arg Phe Ser Gly
100 105 110

Ser Gly Ser Gly Thr Asp Phe Thr Leu Thr Ile Ser Arg Leu Glu Pro
115 120 125

Glu Asp Phe Ala Val Tyr Tyr Cys Gln Gln Tyr Gly Ser Ser Pro Trp
130 135 140

Thr Phe Gly Gln Gly Thr Lys Val Glu Ile Lys Arg Thr Val Ala Ala
145 150 155 160

Pro Ser Val Phe Ile Phe Pro Pro Ser Asp Glu Gln Leu Lys Ser Gly
165 170 175

Thr Ala Ser Val Val Cys Leu Leu Asn Asn Phe Tyr Pro Arg Glu Ala
180 185 190

Lys Val Gln Trp Lys Val Asp Asn Ala Leu Gln Ser Gly Asn Ser Gln
195 200 205

Glu Ser Val Thr Glu Gln Asp Ser Lys Asp Ser Thr Tyr Ser Leu Ser
210 215 220

Ser Thr Leu Thr Leu Ser Lys Ala Asp Tyr Glu Lys His Lys Val Tyr
225 230 235 240

Ala Cys Glu Val Thr His Gln Gly Leu Ser Ser Pro Val Thr Lys Ser
245 250 255

Phe Asn Arg Gly Glu Cys
260

<210> SEQ ID NO 523
<211> LENGTH: 256
<212> TYPE: PRT
<213> ORGANISM: Artificial Sequence
<220> FEATURE:
<223> OTHER INFORMATION: YV55-3001 LC

<400> SEQUENCE: 523

Cys Ala His Ser Ala Tyr Asn Val Cys Leu Asp Pro Gly Gly Gly Ser
1 5 10 15

Ser Gly Gly Ala Val Gly Leu Leu Ala Pro Pro Gly Gly Leu Ser Gly
20 25 30

Arg Ser Asp Asn His Gly Gly Gly Ser Glu Ile Val Leu Thr Gln Ser
35 40 45

Pro Gly Thr Leu Ser Leu Ser Pro Gly Glu Arg Ala Thr Leu Ser Cys
50 55 60

Arg Ala Ser Gln Ser Val Gly Ser Ser Tyr Leu Ala Trp Tyr Gln Gln
65 70 75 80

Lys Pro Gly Gln Ala Pro Arg Leu Leu Ile Tyr Gly Ala Phe Ser Arg
85 90 95

Ala Thr Gly Ile Pro Asp Arg Phe Ser Gly Ser Gly Ser Gly Thr Asp
100 105 110

Phe Thr Leu Thr Ile Ser Arg Leu Glu Pro Glu Asp Phe Ala Val Tyr
115 120 125

Tyr Cys Gln Gln Tyr Gly Ser Ser Pro Trp Thr Phe Gly Gln Gly Thr
130 135 140

Lys Val Glu Ile Lys Arg Thr Val Ala Ala Pro Ser Val Phe Ile Phe

```
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Ser Thr Leu Thr Leu Ser
    210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255


<210> SEQ ID NO 524
<211> LENGTH: 262
<212> TYPE: PRT
<213> ORGANISM: Artificial Sequence
<220> FEATURE:
<223> OTHER INFORMATION: Spacer - YV56-3001 LC

<400> SEQUENCE: 524

Gln Gly Gln Ser Gly Ser Cys Leu His Ser Ala Tyr Asn Val Cys Ala
1               5                   10                  15

Asp Pro Gly Gly Gly Ser Ser Gly Gly Ala Val Gly Leu Leu Ala Pro
            20                  25                  30

Pro Gly Gly Leu Ser Gly Arg Ser Asp Asn His Gly Gly Gly Ser Glu
        35                  40                  45

Ile Val Leu Thr Gln Ser Pro Gly Thr Leu Ser Leu Ser Pro Gly Glu
    50                  55                  60

Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
```

260

<210> SEQ ID NO 525
<211> LENGTH: 256
<212> TYPE: PRT
<213> ORGANISM: Artificial Sequence
<220> FEATURE:
<223> OTHER INFORMATION: YV56-3001 LC

<400> SEQUENCE: 525

Cys Leu His Ser Ala Tyr Asn Val Cys Ala Asp Pro Gly Gly Gly Ser
1 5 10 15

Ser Gly Gly Ala Val Gly Leu Leu Ala Pro Pro Gly Gly Leu Ser Gly
20 25 30

Arg Ser Asp Asn His Gly Gly Gly Ser Glu Ile Val Leu Thr Gln Ser
35 40 45

Pro Gly Thr Leu Ser Leu Ser Pro Gly Glu Arg Ala Thr Leu Ser Cys
50 55 60

Arg Ala Ser Gln Ser Val Gly Ser Ser Tyr Leu Ala Trp Tyr Gln Gln
65 70 75 80

Lys Pro Gly Gln Ala Pro Arg Leu Leu Ile Tyr Gly Ala Phe Ser Arg
85 90 95

Ala Thr Gly Ile Pro Asp Arg Phe Ser Gly Ser Gly Ser Gly Thr Asp
100 105 110

Phe Thr Leu Thr Ile Ser Arg Leu Glu Pro Glu Asp Phe Ala Val Tyr
115 120 125

Tyr Cys Gln Gln Tyr Gly Ser Ser Pro Trp Thr Phe Gly Gln Gly Thr
130 135 140

Lys Val Glu Ile Lys Arg Thr Val Ala Ala Pro Ser Val Phe Ile Phe
145 150 155 160

Pro Pro Ser Asp Glu Gln Leu Lys Ser Gly Thr Ala Ser Val Val Cys
165 170 175

Leu Leu Asn Asn Phe Tyr Pro Arg Glu Ala Lys Val Gln Trp Lys Val
180 185 190

Asp Asn Ala Leu Gln Ser Gly Asn Ser Gln Glu Ser Val Thr Glu Gln
195 200 205

Asp Ser Lys Asp Ser Thr Tyr Ser Leu Ser Ser Thr Leu Thr Leu Ser
210 215 220

Lys Ala Asp Tyr Glu Lys His Lys Val Tyr Ala Cys Glu Val Thr His
225 230 235 240

Gln Gly Leu Ser Ser Pro Val Thr Lys Ser Phe Asn Arg Gly Glu Cys
245 250 255

<210> SEQ ID NO 526
<211> LENGTH: 262
<212> TYPE: PRT
<213> ORGANISM: Artificial Sequence
<220> FEATURE:
<223> OTHER INFORMATION: Spacer - YV57-3001 LC

<400> SEQUENCE: 526

Gln Gly Gln Ser Gly Ser Cys Leu His Ser Ala Tyr Asn Val Cys Leu
1 5 10 15

Ala Pro Gly Gly Gly Ser Ser Gly Gly Ala Val Gly Leu Leu Ala Pro
20 25 30

Pro Gly Gly Leu Ser Gly Arg Ser Asp Asn His Gly Gly Gly Ser Glu
35 40 45

```
Ile Val Leu Thr Gln Ser Pro Gly Thr Leu Ser Leu Ser Pro Gly Glu
    50                  55                  60

Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
            260
```

<210> SEQ ID NO 527
<211> LENGTH: 256
<212> TYPE: PRT
<213> ORGANISM: Artificial Sequence
<220> FEATURE:
<223> OTHER INFORMATION: YV57-3001 LC

<400> SEQUENCE: 527

```
Cys Leu His Ser Ala Tyr Asn Val Cys Leu Ala Pro Gly Gly Gly Ser
1               5                   10                  15

Ser Gly Gly Ala Val Gly Leu Leu Ala Pro Pro Gly Gly Leu Ser Gly
            20                  25                  30

Arg Ser Asp Asn His Gly Gly Gly Ser Glu Ile Val Leu Thr Gln Ser
        35                  40                  45

Pro Gly Thr Leu Ser Leu Ser Pro Gly Glu Arg Ala Thr Leu Ser Cys
    50                  55                  60

Arg Ala Ser Gln Ser Val Gly Ser Ser Tyr Leu Ala Trp Tyr Gln Gln
65                  70                  75                  80

Lys Pro Gly Gln Ala Pro Arg Leu Leu Ile Tyr Gly Ala Phe Ser Arg
                85                  90                  95

Ala Thr Gly Ile Pro Asp Arg Phe Ser Gly Ser Gly Ser Gly Thr Asp
            100                 105                 110

Phe Thr Leu Thr Ile Ser Arg Leu Glu Pro Glu Asp Phe Ala Val Tyr
        115                 120                 125

Tyr Cys Gln Gln Tyr Gly Ser Ser Pro Trp Thr Phe Gly Gln Gly Thr
    130                 135                 140
```

```
Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Ser Thr Leu Thr Leu Ser
    210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255


<210> SEQ ID NO 528
<211> LENGTH: 262
<212> TYPE: PRT
<213> ORGANISM: Artificial Sequence
<220> FEATURE:
<223> OTHER INFORMATION: Spacer - YV58-3001 LC

<400> SEQUENCE: 528

Gln Gly Gln Ser Gly Ser Cys Leu His Ser Ala Tyr Asn Val Cys Leu
1               5                   10                  15

Asp Ala Gly Gly Gly Ser Ser Gly Gly Ala Val Gly Leu Leu Ala Pro
            20                  25                  30

Pro Gly Gly Leu Ser Gly Arg Ser Asp Asn His Gly Gly Gly Ser Glu
        35                  40                  45

Ile Val Leu Thr Gln Ser Pro Gly Thr Leu Ser Leu Ser Pro Gly Glu
    50                  55                  60

Arg Ala Thr Leu Ser Cys Arg Ala Ser Gln Ser Val Gly Ser Ser Tyr
65                  70                  75                  80

Leu Ala Trp Tyr Gln Gln Lys Pro Gly Gln Ala Pro Arg Leu Leu Ile
                85                  90                  95

Tyr Gly Ala Phe Ser Arg Ala Thr Gly Ile Pro Asp Arg Phe Ser Gly
            100                 105                 110

Ser Gly Ser Gly Thr Asp Phe Thr Leu Thr Ile Ser Arg Leu Glu Pro
        115                 120                 125

Glu Asp Phe Ala Val Tyr Tyr Cys Gln Gln Tyr Gly Ser Ser Pro Trp
    130                 135                 140

Thr Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255
```

```
Phe Asn Arg Gly Glu Cys
            260


<210> SEQ ID NO 529
<211> LENGTH: 256
<212> TYPE: PRT
<213> ORGANISM: Artificial Sequence
<220> FEATURE:
<223> OTHER INFORMATION: YV58-3001 LC

<400> SEQUENCE: 529

Cys Leu His Ser Ala Tyr Asn Val Cys Leu Asp Ala Gly Gly Gly Ser
1               5                   10                  15

Ser Gly Gly Ala Val Gly Leu Leu Ala Pro Pro Gly Gly Leu Ser Gly
            20                  25                  30

Arg Ser Asp Asn His Gly Gly Gly Ser Glu Ile Val Leu Thr Gln Ser
        35                  40                  45

Pro Gly Thr Leu Ser Leu Ser Pro Gly Glu Arg Ala Thr Leu Ser Cys
    50                  55                  60

Arg Ala Ser Gln Ser Val Gly Ser Ser Tyr Leu Ala Trp Tyr Gln Gln
65                  70                  75                  80

Lys Pro Gly Gln Ala Pro Arg Leu Leu Ile Tyr Gly Ala Phe Ser Arg
                85                  90                  95

Ala Thr Gly Ile Pro Asp Arg Phe Ser Gly Ser Gly Ser Gly Thr Asp
            100                 105                 110

Phe Thr Leu Thr Ile Ser Arg Leu Glu Pro Glu Asp Phe Ala Val Tyr
        115                 120                 125

Tyr Cys Gln Gln Tyr Gly Ser Ser Pro Trp Thr Phe Gly Gln Gly Thr
    130                 135                 140

Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Ser Thr Leu Thr Leu Ser
    210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255


<210> SEQ ID NO 530
<211> LENGTH: 259
<212> TYPE: PRT
<213> ORGANISM: Artificial Sequence
<220> FEATURE:
<223> OTHER INFORMATION: Spacer - YV39-NSUB LC

<400> SEQUENCE: 530

Gln Gly Gln Ser Gly Ser Cys Arg Thr Gln Leu Tyr Gly Tyr Asn Leu
1               5                   10                  15

Cys Pro Tyr Gly Gly Gly Ser Ser Gly Gly Ser Gly Gly Ser Gly Gly
            20                  25                  30

Ser Gly Gly Gly Ser Gly Gly Gly Ser Gly Gly Ser Glu Ile Val Leu
        35                  40                  45
```

```
Thr Gln Ser Pro Gly Thr Leu Ser Leu Ser Pro Gly Glu Arg Ala Thr
    50                  55                  60

Leu Ser Cys Arg Ala Ser Gln Ser Val Gly Ser Ser Tyr Leu Ala Trp
65                  70                  75                  80

Tyr Gln Gln Lys Pro Gly Gln Ala Pro Arg Leu Leu Ile Tyr Gly Ala
                85                  90                  95

Phe Ser Arg Ala Thr Gly Ile Pro Asp Arg Phe Ser Gly Ser Gly Ser
            100                 105                 110

Gly Thr Asp Phe Thr Leu Thr Ile Ser Arg Leu Glu Pro Glu Asp Phe
        115                 120                 125

Ala Val Tyr Tyr Cys Gln Gln Tyr Gly Ser Ser Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys


<210> SEQ ID NO 531
<211> LENGTH: 253
<212> TYPE: PRT
<213> ORGANISM: Artificial Sequence
<220> FEATURE:
<223> OTHER INFORMATION: YV39-NSUB LC

<400> SEQUENCE: 531

Cys Arg Thr Gln Leu Tyr Gly Tyr Asn Leu Cys Pro Tyr Gly Gly Gly
1               5                   10                  15

Ser Ser Gly Gly Ser Gly Gly Ser Gly Gly Ser Gly Gly Gly Ser Gly
            20                  25                  30

Gly Gly Ser Gly Gly Ser Glu Ile Val Leu Thr Gln Ser Pro Gly Thr
        35                  40                  45

Leu Ser Leu Ser Pro Gly Glu Arg Ala Thr Leu Ser Cys Arg Ala Ser
    50                  55                  60

Gln Ser Val Gly Ser Ser Tyr Leu Ala Trp Tyr Gln Gln Lys Pro Gly
65                  70                  75                  80

Gln Ala Pro Arg Leu Leu Ile Tyr Gly Ala Phe Ser Arg Ala Thr Gly
                85                  90                  95

Ile Pro Asp Arg Phe Ser Gly Ser Gly Ser Gly Thr Asp Phe Thr Leu
            100                 105                 110

Thr Ile Ser Arg Leu Glu Pro Glu Asp Phe Ala Val Tyr Tyr Cys Gln
        115                 120                 125

Gln Tyr Gly Ser Ser Pro Trp Thr Phe Gly Gln Gly Thr Lys Val Glu
    130                 135                 140
```

```
Ile Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250


<210> SEQ ID NO 532
<211> LENGTH: 2
<212> TYPE: PRT
<213> ORGANISM: Artificial Sequence
<220> FEATURE:
<223> OTHER INFORMATION: Linkers
<220> FEATURE:
<221> NAME/KEY: MISC_FEATURE
<222> LOCATION: (1)..(2)
<223> OTHER INFORMATION: sequence may be repeated any number of times

<400> SEQUENCE: 532

Gly Ser
1


<210> SEQ ID NO 533
<211> LENGTH: 3
<212> TYPE: PRT
<213> ORGANISM: Artificial Sequence
<220> FEATURE:
<223> OTHER INFORMATION: Linkers
<220> FEATURE:
<221> NAME/KEY: MISC_FEATURE
<222> LOCATION: (1)..(3)
<223> OTHER INFORMATION: sequence may be repeated any number of times

<400> SEQUENCE: 533

Gly Gly Ser
1


<210> SEQ ID NO 534
<211> LENGTH: 5
<212> TYPE: PRT
<213> ORGANISM: Artificial Sequence
<220> FEATURE:
<223> OTHER INFORMATION: Linkers
<220> FEATURE:
<221> NAME/KEY: MISC_FEATURE
<222> LOCATION: (1)..(5)
<223> OTHER INFORMATION: sequence may be repeated any number of times

<400> SEQUENCE: 534

Gly Ser Gly Gly Ser
1               5


<210> SEQ ID NO 535
<211> LENGTH: 4
<212> TYPE: PRT
<213> ORGANISM: Artificial Sequence
<220> FEATURE:
<223> OTHER INFORMATION: Linkers
```

<220> FEATURE:
<221> NAME/KEY: MISC_FEATURE
<222> LOCATION: (1)..(4)
<223> OTHER INFORMATION: sequence may be repeated any number of times

<400> SEQUENCE: 535

Gly Gly Gly Ser
1

<210> SEQ ID NO 536
<211> LENGTH: 4
<212> TYPE: PRT
<213> ORGANISM: Artificial Sequence
<220> FEATURE:
<223> OTHER INFORMATION: Linkers

<400> SEQUENCE: 536

Gly Gly Ser Gly
1

<210> SEQ ID NO 537
<211> LENGTH: 5
<212> TYPE: PRT
<213> ORGANISM: Artificial Sequence
<220> FEATURE:
<223> OTHER INFORMATION: Linkers

<400> SEQUENCE: 537

Gly Gly Ser Gly Gly
1               5

<210> SEQ ID NO 538
<211> LENGTH: 5
<212> TYPE: PRT
<213> ORGANISM: Artificial Sequence
<220> FEATURE:
<223> OTHER INFORMATION: Linkers

<400> SEQUENCE: 538

Gly Ser Gly Ser Gly
1               5

<210> SEQ ID NO 539
<211> LENGTH: 5
<212> TYPE: PRT
<213> ORGANISM: Artificial Sequence
<220> FEATURE:
<223> OTHER INFORMATION: Linkers

<400> SEQUENCE: 539

Gly Ser Gly Gly Gly
1               5

<210> SEQ ID NO 540
<211> LENGTH: 5
<212> TYPE: PRT
<213> ORGANISM: Artificial Sequence
<220> FEATURE:
<223> OTHER INFORMATION: Linkers

<400> SEQUENCE: 540

Gly Gly Gly Ser Gly
1               5

<210> SEQ ID NO 541
<211> LENGTH: 5
<212> TYPE: PRT

<213> ORGANISM: Artificial Sequence
<220> FEATURE:
<223> OTHER INFORMATION: Linkers

<400> SEQUENCE: 541

Gly Ser Ser Ser Gly
1               5

<210> SEQ ID NO 542
<211> LENGTH: 8
<212> TYPE: PRT
<213> ORGANISM: Artificial Sequence
<220> FEATURE:
<223> OTHER INFORMATION: Linkers

<400> SEQUENCE: 542

Gly Gly Gly Ser Ser Gly Gly Ser
1               5

<210> SEQ ID NO 543
<211> LENGTH: 4
<212> TYPE: PRT
<213> ORGANISM: Artificial Sequence
<220> FEATURE:
<223> OTHER INFORMATION: Linkers

<400> SEQUENCE: 543

Gly Gly Gly Ser
1

<210> SEQ ID NO 544
<211> LENGTH: 7
<212> TYPE: PRT
<213> ORGANISM: Artificial Sequence
<220> FEATURE:
<223> OTHER INFORMATION: Spacer

<400> SEQUENCE: 544

Gln Gly Gln Ser Gly Gln Gly
1               5

<210> SEQ ID NO 545
<211> LENGTH: 6
<212> TYPE: PRT
<213> ORGANISM: Artificial Sequence
<220> FEATURE:
<223> OTHER INFORMATION: Spacer

<400> SEQUENCE: 545

Gly Gln Ser Gly Gln Gly
1               5

<210> SEQ ID NO 546
<211> LENGTH: 6
<212> TYPE: PRT
<213> ORGANISM: Artificial Sequence
<220> FEATURE:
<223> OTHER INFORMATION: Spacer

<400> SEQUENCE: 546

Gln Gly Gln Ser Gly Ser
1               5

<210> SEQ ID NO 547
<211> LENGTH: 6
<212> TYPE: PRT
<213> ORGANISM: Artificial Sequence
<220> FEATURE:
<223> OTHER INFORMATION: Spacer

<400> SEQUENCE: 547

Gln Gly Gln Ser Gly Gln
1 5

<210> SEQ ID NO 548
<211> LENGTH: 5
<212> TYPE: PRT
<213> ORGANISM: Artificial Sequence
<220> FEATURE:
<223> OTHER INFORMATION: Spacer

<400> SEQUENCE: 548

Gln Ser Gly Gln Gly
1 5

<210> SEQ ID NO 549
<211> LENGTH: 5
<212> TYPE: PRT
<213> ORGANISM: Artificial Sequence
<220> FEATURE:
<223> OTHER INFORMATION: Spacer

<400> SEQUENCE: 549

Gly Gln Ser Gly Ser
1 5

<210> SEQ ID NO 550
<211> LENGTH: 5
<212> TYPE: PRT
<213> ORGANISM: Artificial Sequence
<220> FEATURE:
<223> OTHER INFORMATION: Spacer

<400> SEQUENCE: 550

Gln Gly Gln Ser Gly
1 5

<210> SEQ ID NO 551
<211> LENGTH: 4
<212> TYPE: PRT
<213> ORGANISM: Artificial Sequence
<220> FEATURE:
<223> OTHER INFORMATION: Spacer

<400> SEQUENCE: 551

Ser Gly Gln Gly
1

<210> SEQ ID NO 552
<211> LENGTH: 4
<212> TYPE: PRT
<213> ORGANISM: Artificial Sequence
<220> FEATURE:
<223> OTHER INFORMATION: Spacer

<400> SEQUENCE: 552

Gln Ser Gly Ser
1

<210> SEQ ID NO 553
<211> LENGTH: 4
<212> TYPE: PRT
<213> ORGANISM: Artificial Sequence
<220> FEATURE:

<223> OTHER INFORMATION: Spacer

<400> SEQUENCE: 553

Gln Gly Gln Ser
1

<210> SEQ ID NO 554
<211> LENGTH: 15
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (1)..(2)
<223> OTHER INFORMATION: Xaa can be any amino acid
<220> FEATURE:
<221> NAME/KEY: MISC_FEATURE
<222> LOCATION: (4)..(6)
<223> OTHER INFORMATION: Xaa can be any amino acid

<400> SEQUENCE: 554

Xaa Xaa Cys Xaa Xaa Xaa Met Tyr Gly Tyr Asn Leu Cys Pro Tyr
1 5 10 15

<210> SEQ ID NO 555
<211> LENGTH: 15
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (1)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid

<400> SEQUENCE: 555

Xaa Xaa Xaa Cys Xaa His Ser Met Tyr Asn Val Cys Leu Asp Pro
1 5 10 15

<210> SEQ ID NO 556
<211> LENGTH: 19
<212> TYPE: PRT
<213> ORGANISM: Artificial Sequence
<220> FEATURE:
<223> OTHER INFORMATION: Spacer-YV39

<400> SEQUENCE: 556

Gln Gly Gln Ser Gly Ser Cys Arg Thr Gln Leu Tyr Gly Tyr Asn Leu
1 5 10 15

Cys Pro Tyr

<210> SEQ ID NO 557
<211> LENGTH: 5
<212> TYPE: PRT
<213> ORGANISM: Artificial Sequence
<220> FEATURE:
<223> OTHER INFORMATION: CDR1 HC for Ipilimumab

<400> SEQUENCE: 557

Ser Tyr Thr Met His
1 5

<210> SEQ ID NO 558

<211> LENGTH: 17
<212> TYPE: PRT
<213> ORGANISM: Artificial Sequence
<220> FEATURE:
<223> OTHER INFORMATION: CDR2 HC for Ipilimumab

<400> SEQUENCE: 558

Phe Ile Ser Tyr Asp Gly Asn Asn Lys Tyr Tyr Ala Asp Ser Val Lys
1 5 10 15

Gly

<210> SEQ ID NO 559
<211> LENGTH: 9
<212> TYPE: PRT
<213> ORGANISM: Artificial Sequence
<220> FEATURE:
<223> OTHER INFORMATION: CDR3 HC for Ipilimumab

<400> SEQUENCE: 559

Thr Gly Trp Leu Gly Pro Phe Asp Tyr
1 5

<210> SEQ ID NO 560
<211> LENGTH: 12
<212> TYPE: PRT
<213> ORGANISM: Artificial Sequence
<220> FEATURE:
<223> OTHER INFORMATION: CDR1 LC for Ipilimumab

<400> SEQUENCE: 560

Arg Ala Ser Gln Ser Val Gly Ser Ser Tyr Leu Ala
1 5 10

<210> SEQ ID NO 561
<211> LENGTH: 7
<212> TYPE: PRT
<213> ORGANISM: Artificial Sequence
<220> FEATURE:
<223> OTHER INFORMATION: CDR2 LC for Ipilimumab

<400> SEQUENCE: 561

Gly Ala Phe Ser Arg Ala Thr
1 5

<210> SEQ ID NO 562
<211> LENGTH: 9
<212> TYPE: PRT
<213> ORGANISM: Artificial Sequence
<220> FEATURE:
<223> OTHER INFORMATION: CDR3 LC for Ipilimumab

<400> SEQUENCE: 562

Gln Gln Tyr Gly Ser Ser Pro Trp Thr
1 5

<210> SEQ ID NO 563
<211> LENGTH: 146
<212> TYPE: PRT
<213> ORGANISM: Artificial Sequence
<220> FEATURE:
<223> OTHER INFORMATION: YV39-2001 VL

<400> SEQUENCE: 563

Cys Arg Thr Gln Leu Tyr Gly Tyr Asn Leu Cys Pro Tyr Gly Gly Gly
1 5 10 15

Ser Ser Gly Gly Ser Ile Ser Ser Gly Leu Leu Ser Gly Arg Ser Asp

```
            20                  25                  30

Asn His Gly Gly Gly Ser Glu Ile Val Leu Thr Gln Ser Pro Gly Thr
        35                  40                  45

Leu Ser Leu Ser Pro Gly Glu Arg Ala Thr Leu Ser Cys Arg Ala Ser
    50                  55                  60

Gln Ser Val Gly Ser Ser Tyr Leu Ala Trp Tyr Gln Gln Lys Pro Gly
65                  70                  75                  80

Gln Ala Pro Arg Leu Leu Ile Tyr Gly Ala Phe Ser Arg Ala Thr Gly
                85                  90                  95

Ile Pro Asp Arg Phe Ser Gly Ser Gly Ser Gly Thr Asp Phe Thr Leu
            100                 105                 110

Thr Ile Ser Arg Leu Glu Pro Glu Asp Phe Ala Val Tyr Tyr Cys Gln
        115                 120                 125

Gln Tyr Gly Ser Ser Pro Trp Thr Phe Gly Gln Gly Thr Lys Val Glu
    130                 135                 140

Ile Lys
145


<210> SEQ ID NO 564
<211> LENGTH: 146
<212> TYPE: PRT
<213> ORGANISM: Artificial Sequence
<220> FEATURE:
<223> OTHER INFORMATION: YV39-2011 VL

<400> SEQUENCE: 564

Cys Arg Thr Gln Leu Tyr Gly Tyr Asn Leu Cys Pro Tyr Gly Gly Gly
1               5                   10                  15

Ser Ser Gly Gly Ser Ile Ser Ser Gly Leu Leu Ser Gly Arg Ser Asp
            20                  25                  30

Asn Pro Gly Gly Gly Ser Glu Ile Val Leu Thr Gln Ser Pro Gly Thr
        35                  40                  45

Leu Ser Leu Ser Pro Gly Glu Arg Ala Thr Leu Ser Cys Arg Ala Ser
    50                  55                  60

Gln Ser Val Gly Ser Ser Tyr Leu Ala Trp Tyr Gln Gln Lys Pro Gly
65                  70                  75                  80

Gln Ala Pro Arg Leu Leu Ile Tyr Gly Ala Phe Ser Arg Ala Thr Gly
                85                  90                  95

Ile Pro Asp Arg Phe Ser Gly Ser Gly Ser Gly Thr Asp Phe Thr Leu
            100                 105                 110

Thr Ile Ser Arg Leu Glu Pro Glu Asp Phe Ala Val Tyr Tyr Cys Gln
        115                 120                 125

Gln Tyr Gly Ser Ser Pro Trp Thr Phe Gly Gln Gly Thr Lys Val Glu
    130                 135                 140

Ile Lys
145


<210> SEQ ID NO 565
<211> LENGTH: 146
<212> TYPE: PRT
<213> ORGANISM: Artificial Sequence
<220> FEATURE:
<223> OTHER INFORMATION: YV39-2012 VL

<400> SEQUENCE: 565

Cys Arg Thr Gln Leu Tyr Gly Tyr Asn Leu Cys Pro Tyr Gly Gly Gly
1               5                   10                  15
```

```
Ser Ser Gly Gly Ser Ile Ser Ser Gly Leu Leu Ser Gly Arg Ser Ala
            20                  25                  30

Asn Pro Gly Gly Gly Ser Glu Ile Val Leu Thr Gln Ser Pro Gly Thr
        35                  40                  45

Leu Ser Leu Ser Pro Gly Glu Arg Ala Thr Leu Ser Cys Arg Ala Ser
    50                  55                  60

Gln Ser Val Gly Ser Ser Tyr Leu Ala Trp Tyr Gln Gln Lys Pro Gly
65                  70                  75                  80

Gln Ala Pro Arg Leu Leu Ile Tyr Gly Ala Phe Ser Arg Ala Thr Gly
                85                  90                  95

Ile Pro Asp Arg Phe Ser Gly Ser Gly Ser Gly Thr Asp Phe Thr Leu
            100                 105                 110

Thr Ile Ser Arg Leu Glu Pro Glu Asp Phe Ala Val Tyr Tyr Cys Gln
        115                 120                 125

Gln Tyr Gly Ser Ser Pro Trp Thr Phe Gly Gln Gly Thr Lys Val Glu
    130                 135                 140

Ile Lys
145


<210> SEQ ID NO 566
<211> LENGTH: 12
<212> TYPE: PRT
<213> ORGANISM: Artificial Sequence
<220> FEATURE:
<223> OTHER INFORMATION: MM Consensus Sequence 1
<220> FEATURE:
<221> NAME/KEY: MISC_FEATURE
<222> LOCATION: (2)..(2)
<223> OTHER INFORMATION: Xaa can be L, M, V or T
<220> FEATURE:
<221> NAME/KEY: MISC_FEATURE
<222> LOCATION: (4)..(4)
<223> OTHER INFORMATION: Xaa can be S, V or I
<220> FEATURE:
<221> NAME/KEY: MISC_FEATURE
<222> LOCATION: (5)..(5)
<223> OTHER INFORMATION: Xaa can be F, L, M or A
<220> FEATURE:
<221> NAME/KEY: MISC_FEATURE
<222> LOCATION: (6)..(6)
<223> OTHER INFORMATION: Xaa can be Y or F
<220> FEATURE:
<221> NAME/KEY: MISC_FEATURE
<222> LOCATION: (8)..(8)
<223> OTHER INFORMATION: Xaa can be V or I

<400> SEQUENCE: 566

Cys Xaa Tyr Xaa Xaa Xaa Asn Xaa Cys Leu Asp Pro
1               5                   10


<210> SEQ ID NO 567
<211> LENGTH: 13
<212> TYPE: PRT
<213> ORGANISM: Artificial Sequence
<220> FEATURE:
<223> OTHER INFORMATION: MM Consensus Sequence 2
<220> FEATURE:
<221> NAME/KEY: MISC_FEATURE
<222> LOCATION: (11)..(11)
<223> OTHER INFORMATION: Xaa can be P or A
<220> FEATURE:
<221> NAME/KEY: MISC_FEATURE
<222> LOCATION: (12)..(12)
<223> OTHER INFORMATION: Xaa can be H, R or A

<400> SEQUENCE: 567

Cys Ala Gln Met Tyr Gly Tyr Ser Met Cys Xaa Xaa Thr
```

```
1               5                   10


<210> SEQ ID NO 568
<211> LENGTH: 13
<212> TYPE: PRT
<213> ORGANISM: Artificial Sequence
<220> FEATURE:
<223> OTHER INFORMATION: MM Consensus Sequence 3
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (3)..(3)
<223> OTHER INFORMATION: Xaa can be M, I, Y, L, N or F
<220> FEATURE:
<221> NAME/KEY: MISC_FEATURE
<222> LOCATION: (4)..(4)
<223> OTHER INFORMATION: Xaa can be Y, W, F, Q or T
<220> FEATURE:
<221> NAME/KEY: MISC_FEATURE
<222> LOCATION: (5)..(5)
<223> OTHER INFORMATION: Xaa can be M or Y
<220> FEATURE:
<221> NAME/KEY: MISC_FEATURE
<222> LOCATION: (8)..(8)
<223> OTHER INFORMATION: Xaa can be Y, V or F
<220> FEATURE:
<221> NAME/KEY: MISC_FEATURE
<222> LOCATION: (9)..(9)
<223> OTHER INFORMATION: Xaa can be N or D
<220> FEATURE:
<221> NAME/KEY: MISC_FEATURE
<222> LOCATION: (13)..(13)
<223> OTHER INFORMATION: Xaa can be Y or F

<400> SEQUENCE: 568

Cys Xaa Xaa Xaa Xaa Tyr Gly Xaa Xaa Leu Cys Pro Xaa
1               5                   10


<210> SEQ ID NO 569
<211> LENGTH: 12
<212> TYPE: PRT
<213> ORGANISM: Artificial Sequence
<220> FEATURE:
<223> OTHER INFORMATION: MM Consensus Sequence 4
<220> FEATURE:
<221> NAME/KEY: MISC_FEATURE
<222> LOCATION: (1)..(1)
<223> OTHER INFORMATION: Xaa can be N or T
<220> FEATURE:
<221> NAME/KEY: MISC_FEATURE
<222> LOCATION: (2)..(2)
<223> OTHER INFORMATION: Xaa can be S, T, M or A
<220> FEATURE:
<221> NAME/KEY: MISC_FEATURE
<222> LOCATION: (5)..(5)
<223> OTHER INFORMATION: Xaa can be N or Y
<220> FEATURE:
<221> NAME/KEY: MISC_FEATURE
<222> LOCATION: (8)..(8)
<223> OTHER INFORMATION: Xaa can be M or L
<220> FEATURE:
<221> NAME/KEY: MISC_FEATURE
<222> LOCATION: (10)..(10)
<223> OTHER INFORMATION: Xaa can be H, F or Y
<220> FEATURE:
<221> NAME/KEY: MISC_FEATURE
<222> LOCATION: (12)..(12)
<223> OTHER INFORMATION: Xaa can be Y, F or W

<400> SEQUENCE: 569

Xaa Xaa Cys Pro Xaa His Pro Xaa Cys Xaa Asp Xaa
1               5                   10
```

-continued

```
<210> SEQ ID NO 570
<211> LENGTH: 14
<212> TYPE: PRT
<213> ORGANISM: Artificial Sequence
<220> FEATURE:
<223> OTHER INFORMATION: Protease Resistant Linker

<400> SEQUENCE: 570

Gly Gly Ser Gly Gly Ser Gly Gly Gly Ser Gly Gly Gly Ser
1               5                   10
```